United States Patent
Poitout et al.

(10) Patent No.: US 7,332,517 B2
(45) Date of Patent: Feb. 19, 2008

(54) DERIVATIVES OF HYDANTOINS, THIOHYDANTOINS, PYRIMIDINEDIONES AND THIOXOPYRIMIDINONES, THEIR PREPARATION PROCESSES AND THEIR USE AS MEDICAMENTS

(75) Inventors: Lydie Poitout, Le Kremlin Bicetre (FR); Valérie Brault, Gif-sur-Yvette (FR); Christophe Thurieau, Paris (FR)

(73) Assignee: Société de Conseils de Recheres et d'Applications Scientifiques (SCRAS), Paris (FR)

( * ) Notice: Subject to any disclaimer, the term of this patent is extended or adjusted under 35 U.S.C. 154(b) by 0 days.

(21) Appl. No.: 11/444,769

(22) Filed: Jun. 1, 2006

(65) Prior Publication Data

US 2007/0021420 A1    Jan. 25, 2007

Related U.S. Application Data

(62) Division of application No. 10/813,139, filed on Mar. 30, 2004, now Pat. No. 7,199,145, which is a division of application No. 10/048,144, filed as application No. PCT/FR00/002164 on Jul. 28, 2000, now Pat. No. 6,759,415.

(30) Foreign Application Priority Data

Jul. 30, 1999    (FR)    .................................. 99 09886

(51) Int. Cl.
*A61K 31/4178*    (2006.01)

(52) U.S. Cl. ..................................... 514/392; 514/235.8
(58) Field of Classification Search ................ 514/392, 514/235.8
See application file for complete search history.

*Primary Examiner*—Kahsay Habte
(74) *Attorney, Agent, or Firm*—Charles A. Muserlian

(57) ABSTRACT

A method of treating a disorder selected from the group consisting of acromegaly, hypophyseal adenomas, endocrine gastroenteropancreatic tumors including carcinoid syndrome and gastrointestinal bleeding in warm-blooded animals comprising administering to warm-blooded animals in need thereof an amount of a compound of the formula

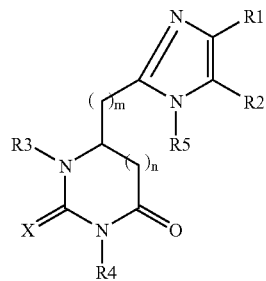

in racemic or enantiomeric form.

5 Claims, No Drawings

DERIVATIVES OF HYDANTOINS, THIOHYDANTOINS, PYRIMIDINEDIONES AND THIOXOPYRIMIDINONES, THEIR PREPARATION PROCESSES AND THEIR USE AS MEDICAMENTS

This application is a division of U.S. patent application Ser. No. 10/813,139 filed Mar. 30,2004, now U.S. Pat. No. 7,199,145 which is a division of U.S. patent application Ser. No. 10/048,144 filed Jan. 23, 2002, now U.S. Pat. No. 6,759,415 which is a 371 of PCT/FR00/02164 filed Jul. 28, 2000.

The invention relates to new derivatives of hydantoins, thiohydantoins, pyrimidinediones and thioxopyrimidinones of general formula (I) represented below, their preparation processes and their use as medicaments. These compounds have a good affinity with certain sub-types of somatostatin receptors and therefore have useful pharmacological properties. The invention also relates to the pharmaceutical compositions containing said compounds and their use for the preparation of a medicament intended to treat pathological states or diseases in which one (or more) somatostatin receptors are involved.

Somatostatin (SST) is a cyclic tetradecapeptide which was isolated for the first time from the hypothalamus as a substance which inhibits the growth hormone (Brazeau P. et al., *Science* 1973, 179, 77-79). It also operates as a neurotransmitter in the brain (Reisine T. et al., *Neuroscience* 1995, 67, 777-790; Reisine T. et al., *Endocrinology* 1995, 16, 427-442). Molecular cloning has allowed it to be shown that the bioactivity of somatostatin depends directly on a family of five receptors linked to the membrane.

The heterogeneity of the biological functions of somatostatin has led to studies which try to identify the structure-activity relationships of peptide analogues on somatostatin receptors, which has led to the discovery of 5 sub-types of receptors (Yamada et al., *Proc. Natl. Acad. Sci.* U.S.A, 89, 251-255, 1992; Raynor, K. et al, *Mol. Pharmacol.*, 44, 385-392, 1993). The functional roles of these receptors are currently being actively studied. The affinities with different sub-types of somatostatin receptors have been associated with the treatment of the following disorders/diseases. Activation of sub-types 2 and 5 has been associated with suppression of the growth hormone (GH) and more particularly with that of adenomas secreting GH (acromegalia) and those secreting hormone TSH. Activation of sub-type 2 but not sub-type 5 has been associated with the treatment of adenomas secreting prolactin. Other indications associated with the activation of sub-types of somatostatin receptors are the recurrence of stenosis, inhibition of the secretion of insulin and/or of glucagon and in particular diabetes mellitus, hyperlipidemia, insensiblity to insulin, Syndrome X, angiopathy, proliferative retinopathy, dawn phenomenon and nephropathy; inhibition of the secretion of gastric acid and in particular peptic ulcers, enterocutaneous and pancreaticocutaneous fistulae, irritable colon syndrome, dumping syndrome, aqueous diarrhoea syndrome, diarrhoea associated with AIDS, diarrhoea induced by chemotherapy, acute or chronic pancreatitis and secretory gastrointestinal tumours; the treatment of cancer such as hepatomas; the inhibition of angiogenesis, the treatment of inflammatory disorders such as arthritis; chronic rejection of allografts; angioplasty; the prevention of bleeding of grafted vessels and gastrointestinal bleeding. The agonists of somatostatin can also be used to reduce the weight of a patient.

Among the pathological disorders associated with somatostatin (Moreau J. P. et al., Life Sciences 1987, 40, 419; Harris A. G. et al., *The European Journal of Medicine*, 1993, 2, 97-105), there can be mentioned for example: acromegalia, hypophyseal adenomas, Cushing's disease, gonadotrophinomas and prolactinomas, catabolic side-effects of glucocorticoids, insulin dependent diabetes, diabetic retinopathy, diabetic nephropathy, hyperthyroidism, gigantism, endocrinic gastroenteropancreatic tumours including carcinoid syndrome, VIPoma, insulinoma, nesidioblastoma, hyperinsulinemia, glucagonoma, gastrinoma and Zollinger-Ellison's syndrome, GRFoma as well as acute bleeding of the esophageal varices, gastroesophageal reflux, gastroduodenal reflux, pancreatitis, enterocutaneous and pancreatic fistulae but also diarrhoeas, refractory diarrhoeas of acquired immunodeficiency syndrome, chronic secretary diarrhoea, diarrhoea associated with irritable bowel syndrome, disorders linked with gastrin releasing peptide, secondary pathologies with intestinal grafts, portal hypertension as well as haemorrhages of the varices in patients with cirrhosis, gastro-intestinal haemorrhage, haemorrhage of the gastroduodenal ulcer, Crohn's disease, systemic scleroses, dumping syndrome, small intestine syndrome, hypotension, scleroderma and medullar thyroid carcinoma, illnesses linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and other therapeutic fields such as, for example, cephaleas including cephalea associated with hypophyseal tumours, pain, panic attacks, chemotherapy, cicatrization of wounds, renal insufficiency resulting from delayed development, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukaemia, meningioma, cancerous cachexia, inhibition of H pylori, psoriasis, as well as Alzheimer's disease. Osteoporosis can also be mentioned.

The Applicant found that the compounds of general formula (I) described hereafter have an affinity and a selectivity for the somatostatin receptors. As somatostatin and its peptide analogues. often have a poor bioavailability by oral route and a low selectivity (Robinson, C., *Drugs of the Future*, 1994, 19, 992; Reubi, J. C. et al., *TIPS*, 1995, 16, 110), said compounds, non-peptide agonists or antagonists of somatostatin, can be advantageously used to treat pathological states or illnesses as presented above and in which one (or more) somatostatin receptors are involved. Preferably, said compounds can be used for the treatment of acromegalia, hypophyseal adenomas or endocrine gastroenteropancreatic tumours including carcinoid syndrome.

The compounds of the present invention correspond to general formula (I)

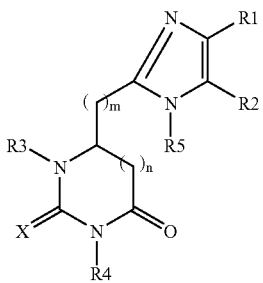

(I)

in racemic, enantiomeric form or all combinations of these forms, in which:

R1 represents a $(C_1-C_{12})$alkyl, $(C_0-C_6)$alkyl-C(O)—O-Z1, $(C_0-C_6)$alkyl-C(O)—NH—$(CH_2)_p$-Z2 or aryl radical optionally substituted, Z1 represents H, a $(C_1-C_6)$ alkyl, —$(CH_2)_p$-aryl radical;

Z2 represents an amino, $(C_1-C_{12})$alkylamino, $(C_3-C_8)$cycloalkylamino, N,N-di-$(C_1-C_{12})$alkylamino, NH—C(O)—O—$(CH_2)_p$-phenyl, NH—C(O)—O—$(CH_2)_p$—$(C_1-C_6)$alkyl radical, an optionally substituted carbocyclic or heterocyclic aryl radical or an optionally substituted heterocyclic non aromatic radical;

R2 represents H, $(C_1-C_{12})$alkyl or aryl optionally substituted;

R3 represents H or $(CH_2)_p$-Z3;

Z3 represents $(C_1-C_{12})$alkyl, $(C_1-C_{12})$alkenyl, $(C_3-C_8)$cycloalkyl, —Y1—$(CH_2)_p$-phenyl-$(X1)_n$, —S—$(C_1-C_{12})$alkyl, S—$(C_1-C_{12})$alkyl-S—S—$(C_1-C_{12})$alkyl, an optionally substituted carbocyclic or heterocyclic aryl radical, and in particular one of the radicals represented below

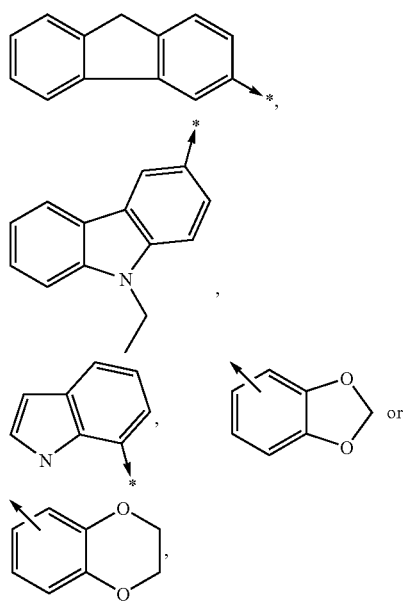

an optionally substituted heterocyclic non aromatic radical, a bis-arylalkyl or di-arylalkyl radical or also the radical

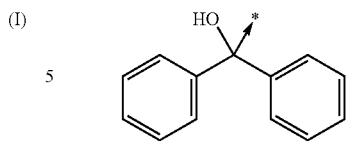

Y1 represents O, S, NH or is absent;

R4 represents $(CH_2)_p$-Z4;

Z4 represents amino, $(C_1-C_{12})$alkyl, $(C_3-C_8)$cycloalkyl, $(C_1-C_{12})$alkylamino, N,N-di-$(C_1-C_{12})$alkylamino, amino$(C_3-C_6)$cycloalkyl, amino$(C_1-C_6)$alkyl$(C_3-C_6)$cycloalkyl$(C_1-C_6)$alkyl, carbocyclic or heterocyclic aminoaryl, $(C_1-C_{12})$ alkoxy, $(C_1-C_{12})$alkenyl, N—C(O)O$(C_1-C_6)$alkyl, an optionally substituted carbocyclic or heterocyclic aryl radical, an optionally substituted heterocyclic non aromatic radical, bis-arylalkyl, di-arylalkyl or one of the radicals represented below

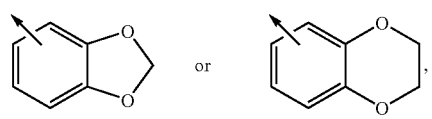

or also Z4 represents an N(R6)(R7) radical in which R6 and R7 taken together with the nitrogen atom which they carry form together a heterocycle with 5 to 7 members;

R5 represents H, —$(CH_2)_p$—C(O)—$(CH_2)_p$-Z5, —$(CH_2)_p$-Z5, —$(CH_2)_p$—OZ5 or —$(C_0-C_6)$alkyl-C(O)—NH—$(CH_2)_p$-Z5, Z5 representing an optionally substituted radical chosen from the group constituted by the —$(C_1-C_{12})$alkyl, benzo[b]thiophene, phenyl, naphthyl, benzo[b]furannyl, thiophene, isoxazolyl, indolyl radicals, and

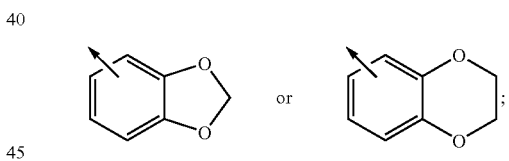

it being understood that an optionally substituted radical or an optionally substituted phenyl is optionally substituted by one or more substituent, each preferably chosen independently from the group constituted by the Cl, F, Br, I, $CF_3$, $NO_2$, OH, $NH_2$, CN, $N_3$, —$OCF_3$, $(C_1-C_{12})$alkyl, $(C_1-C_{12})$alkoxy, —$(CH_2)_p$-phenyl-$(X1)_q$, —NH—CO—$(C_{1-C6})$alkyl, —NH—C(O)O—$(C_1-C_6)$alkyl, —S—$(C_1-C_6)$alkyl, —S-phenyl-$(X1)_q$, —O—$(CH_2)_p$-phenyl-$(X1)_q$, —$(CH_2)_p$—C(O)—O—$(C_1-C_6)$alkyl, —$(CH_2)_p$—C(O)—$(C_1-C_6)$alkyl, —O—$(CH_2)_p$—$NH_2$, —O—$(CH_2)_p$—NH—$C_1-C_6)$alkyl, —O—$(CH_2)_p$—N-di-$((C_1-C_6)$alkyl) and —$((C_0-C_{12}))$alkyl-$(X1)_q$ radicals;

X1, each time that it occurs, is independently chosen from the group constituted by the H, Cl, F, Br, I, $CF_3$, $NO_2$, OH, $NH_2$, CN, $N_3$, —$OCF_3$, $(C_1-C_{12})$alkyl, $(C_1-C_{12})$alkoxy, —S—$(C_1-C_6)$alkyl, —$(CH_2)_p$-amino, —$(CH_2)_p$—NH—$(C_1-C_6)$alkyl, —$(CH_2)_p$—N-di-$((C_1-C_6)$alkyl), —$(CH_2)_p$ and —$(CH_2)_p$—NH—$(C_3-C_6)$cycloalkyl radicals;

p each time that it occurs is independently 0 or an integer from 1 to 6;

q each time that it occurs is independently an integer from 1 to 5.

X represents O or S;

n represents 0 or 1; and finally when n represents 0, m represents 1, 2 or 3, and when n represents 1, m represents 0 or 1.

According to a preferred variant of the invention, the compounds of general formula (I) are such that R5 represents H.

The compounds of general formula (I) can, if appropriate, contain more than one asymmrnetrical centre. If this happens, the diastereomers or any mixture of diastereomers are also included in the invention. For example, when the compound of general formula (I) has two asymmetrical centres, the invention will include the compounds of general formula (I) of "R,S", "S,R", "R,R" and "S,S" configurations, as well as a mixture in whatever proportions of the latter.

In the present invention, the alkyl radicals can be linear or branched. By alkyl, unless specified otherwise, is meant a linear or branched alkyl radical containing 1 to 6 carbon atoms. By cycloalkyl, unless specified otherwise, is meant a monocyclic carbon system containing 3 to 7 carbon atoms. By alkenyl, unless specified otherwise, is meant a linear or branched alkyl radical containing 1 to 6 carbon atoms and having at least one unsaturation (double bond). By alkynyl, unless specified otherwise, is meant a linear or branched alkyl radical containing 1 to 6 carbon atoms and having at least one double unsaturation (triple bond). By carbocyclic or heterocyclic aryl, is meant a carbocyclic or heterocyclic system containing at least one aromatic ring, a system being called heterocyclic when at least one of the rings which comprise it contains a heteroatom (O, N or S). By aryl, unless specified otherwise, is meant a carbocyclic system comprising at least one aromatic ring. By haloalkyl, is meant an alkyl radical of which at least one of the hydrogen atoms (and optionally all) is replaced by a halogen atom. By heterocyclic non aromatic radical, is meant a heterocyclic system containing no aromatic ring, at least one of the rings comprising said system containing at least one heteroatom (O, N or S).

By alkylthio, alkoxy, haloalkyl, haloalkoxy, aminoalkyl, alkylamino, alkenyl, alkynyl and aralkyl radicals, is meant respectively the alkylthio, alkoxy, haloalkyl, haloalkoxy, aminoalkyl, alkylmino, alkenyl, alkynyl and aralkyl radicals the alkyl radical of which has the meaning indicated previously.

By N,N-di-($C_1$-$C_{12}$)alkylamino radical, is meant a dialkylamino radical of which the two alkyl radicals substituting the nitrogen atom can have independently 1 to 12 carbon atoms.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By cycloalkyl, is meant in particular the cyclopropanyl, cyclobutanyl, cyclopentanyl, cyclohexyl and cycloheptanyl radicals. By carbocyclic or heterocyclic aryl, is meant in particular the phenyl, naphthyl, pyridinyl, furannyl, pyrrolyl, thiophenyl, thiazolyl, indanyl, indolyl, imidazolyl, benzofurannyl, benzothiophenyl, phthalimidyl radicals. By carbocyclic or heterocyclic aralkyl, is meant in particular the benzyl, phenylethyl, phenylpropyl, phenylbutyl, indolylalkyl, phthalimidoalkyl radicals.

When an arrow emanates from a chemical structure, said arrow indicates the attachment point. For example:

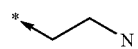

represents the aminoethyl radical.

When an arrow is drawn through a bi- or tricyclic group, said arrow indicates that said bi- or tricyclic group can be attached by any of the available attachment points on any aromatic ring of said group. For example:

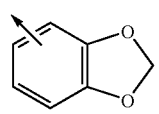

represents a radical which is attached at any position on the benzene rinag

In particular, the compounds of general formula (I) according to the invention can be chosen such that:

R1 represents an optionally substituted aryl radical;

R2 represents H or an alkyl radical;

R3 represents one of the following radicals:

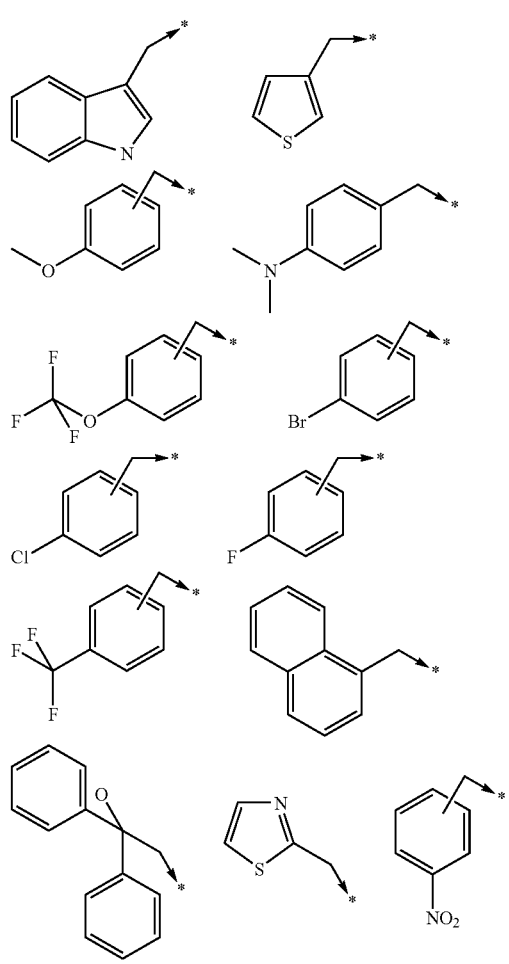

-continued
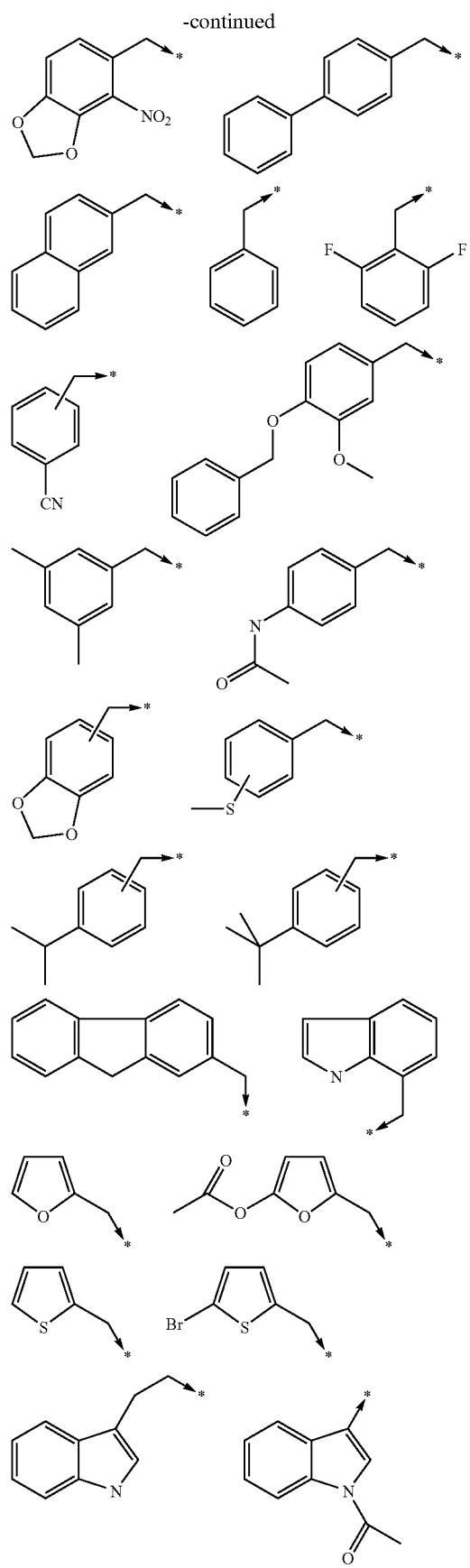
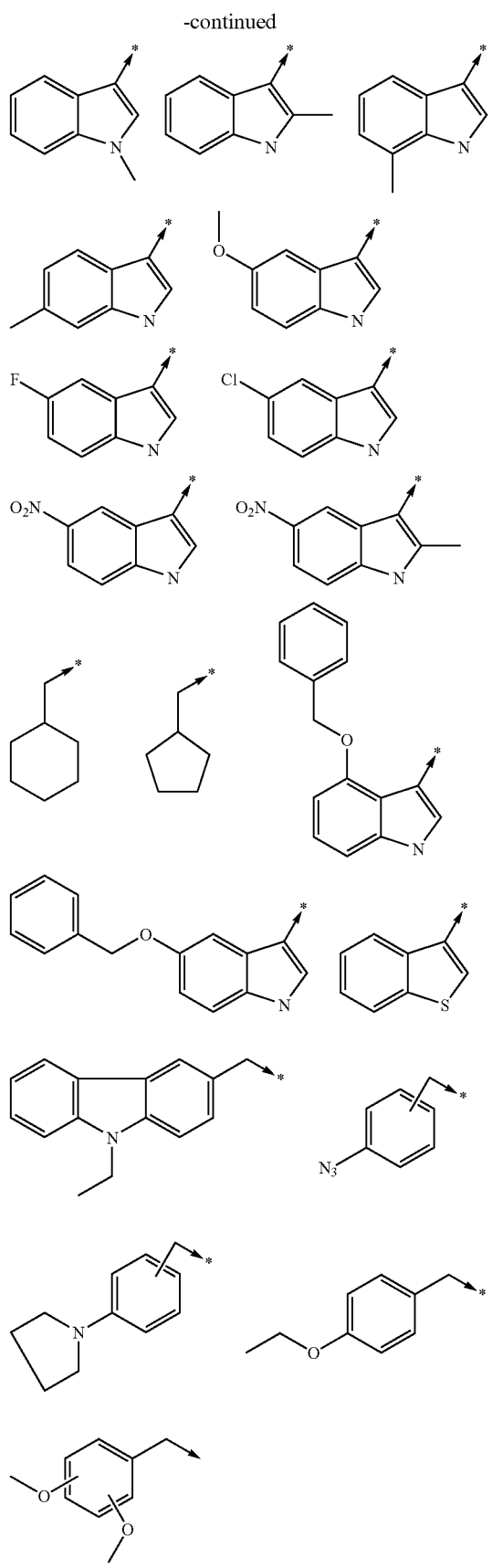

R4 represents one of the following radicals:
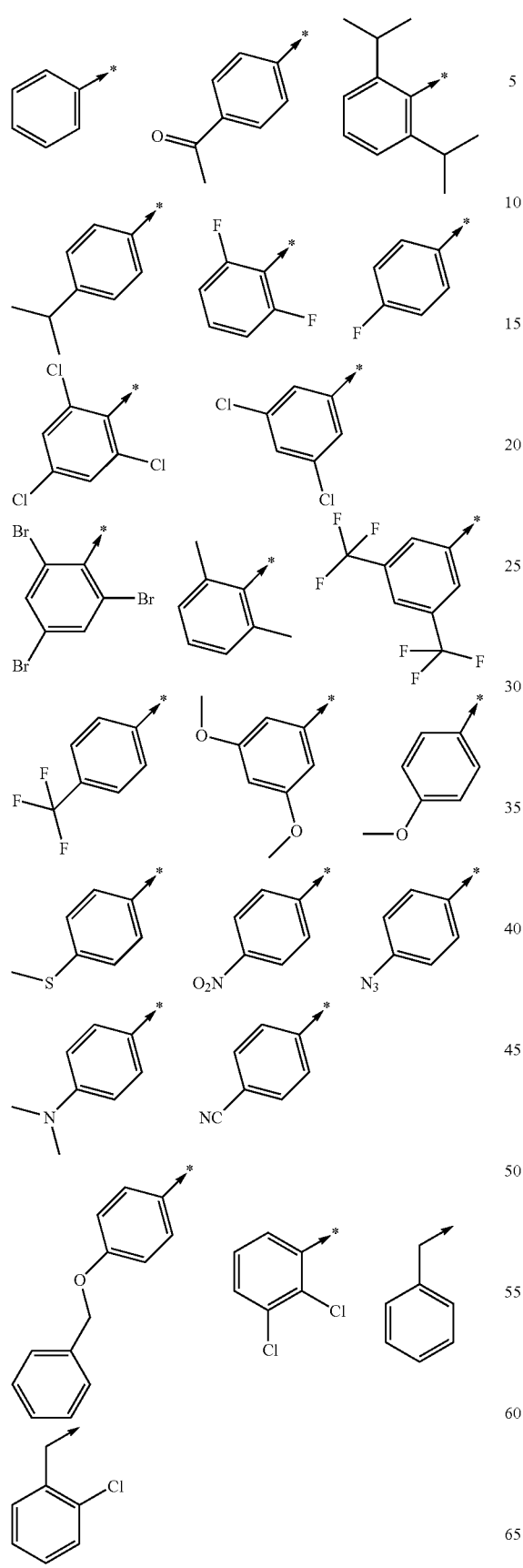
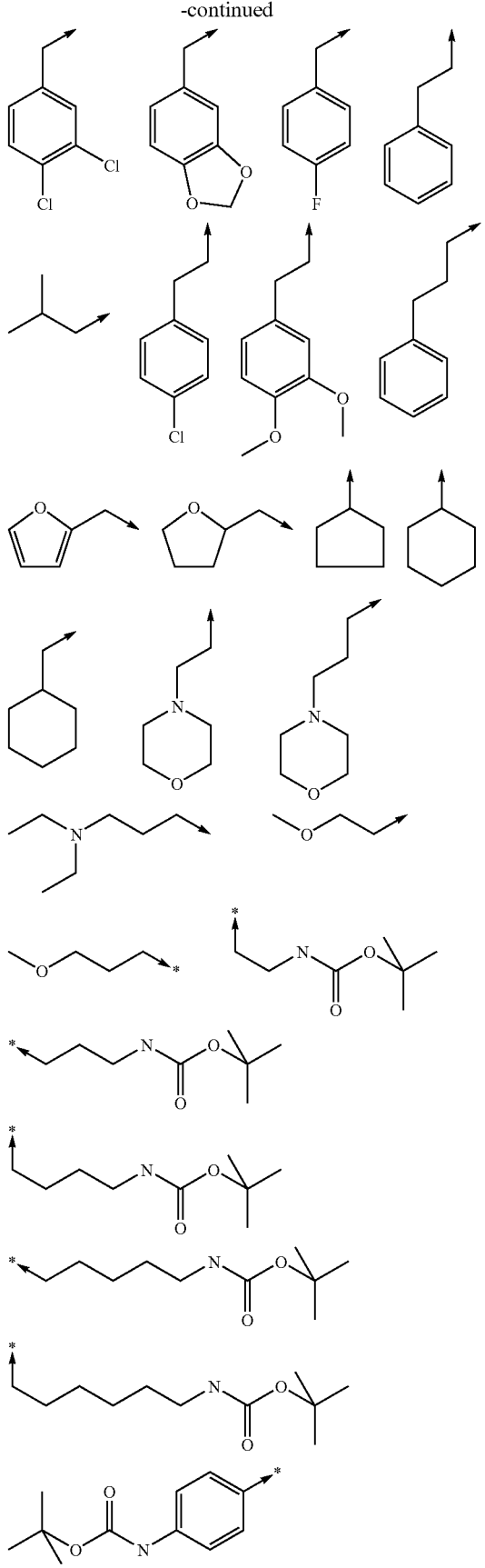

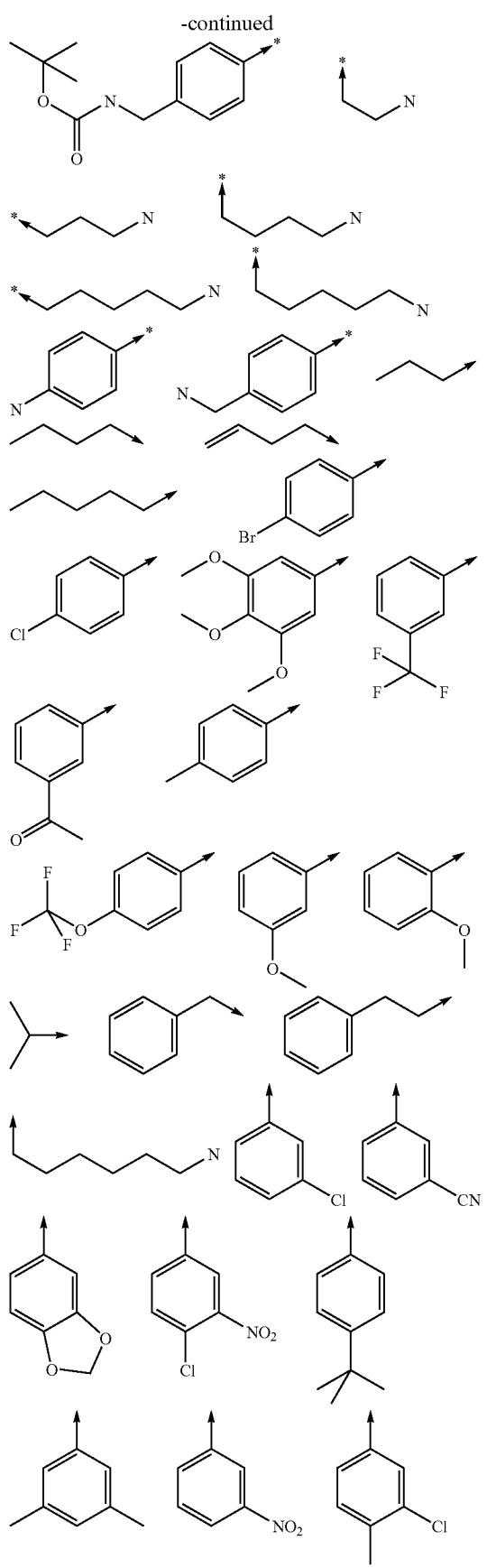

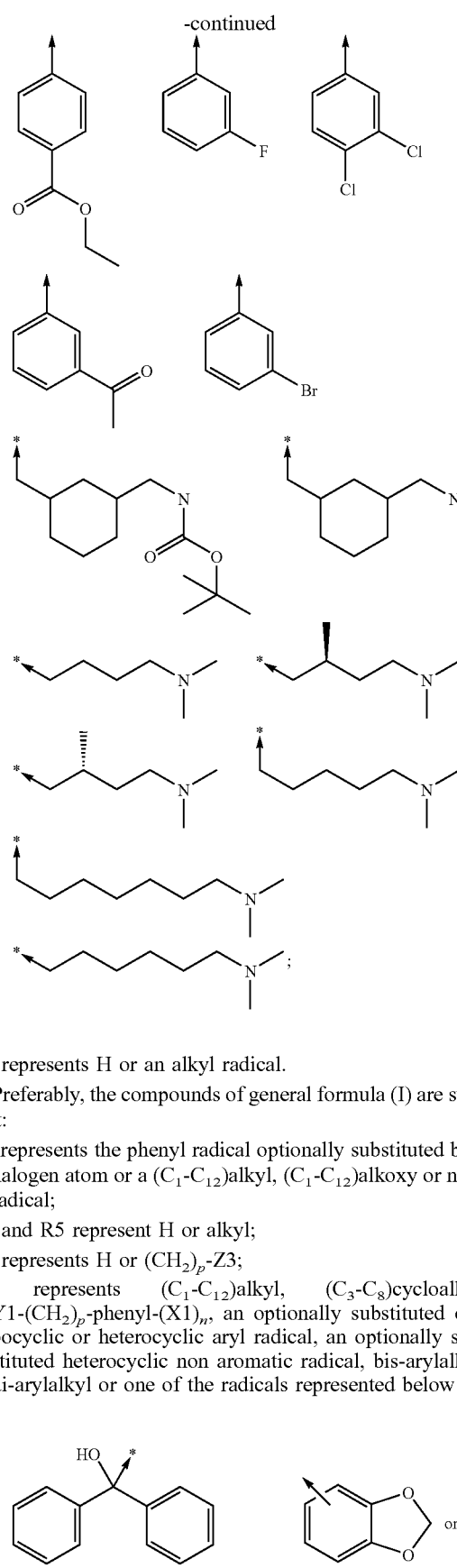

R5 represents H or an alkyl radical.

Preferably, the compounds of general formula (I) are such that:

R1 represents the phenyl radical optionally substituted by a halogen atom or a $(C_1-C_{12})$alkyl, $(C_1-C_{12})$alkoxy or nitro radical;

R2 and R5 represent H or alkyl;

R3 represents H or $(CH_2)_p$-Z3;

Z3 represents $(C_1-C_{12})$alkyl, $(C_3-C_8)$cycloalkyl, Y1-$(CH_2)_p$-phenyl-$(X1)_n$, an optionally substituted carbocyclic or heterocyclic aryl radical, an optionally substituted heterocyclic non aromatic radical, bis-arylalkyl, di-arylalkyl or one of the radicals represented below -continued

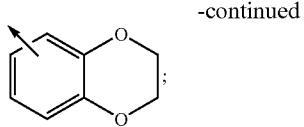

Y1 represents O, S, NH or is absent;
R4 represents (CH$_2$)$_p$-Z4;
Z4 represents amino, (C$_3$-C$_8$)cycloalkyl, (C$_1$-C$_{12}$)alkylamino, N,N-di-(C$_1$-C$_{12}$)alkylamino, amino(C$_3$-C$_6$)cycloalkyl, amino(C$_1$-C$_6$)alkyl(C$_3$-C$_6$)cycloalkyl(C$_1$-C$_6$)alkyl, carbocyclic or heterocyclic aminoaryl, an optionally substituted carbocyclic or heterocyclic aryl radical, an optionally substituted heterocyclic non aromatic radical, bis-arylalkyl, di-arylalkyl or one of the radicals represented below

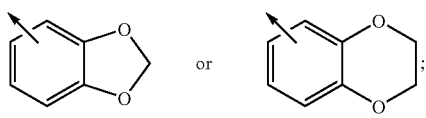

it being understood that an optionally substituted radical or an optionally substituted phenyl is optionally substituted by one or more substituent, each preferably chosen independently from the group constituted by the Cl, F, Br, I, CF$_3$, NO$_2$, OH, NH$_2$, CN, N$_3$, —OCF$_3$, (C$_1$-C$_{12}$)alkyl, (C$_1$-C$_{12}$)alkoxy, —(CH$_2$)$_p$-phenyl-(X1)$_q$, —NH—CO—(C$_1$-C$_6$)alkyl, —NH—C(O)O—(C$_1$-C$_6$)alkyl, —S—(C$_1$-C$_6$)alkyl, —S-phenyl-(X1)$_q$, —O—(CH$_2$)$_p$-phenyl-(X1)$_q$, —(CH$_2$)$_p$—C(O)—O—(C$_1$-C$_6$)alkyl, —(CH$_2$)$_p$—C(O)—(C$_1$-C$_6$)alkyl, —O—(CH$_2$)$_p$—NH$_2$, —O—(CH$_2$)$_p$—NH—(C$_1$-C$_6$)alkyl, —O—(CH$_2$)$_p$—N-di-((C$_1$-C$_6$)alkyl) and —((C$_0$-C$_{12}$))alkyl-(X1)$_q$ radicals;
X1, each time that it occurs, is independently chosen from the group constituted by the H, Cl, F, Br, I, CF$_3$, NO$_2$, OH, NH$_2$, CN, N$_3$, —OCF$_3$, (C$_1$-C$_{12}$)alkyl, (C$_1$-C$_{12}$)alkoxy, —S—(C$_1$-C$_6$)alkyl, —(CH$_2$)$_p$-amino, —(CH$_2$)$_p$—NH—(C$_1$-C$_6$)alkyl, —(CH$_2$)$_p$—N-di-((C$_1$-C$_6$)alkyl), —(CH$_2$)$_p$-phenyl and —(CH$_2$)$_p$—NH—(C$_3$-C$_6$)cycloalkyl radicals;
p each time that it occurs is independently 0 or an integer from 1 to 6;
q each time that it occurs is independently an integer from 1 to 5.
X represents O or S;
n represents 0 or 1; and finally
when n represents 0, m represents 1, 2 or 3, and when n represents 1, m represents 0 or 1.
More preferentially, the compounds of general formula (I) are such that:
R1 represents the phenyl radical optionally substituted by a halogen atom or a (C$_1$-C$_{12}$)alkyl, (C$_1$-C$_{12}$)alkoxy or nitro radical;
R2 and R5 represent H or alkyl;
R3 represents (CH$_2$)$_p$-Z3,
Z3 representing a (C$_3$-C$_8$)cycloalkyl radical or an optionally substituted radical chosen from the phenyl, naphthyl, furannyl, thiophene, indolyl, pyrrolyl and benzothiophene radicals;
R4 represents (CH$_2$)$_p$-Z4;
Z4 representing amino, (C$_1$-C$_{12}$)alkylamino, N,N-di-(C$_1$-C$_{12}$)alkylamino or amino(C$_1$-C$_6$)alkyl(C$_3$-C$_6$)cycloakyl—(C$_1$-C$_6$)alkyl;

X represents S;
p each time that it occurs is independently 0 or an integer from 1 to 6;
m represents 0, 1 or 2; and finally n represents 0 or 1.
Yet more preferentially, the compounds of the present invention are of the compounds:
of general sub-formula (I)a represented below:

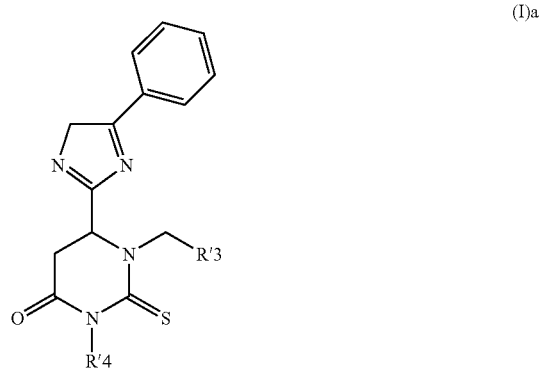

in which:
R'3 represents one of the radicals represented below:

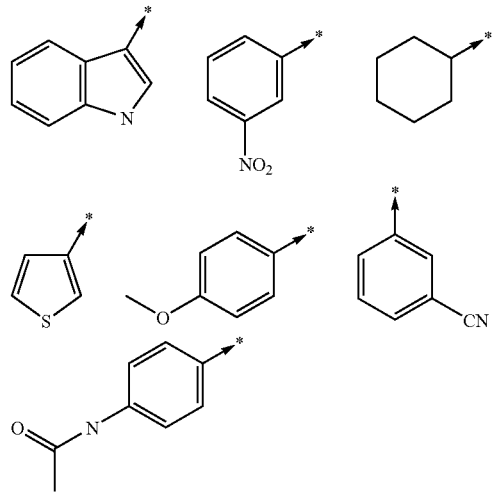

and R'4 represents one of the radicals represented below:

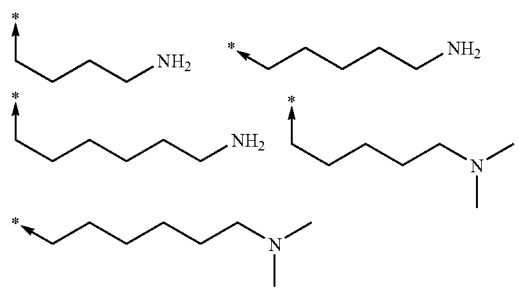

-continued

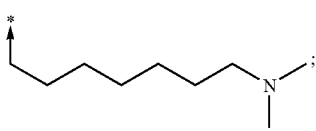

of general sub-formula (I)b represented below:

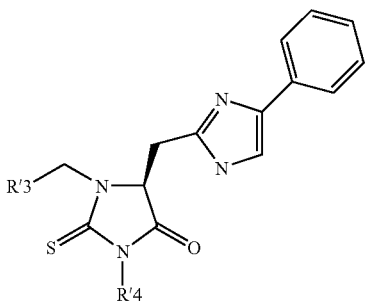
(I)b in which:
R'3 represents one of the radicals represented below:

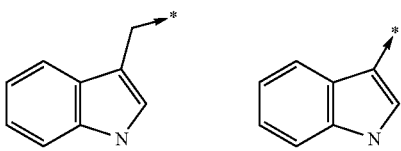

and R'4 represents one of the radicals represented below:

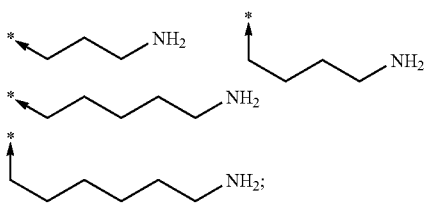

of general sub-formula (I)c represented below:

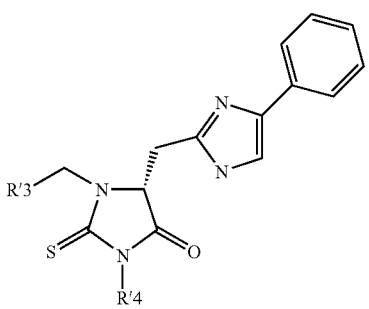
(I)c in which:
R'3 represents one of the radicals represented below:

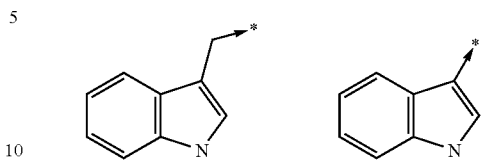

and R'4 represents one of the radicals represented below:

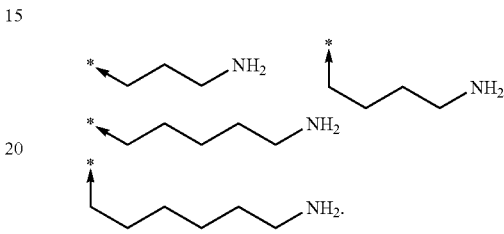

The invention relates moreover to the preparation processes for the compounds of general formula (I) described previously (also applicable to the corresponding compounds of general sub-formulae (I)a, (I)b and (I)c).

The compounds of general formula (I) described previously for which n represents 0 and X represents O or S can be prepared by the reaction in an aprotic solvent of the compound of general formula (II) represented below

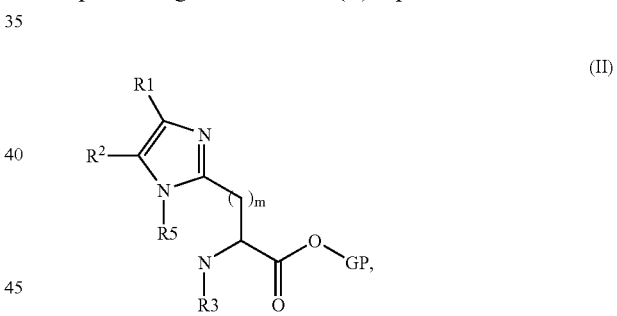
(II)

in which m, R1, R2, R3 and R5 have the same meaning as in general formula (I), and the O-GP radical is a parting protective group derived from an alcohol and in particular benzyloxy, methoxy or tert-butoxy, with an isocyanate or isothiocyanate of general formula (III)

$$R4\text{-}N=C=X,$$ 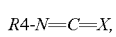 (III)

in which R4 and X have the same meaning as in general formula (I), preferably in the presence of a tertiary base for a duration of approximately 1 to 24 hours and at a temperature preferably comprised between 20 and 60° C.

The compounds of general formula (I) described previously for which n represents 1 and X represents O or S can be prepared by the reaction in an aprotic solvent of the compound of general formula (IV) represented below

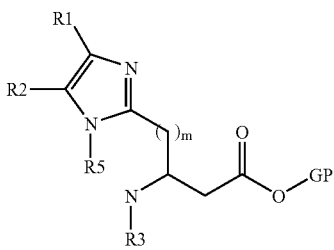

(IV)

in which m, R1, R2, R3 and R5 have the same meaning as in general formula (I), and the O-GP radical is a parting protective group derived from an alcohol and in particular benzyloxy, methoxy or tert-butoxy, with an isocyanate or isothiocyanate of general formula (III)

R4-N=C=X     (III)

in which R4 and X have the same meaning as in general formula (I), preferably in the presence of a tertiary base for a duration of approximately 1 to 48 hours and at a temperature comprised between 20 and 70° C.

For the above processes, the aprotic solvent is preferably polar and can in particular be THF or dichloromethane. The tertiary base will be for example triethylamine or N,N-diisopropylethylamine.

Moreover the invention offers new synthesis intermediates which are useful for the preparation of the compounds of general formula (I). These compounds, precursors of the compounds of general formula (II) and (IV), correspond to general formula (V):

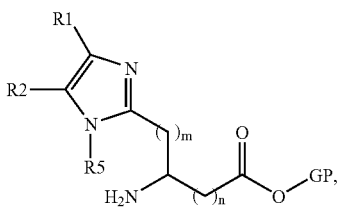

(V)

in which
R1, R2, R5, m and n have the same meaning as in general formula (I);

and the O-GP radical is a parting protective group derived from an alcohol and in particular benzyloxy, methoxy or tert-butoxy.

The following compounds corresponding to general formula (V) are the preferred intermediates:
- benzyl (2S)-2-amino-3-[(4-phenyl)-1H-imidazol-2-yl]propanoate;
- benzyl (2R)-2-amino-3-[(4-phenyl)-1H-imidazol-2-yl]propanoate;
- benzyl (2S)-2-amino-4-[(4-phenyl)-1H-imidazol-2-yl]butanoate;
- benzyl (2R)-2-amino-4-[(4-phenyl)-1H-imidazol-2-yl]butanoate;
- benzyl (3R)-3-amino-4-[(4-phenyl)-1H-imidazol-2-yl]propanoate;
- benzyl (3S)-3-amino-4-[(4-phenyl)-1H-imidazol-2-yl]propanoate.

A subject of the invention is also, as medicaments, the compounds of general formulae (I), (I)a, (I)b and (I)c described previously or their pharmaceutically acceptable salts. It also relates to the pharmaceutical compositions containing said compounds or their pharmaceutically acceptable salts, and their use for the preparation of a medicament intended to treat the pathological states or diseases in which one (or more) of the somatostatin receptors are involved.

In particular, the compounds of general formulae (I), (I)a, (I)b and (I)c described previously or their pharmaceutically acceptable salts can be used for the preparation of a medicament intended to treat the pathological states or diseases chosen from the group comprising the following pathological states or diseases: acromegalia, hypophyseal adenomas, Cushing's disease, gonadotrophinomas and prolactinomas, catabolic side-effects of glucocorticoids, insulin dependent diabetes, diabetic retinopathy, diabetic nephropathy, syndrome X, dawn phenomena, angiopathy, angioplasty, hyperthyroidism, gigantism, endocrinic gastroenteropancreatic tumours including carcinoid syndrome, VIPoma, insulinoma, nesidioblastoma, hyperinsulinemia, glucagonoma, gastrinoma and Zollinger-Ellison's syndrome, GRFoma as well as acute bleeding of the esophageal varices, ulcers, gastroesophageal reflux, gastroduodenal reflux, pancreatitis, -enterocutaneous and pancreatic fistulae but also diarrhoeas, refractory diarrhoeas of acquired immunodeficiency syndrome, chronic secretary diarrhoea, diarrhoea associated with irritable bowel syndrome, diarrhoeas induced by chemotherapy, disorders linked with gastrin releasing peptide, secondary pathologies with intestinal grafts, portal hypertension as well as haemorrhages of the varices in patients with cirrhosis, gastro-intestinal haemorrhage, haemorrhage of the gastroduodenal ulcer, bleeding of grafted vessels, Crohn's disease, systemic scleroses, dumping syndrome, small intestine syndrome, hypotension, scleroderma and medullar thyroid carcinoma, illnesses linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and in other therapeutic fields, cephaleas including cephalea associated with hypophyseal tumours, pain, inflammatory disorders such as arthritis, panic attacks, chemotherapy, cicatrization of wounds, renal insufficiency resulting from delayed development, hyperlipidemia, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukaemia, meningioma, cancerous cachexia, inhibition of H pylori, psoriasis, chronic rejection of allografts as well as Alzheimer's disease and finally osteoporosis.

Preferably, the compounds of general formulae (I), (I)a, (I)b and (I)c described previously or their pharmaceutically acceptable salts can be used for the preparation of a medicament intended to treat the pathological states or diseases chosen from the group comprising the following pathological states or diseases: acromegalia, bypophyseal adenomas or endocrinic gastroenteropancreatic tumours including carcinoid syndrome, and gastrointestinal bleeding.

By pharmaceutically acceptable salt is meant in particular addition salts of inorganic acids such as hydrochloride, sulphate, phosphate, diphosphate, hydrobromide and nitrate, or of organic acids, such as acetate, maleate, fumarate, tartarate, succinate, citrate, lactate, methanesulphonate, p-toluenesulphonate, pamoate, oxalate and stearate.

The salts formed from bases such as sodium or potassium hydroxide also fall within the scope of the present invention, when they can be used. For other examples of pharmaceutically acceptable salts, reference can be made to "Pharmaceutical salts", J. Pharm. Sci. 66:1 (1977).

The pharmaceutical composition can be in the form of a solid, for example powders, granules, tablets, capsules, liposomes or suppositories. Appropriate solid supports can be for example calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in the form of a liquid, for example, solutions, emulsions, suspensions or syrups. Appropriate liquid supports can be, for example, water, organic solvents such as glycerol or the glycols, as well as their mixtures, in varying proportions, in water. The suspensions contain in particular suspensions of sustained release microparticles loaded with active ingredient (in particular microparticles of polylactide-co-glycolide or PLGA-cf. for example the U.S. Pat. No. 3,773,919, EP 52 510 or EP 58 481 or the patent application PCT WO 98/47489), which allow the administration of a determined daily dose over a period of several days to several weeks.

The administration of a medicament according to the invention can be done by topical, oral, parenteral route, by intramuscular injection, etc.

The administration dose envisaged for a medicament according to the invention is comprised between 0.1 mg to 10 g according to the type of active compound used.

These compounds are prepared according to the following procedures.

Preparation of the Compounds of the Invention

Preparation of Imidazolyl Derivatives

General Procedure:

i) Cyclization in order to obtain the imidazole group:

An amino acid is converted to its cesium salt using cesium carbonate in a polar solvent such as a DMF/H$_2$O (1:1) or EtOH/H$_2$O (1:1) mixture. An ester is then obtained using an appropriate bromoketone in an aprotic polar solvent such as anhydrous DMF. The cesium bromide formed is eliminated by filtration and ammonium acetate is added in an aprotic solvent having a high boiling temperature such as xylene or toluene or in an acidic aprotic solvent such as acetic acid. The mixture is maintained under reflux using a Dean-Stark trap for 30 minutes to one hour. In the diagram directly below, PG1 is a protective group, preferably a carbamate, such as t-Boc or benzylcarbamate, and PG2 is also a protective group, preferably a benzyl group.

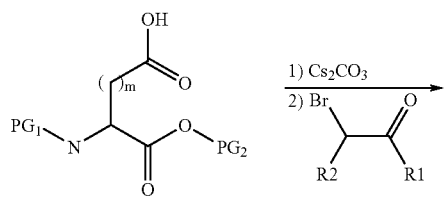

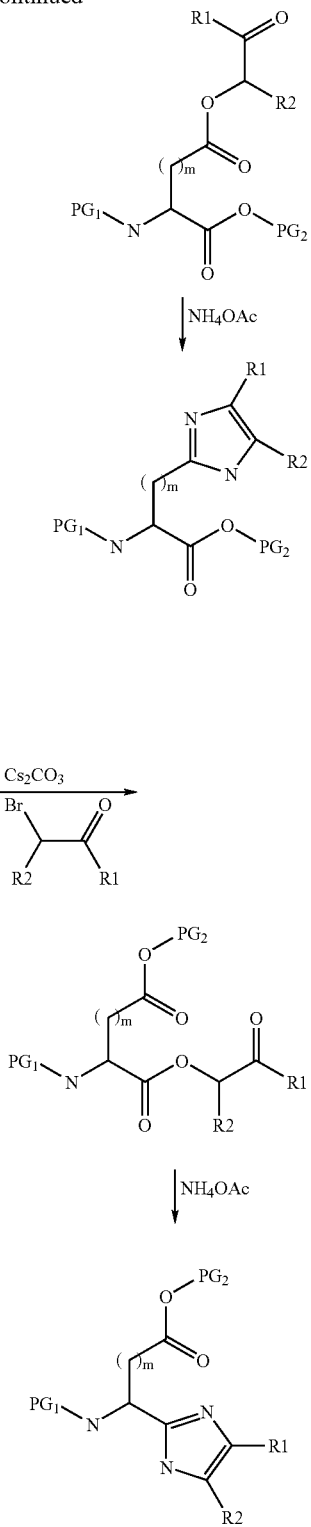

ii) N-substitution on the Imidazole Group:

If appropriate, the N-substitution on the imidazole group is carried out by the reaction described hereafter for the compounds of general formula (I) for which R5 does not represent H.

A solution of the intermediate obtained in the preceding stage, an alkylating agent such as an -bromoketone, an -bromoester, an alkyl or aryl bromide, is heated to a temperature of 20 to 80° C. for a duration of 2 to 48 hours in the presence of an organic or inorganic base (optionally supported on a resin such as polystyrene resin), in an aprotic solvent such as THF, acetonitrile or DMF.

Preparation of Benzyl (2S)-2-[(Tert-butoycarbonyl)amino]-3-(4-phenyl-1H-imidazol-2-yl)propanoate A solution of Boc-L-Asp-OBn (12 g; 37.1 mmol) and cesium carbonate (6.05 g; 0.5 eq.) is stirred for approximately 30 minutes at approximately 20° C. in EtOH/H$_2$O (1:1, 7 ml), then concentrated under reduced pressure at approximately 40° C.

25 ml of a solution of 2-bromoacetophenone (7.38 g; 1 eq.) in dry DMF is added to the resulting salt dissolved in 130 ml of dry DMF. The mixture is stirred for approximately 1 hour at approximately 20° C. under an argon atmosphere then concentrated under reduced pressure. Ethyl acetate is added (100 ml) and the mixture filtered, CsBr being washed with ethyl acetate. The filtrate is then concentrated under reduced pressure. A solution of the residue obtained and ammonium acetate (58 g; 20 eq.) in xylene,(280 ml) is maintained under reflux for approximately 30 minutes at approximately 140° C. The excess NH$_4$OAc and water are eliminated using a Dean-Stark trap. The progress of the reaction is monitored by thin layer chromatography (TLC; eluent: ethyl acetate/heptane 1:1). The mixture is then taken to approximately 20° C. then washed successively with water, a saturated solution of NaHCO$_3$ solution until a basic pH is obtained then with salt water until a neutral pH is obtained. The organic phase is then dried over Na$_2$SO$_4$ and concentrated under reduced pressure.

Purification of the resulting residue by flash chromatography on silica gel (eluent: ethyl acetate/heptane 1:1) yields the expected compound (8.2 g; 52%).

NMR ($^1$H, 400 MHz, CDCl$_3$): 7.64-7.14 (m, 11H, arom H); 5.95 (d, 1H, NHBoc); 5.21-5.13 (AB, 2H, OCH$_2$Ph, J$_{AB}$=12 Hz); 4.73 (m, 1H, CH); 3.30 (m, 2H, CH$_2$); 1.42 (s, 9H, (CH$_3$)$_3$C).

MS/LC: calculated MM=421.2; m/z=422.2 (M+H).

The following compounds are prepared in an analogous fashion to the procedure described for benzyl (2S)-2-[(tert-butoxycarbonyl)amino)]-3-(4-phenyl-1H-imidazol-2-yl) propanoate:

-continued

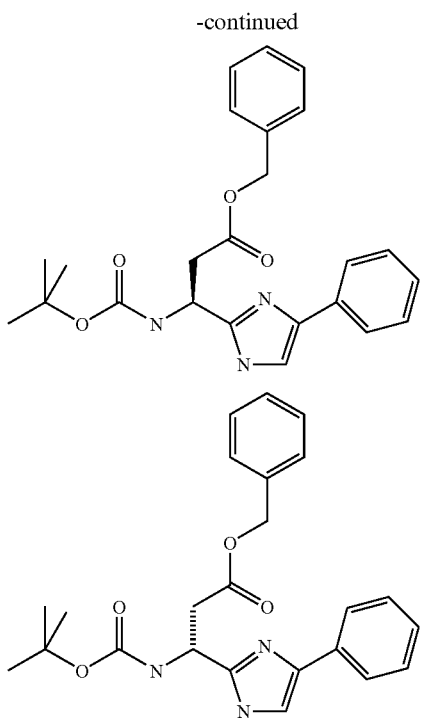

Deprotection Stage

acid treatment

acid treatment

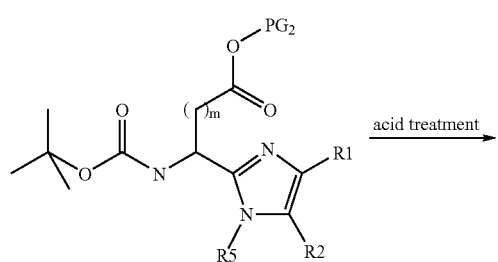

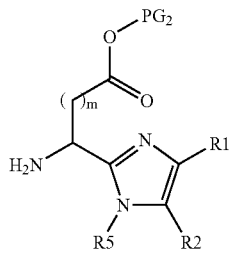

General procedure: the imidazolyl derivatives protected by N-Boc are treated with an organic or inorganic acid such as trifluoroacetic acid or hydrogen chloride (aqueous or in gaseous form) in an aprotic solvent such as dichloromethane or ethyl acetate at a temperature comprised between 0° C. and 25° C. for 0.5 to 5 hours.

Preparation of the Dihydrochloride of Benzyl (3S)-3-(4-phenyl-1H-imidazol-2-yl)-3-amino-propanoate

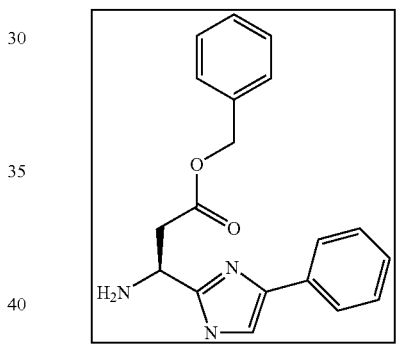

A flow of dry HCl is passed through a solution of benzyl (3S)-3-(4-phenyl-1H-imidazol-2-yl)-3-[(tert-butoxycarbonyl)amino propanoate (5 g) in ethyl acetate (120 ml) at 0° C. until the TLC (eluent: 100% ethyl acetate) shows that the starting compound has completely disappeared. The resulting mixture is then evaporated under reduced pressure. Diethylether is added to the solid obtained and the mixture is filtered. The hydrochloride is washed several times with dichloromethane then diethylether and dried under reduced pressure to produce 4.6 g of expected compound (98% yield).

NMR ($^1$H, 400 MHz, DMSOd6): 9.21 (broad s, 2H, NH); 8.03-7.28 (m, arom. H, 11H); 5.10 (s, 1H, OCH$_2$Ph); 5.04 (m, 1H, CH); 3.61 (dd, 1H, CH$_2$, 3J=9 Hz, 2J=17.0 Hz); 3.39 (dd, 1H, CH$_2$', 3J=5.5 Hz, 2J=17.0 Hz).

MS/LC: Calculated MM=321.2; m/z=322.1 (M+H).

The following compounds are prepared in an analogous fashion to the procedure described for the dihydrochloride of benzyl (3S)-3-(4-phenyl-1H-imidazol-2-yl)-3-amino-propanoate.

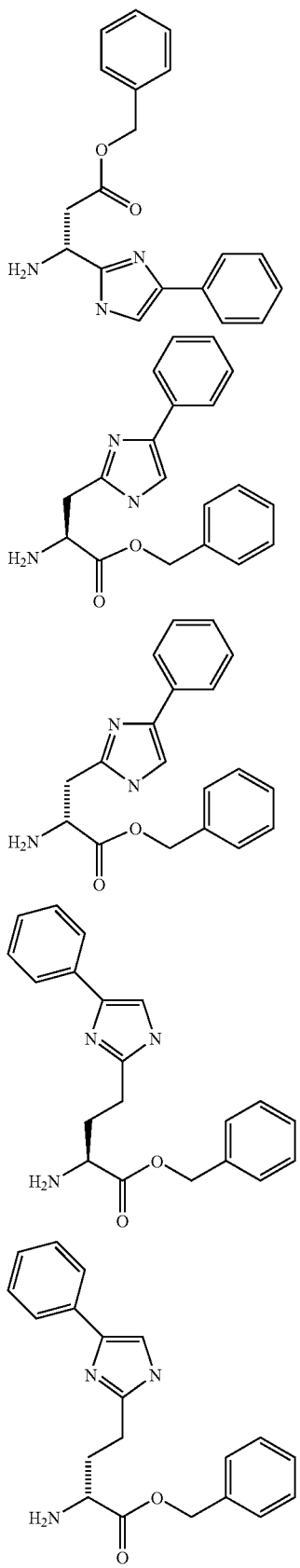

N-Alkylation Reaction

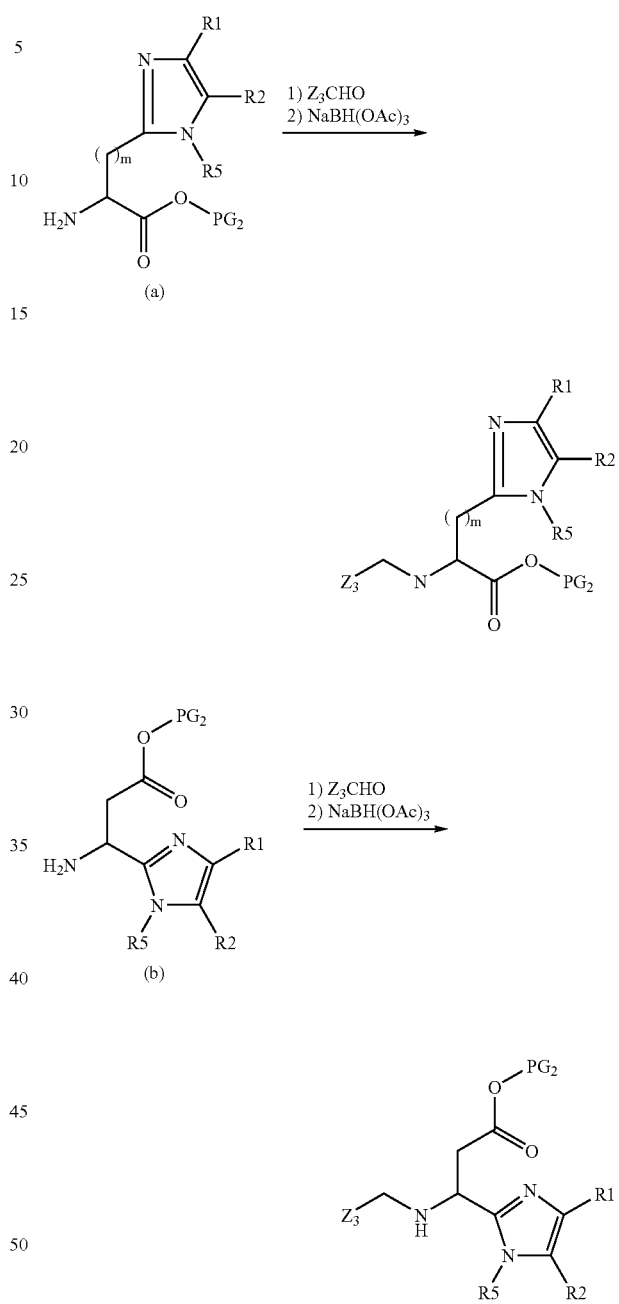

General procedure: A free amine of formula (a) or (b) is treated with an aldehyde in a protic or aprotic solvent, preferably dichloromethane or tetrahydrofuran, for a duration of 1 to 15 hours at 20-50° C. The resulting imine is then reduced using a reducing agent, preferably sodium triacetoxyborohydride or sodium cyanoborohydride with or without the presence of an acid such as acetic acid, at a temperature comprised between 20 and 50° C. for a duration of 0.2 to 5 hours. The N-alkylated compound is isolated by adding water and extraction followed by flash chromatography on silica gel or by crystallization.

Preparation of Benzyl (2S)-4-(4-phenyl-1H-imidazol-2-yl)-2-[(3-thienylmethyl)amino]butanoate

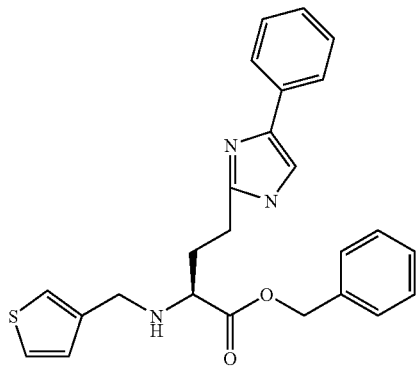

Thiophene-3-carboxaldehyde (1 ml; 1 eq.) is added to a solution of benzyl (2S)-2-amino-4-(4-phenyl-1H-imidazol-2yl)butanoate in the form of a free base (3.6 g; 1 eq.) in tetrahydrofuran (hereafter THF, 40 ml). The mixture is stirred for 15 hours at approximately 20° C. and diluted by adding 50 ml of tetrahydrofuran. NaBH(OAc)$_3$ (4.73 g; 2 eq.) is then added. After 1 hour of stirring at approximately 20° C., the reaction is stopped by adding water (40 ml) and ethyl acetate is then added (100 ml). After decantation and extraction, the combined organic phases are washed with salt water, dried over Na$_2$SO$_4$ then evaporated under reduced pressure at 40° C. Flash chromatography purification on silica gel (eluent: ethyl acetate/heptane 9:1) yields the expected compound in the form of a yellow oil (3.08 g; 66% yield).

NMR ($^1$H, 400 MHz, CDCl$_3$): 7.62-7.04 (m, 15H, arom. H, NH); 5.18 (s, 2H, OCH$_2$); 3.87-3.69 (AB, 2H, CH$_2$NH, 2J$_{AB}$=13 Hz); 3.38 (dd, 1H, CHNH, 3J=4.5 Hz, 2j=8.5 Hz); 2.98 (m, 1H, CH$_2$CH); 2.88 (m, 1H, CH$_2$CH); 2.17 (m, 1H, CH$_2$); 1.97 (m, 1H, CH$_2$).

MS/LC: Calculated MM=431.2; m/z=432.2 (M+H); m/z=430.8 (M−H).

The following compounds (in their two enantiomer forms) are prepared in an analogous fashion to the procedure described for benzyl (2S)-4-(4-phenyl-1H-imidazol-2-yl)-2-[(3-thienylmethy]butanoate:

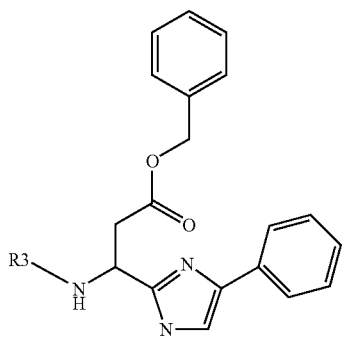

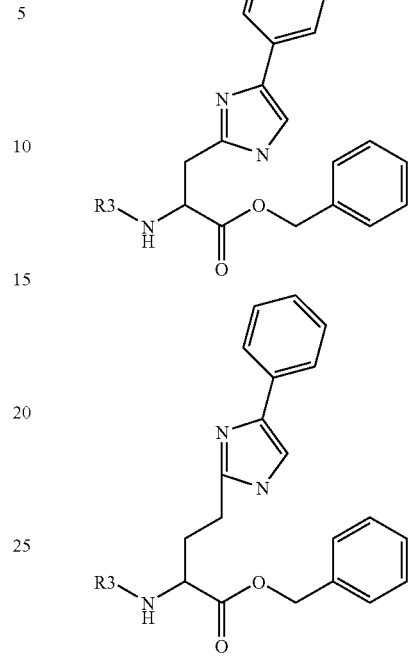

In the above formulae, R3 represents one of the following radicals:

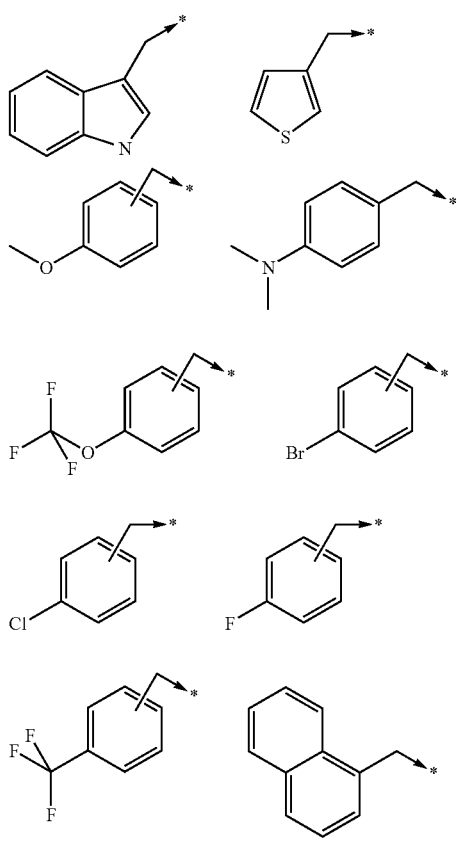

-continued
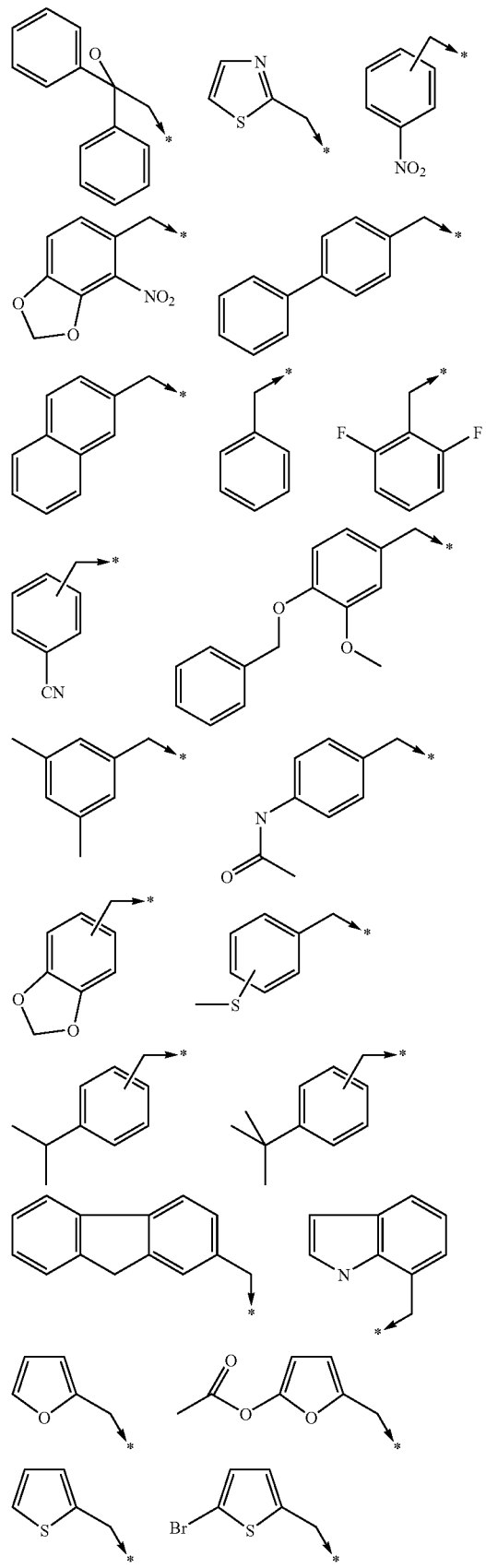
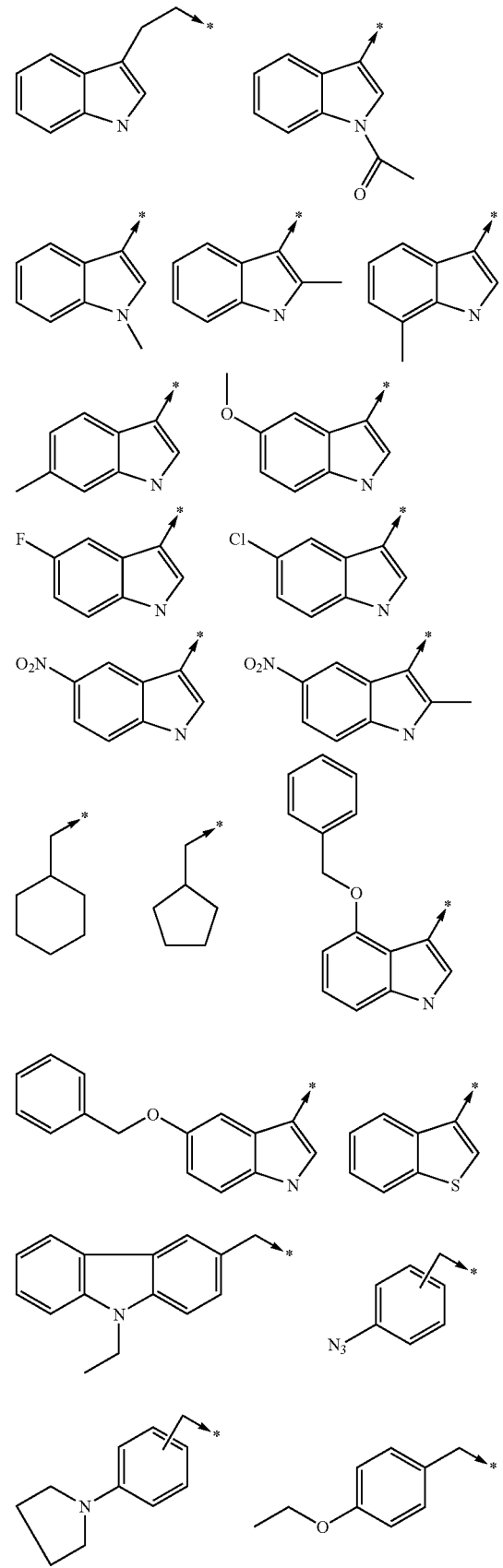

-continued

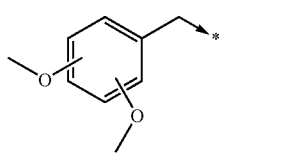

Preparation of Hydantoins and Thiodydantoins

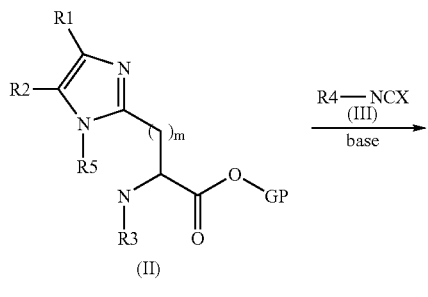

X = O or S; n = 0

General Procedure:

An amine of formula (II), in which m, R1, R2, R3 and R5 have the same meanings as in general formula (I) and the O-GP radical is a parting protective group derived from an alcohol and in particular benzyloxy, methoxy or tert-butoxy, is treated with an isocyanate or a isothiocyanate of general formula R4-NCX in which R4 has the same meaning as in general formula (I), in the presence or in the absence of a tertiary base such as triethylamine or N,N-diisopropylethylamine, in an aprotic solvent, preferably tetrahydrofuran or dichloromethane, at a temperature comprised between approximately 20 and 60° C. and for 1 to 24 hours. The resulting hydantoin or thiohydandoin can be isolated with a yield of 60 to 95%, either by flash chromatography on silica gel or by addition to the reaction mixture of a nucleophilic reagent carried by a polymer such as for example an aminomethylpolystyrene resin (acquired from Novabiochem) followed by filtration and evaporation of the filtrate.

When R4 represents a radical comprising a primary amino termination (for example R4 represents aminoethyl, aminopropyl, etc.), the reagent is not R4-NCX but the corresponding compound the amino group of which is protected by a suitable protective group, for example a tert-butoxycarbonyl group. A subsequent deprotection stage (carried out under standard conditions, namely an acid treatment) must therefore be carried out in order to obtain the compound of general formula (I).

Preparation of Certain Non-Commercial Isothiocyanates of General Formula (III):

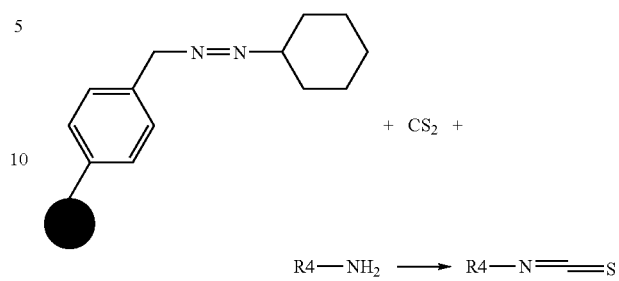

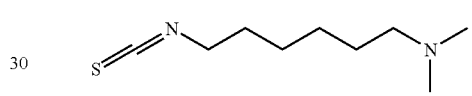

These compounds are prepared as follows: a primary amine of general formula R4-NH$_2$ is treated with a mixture of carbon disulphide and N-cyclohexylcarbodiimide N-methyl polystyrene resin, in an aprotic solvent, preferably tetrahydrofuran or dichloromethane, for a duration of 1 hour to 18 hours at 20-50° C. The resulting isothiocyanate is isolated after filtration on frit and evaporation of the filtrate.

Preparation of 6-isothiocyanato-N,N-dimethyl-1-hexanamine

Carbon disulphide (8.3 mL, 10 eq) and a solution of N,N-dimethyl-1,6-hexanediamine (2 g, 1 eq) in THF (10 mL) are added successively dropwise to a suspension of N-cyclohexylcarbodiimide N-methyl polystyrene resin (7.8 g, 1.1 eq; acquired from Novabiochem, load 1.95 mmol/g) in anhydrous THF (120 mL). The suspension is stirred for 2 hours at approximately 20° C. then filtered on frit. The filtrate is then concentrated to dryness under reduced pressure at 40° C. in order to produce the expected isothiocyanate derivative (2.6 g, 93% yield).

NMR $^1$H, 400 MHz, CDCl$_3$, ): 3.50 (t, 2H); 2.24 (t, 2H), 2.20 (s, 6H), 1.68 (q, 2H), 1.50-1.31 (m, 6H).

The following compounds are prepared in an analogous fashion to the procedure described for 6-isothiocyanato-N,N-dimethyl-1-hexanamine:

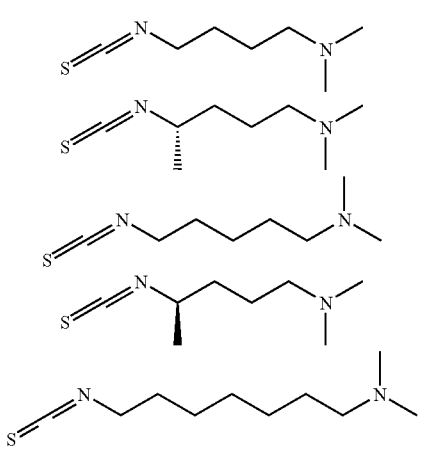

-continued

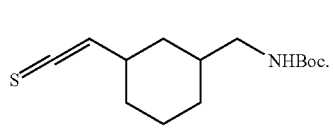

Preparation of (5S)-1-(1H-indol-3-ylmethyl)-3-(4-nitrophenyl)-5-[2-(4-phenyl-1H-imidazol-2-yl)ethyl]-2thioxo-4imidazolidinone

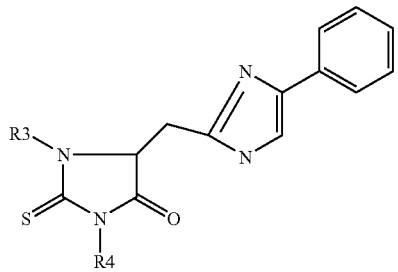

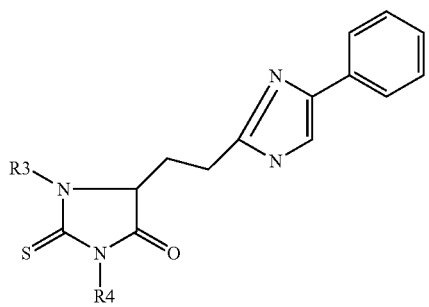

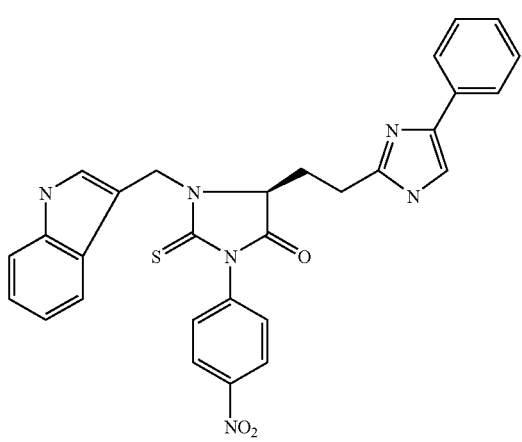

4-nitro-phenylisothiocyanate (43 mg; 1.2 eq.) is added to a solution of benzyl (2S)-2-[(1H-indol-3ylmethyl)amino]-4 (4-phenyl-1H-imidazol-2-yl)butanoate (93 mg; 1 eq.) in THF (2 ml). The mixture is stirred for 2 hours at approximately 20° C. then diluted with 4 ml of THF. Aminomethylpolystyrene resin (acquired from Novabiochem, load 3.2 mmol/g, 125 mg, 2 eq.) is added, then triethylamine (200 μl). The mixture is stirred for 15 hours at approximately 20° C. then filtered on frit. The filtrate is concentrated to dryness under reduced pressure at 40° C. (a co-evaporation with dichloromethane is necessary to eliminate the excess triethylamine). Purification of the residue by flash chromatography on silica gel (eluent: ethyl acetate/heptane 9:1) yields the expected compound (90 mg; 84% yield).

NMR ($^1$H, 400 MHz, CDCl$_3$): 8.24-7.09 (m, 17H, arom H, NH); 5.88, 4.64 (AB, 2H, CH$_2$N, 2J$_{AB}$=15 Hz); 3.38 (dd, 1H, CH, 3J=3.0 Hz, 2J=8.5 Hz); 2.92 (m, 2H, CH$_2$CH); 2.74 (m, 1H, CH$_2$); 2.24 (m, 1H, CH$_2$).

MS/LC: Calculated MM=536.2; m/z=537.1 (M+H).

The following compounds (in their two enantiomer forms) are prepared in an analogous fashion to the procedure described for (5S)-1-(1H-indol-3-ylmethyl)-3-(4-nitrophenyl)-5-[2-(4phenyl-1H-imidazol-2-yl)ethyl]2-thioxo-4-imidazolidinone (apart from the final purification by flash chromatography on silica gel which is optional):

In the above formulae, R3 represents one of the following radicals:

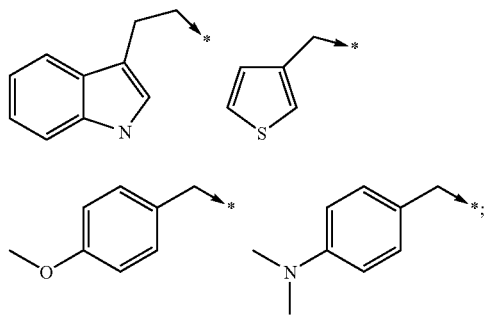

and R4 represents one of the following radicals:

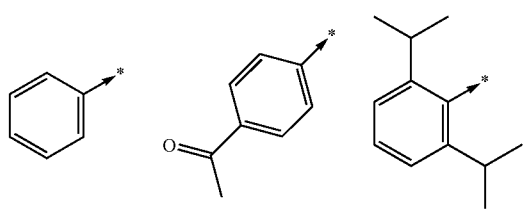

-continued
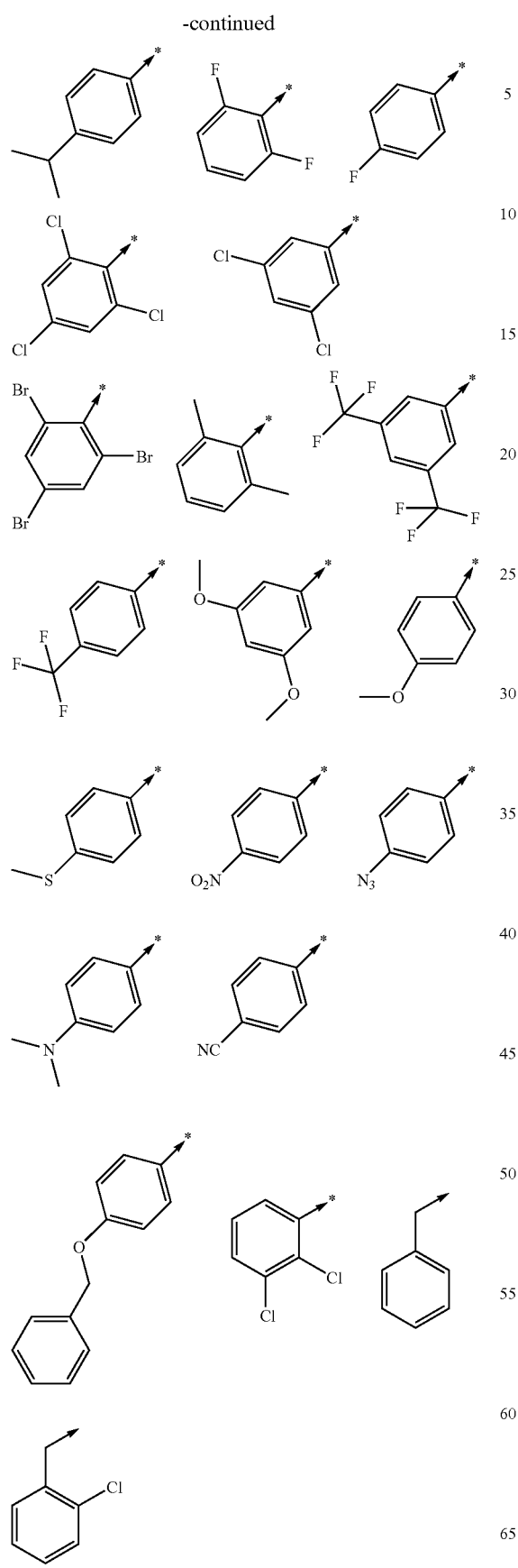
-continued
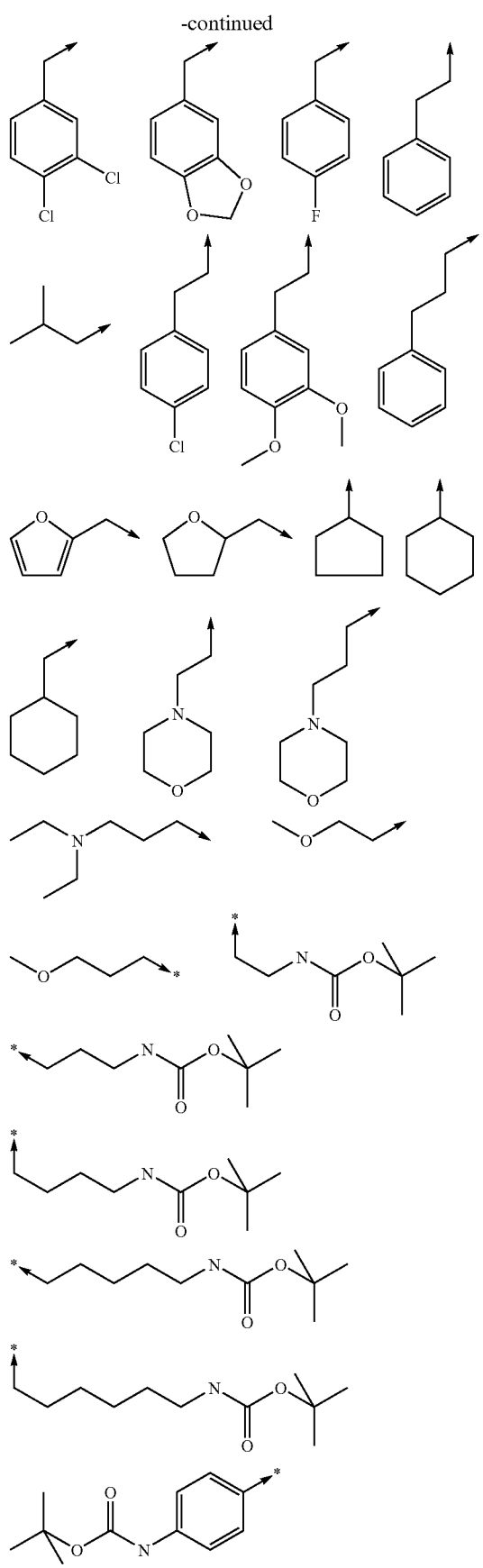

-continued

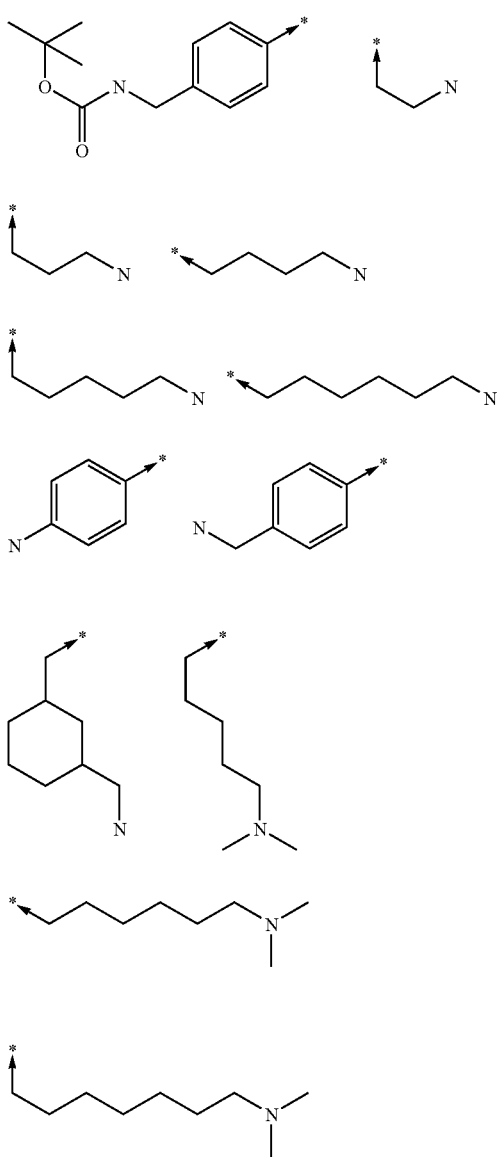

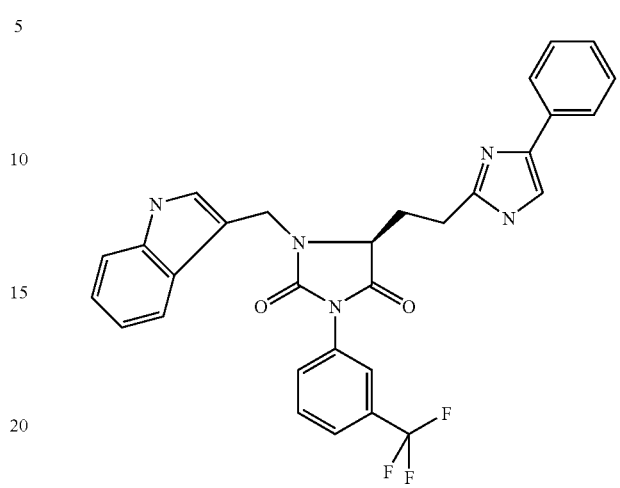

Preparation of (5S)-1-(1H-indol-3-ylmethyl)-5-[2-(4-phenyl-1H-imidazol-2-yl)ethyl]-3-3-(trifluoromethyl)phenyl]-2,4-imidazolidinedione 3-trifluoromethyl-phenylisocyanate (11 mg, 1.2 eq.) is added to a solution of benzyl (2S)-2-[(1H-indol-3-ylmethyl)amino]-4-(4-phenyl-1H-imidazol-2-yl)butanoate (23 mg, 1 eq.) in 2 ml of THF. The mixture is stirred for 2 hours at approximately 20° C. then diluted with 2 ml of THF. Aminomethylpolystyrene resin (acquired from Novabiochem, load 3.2 mmol/g, 125 mg, 2 eq.) is added, then triethylamine (200 μl). The mixture is stirred for 15 hours at approximately 20° C. then filtered on frit. The filtrate is then concentrated to dryness under reduced pressure at 40° C. (a co-evaporation with dichloromethane is necessary to eliminate the excess triethylamine) in order to produce the expected compound (25 mg, 92% yield).

NMR ($^1$H, 400 MHz, CDCl$_3$): 7.75-6.99 (m, 17H, arom H, NH); 5.25, 4.44 (AB, 2H, CH$_2$N, J$_{AB}$=15 Hz); 3.77 (m, 1H, CH); 2.92 (m, 1H, CH$_2$CH); 2.88 (m, 1H, CH$_2$CH); 2.72 (m, 1H, CH$_2$); 2.17 (m, 1H, CH$_2$).

MS/LC: Calculated MM=543.2; m/z=544.2 (M+H).

The following compounds (in their two enantiomer forms) are prepared in an analogous fashion to the procedure described for (5S)-1-(1H-indol-3-ylmethyl)-5-[2-(4-phenyl-1H-imidazol-2yl)ethyl]-3-[3-(trifluoromethyl)phenyl]-2,4imidazolidinedione:

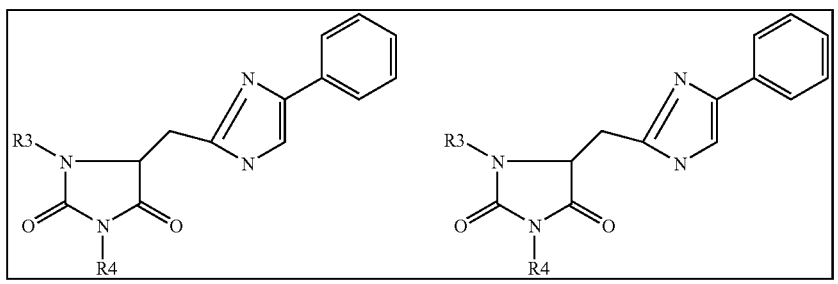

In the above formulae, R3 represents one of the following radicals:
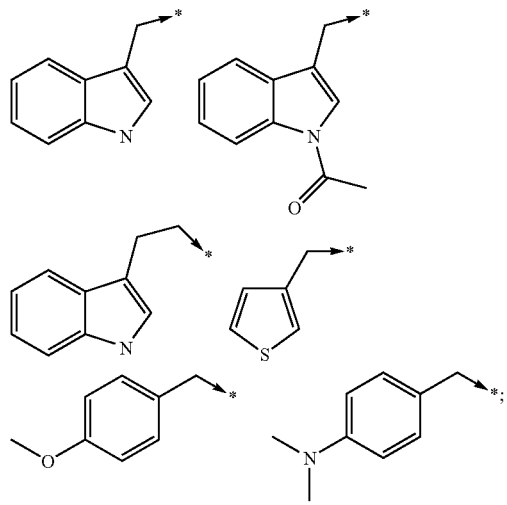
and R4 represents one of the following radicals:
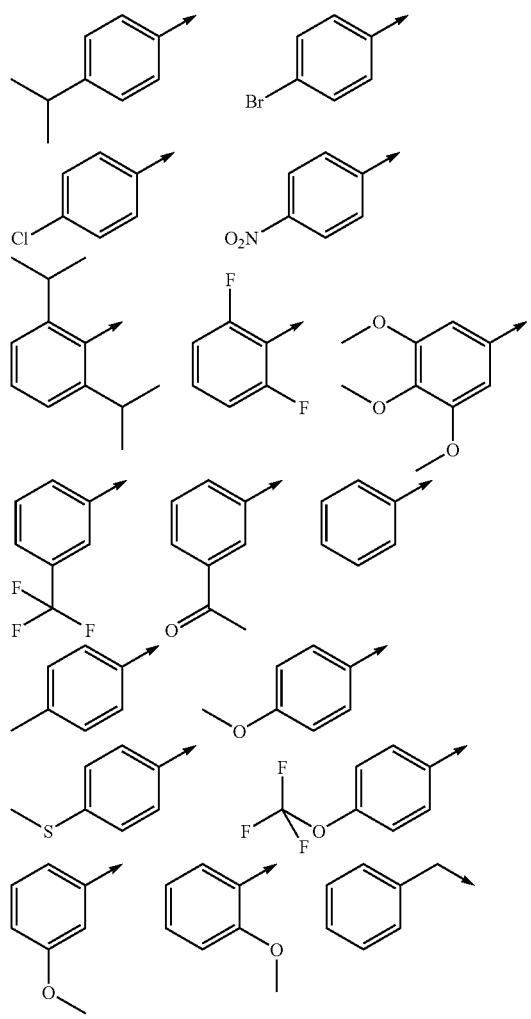
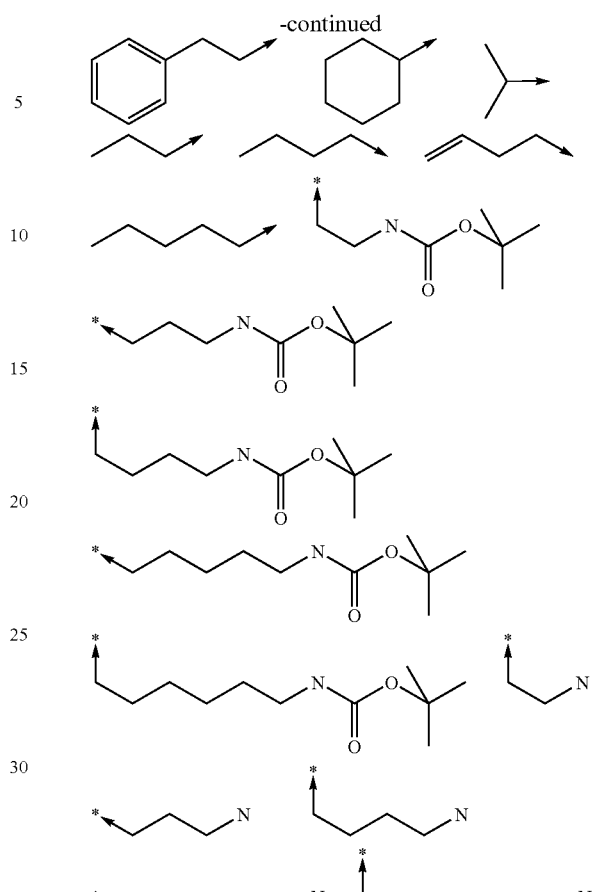
Preparation of Dihydropyrimidine-2,4-diones and 2-thioxo-tetrahydro-4-pyrimidinones
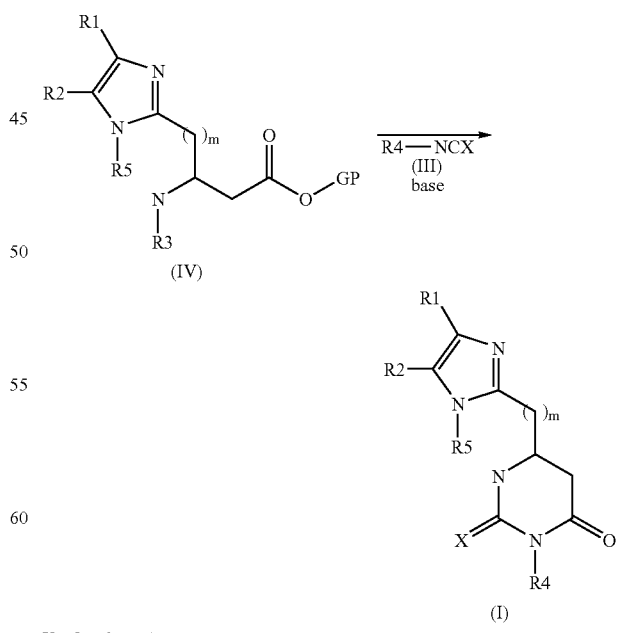
X = O or S; n = 1

General Procedure:

An amine of general formula (IV), in which m, R1, R2, R3 and R5 have the same meanings as in general formula (I) and the O-GP radical is a parting protective group derived from alcohol and in particular benzyloxy, methoxy or tert-butoxy, is treated with an isocyanate or isothiocyanate R4-NCX in the presence of a tertiary base such as triethylamine or N,N-diisopropylethylamine in an aprotic solvent, preferably THF or dichloromethane, at a temperature comprised between 20 and 70° C. for 1 to 48 hours. The compound obtained can be isolated with a yield of 40 to 90%, either by flash chromatography on silica gel or by addition to the reaction mixture of a nucleophilic reagent carried by a polymer such as for example an aminomethylpolystyrene resin (acquired from Novabiochem) followed by filtration and evaporation of the filtrate.

When R4 represents a radical comprising a primary amino termination (for example R4 represents aminoethyl, aminopropyl, etc.), the reagent is not R4-NCX but the corresponding compound the amino group of which is protected by a suitable protective group, for example a tert-butoxycarbonyl group. A subsequent deprotection stage (carried out under standard conditions, namely an acid treatment) must therefore be carried out in order to obtain the compound of general formula (I).

Preparation of (6S)-1-(1H-indol-3-ylmethyl)-3-propyl-6-(4-phenyl-1H-imidazol-2-yl)-2-thioxotetrahydro-4(1H)-pyrimidinone

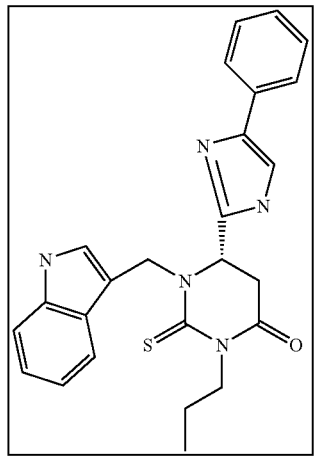

Propylisothiocyanate (25 µl, 1.2 eq.) is added to a solution of benzyl (3S)-3-[(1H-indol-3-ylmethyl)amino]-3(4phenyl-1H-imidazol-2-yl)propanoate (90 mg, 1 eq.) in 2 ml of THF. The mixture is stirred for 15 hours at a temperature of approximately 40° C. then diluted with 2 ml of THF. An aminomethylpolystyrene resin (acquired from Novabiochem, load 3.2 mmol/g, 125 mg, 2 eq.) is added. The mixture is stirred for 5 hours at a temperature of approximately 20° C. then filtered on frit. The filtrate is concentrated under reduced pressure at 40° C. 1 ml of THF and 1 ml of triethylamine are added to the residue. The mixture is stirred for 15 hours at a temperature of approximately 40° C. then concentrated under reduced pressure. Purification by flash chromatography on silica gel (eluent: ethyl acetate/heptane 8:2)-yields the expected compound (72 mg, yield 82%).

NMR ($^1$H, 400 MHz, CDCl$_3$): mixture of 2 atropisomers: 8.69-6.45 (m, 12H, H arom, NH); 6.42, 4.89 (AB, 1H, CH$_2$, $J_{AB}$=14.5 Hz); 5.78, 5.42 (AB, 1H, CH$_2$, $J_{AB}$=14.5 Hz); 4.99 (m, 1H, CH); 4.41-4.36 (m, 1H, CH$_2$); 4.20-4.11 (m, 1H, CH$_2$); 3.49, 2.94 (AB, 1H, CH$_2$CO, $J_{AB}$=16 Hz); 3.28, 2.80 (AB, 1H, CH$_2$CO, $J_{AB}$=16 Hz); 1.52 (m, 1H, CH$_2$); 1.40 (m, 1H, CH$_2$); 0.76, 0.62 (2m, 3H, CH$_3$).

MS/LC: Calculated MM=443.2; m/z=444.2 (M+H).

The following compounds (in their two enantiomer forms) are prepared in an analogous fashion to the procedure described for (6S)-1-(1H-indol-3-ylmethyl)-3-propyl-6-(4-phenyl-1H-imidazol-2-yl)-2-thioxotetrahydro-4(1H)-pyrimidinone (except for the final purification by flash chromatography on silica gel which is optional):

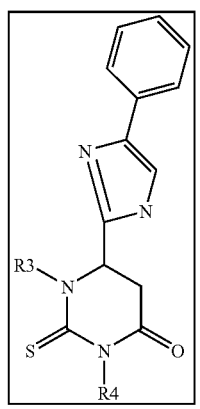

In the above formula, R3 represents one of the following radicals:

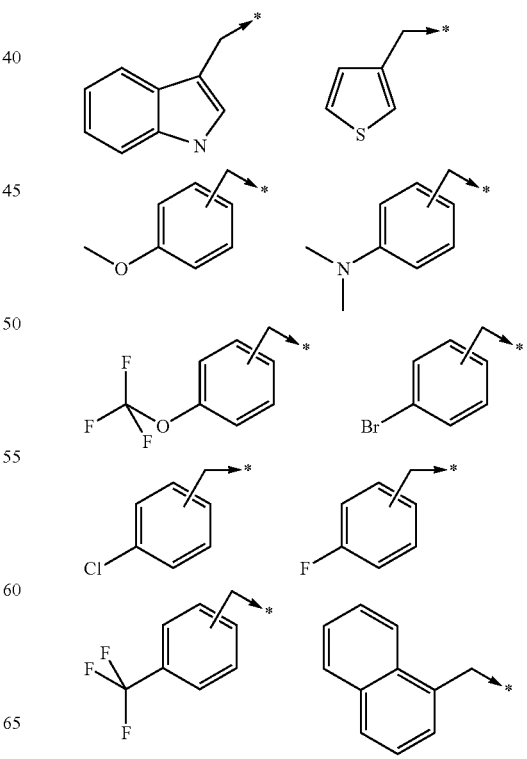

-continued
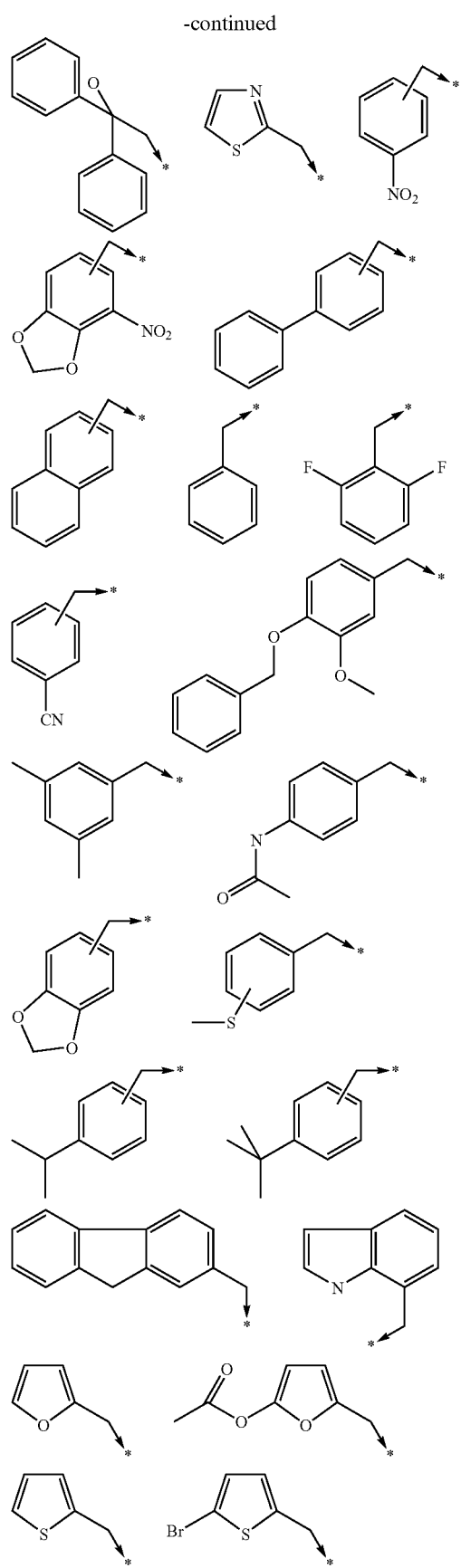
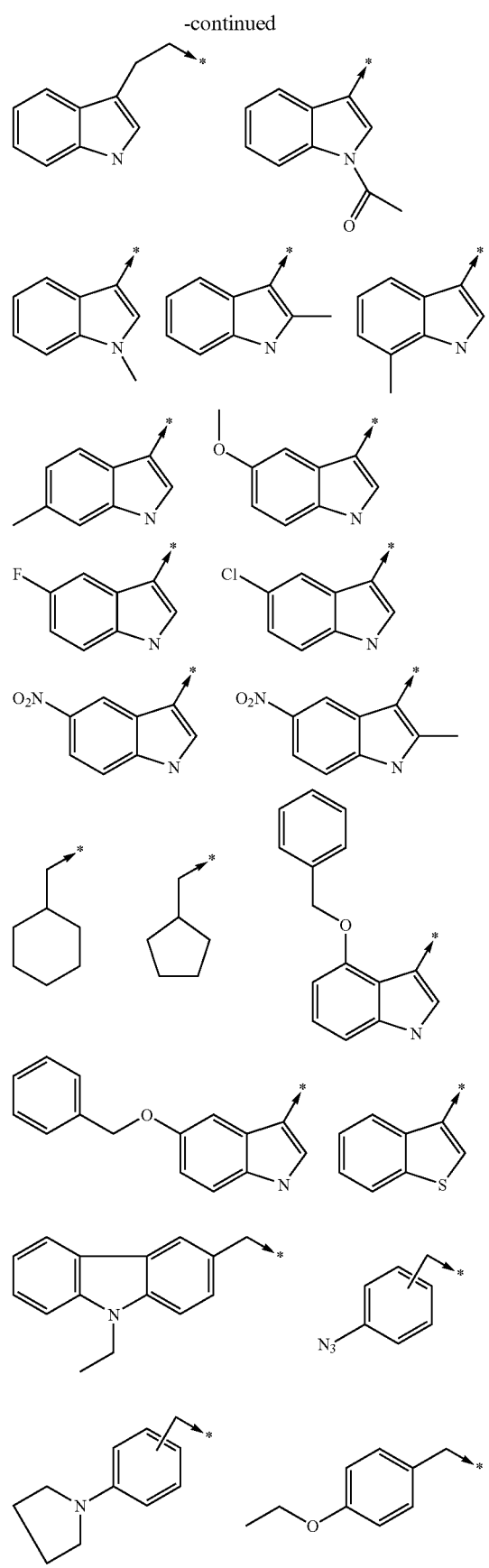

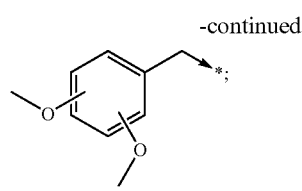
and R4 represents one of the following radicals:
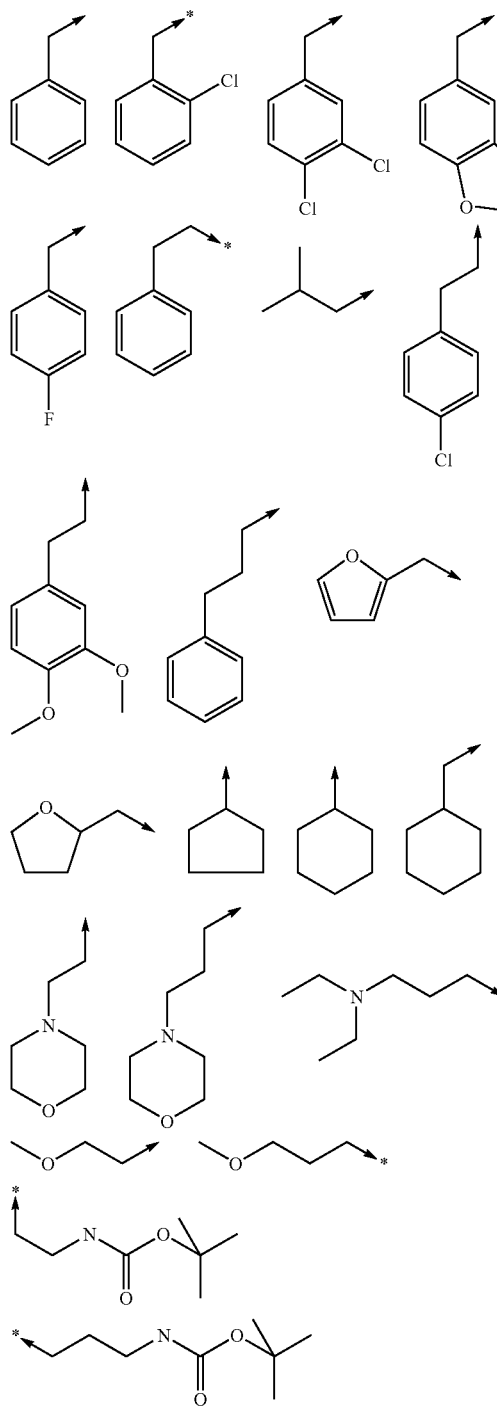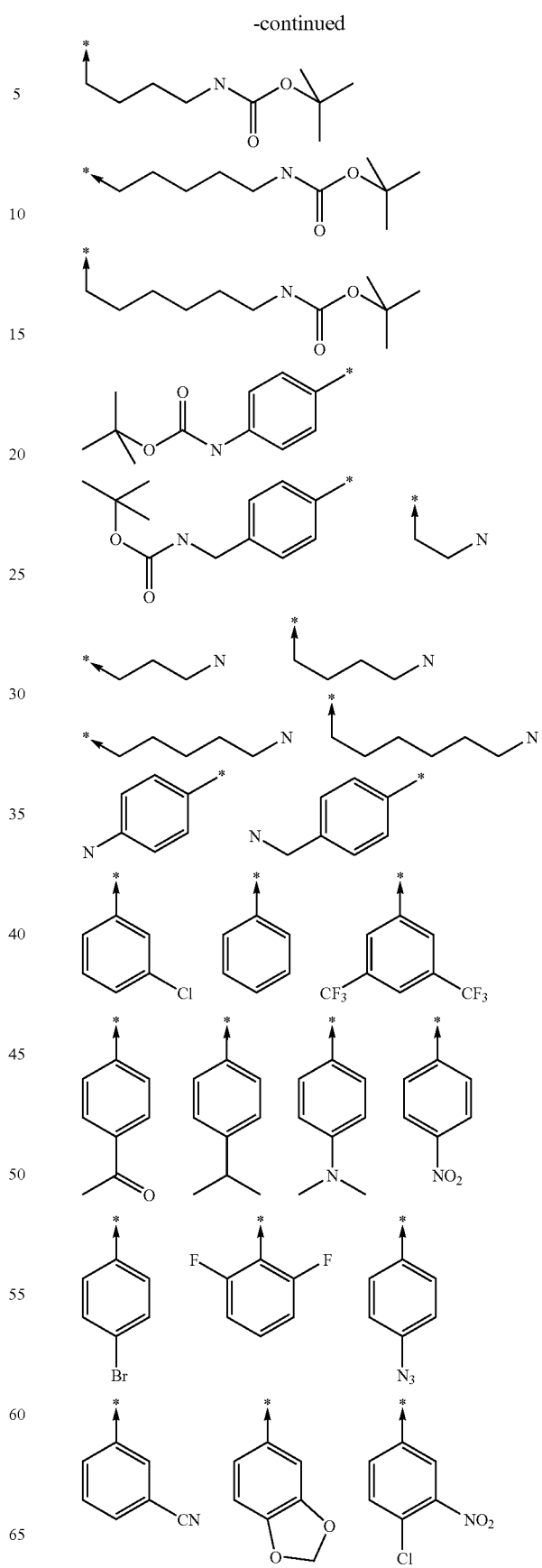

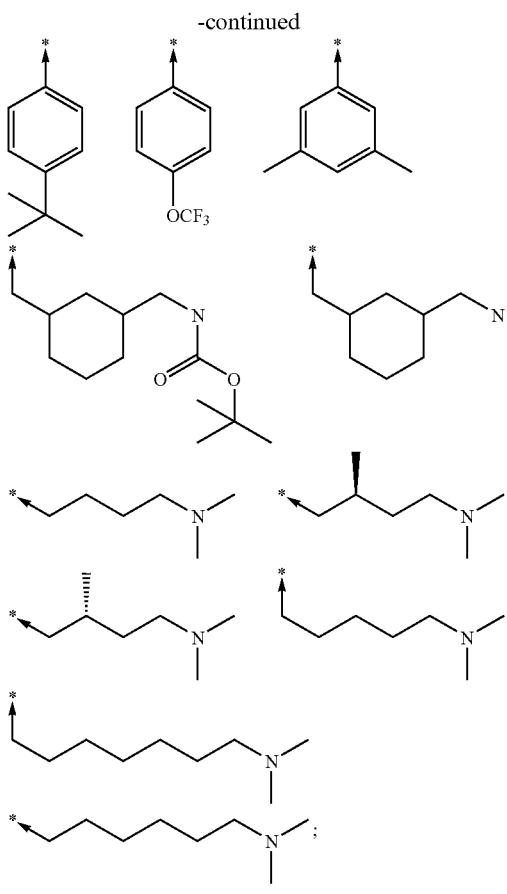

Preparation of (6S)-1-(1H-indol-3-ylmethyl)-3-(4-methoxyphenyl)-6-(4-phenyl-1H-imidazol-2-yl)dihydro-2,4(1H,3H)-pyimidinedione

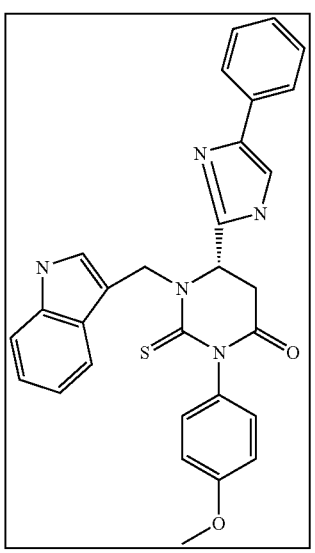

4-methoxyphenylisocyanate (40 μl, 1.2 eq.) is added to a solution of benzyl (3S)-3-[(1H-indol-3-ylmethyl)amino]-3-(4-phenyl-1H-imidazol-2-yl)propanoate (100 mg, 1 eq.) in THF (2 ml). The mixture is stirred for 5 hours at a temperature of approximately 20° C. then diluted with 2 ml of THF. An aminomethylpolystyrene resin (acquired from Novabiochem, load 3.2 mmol/g, 138 mg, 2 eq.) is added. The mixture is stirred for 3 hours at a temperature of approximately 20° C. then filtered on frit. The filtrate is concentrated under reduced pressure at 40° C. 2 ml of THF and 2 ml of triethylamine are added to the residue. The mixture is taken to reflux for 24 hours then concentrated under reduced pressure. Purification of the residue by flash chromatography on silica gel (eluent: ethyl acetate/heptane 8:2) yields the expected compound (80 mg, yield 74%).

NMR ($^1$H, 400 MHz, CDCl$_3$): mixture of 2 atropisomers: 9.67-8.96 (2s, 1H, NH); 8.49 (s, 1H, NH); 5.15, 4.36 (AB, 1H, CH$_2$, J$_{AB}$=15 Hz); 5.08, 4.69 (AB, 1H, CH$_2$, J$_{AB}$=15 Hz); 4.67, 4.57 (2m, 1H, CH); 3.72 (s, 3H, OCH$_3$); 3.29-2.79 (m, 2H, CH$_2$CO).

MS/LC: Calculated MM=491.2; m/z=492.3 (M+H).

The following compounds (in their two enantiomer forms) are prepared in an analogous fashion to the procedure described for (6S)-1-(1H-indol-3-ylmethyl)-3-(4-methoxyphenyl)-6-(4-phenyl-1H-imidazol-2-yl)dihydro-2.4(1H, 3H)-pyrimidinedione (except for the final purification by flash chromatography on silica gel which is optional):

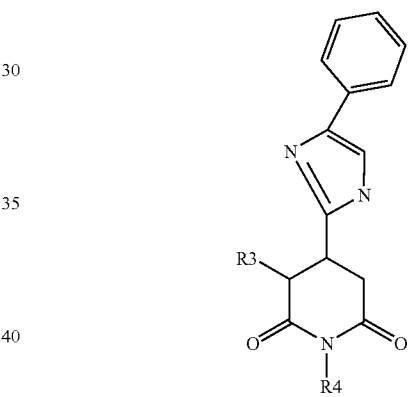

In the above formula, R3 represents one of the following radicals:

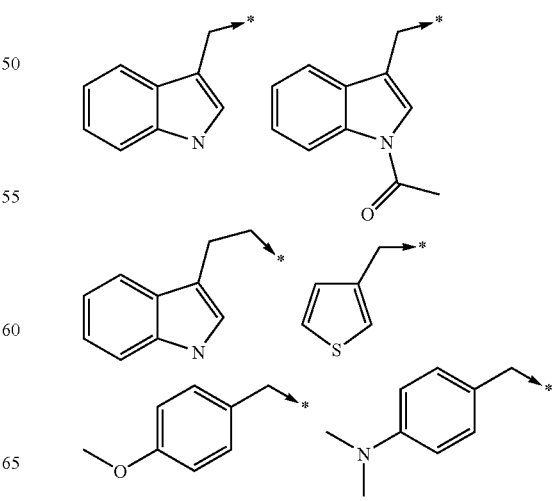

-continued

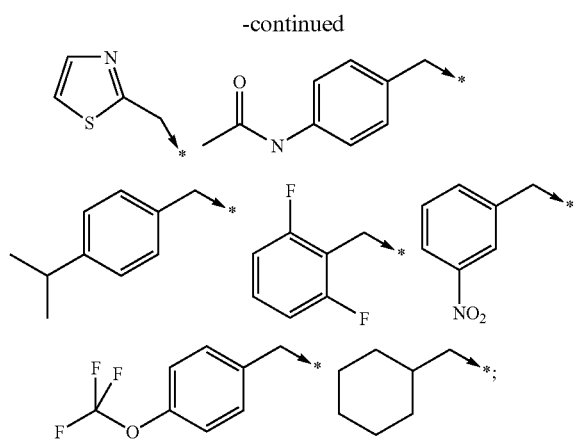

and R4 represents one of the following radicals:

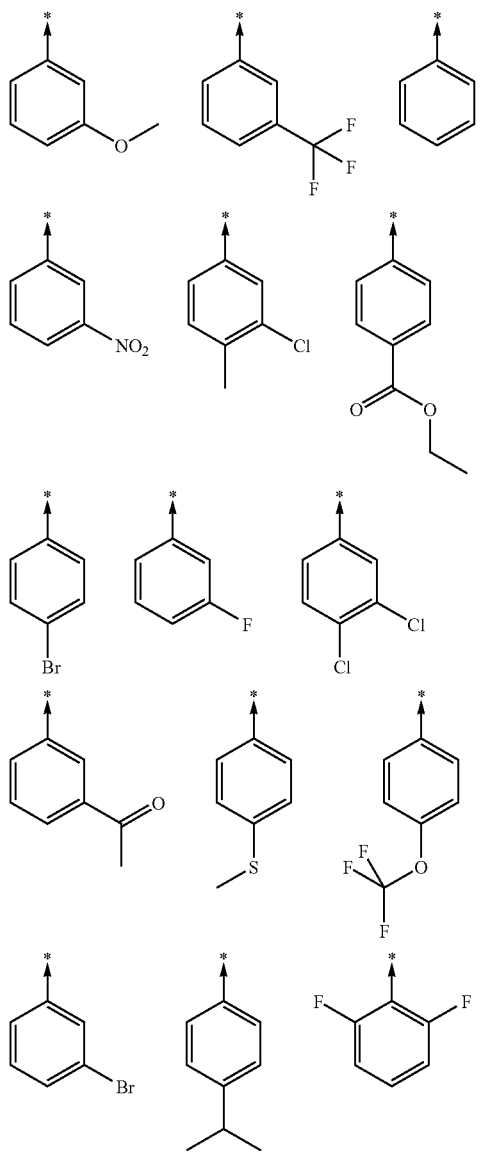

-continued

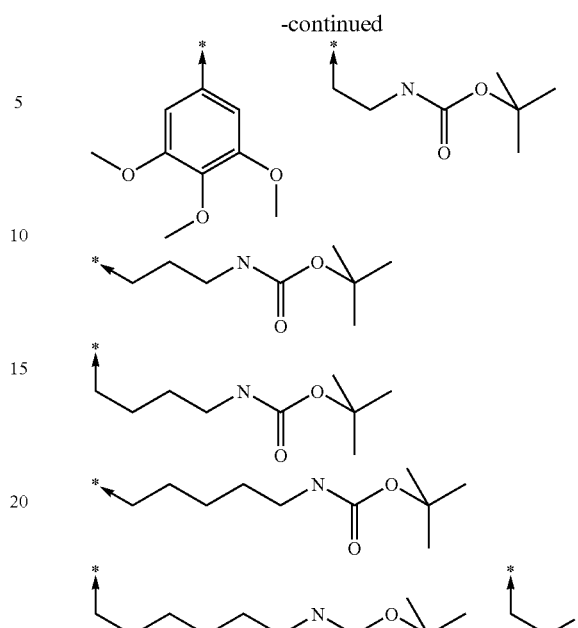

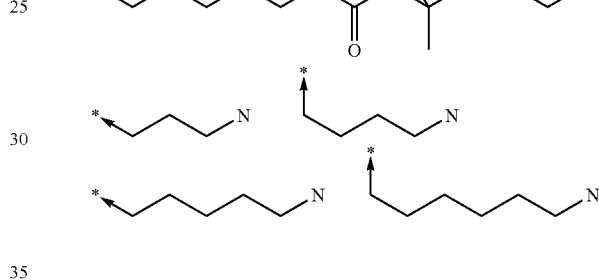

EXAMPLES

The examples prepared according to the synthesis methods described above are shown in tables below. These examples are presented to illustrate the above procedures and should in no case be considered as limiting the scope of the invention.

Analytical Methods used for the Characterization of the Compounds

The compounds obtained have been characterized according to their retention time (rt) and to their mass spectrometry (MH+).

1) Mass Spectrometry

For the mass spectrometry, a single quadrupole mass spectrometer (Micromass, platform model) equipped with an electrospray source is used with a resolution of 0.8 Da at 50% valley.

Calibration is carried out monthly between the masses 80 and 1000 Da using a calibration mixture of sodium and rubidium iodide in solution in an isopropanol/water mixture (1/1 Vol.).

2) High Performance Liquid Chromatography (HPLC)

For the liquid chromatography, an HPLC HP1100 system (Hewlett-Packard) including an in-line degasser, a quaternary pump, a column oven and a diode array UV detector is used.

Different elution conditions are used according to the examples:

Conditions (i):

Eluants:

A water+0.04% trifluoroacetic acid

B acetonitrile

| T (min) | A % | B % |
|---|---|---|
| 0 | 100 | 0 |
| 1 | 100 | 0 |
| 8 | 30 | 70 |
| 10 | 30 | 70 |

Flow rate: 1.1 ml/min

Injection: 5 μl

Column: Uptisphere ODS 3 μm 33*4.6 mm i.d.

Temperature: 40° C.

Conditions (ii):

Eluants:

A water+0.04% trifluoroacetic acid

B acetonitrile

| T (min) | A % | B % |
|---|---|---|
| 0 | 90 | 10 |
| 6 | 15 | 85 |
| 10 | 15 | 85 |

Flow rate: 1 ml/min

Injection: 5 μl

Column: Uptisphere ODS 3 μm 50*4.6 mm i.d.

Temperature: 40° C.

Elution conditions (i) are used for the characterization of Examples 1 to 479, 560 to 572 and 733 to 1040. As regards conditions (ii) they are used for Examples 480 to 559, 573 to 732 and 1041 to 1234. The UV detection is carried out at a wavelength of 220 nm for all the examples.

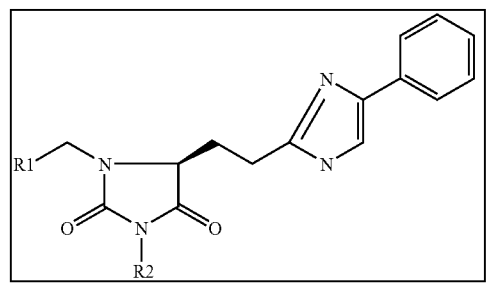

| Ex. No. | Formula | R1 | R2 | Purity | rt (min) | [M + H]⁺ |
|---|---|---|---|---|---|---|
| 1 | C29H25N5O2 | indol-3-yl | phenyl | 89.6% | 6.2 | 476.2 |
| 2 | C30H27N5O2 | indol-3-yl | 4-methylphenyl | 91.0% | 6.4 | 490.3 |
| 3 | C30H27N5O3 | indol-3-yl | 4-methoxyphenyl | 90.1% | 6.2 | 506.3 |
| 4 | C30H27N5O2S | indol-3-yl | 4-(methylthio)phenyl | 91.0% | 6.6 | 522.2 |

Analyses

-continued
| | | | | | | |
|---|---|---|---|---|---|---|
| 5 | C30H24F3N5O3 | 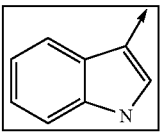 | 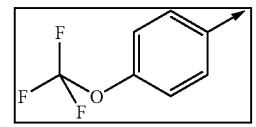 | 83.1% | 7.0 | 560.2 |
| 6 | C32H31N5O2 | 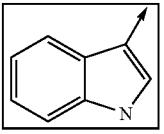 | 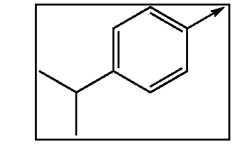 | 84.9% | 7.0 | 518.3 |
| 7 | C29H24BrN5O2 | 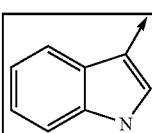 | 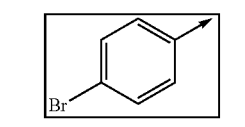 | 81.9% | 6.7 | 556.1 |
| 8 | C29H24ClN5O2 | 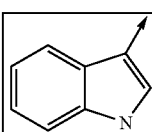 | 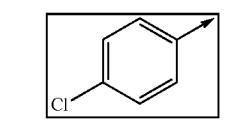 | 79.1% | 6.6 | 510.2 |
| 9 | C29H24N6O4 | 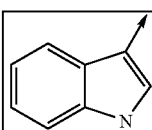 | 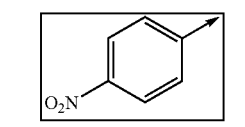 | 87.3% | 6.4 | 521.2 |
| 10 | C35H37N5O2 | 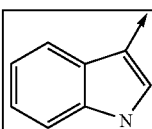 | 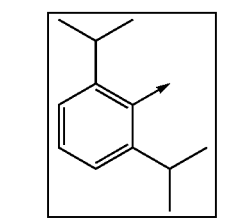 | 94.1% | 7.3 | 560.3 |
| 11 | C29H23F2NSO2 | 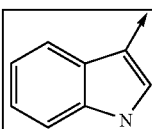 | 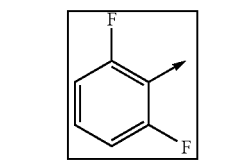 | 96.9% | 6.3 | 512.2 |
| 12 | C30H27N5O2 | 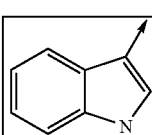 | 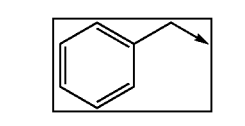 | 96.3% | 6.4 | 490.2 |
| 13 | C31H29N5O2 | 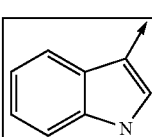 | 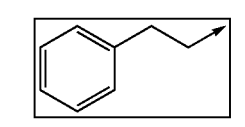 | 92.0% | 6.5 | 504.2 |
| 14 | C29H31N5O2 | 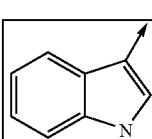 | 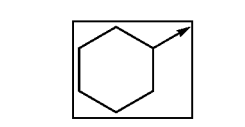 | 85.7% | 6.6 | 482.3 |

-continued

| | | | | | | |
|---|---|---|---|---|---|---|
| 15 | C26H27N5O2 | (indole) | (propyl chain) | 94.2% | 5.9 | 442.3 |
| 16 | C27H29N5O2 | (indole) | (butyl chain) | 91.7% | 6.3 | 456.3 |
| 17 | C26H25N5O2 | (indole) | (allyl chain) | 96.6% | 5.8 | 440.2 |
| 18 | C28H31N5O2 | (indole) | (pentyl chain) | 87.2% | 6.6 | 470.3 |
| 19 | C26H27N5O2 | (indole) | (isobutyl) | 89.1% | 6.0 | 442.2 |
| 20 | C32H31N5O5 | (indole) | (trimethoxyphenyl) | 80.5% | 6.1 | 566.2 |
| 21 | C25H22N4O2S | (thiophene) | (phenyl) | 92.3% | 5.9 | 443.2 |
| 22 | C26H24N4O2S | (thiophene) | (4-methylphenyl) | 90.2% | 6.2 | 457.2 |
| 23 | C26H24N4O3S | (thiophene) | (4-methoxyphenyl) | 92.1% | 6.0 | 473.2 |
| 24 | C26H24N4O2S2 | (thiophene) | (4-methylthiophenyl) | 92.8% | 6.4 | 489.2 |

| | | | | | | |
|---|---|---|---|---|---|---|
| 25 | C26H21F3N4O3S | 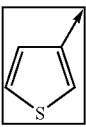 | 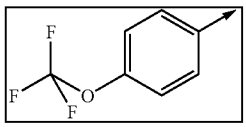 | 87.7% | 6.8 | 527.2 |
| 26 | C28H28N4O2S | 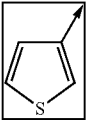 | 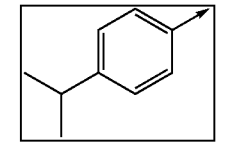 | 87.8% | 6.8 | 485.3 |
| 27 | C25H21BrN4O2S | 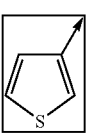 | 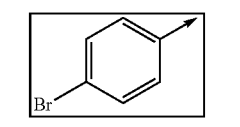 | 84.3% | 6.5 | 523.1 |
| 28 | C25H21ClN4O2S | 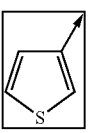 | 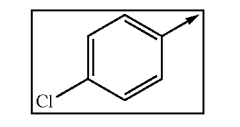 | 84.9% | 6.4 | 477.2 |
| 29 | C25H21N5O4S | 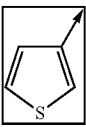 | 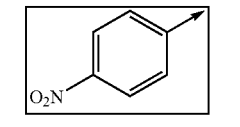 | 94.0% | 6.2 | 488.2 |
| 30 | C31H34N4O2S | 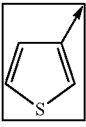 | 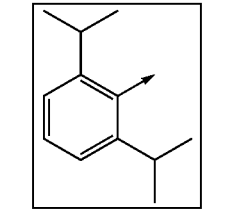 | 97.2% | 7.2 | 527.3 |
| 31 | C25H20F2N4O2S | 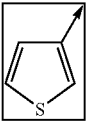 | 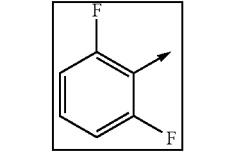 | 96.7% | 6.1 | 479.2 |
| 32 | C26H24N4O2S | 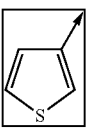 | 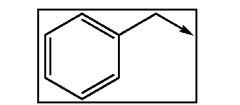 | 95.3% | 6.2 | 457.2 |
| 33 | C27H26N4O2S | 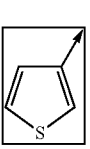 | 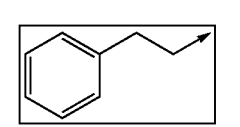 | 93.0% | 6.4 | 471.2 |
| 34 | C25H28N4O2S | 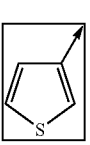 | 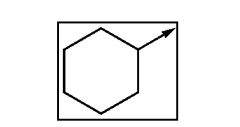 | 88.3% | 6.4 | 449.2 |

| 35 | C22H24N4O2S | 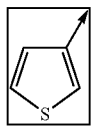 | 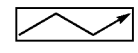 | 90.8% | 5.7 | 409.2 |
| 36 | C23H26N4O2S | 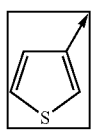 | 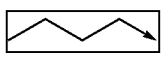 | 91.8% | 6.1 | 423.2 |
| 37 | C22H22N4O2S | 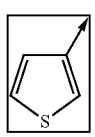 | 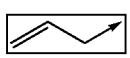 | 97.9% | 5.6 | 407.2 |
| 38 | C24H28N4O2S | 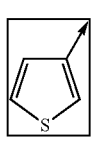 | 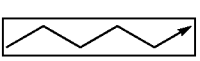 | 84.3% | 6.4 | 437.2 |
| 39 | C22H24N4O2S | 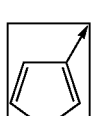 |  | 87.2% | 5.7 | 409.2 |
| 40 | C28H28N4O5S | 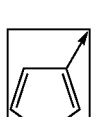 | 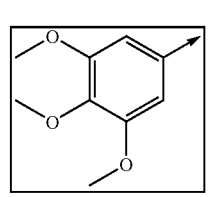 | 92.2% | 5.9 | 533.2 |
| 41 | C28H26N4O3 | 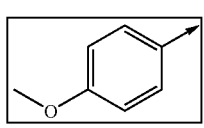 | 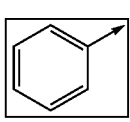 | 93.9% | 6.1 | 467.2 |
| 42 | C29H28N4O3 | 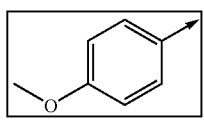 | 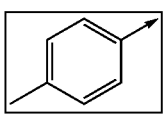 | 95.8% | 6.3 | 481.3 |
| 43 | C29H28N4O4 | 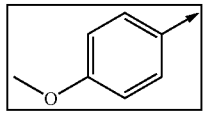 |  | 93.0% | 6.1 | 497.3 |
| 44 | C29H28N4O3S | 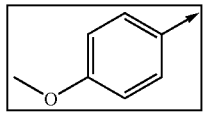 | 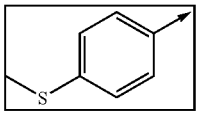 | 94.5% | 6.5 | 513.2 |
| 45 | C29H25F3N4O4 | 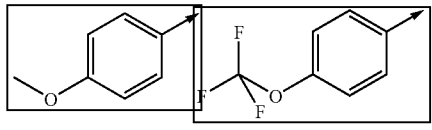 | | 90.4% | 6.9 | 551.2 |

-continued
| 46 | C31H32N4O3 | 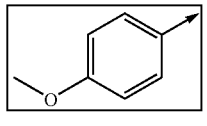 | 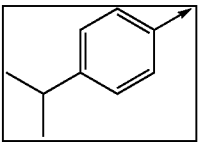 | 87.7% | 6.9 | 509.3 |
| 47 | C28H25BrN4O3 | 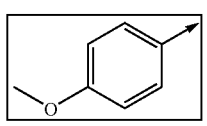 | 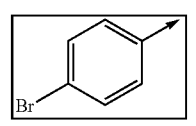 | 84.2% | 6.6 | 547.1 |
| 48 | C28H25ClN4O3 | 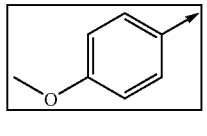 | 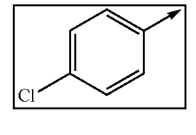 | 86.6% | 6.5 | 501.2 |
| 49 | C28H25N5O5 | 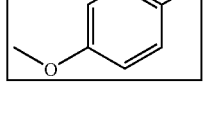 | 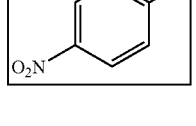 | 93.9% | 6.3 | 512.2 |
| 50 | C34H38N4O3 | 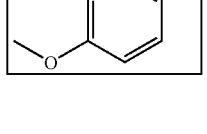 | 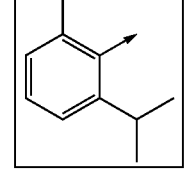 | 98.3% | 7.2 | 551.3 |
| 51 | C28H24F2N4O3 | 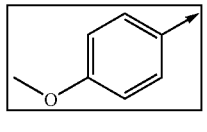 | 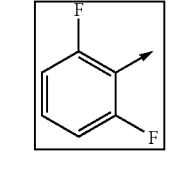 | 98.0% | 6.2 | 503.2 |
| 52 | C29H28N4O3 | 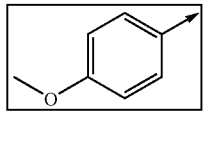 | 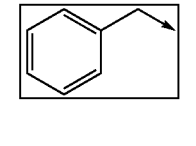 | 94.6% | 6.4 | 481.2 |
| 53 | C30H30N4O3 | 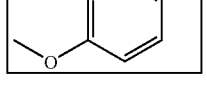 | 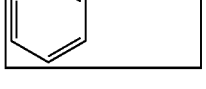 | 91.5% | 6.4 | 495.3 |
| 54 | C28H32N4O3 | 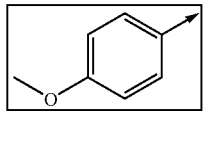 | 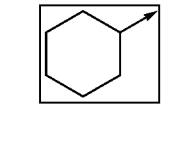 | 85.8% | 6.5 | 473.3 |
| 55 | C25H28N4O3 | 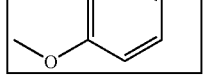 |  | 89.7% | 5.8 | 433.3 |

-continued
| | | | | | | |
|---|---|---|---|---|---|---|
| 56 | C26H30N4O3 | 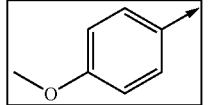 | 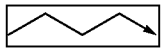 | 90.6% | 6.2 | 447.3 |
| 57 | C25H26N4O3 | 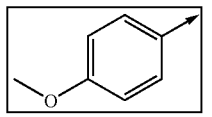 | 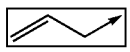 | 97.1% | 5.7 | 431.2 |
| 58 | C27H32N4O3 | 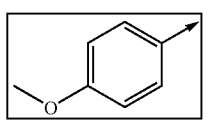 | 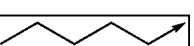 | 75.3% | 6.5 | 461.3 |
| 59 | C25H28N4O3 | 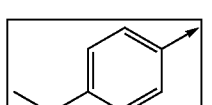 | 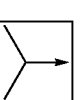 | 86.1% | 5.9 | 433.3 |
| 60 | C31H32N4O6 | 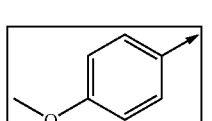 | 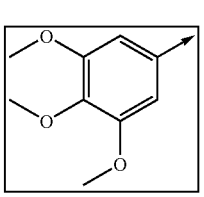 | 83.5% | 6.0 | 557.2 |
| 61 | C29H29N5O2 | 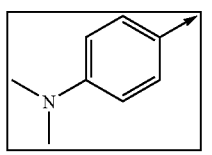 | 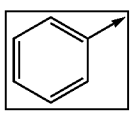 | 92.62%* | 5.3 | 480.3 |
| 62 | C30H31N5O2 | 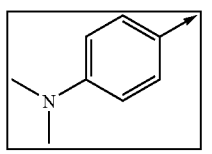 | 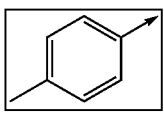 | 93.25%* | 5.6 | 494.3 |
| 63 | C30H31N5O3 | 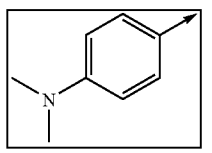 | 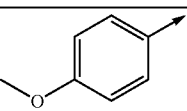 | 94.39%* | 5.4 | 510.3 |
| 64 | C30H31N5O2S | 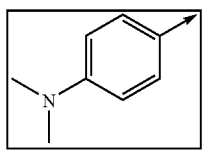 | 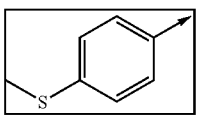 | 95.36%* | 5.8 | 526.3 |
| 65 | C30H28F3N5O3 | 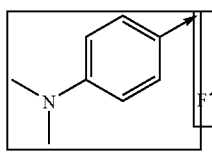 | 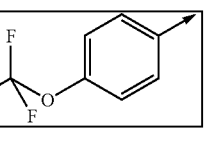 | 89.2% | 6.3 | 564.2 |

-continued
| | | | | | | |
|---|---|---|---|---|---|---|
| 66 | C32H35N5O2 |  |  | 86.35%* | 6.3 | 522.3 |
| 67 | C29H28BrN5O2 | 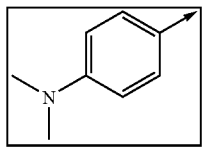 | 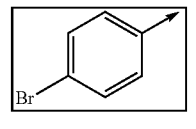 | 84.14%* | 5.9 | 560.1 |
| 68 | C29H28ClN5O2 | 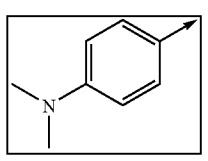 | 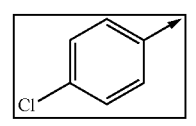 | 85.8% | 5.8 | 514.2 |
| 69 | C29H28N6O4 | 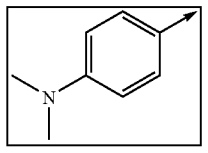 | 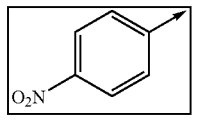 | 94.4% | 5.6 | 525.3 |
| 70 | C35H41N5O2 | 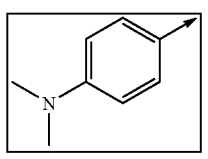 | 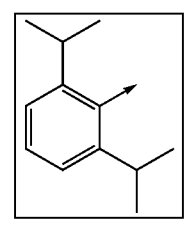 | 95.76%* | 6.8 | 564.3 |
| 71 | C29H27F2N5O2 | 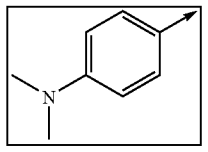 |  | 96.29%* | 5.5 | 516.3 |
| 72 | C30H31N5O2 | 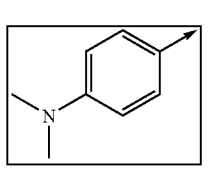 |  | 97.59%* | 5.6 | 494.3 |
| 73 | C31H33N5O2 | 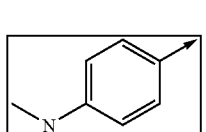 | 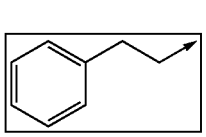 | 94.87%* | 5.7 | 508.3 |
| 74 | C29H35N5O2 | 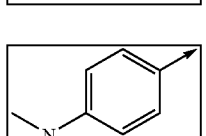 | 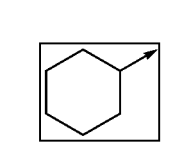 | 87.63%* | 5.8 | 486.3 |

-continued
| | | | | Purity | rt (min) | [M + H]+ |
|---|---|---|---|---|---|---|
| 75 | C26H31N5O2 | 4-(dimethylamino)phenyl | cyclohexyl | 87.69%* | 5.0 | 446.3 |
| 76 | C27H33N5O2 | 4-(dimethylamino)phenyl | n-hexyl | 86.66%* | 5.4 | 460.3 |
| 77 | C26H29N5O2 | 4-(dimethylamino)phenyl | cyclohexenyl | 93.78%* | 4.9 | 444.3 |
| 78 | C28H35N5O2 | 4-(dimethylamino)phenyl | n-heptyl | 85%* | 5.8 | 474.3 |
| 79 | C26H31N5O2 | 4-(dimethylamino)phenyl | isopropyl-cyclopropyl | 87.49%* | 5.0 | 446.3 |
| 80 | C32H35N5O5 | 4-(dimethylamino)phenyl | 3,4,5-trimethoxyphenyl | 87.6% | 5.3 | 570.3 |
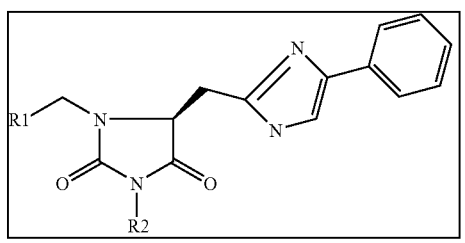
| | | | | Analyses | | |
|---|---|---|---|---|---|---|
| Ex. No. | Formula | R1 | R2 | Purity | rt (min) | [M + H]+ |
| 81 | C28H23N5O2 | indol-3-yl | phenyl | 92% | 6.2 | 462.2 |

-continued
| 82 | C29H25N5O2 | 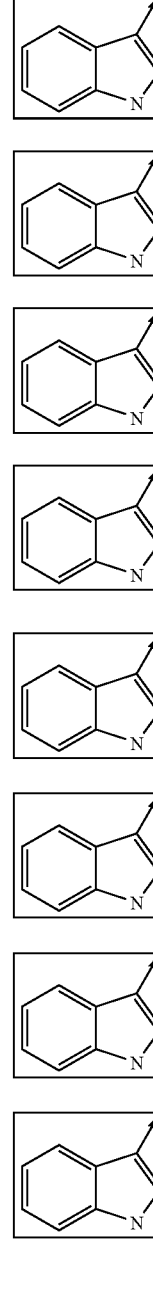 | 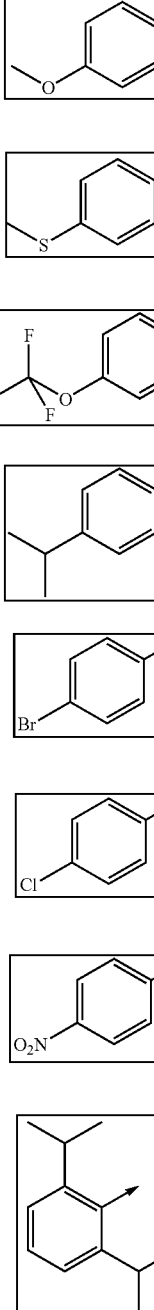 | 93% | 6.5 | 476.2 |
| 83 | C29H25N5O3 | 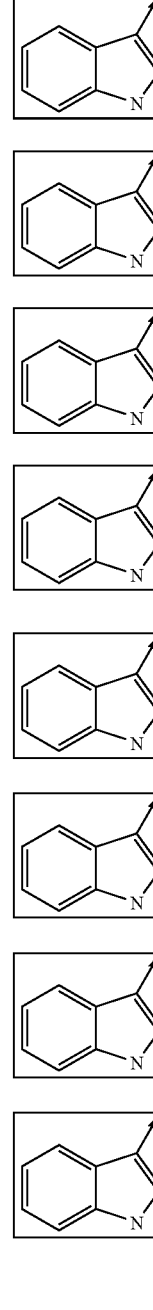 | 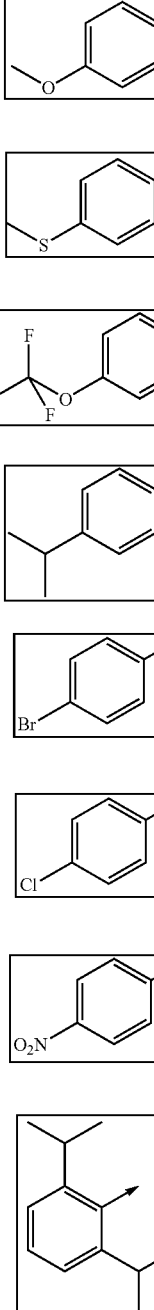 | 94% | 6.2 | 492.2 |
| 84 | C29H25N5O2S | 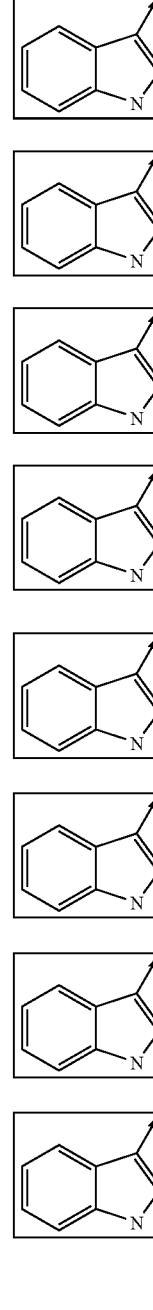 | 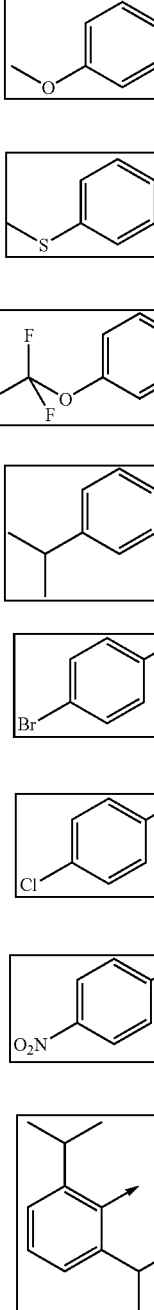 | 92% | 6.6 | 508.2 |
| 85 | C29H22F3N5O3 | 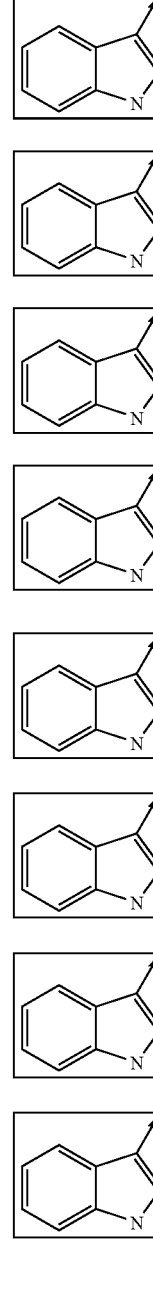 | 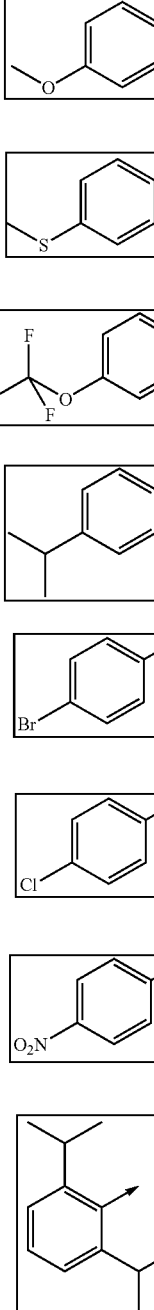 | 92% | 7.0 | 546.2 |
| 86 | C31H29N5O2 | 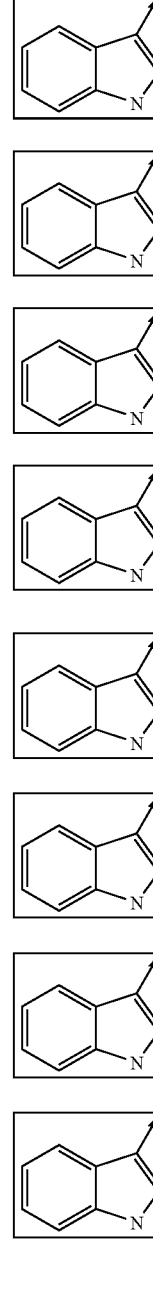 | 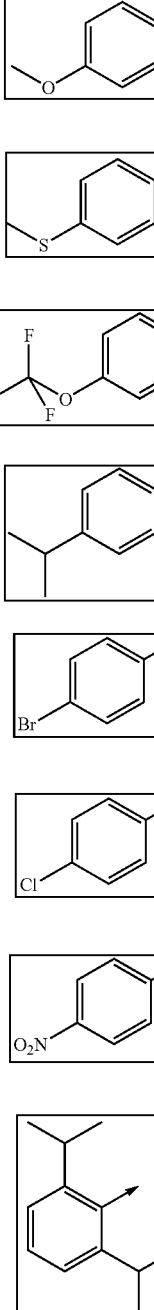 | 92% | 7.1 | 504.3 |
| 87 | C28H22BrN5O2 | 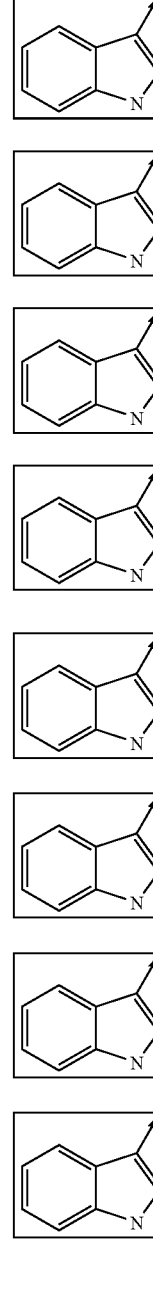 | 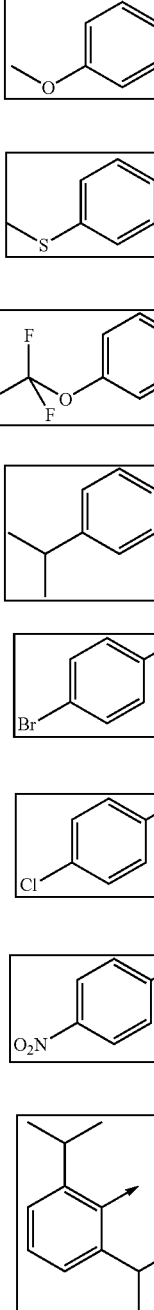 | 92% | 6.8 | 542.1 |
| 88 | C28H22ClN5O2 | 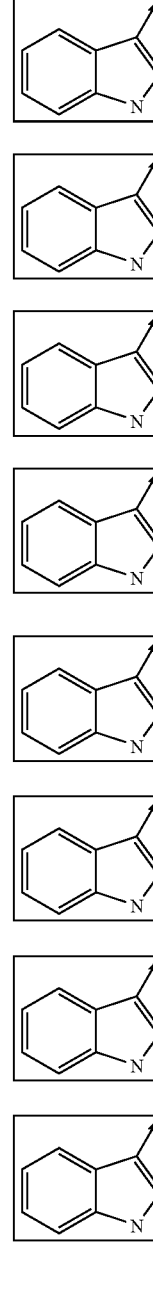 | 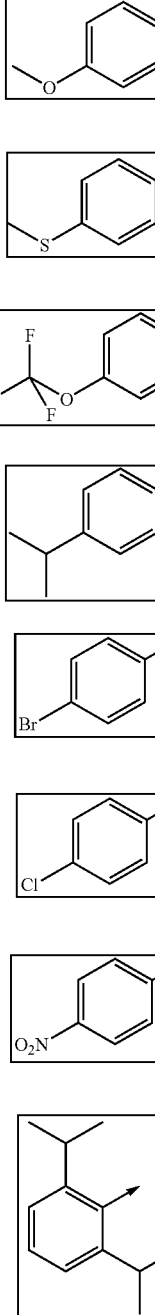 | 92% | 6.7 | 496.2 |
| 89 | C28H22N6O4 | 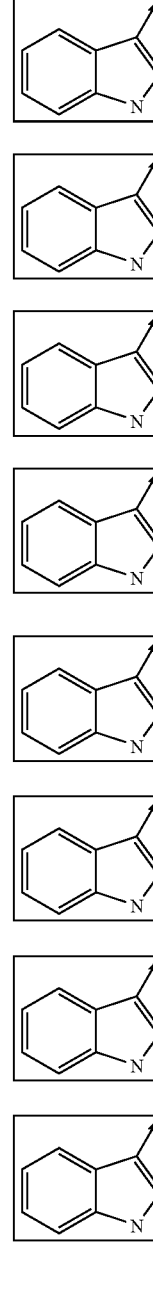 | 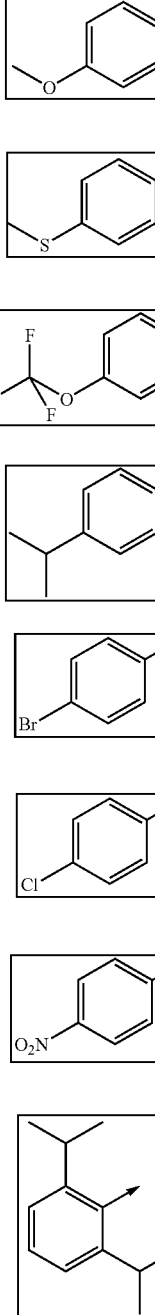 | 82% | 6.5 | 507.2 |
| 90 | C34H35N5O2 | 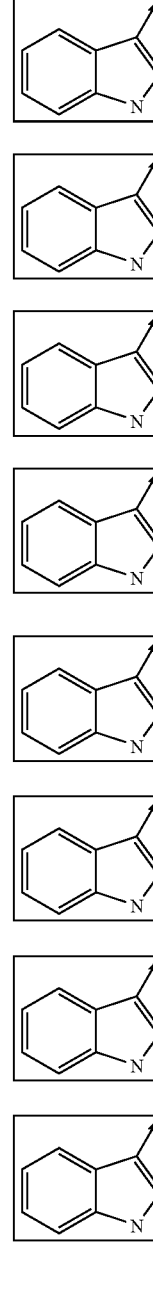 | 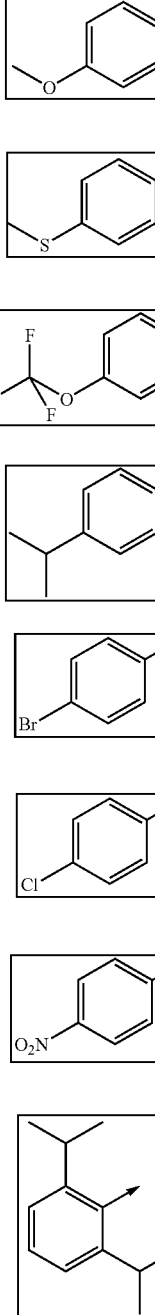 | 92% | 7.3 | 546.3 |
| 91 | C28H21F2N5O2 | 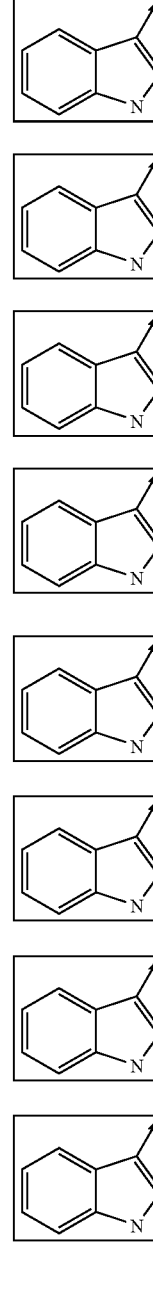 | 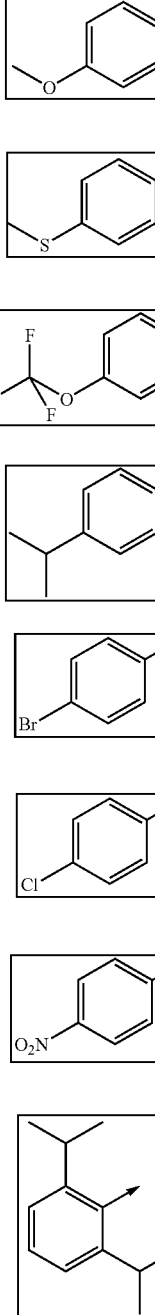 | 90% | 6.2 | 498.2 |

| | | | | | | |
|---|---|---|---|---|---|---|
| 92 | C31H29N5O5 | 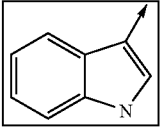 | 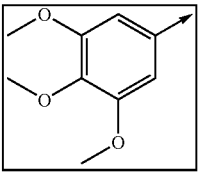 | 82% | 6.2 | 552.2 |
| 93 | C29H22F3N5O2 | 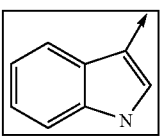 | 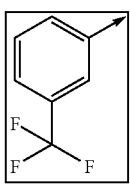 | 92% | 6.9 | 530.2 |
| 94 | C30H25N5O3 | 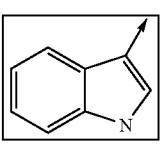 | 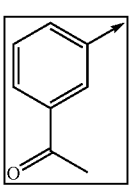 | 89% | 6.1 | 504.2 |
| 95 | C29H25N5O2 | 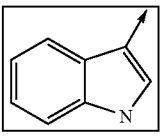 | 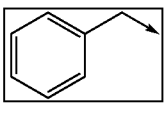 | 92% | 6.4 | 476.2 |
| 96 | C30H27N5O2 | 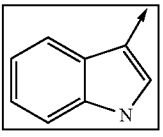 | 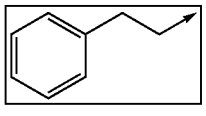 | 93% | 6.6 | 490.3 |
| 97 | C25H25N5O2 | 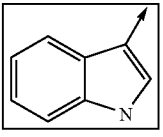 |  | 95% | 5.9 | 428.2 |
| 98 | C26H27N5O2 | 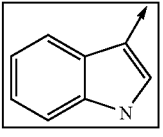 |  | 95% | 6.3 | 442.3 |
| 99 | C25H23N5O2 | 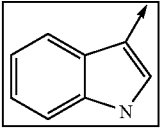 | 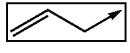 | 95% | 5.8 | 426.2 |
| 100 | C27H29N5O2 | 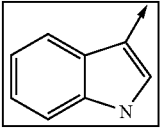 | 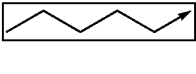 | 94% | 6.6 | 456.3 |

-continued
| | | | | | | | |
|---|---|---|---|---|---|---|---|
| 101 | C24H20N4O2S | 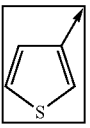 | | 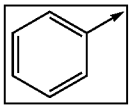 | 92% | 5.9 | 429.2 |
| 102 | C25H22N4O2S | 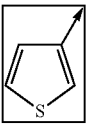 | | 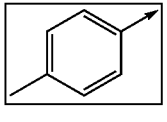 | 91% | 6.2 | 443.2 |
| 103 | C25H22N4O3S | 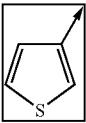 | | 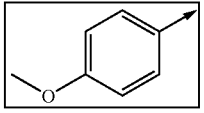 | 90% | 6.0 | 459.2 |
| 104 | C25H22N4O2S2 | 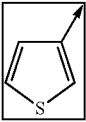 | | 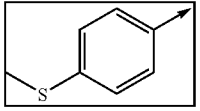 | 87% | 6.4 | 475.2 |
| 105 | C25H19F3N4O3S | 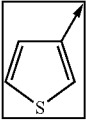 | | 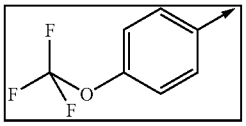 | 89% | 6.8 | 513.2 |
| 106 | C27H26N4O2S | 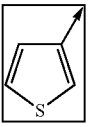 | | 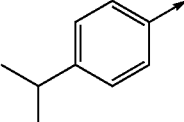 | 89% | 6.9 | 471.2 |
| 107 | C24H19BrN4O2S | 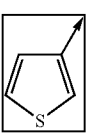 | | 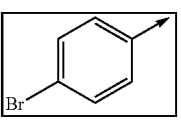 | 91% | 6.5 | 509.1 |
| 108 | C24H19ClN4O2S | 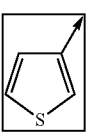 | | 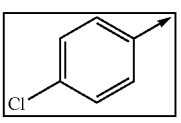 | 90% | 6.4 | 463.1 |
| 109 | C24H19N5O4S | 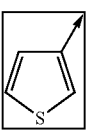 | | 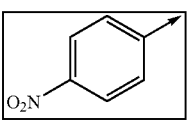 | 76% | 6.3 | 474.2 |
| 110 | C30H32N4O2S | 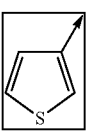 | | 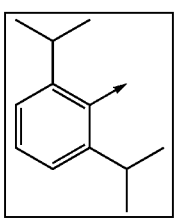 | 90% | 7.1 | 513.3 |

-continued
| | | | | | | |
|---|---|---|---|---|---|---|
| 111 | C24H18F2N4O2S | 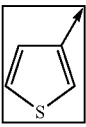 | 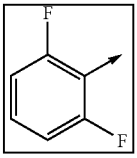 | 82% | 6.0 | 465.2 |
| 112 | C27H26N4O5S | 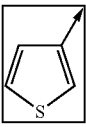 | 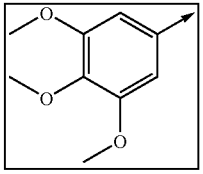 | 77% | 5.8 | 519.2 |
| 113 | C25H19F3N4O2S | 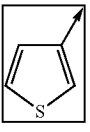 | 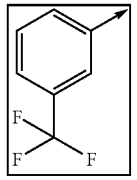 | 89% | 6.7 | 497.2 |
| 114 | C26H22N4O3S | 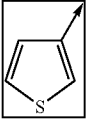 | 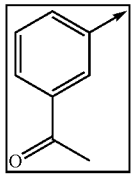 | 86% | 5.8 | 471.2 |
| 115 | C25H22N4O2S |  | 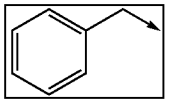 | 85% | 6.1 | 443.2 |
| 116 | C26H24N4O2S | 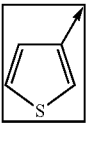 | 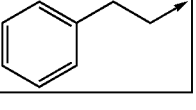 | 82% | 6.3 | 457.2 |
| 117 | C21H22N4O2S | 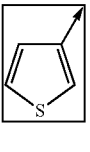 | 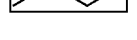 | 84% | 5.6 | 395.2 |
| 118 | C22H24N4O2S | 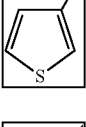 | 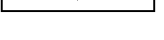 | 93% | 5.9 | 409.2 |
| 119 | C21H20N4O2S | 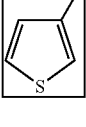 | 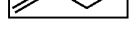 | 89% | 5.4 | 393.2 |
| 120 | C23H26N4O2S | 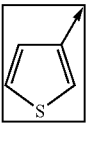 | 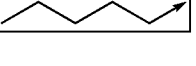 | 81% | 6.3 | 423.2 |

-continued
| | | | | | | |
|---|---|---|---|---|---|---|
| 121 | C27H24N4O3 | 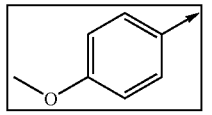 | 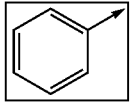 | 91% | 6.0 | 453.2 |
| 122 | C28H26N4O3 | 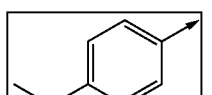 | 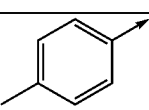 | 92% | 6.3 | 467.2 |
| 123 | C28H26N4O4 | 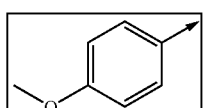 | 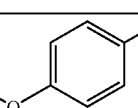 | 91% | 6.0 | 483.3 |
| 124 | C28H26N4O3S | 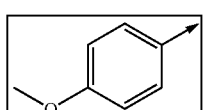 | 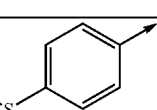 | 88% | 6.4 | 499.2 |
| 125 | C28H23F3N4O4 | 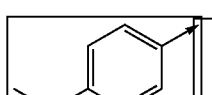 | 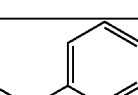 | 91% | 6.9 | 537.2 |
| 126 | C30H30N4O3 | 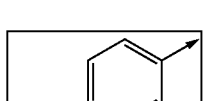 | 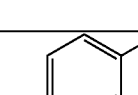 | 90% | 6.9 | 495.2 |
| 127 | C27H23BrN4O3 | 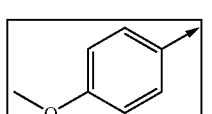 | 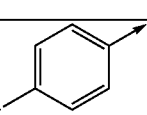 | 89% | 6.6 | 533.1 |
| 128 | C27H23ClN4O3 | 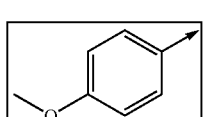 | 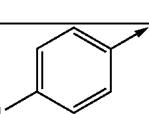 | 91% | 6.5 | 487.2 |
| 129 | C27H23N5O5 | 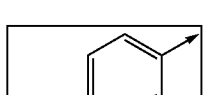 |  | 75% | 6.4 | 498.2 |
| 130 | C33H36N4O3 |  | 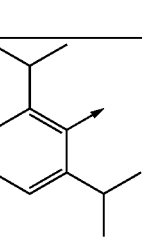 | 90% | 7.2 | 537.3 |

-continued
| 131 | C27H22F2N4O3 | 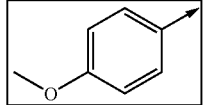 | 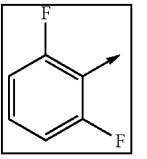 | 82% | 6.1 | 489.2 |
| 132 | C30H30N4O6 | 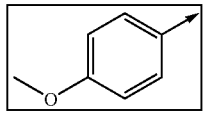 | 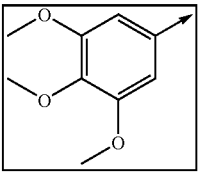 | 79% | 6.0 | 543.2 |
| 133 | C28H23F3N4O3 | 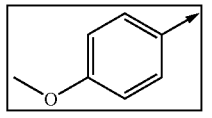 | 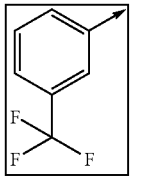 | 90% | 6.8 | 521.2 |
| 134 | C29H26N4O4 | 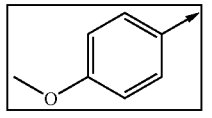 | 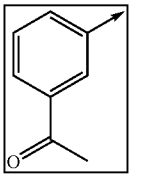 | 85% | 5.9 | 495.2 |
| 135 | C28H26N4O3 | 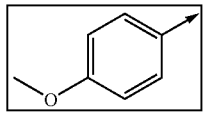 | 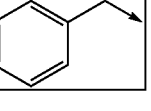 | 89% | 6.2 | 467.2 |
| 136 | C29H28N4O3 | 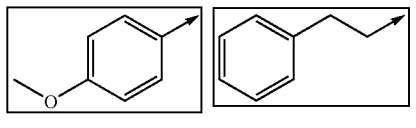 |  | 89% | 6.4 | 481.2 |
| 137 | C24H26N4O3 | 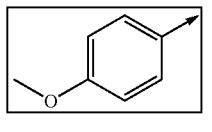 | 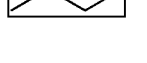 | 88% | 5.7 | 419.3 |
| 138 | C25H28N4O3 | 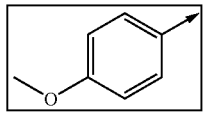 |  | 90% | 6.1 | 433.3 |
| 139 | C24H24N4O3 | 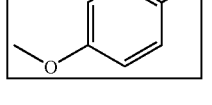 | 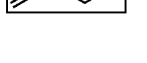 | 92% | 5.6 | 417.3 |
| 140 | C26H30N4O3 | 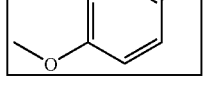 |  | 87% | 6.4 | 447.3 |

|     |              |                      |                      |         |     |       |
|-----|--------------|----------------------|----------------------|---------|-----|-------|
| 141 | C28H27N5O2   |  | 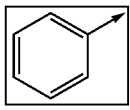 | 89%     | 5.1 | 466.2 |
| 142 | C29H29N5O2   |  | 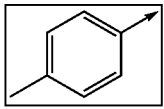 | 89%     | 5.5 | 480.3 |
| 143 | C29H29N5O3   |  | 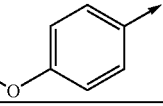 | 90%     | 5.2 | 496.3 |
| 144 | C29H29N5O2S  |  | 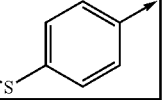 | 86%     | 5.7 | 512.2 |
| 145 | C29H26F3N5O3 |  | 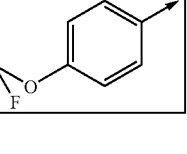 | 87%    | 6.2 | 550.2 |
| 146 | C31H33N5O2   |  | 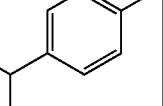 | 87%   | 6.2 | 508.3 |
| 147 | C28H26BrN5O2 |  | 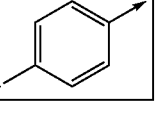 | 88%   | 5.8 | 546.1 |
| 148 | C28H26ClN5O2 | 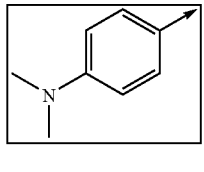 | 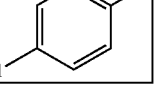 | 88%   | 5.7 | 500.2 |
| 149 | C28H26N6O4   | 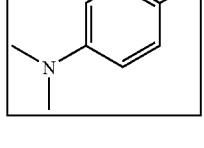 | 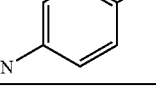 | 74.76%* | 5.6 | 511.2 |

| | | | | | | |
|---|---|---|---|---|---|---|
| 150 | C34H39N5O2 | 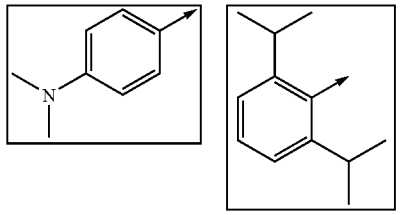 | | 85% | 6.7 | 550.3 |
| 151 | C28H25F2N5O2 | 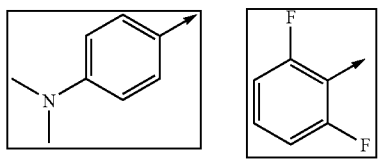 | | 81% | 5.3 | 502.2 |
| 152 | C31H33N5O5 | 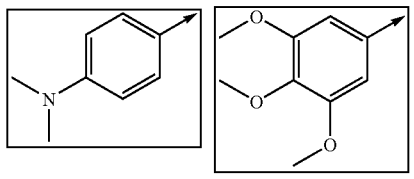 | | 79% | 5.2 | 556.3 |
| 153 | C29H26F3N5O2 | 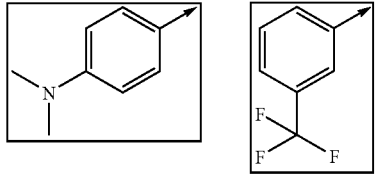 | | 88% | 6.1 | 534.2 |
| 154 | C30H29N5O3 | 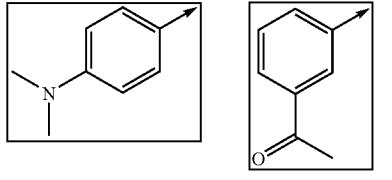 | | 85% | 5.1 | 508.3 |
| 155 | C29H29N5O2 | 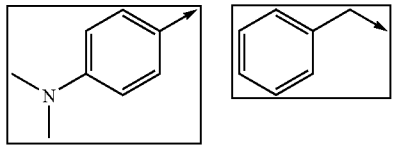 | | 86% | 5.4 | 480.3 |
| 156 | C30H31N5O2 | 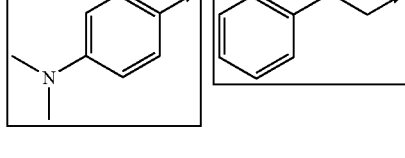 | | 86% | 5.6 | 494.3 |
| 157 | C25H29N5O2 |  | | 85% | 4.8 | 432.3 |

-continued
| Ex. No. | Formula | R1 | R2 | Purity | rt (min) | [M + H]+ |
|---|---|---|---|---|---|---|
| 158 | C26H31N5O2 | 4-(dimethylamino)phenyl | cyclohexyl-CH2 | 84% | 5.2 | 446.3 |
| 159 | C25H27N5O2 | 4-(dimethylamino)phenyl | allyl-CH2 | 86% | 4.7 | 430.3 |
| 160 | C27H33N5O2 | 4-(dimethylamino)phenyl | n-pentyl | 88% | 5.6 | 460.3 |
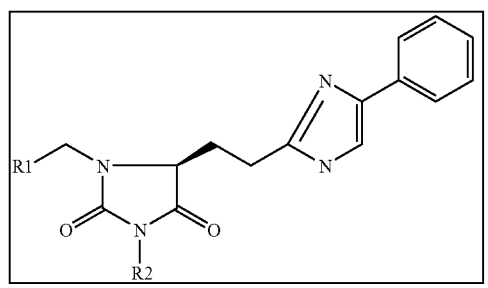
| | | | | Analyses | | |
|---|---|---|---|---|---|---|
| Ex. No. | Formula | R1 | R2 | Purity | rt (min) | [M + H]+ |
| 161 | C30H27N5OS | indol-3-yl | benzyl | 80% | 7.1 | 506.2 |
| 162 | C30H26ClN5OS | indol-3-yl | 2-chlorobenzyl | 83% | 7.3 | 540.2 |
| 163 | C30H25Cl2N5OS | indol-3-yl | 3,4-dichlorobenzyl | 81% | 7.7 | 574.1 |

| | | | | | | |
|---|---|---|---|---|---|---|
| 164 | C31H27N5O3S | 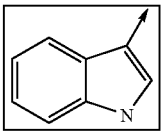 | 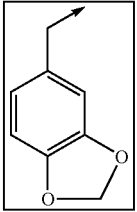 | 81% | 7.0 | 550.2 |
| 165 | C30H26FN5OS | 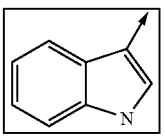 | 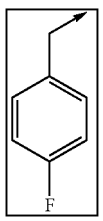 | 82% | 7.1 | 524.3 |
| 166 | C31H29N5OS | 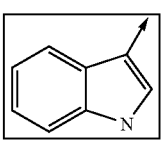 | 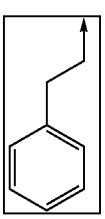 | 81% | 7.3 | 520.3 |
| 167 | C31H28ClN5OS | 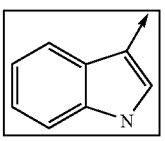 | 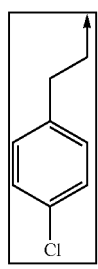 | 83% | 7.6 | 554.2 |
| 168 | C33H33N5O3S | 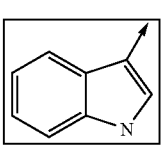 | 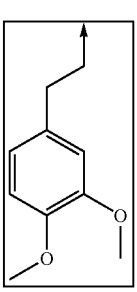 | 80% | 7.0 | 580.3 |
| 169 | C32H31N5OS | 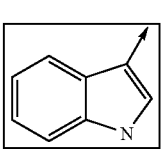 | 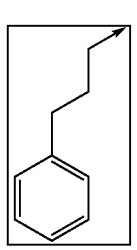 | 78% | 7.4 | 534.3 |

| | | | | | | |
|---|---|---|---|---|---|---|
| 170 | C28H25N5O2S | 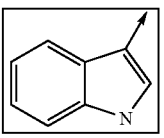 | 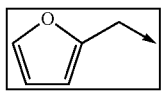 | 85% | 6.7 | 496.3 |
| 171 | C28H29N5O2S | 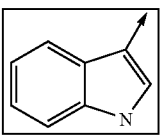 | 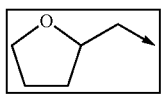 | 81% | 6.6 | 500.3 |
| 172 | C28H29N5OS | 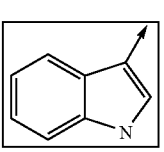 | 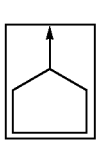 | 71% | 7.1 | 484.3 |
| 173 | C29H31N5OS | 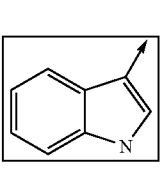 | 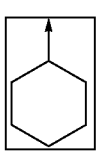 | 61% | 7.3 | 498.3 |
| 174 | C30H33N5OS | 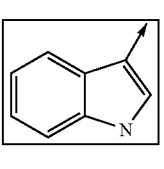 | 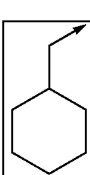 | 64% | 7.6 | 512.3 |
| 175 | C29H32N6O2S | 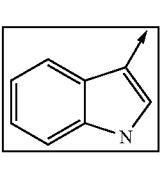 | 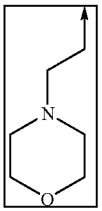 | 84% | 5.0 | 529.3 |
| 176 | C30H34N6O2S | 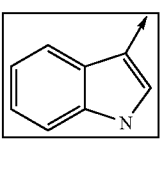 | 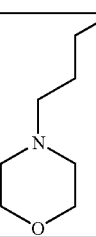 | 86% | 5.0 | 543.3 |
| 177 | C30H36N6OS | 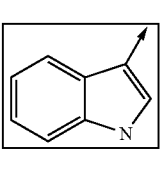 | 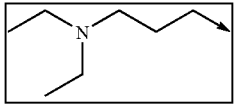 | 83% | 5.2 | 529.3 |
| 178 | C26H27N5O2S | 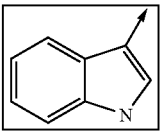 | 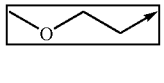 | 82% | 6.3 | 474.3 |

-continued

| # | Formula | R1 | R2 | Yield | RT | MS |
|---|---|---|---|---|---|---|
| 179 | C27H29N5O2S | indol-3-yl | -CH2CH2CH2-O-CH3 | 80% | 6.4 | 438.3 |
| 180 | C27H29N5OS | indol-3-yl | -CH2-CH(CH3)2 | 74% | 7.0 | 472.3 |
| 181 | C26H24N4OS2 | thien-3-yl | -CH2-Ph | 77% | 6.9 | 473.2 |
| 182 | C26H23ClN4OS2 | thien-3-yl | -CH2-(2-Cl-Ph) | 78% | 7.1 | 507.2 |
| 183 | C26H22Cl2N4OS2 | thien-3-yl | -CH2-(3,4-diCl-Ph) | 84% | 7.6 | 541.1 |
| 184 | C27H24N4O3S2 | thien-3-yl | -CH2-(3,4-methylenedioxy-Ph) | 80% | 6.9 | 517.2 |
| 185 | C26H23FN4OS2 | thien-3-yl | -CH2-(4-F-Ph) | 75% | 7.0 | 491.2 |
| 186 | C27H26N4OS2 | thien-3-yl | -CH2CH2-Ph | 80% | 7.1 | 487.2 |

-continued
| | | | | | | |
|---|---|---|---|---|---|---|
| 187 | C27H25ClN4OS2 | 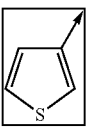 | 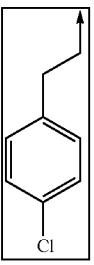 | 85% | 7.4 | 521.2 |
| 188 | C29H30N4O3S2 | 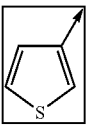 | 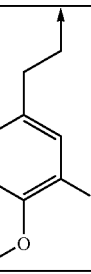 | 87% | 6.8 | 547.2 |
| 189 | C28H28N4OS2 | 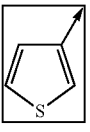 | 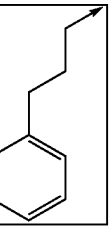 | 77% | 7.3 | 501.2 |
| 190 | C24H22N4O2S2 |  | 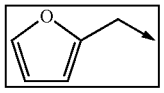 | 86% | 6.5 | 463.2 |
| 191 | C24H26N4O2S2 | 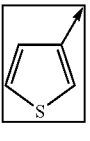 | 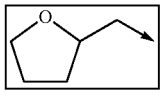 | 58.9% + 19.6% | 6.4 | 467.2 |
| 192 | C24H26N4OS2 | 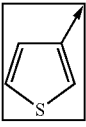 | 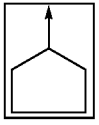 | 75% | 6.9 | 451.2 |
| 193 | C25H28N4OS2 | 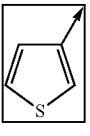 | 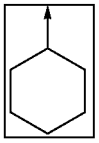 | 77% | 7.2 | 465.2 |
| 194 | C26H30N4OS2 | 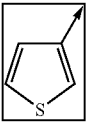 | 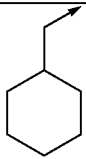 | 76% | 7.5 | 479.3 |

| | | | | | | |
|---|---|---|---|---|---|---|
| 195 | C25H29N5O2S2 | 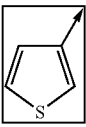 | 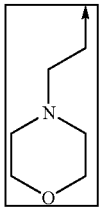 | 81% | 4.8 | 496.3 |
| 196 | C26H31N5O2S2 | 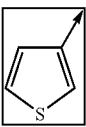 | 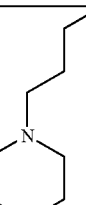 | 82% | 4.9 | 510.3 |
| 197 | C26H33N5OS2 | 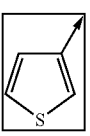 | 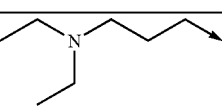 | 71% | 5.0 | 496.3 |
| 198 | C22H24N4O2S2 | 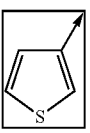 |  | 81% | 6.1 | 441.2 |
| 199 | C23H25N4O2S2 | 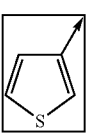 | 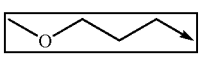 | 78% | 6.2 | 455.2 |
| 200 | C23H26N4OS2 | 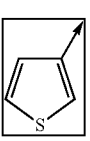 | 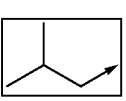 | 79% | 6.8 | 551.2 |
| 201 | C29H28N4O2S | 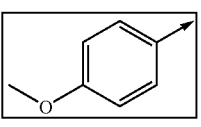 | 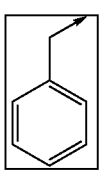 | 80% | 7.0 | 497.3 |
| 202 | C29H27ClN4O2S | 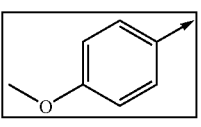 | 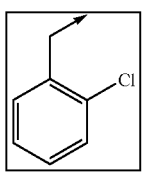 | 81% | 7.2 | 643.2 |

-continued

| # | Formula | R1 | R2 | Yield | RT | MS |
|---|---|---|---|---|---|---|
| 203 | C29H26Cl2N4O2S | 4-methoxyphenyl | 3,4-dichlorobenzyl | 86% | 7.6 | 677.2 |
| 204 | C30H28N4O4S | 4-methoxyphenyl | 3,4-methylenedioxybenzyl | 82% | 7.0 | 653.2 |
| 205 | C29H27FN4O2S | 4-methoxyphenyl | 4-fluorobenzyl | 72% | 7.1 | 627.2 |
| 206 | C30H30N4O2S | 4-methoxyphenyl | phenethyl | 83% | 7.2 | 511.3 |
| 207 | C30H29ClN4O2S | 4-methoxyphenyl | 4-chlorophenethyl | 87% | 7.5 | 657.2 |
| 208 | C32H34N4O4S | 4-methoxyphenyl | 3,4-dimethoxyphenethyl | 87% | 6.9 | 571.3 |

-continued
| | | | | | | |
|---|---|---|---|---|---|---|
| 209 | C31H32N4O2S | 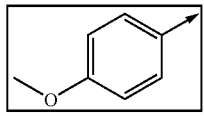 | 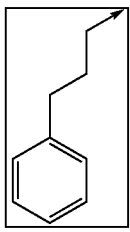 | 83% | 7.4 | 637.3 |
| 210 | C27H26N4O3S | 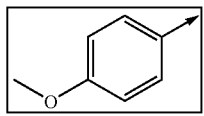 | 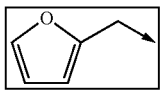 | 87% | 6.6 | 599.2 |
| 211 | C27H30N4O3S | 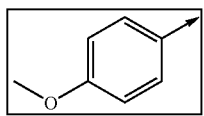 | 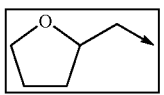 | 59% + 20% | 6.5 + 6.6 | 491.2 |
| 212 | C27H30N4O2S | 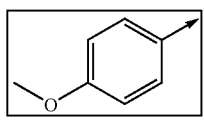 | 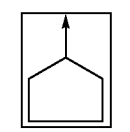 | 81% | 7.0 | 475.5 |
| 213 | C28H32N4O2S | 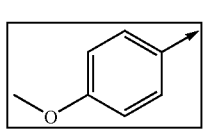 | 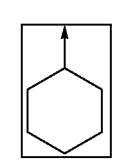 | 82% | 7.2 | 601.2 |
| 214 | C29H34N4O2S | 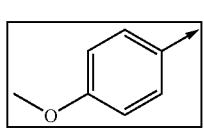 | 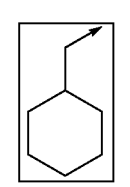 | 83% | 7.5 | 615.3 |
| 215 | C28H33N5O3S | 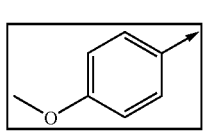 | 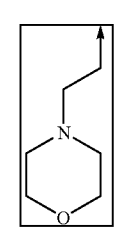 | 86% | 5.0 | 520.3 |
| 216 | C29H35N5O3S | 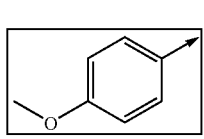 | 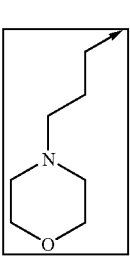 | 86% | 5.0 | 646.3 |
| 217 | C29H37N5O2S | 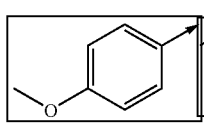 | 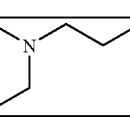 | 78% | 5.1 | 632.3 |

-continued

| | | | | | | |
|---|---|---|---|---|---|---|
| 218 | C25H28N4O3S | 4-methoxyphenyl | -CH2CH2-O-CH3 | 87% | 6.2 | 577.2 |
| 219 | C26H30N4O3S | 4-methoxyphenyl | -CH2CH2CH2-O-CH3 | 80% | 6.4 | 591.3 |
| 220 | C26H30N4O2S | 4-methoxyphenyl | isobutyl | 85% | 6.9 | 575.2 |
| 221 | C30H31N5OS | 4-(dimethylamino)phenyl | benzyl | 77% | 6.5 | 510.3 |
| 222 | C30H30ClN5OS | 4-(dimethylamino)phenyl | 2-chlorobenzyl | 66% | 6.8 | 544.3 |
| 223 | C30H29Cl2N5OS | 4-(dimethylamino)phenyl | 3,4-dichlorobenzyl | 69% | 7.3 | 690.2 |
| 224 | C31H31N5O3S | 4-(dimethylamino)phenyl | 1,3-benzodioxol-5-ylmethyl | 75% | 6.4 | 666.3 |
| 225 | C30H30FN5OS | 4-(dimethylamino)phenyl | 4-fluorobenzyl | 52% | 6.6 | 528.5 |

-continued
| | | | | | | |
|---|---|---|---|---|---|---|
| 226 | C31H33N5OS | 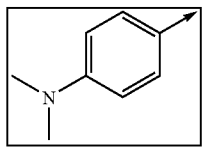 | 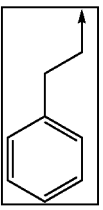 | 82% | 6.7 | 636.3 |
| 227 | C31H32ClN5OS | 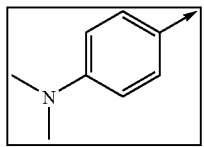 | 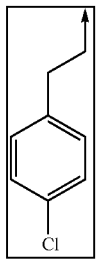 | 85% | 7.1 | 670.3 |
| 228 | C33H37N5O3S | 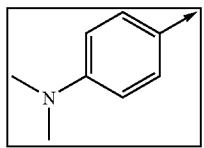 | 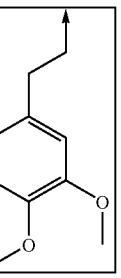 | 82% | 6.4 | 696.3 |
| 229 | C32H35N5OS | 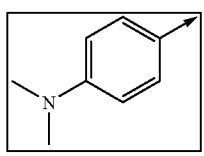 | 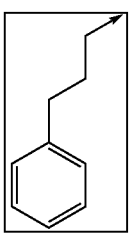 | 66% | 7.0 | 650.3 |
| 230 | C28H29N5O2S | 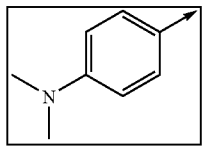 |  | 77% | 6.1 | 612.2 |
| 231 | C28H33N5O2S | 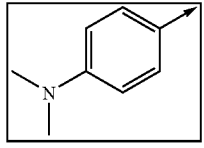 | 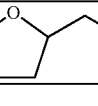 | 26% + 48 | 5.8 + 5.9 | 616.3 |
| 232 | C28H33N5OS | 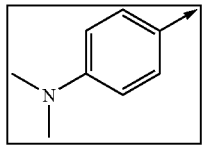 | 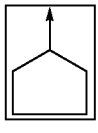 | 76% | 6.4 | 600.3 |

-continued
| | | | | | | |
|---|---|---|---|---|---|---|
| 233 | C29H35N5OS | 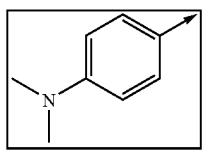 | 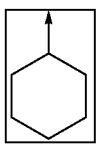 | 78% | 6.7 | 614.3 |
| 234 | C30H37N5OS | 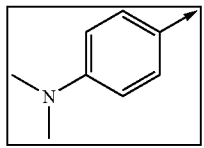 | 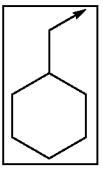 | 77% | 4.6 | 645.3 |
| 235 | C29H36N6O2S | 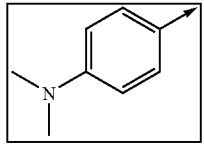 | 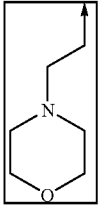 | 85% | 4.6 | 659.4 |
| 236 | C30H38N6O2S | 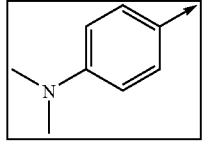 | 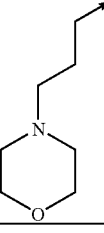 | 84% | 4.8 | 532.3 |
| 237 | C30H40N5OS | 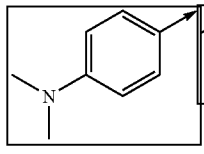 | 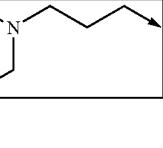 | 36% | 5.5 | 590.3 |
| 238 | C26H31N5O2S | 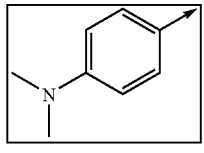 | 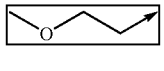 | 79% | 5.7 | 492.3 |
| 239 | C27H33N5O2S | 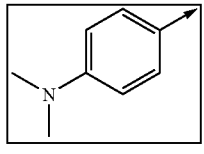 | 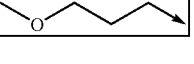 | 69% | 6.3 | 588.3 |
| 240 | C27H33N5OS | 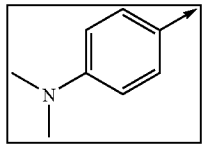 | 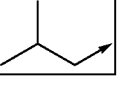 | 78% | 6.3 | 476.3 |

-continued
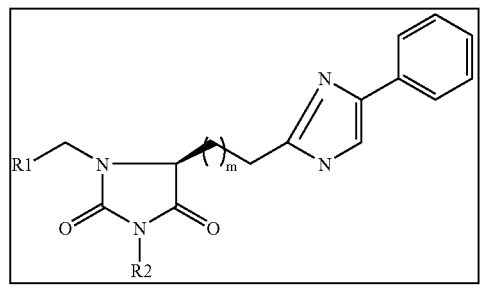
| Ex. No. | Formula | m | R1 | R2 | Purity | rt (min) | [M + H]+ |
|---|---|---|---|---|---|---|---|
| 241 | C29H25N5OS | 2 | indole | phenyl | 93% | 6.7 | 492.2 |
| 242 | C31H27N5O2S | 2 | indole | 4-acetylphenyl | 87% | 6.6 | 534.2 |
| 243 | C35H37N5OS2 | 2 | indole | 2,6-diisopropylphenyl | 68% | 7.9 | 576.3 |
| 244 | C32H31N5OS | 2 | indole | 4-isopropylphenyl | 88% | 7.5 | 534.2 |
| 245 | C29H23F2N5OS | 2 | indole | 2,6-difluorophenyl | 92% | 6.9 | 528.2 |
| 246 | C29H24FN5OS | 2 | indole | 4-fluorophenyl | 92% | 6.8 | 510.2 |

| | | | | | | | |
|---|---|---|---|---|---|---|---|
| 247 | C29H22Cl3N5OS | 2 | 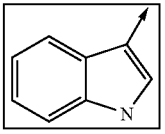 | 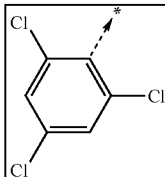 | 82% | 7.6 | 594.1 |
| 248 | C29H23Cl2N5OS | 2 | 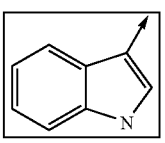 | 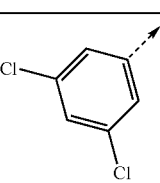 | 86% | 7.5 | 560.1 |
| 249 | C29H22Br3N5OS | 2 | 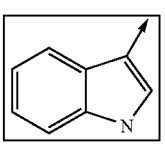 |  | 76% | 7.8 | 725.9 |
| 250 | C31H29N5OS | 2 | 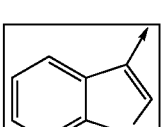 | 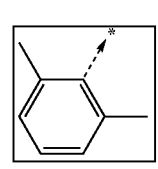 | 47% | 7.1 | 520.2 |
| 251 | C31H23F6N5OS | 2 | 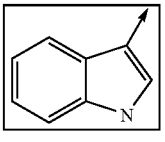 | 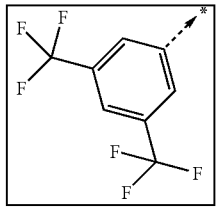 | 88% | 7.8 | 628.2 |
| 252 | C30H24F3N5OS | 2 | 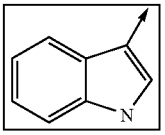 | 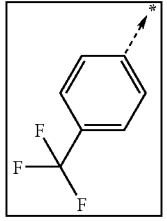 | 90% | 7.3 | 560.2 |
| 253 | C31H29N5O3S | 2 | 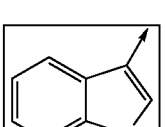 | 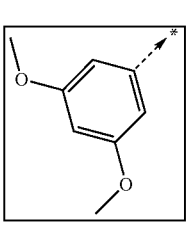 | 86% | 6.9 | 552.2 |

-continued
| | | | | | | | |
|---|---|---|---|---|---|---|---|
| 254 | C30H27N5O2S | 2 | 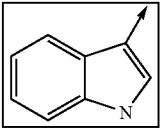 | 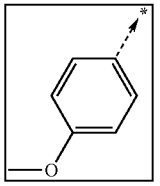 | 93% | 6.8 | 522.2 |
| 255 | C30H27N5OS2 | 2 | 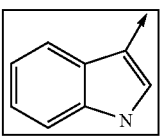 | 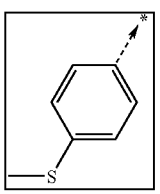 | 88% | 7.1 | 538.2 |
| 256 | C29H24N6O3S | 2 | 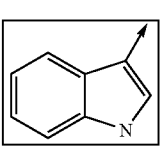 | 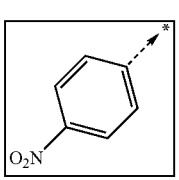 | 92% | 6.9 | 537.2 |
| 257 | C29H24N8OS | 2 | 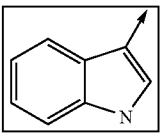 | 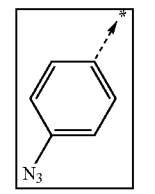 | 92% | 7.1 | 533.2 |
| 258 | C31H30N6OS | 2 | 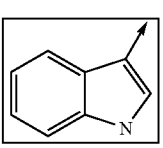 | 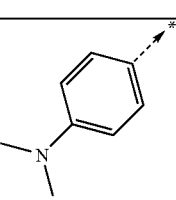 | 67% | 6.7 | 268.2 |
| 259 | C30H24N6OS | 2 | 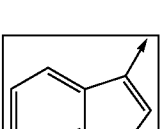 | 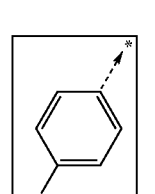 | 82% | 6.7 | 517.2 |
| 260 | C36H31N5O2S | 2 | 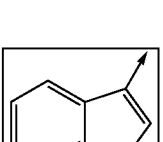 | 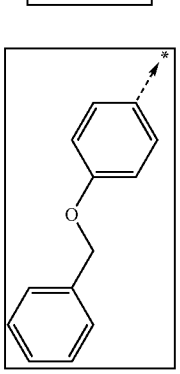 | 85% | 7.6 | 598.2 |

-continued
| | | | | | | | |
|---|---|---|---|---|---|---|---|
| 261 | C29H29N5OS | 2 | 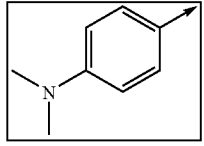 | 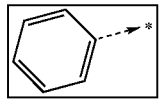 | 78% | 6.1 | 248.7 |
| 262 | C31H31N5O2S | 2 | 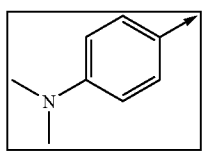 | 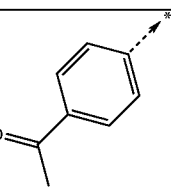 | 65% | 6.0 | 269.7 |
| 263 | C35H41N5OS | 2 | 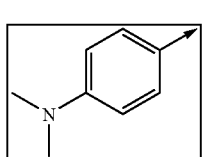 | 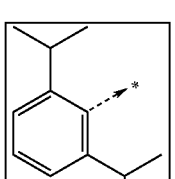 | 53% | 7.5 | 290.8 |
| 264 | C32H35N5OS | 2 | 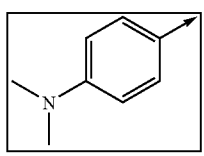 | 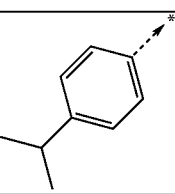 | 82% | 7.0 | 269.8 |
| 265 | C29H27F2N5OS | 2 | 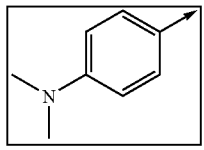 | 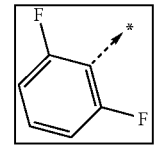 | 79% | 6.4 | 266.7 |
| 266 | C29H28FN5OS2 | 2 | 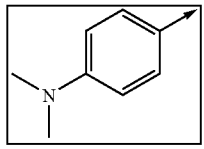 | 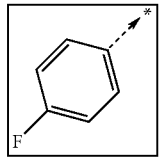 | 73% | 6.2 | 257.7 |
| 267 | C29H26Cl3N5OS | 2 | 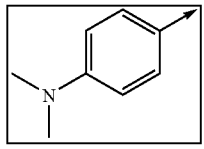 | 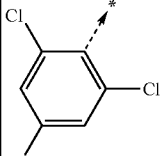 | 87% | 7.2 | 299.6 |
| 268 | C29H27Cl2N5OS | 2 | 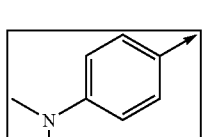 | 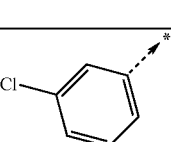 | 70% | 7.1 | 282.6 |

-continued
| | | | | | | | |
|---|---|---|---|---|---|---|---|
| 269 | C29H26Br3N5OS | 2 | 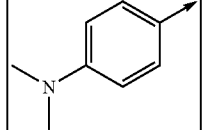 | 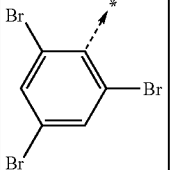 | 78% | 7.3 | 365.5 |
| 270 | C31H33N5OS2 | 2 | 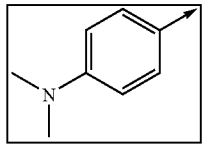 | 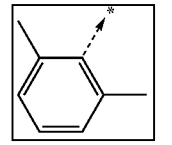 | 3% | 6.6 | 262.7 |
| 271 | C31H27F6N5OS | 2 | 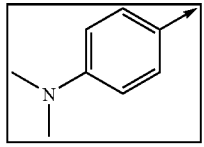 | 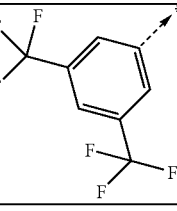 | 39% | 7.5 | 316.8 |
| 272 | C30H28F3N5OS | 2 | 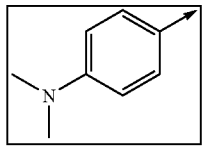 | 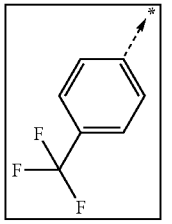 | 64% | 6.9 | 282.7 |
| 273 | C31H33N5O3S | 2 | 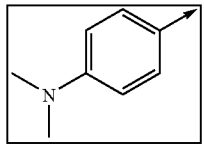 | 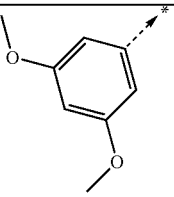 | 78% | 6.3 | 278.7 |
| 274 | C30H31N5O2S | 2 | 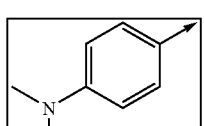 | 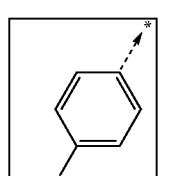 | 45% | 6.2 | 263.7 |
| 275 | C30H31N5OS2 | 2 | 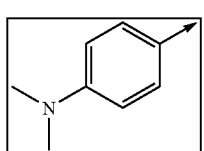 | 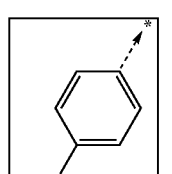 | 66% | 6.5 | 271.7 |

| | | | | | | | |
|---|---|---|---|---|---|---|---|
| 276 | C29H28N6O3S | 2 | 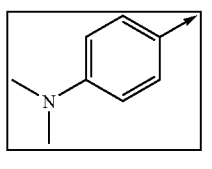 | 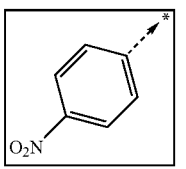 | 67% | 6.4 | 271.2 |
| 277 | C29H28N8OS | 2 | 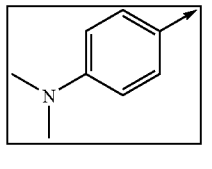 | 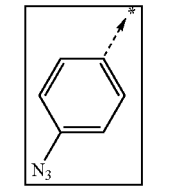 | 62% | 6.5 | 269.2 |
| 278 | C31H34N6OS | 2 | 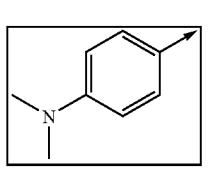 | 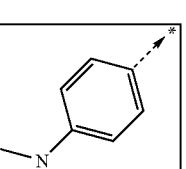 | 37% | 6.1 | 270.2 |
| 279 | C30H28N6OS | 2 | 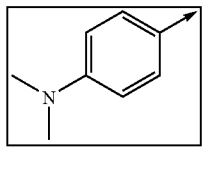 | 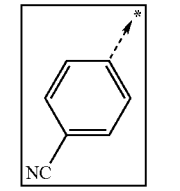 | 49% | 6.1 | 261.3 |
| 280 | C36H35N5O2S | 2 | 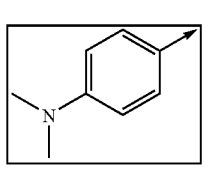 | 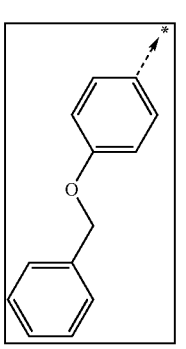 | 73% | 7.2 | 301.8 |
| 281 | C24H20N4OS2 | 1 | 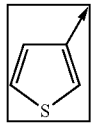 | 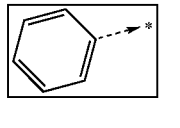 | 89% | 6.6 | 445.1 |
| 282 | C26H22N4O2S2 | 1 | 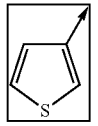 | 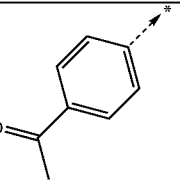 | 88% | 6.6 | 487.2 |

-continued

| | | | | | | | |
|---|---|---|---|---|---|---|---|
| 283 | C30H32N4OS2 | 1 | (thiophene) | (2,6-diisopropylphenyl) | 86% | 7.9 | 529.2 |
| 284 | C27H26N4OS2 | 1 | (thiophene) | (4-isopropylphenyl) | 96% | 7.5 | 487.2 |
| 285 | C24H18F2N4OS2 | 1 | (thiophene) | (2,6-difluorophenyl) | 93% | 6.7 | 481.1 |
| 286 | C24H19FN4OS2 | 1 | (thiophene) | (4-fluorophenyl) | 90% | 6.8 | 463.1 |
| 287 | C24H17Cl3N4OS2 | 1 | (thiophene) | (2,4,6-trichlorophenyl) | 97% | 7.5 | 547.0 |
| 288 | C24H18Cl2N4OS2 | 1 | (thiophene) | (3,5-dichlorophenyl) | 90% | 7.8 | 513.1 |
| 289 | C24H17Br3N4OS2 | 1 | (thiophene) | (2,4,6-tribromophenyl) | 92% | 7.7 | 678.9 |
| 290 | C26H24N4OS2 | 1 | (thiophene) | (2,6-dimethylphenyl) | 87% | 7.0 | 473.2 |

-continued
| 291 | C26H18F6N4OS2 | 1 | 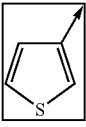 | 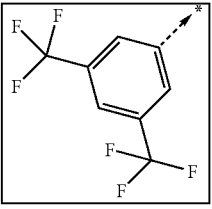 | 91% | 8.2 | 581.1 |
| 292 | C25H19F3N4OS2 | 1 | 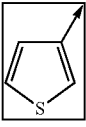 | 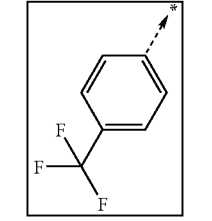 | 87% | 7.5 | 513.1 |
| 293 | C26H24N4O3S2 | 1 | 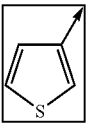 | 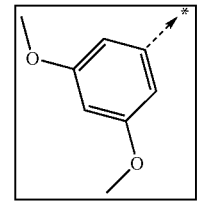 | 95% | 6.8 | 505.2 |
| 294 | C25H22N4O2S2 | 1 | 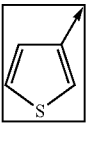 | 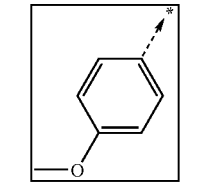 | 92% | 6.7 | 475.1 |
| 295 | C25H22N4OS3 | 1 | 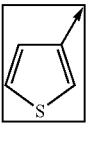 | 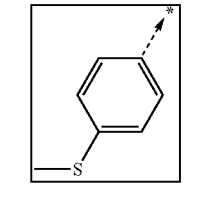 | 89% | 7.1 | 491.1 |
| 296 | C24H19N5O3S2 | 1 | 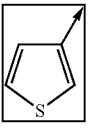 | 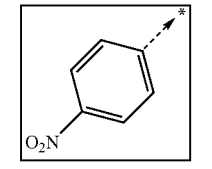 | 88% | 7.0 | 490.1 |
| 297 | C24H19N7OS2 | 1 | 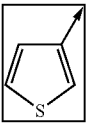 | 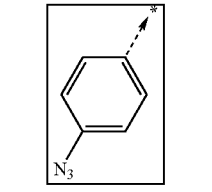 | 90% | 7.1 | 486.2 |

-continued

| | | | | | | | |
|---|---|---|---|---|---|---|---|
| 298 | C26H25N5OS2 | 1 | (3-thienyl) | (4-dimethylamino-phenyl)* | 86% | 6.6 | 244.7 |
| 299 | C25H19N5OS2 | 1 | (3-thienyl) | (4-cyanophenyl)* | 89% | 6.8 | 470.1 |
| 300 | C31H26N4O2S2 | 1 | (3-thienyl) | (4-benzyloxyphenyl)* | 88% | 7.7 | 551.2 |
| 301 | C27H24N4O2S | 1 | (4-methoxyphenyl) | (phenyl)* | 92% | 6.7 | 459.2 |
| 302 | C29H26N4O3S | 1 | (4-methoxyphenyl) | (4-acetylphenyl)* | 91% | 6.7 | 511.2 |
| 303 | C33H36N4O2S | 1 | (4-methoxyphenyl) | (2,6-diisopropylphenyl)* | 89% | 8.0 | 553.3 |
| 304 | C30H30N4O2S | 1 | (4-methoxyphenyl) | (4-isopropylphenyl)* | 95% | 7.6 | 511.2 |

-continued
| 305 | C27H22F2N4O2S | 1 | 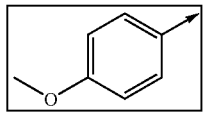 | 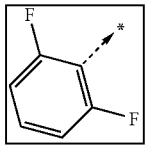 | 95% | 6.8 | 505.2 |
| 306 | C27H23FN4O2S | 1 | 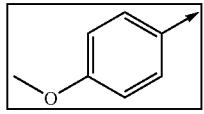 | 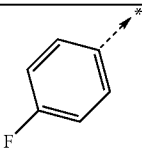 | 93% | 6.9 | 487.2 |
| 307 | C27H21Cl3N4O2S | 1 | 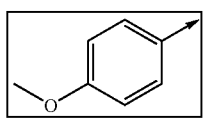 | 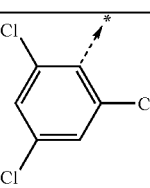 | 93% | 7.6 | 571.1 |
| 308 | C27H22Cl2N4O2S | 1 | 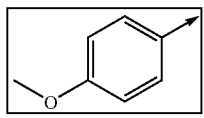 | 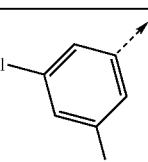 | 85% | 7.9 | 537.1 |
| 309 | C27H21Br3N4O2S | 1 | 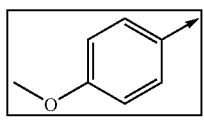 | 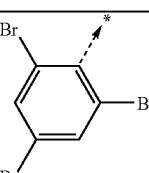 | 93% | 7.8 | 702.9 |
| 310 | C29H28N4O2S | 1 | 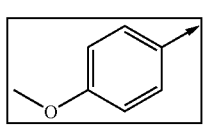 | 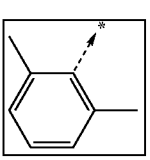 | 86% | 7.1 | 497.2 |
| 311 | C29H22F6N4O2S | 1 | 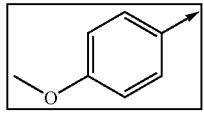 | 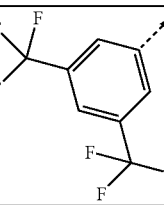 | 93% | 8.3 | 605.2 |
| 312 | C28H23F3N4O2S | 1 | 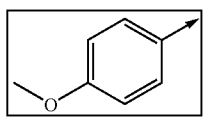 | 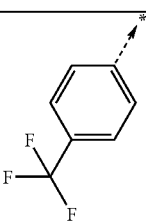 | 93% | 7.5 | 537.1 |

-continued

| # | Formula | n | R1 | R2 | % | t | M |
|---|---|---|---|---|---|---|---|
| 313 | C29H28N4O4S | 1 | 4-methoxyphenyl | 3,5-dimethoxyphenyl | 96% | 6.9 | 529.2 |
| 314 | C28H26N4O3S | 1 | 4-methoxyphenyl | 4-methoxyphenyl | 97% | 6.8 | 499.2 |
| 315 | C28H26N4O2S2 | 1 | 4-methoxyphenyl | 4-methylthiophenyl | 84% | 7.2 | 515.2 |
| 316 | C27H23N5O4S | 1 | 4-methoxyphenyl | 4-nitrophenyl | 88% | 7.1 | 514.2 |
| 317 | C27H23N7O2S | 1 | 4-methoxyphenyl | 4-azidophenyl | 94% | 7.2 | 510.2 |
| 318 | C29H29N5O2S | 1 | 4-methoxyphenyl | 4-dimethylaminophenyl | 89% | 6.7 | 256.7 |
| 319 | C28H23N5O2S | 1 | 4-methoxyphenyl | 4-cyanophenyl | 90% | 6.8 | 494.2 |

-continued
| 320 | C34H30N4O3S | 1 | 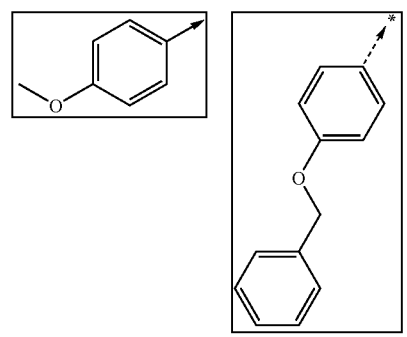 | | 89% | 7.7 | 575.2 |
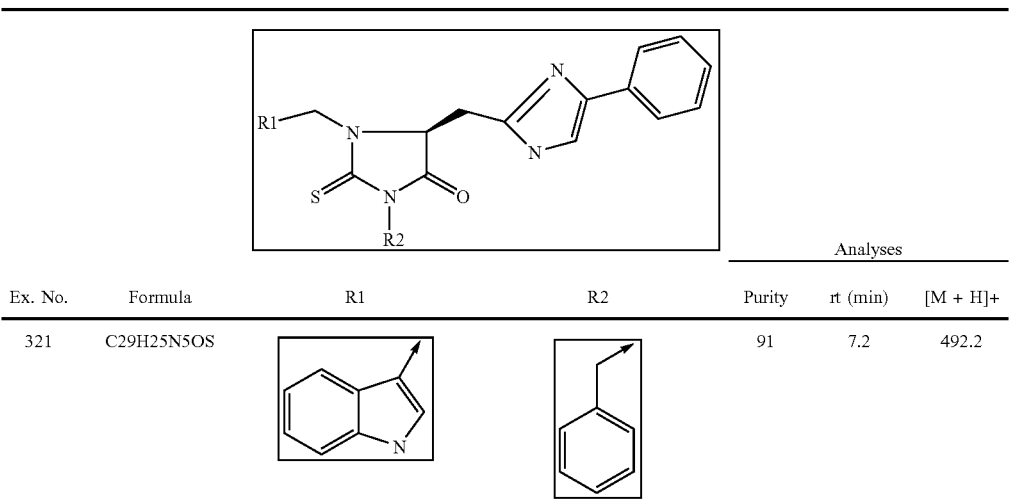
| | | | | Analyses | | |
|---|---|---|---|---|---|---|
| Ex. No. | Formula | R1 | R2 | Purity | rt (min) | [M + H]+ |
| 321 | C29H25N5OS | 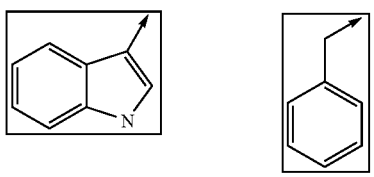 | 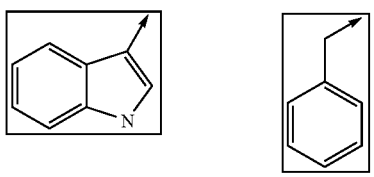 | 91 | 7.2 | 492.2 |
| 322 | C29H24ClN5OS | 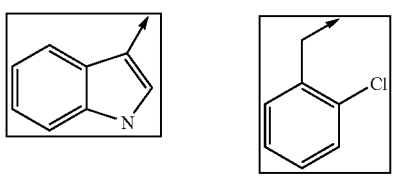 | 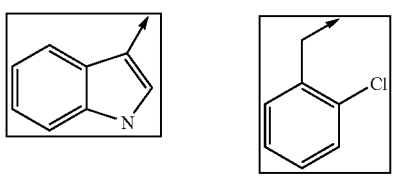 | 91 | 7.5 | 526.2 |
| 323 | C29H23Cl2N5OS | 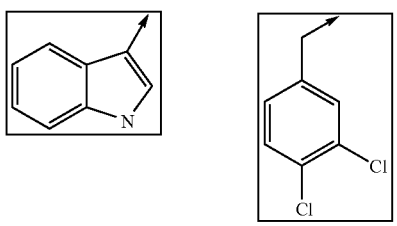 | 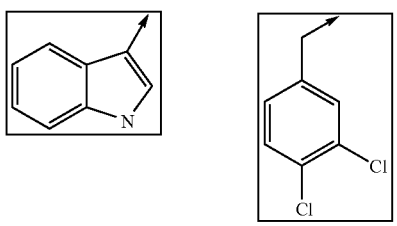 | 91 | 7.9 | 560.1 |
| 324 | C30H25N5O3S | 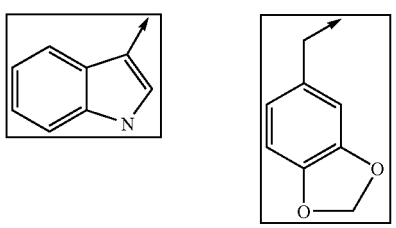 | 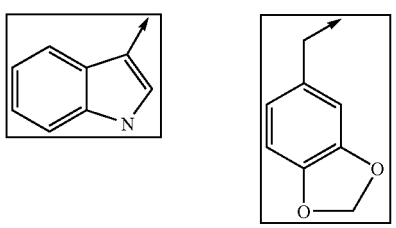 | 92 | 7.0 | 536.2 |

-continued
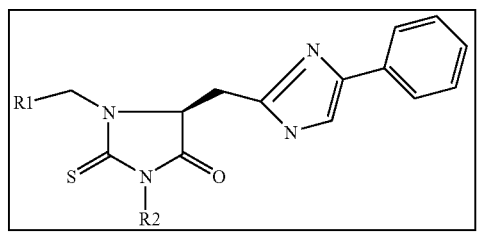
| Ex. No. | Formula | R1 | R2 | Purity | rt (min) | [M + H]+ |
|---|---|---|---|---|---|---|
| | | | | | Analyses | |
| 325 | C29H24FN5OS | indol-3-yl | 4-fluorobenzyl | 93 | 7.3 | 510.2 |
| 326 | C30H27N5OS | indol-3-yl | phenethyl | 92 | 7.4 | 506.2 |
| 327 | C30H26ClN5OS | indol-3-yl | 4-chlorophenethyl (90) | 91 | 7.8 | 540.2 |
| 328 | C32H31N5O3S | indol-3-yl | 3,4-dimethoxyphenethyl (91) | 90 | 7.1 | 566.2 |
| 329 | C31H29N5OS | indol-3-yl | 3-phenylpropyl | 91 | 7.6 | 520.2 |

-continued
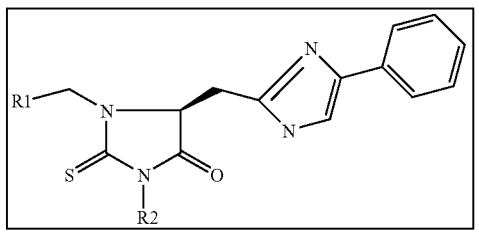
| Ex. No. | Formula | R1 | R2 | Purity | rt (min) | [M + H]+ |
|---|---|---|---|---|---|---|
| 330 | C27H23N5O2S | indol-3-yl | furan-2-ylmethyl | 92 | 6.8 | 482.2 |
| 331 | C27H27N5O2S | indol-3-yl | tetrahydrofuran-2-ylmethyl | 35 + 51 | 6.64 + 6.76 | 486.2 |
| 332 | C27H27N5OS | indol-3-yl | cyclopentyl | 90 | 7.2 | 470.2 |
| 333 | C28H29N5OS | indol-3-yl | cyclohexyl | 89 | 7.4 | 484.3 |
| 334 | C29H31N5OS | indol-3-yl | cyclohexylmethyl | 90 | 7.7 | 498.3 |
| 335 | C28H30N6O2S | indol-3-yl | 2-morpholinoethyl | 94 | 5.2 | 258.3 |
| 336 | C29H32N6O2S | indol-3-yl | 3-morpholinopropyl | 93 | 5.1 | 265.3 |

-continued
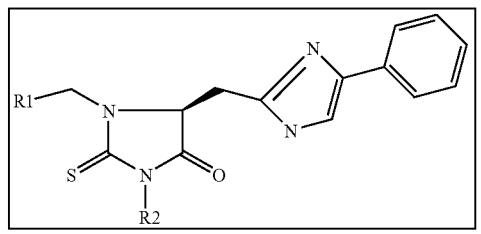
| Ex. No. | Formula | R1 | R2 | Purity | rt (min) | [M + H]+ |
|---|---|---|---|---|---|---|
| 353 | C24H26N4OS2 | 3-thienyl | cyclohexyl | 84 | 7.3 | 451.2 |
| 354 | C25H28N4OS2 | 3-thienyl | cyclohexylmethyl | 86 | 7.5 | 465.2 |
| 355 | C24H27N5O2S2 | 3-thienyl | 2-morpholinoethyl | 91 | 5.0 | 241.7 |
| 356 | C25H29N5O2S2 | 3-thienyl | 3-morpholinopropyl | 88 | 5.0 | 248.8 |
| 357 | C25H31N5OS2 | 3-thienyl | 3-(diethylamino)propyl | 61 | 5.1 | 241.8 |
| 358 | C21H22N4O2S2 | 3-thienyl | 2-methoxyethyl | 88 | 6.1 | 427.1 |
| 359 | C22H24N4O2S2 | 3-thienyl | 3-methoxypropyl | 87 | 6.3 | 441.1 |

-continued
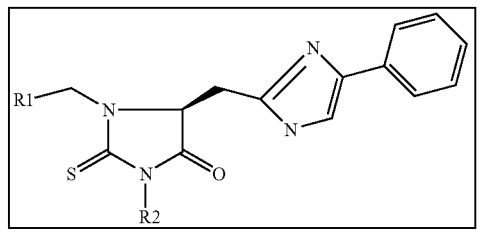
| Ex. No. | Formula | R1 | R2 | Purity | rt (min) | [M + H]+ |
|---|---|---|---|---|---|---|
| 360 | C22H24N4OS2 | 3-thienyl | isobutyl | 84 | 6.9 | 425.2 |
| 361 | C28H26N4O2S | 4-methoxyphenyl | benzyl | 89 | 7.1 | 483.2 |
| 362 | C28H25ClN4O2S | 4-methoxyphenyl | 2-chlorobenzyl | 89 | 7.5 | 517.2 |
| 363 | C28H24Cl2N4O2S | 4-methoxyphenyl | 3,4-dichlorobenzyl | 91 | 7.8 | 551.1 |
| 364 | C29H26N4O4S | 4-methoxyphenyl | 3,4-methylenedioxybenzyl | 89 | 7.0 | 527.2 |
| 365 | C28H25FN4O2S | 4-methoxyphenyl | 4-fluorobenzyl | 95 | 7.2 | 501.2 |

-continued
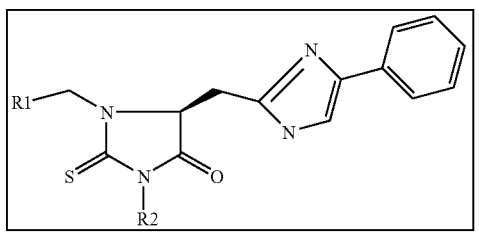
| Ex. No. | Formula | R1 | R2 | Purity | rt (min) | [M + H]+ |
|---|---|---|---|---|---|---|
| 366 | C29H28N4O2S | 4-methoxyphenyl | 2-phenylethyl | 90 | 7.3 | 497.2 |
| 367 | C29H27ClN4O2S | 4-methoxyphenyl | 2-(4-chlorophenyl)ethyl | 89 | 7.7 | 531.2 |
| 368 | C31H32N4O4S | 4-methoxyphenyl | 2-(3,4-dimethoxyphenyl)ethyl | 90 | 7.0 | 557.2 |
| 369 | C30H30N4O2S | 4-methoxyphenyl | 3-phenylpropyl | 91 | 7.5 | 511.2 |
| 370 | C26H24N4O3S | 4-methoxyphenyl | furan-2-ylmethyl | 92 | 6.7 | 473.2 |
| 371 | C26H28N4O3S | 4-methoxyphenyl | (tetrahydrofuran-2-yl)methyl | 39 + 45 | 6.44 + 6.56 | 477.2 |

-continued
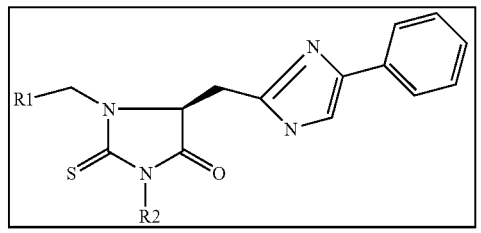
| | | | | | Analyses | |
|---|---|---|---|---|---|---|
| Ex. No. | Formula | R1 | R2 | Purity | rt (min) | [M + H]+ |
| 372 | C26H28N4O2S | 4-methoxyphenyl | cyclopentyl | 89 | 7.1 | 461.2 |
| 373 | C27H30N4O2S | 4-methoxyphenyl | cyclohexyl | 90 | 7.3 | 475.2 |
| 374 | C28H32N4O2S | 4-methoxyphenyl | cyclohexylmethyl | 90 | 7.6 | 489.3 |
| 375 | C27H31N5O3S | 4-methoxyphenyl | 2-morpholinoethyl | 93 | 5.1 | 253.7 |
| 376 | C28H33N5O3S | 4-methoxyphenyl | 3-morpholinopropyl | 90 | 5.1 | 260.8 |
| 377 | C28H35N5O2S | 4-methoxyphenyl | 3-(diethylamino)propyl | 73 | 5.3 | 253.8 |
| 378 | C24H26N4O3S | 4-methoxyphenyl | oxiranylmethyl | 91 | 6.2 | 451.2 |

-continued

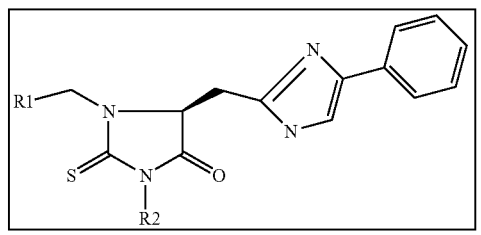

| | | | | Analyses | | |
|---|---|---|---|---|---|---|
| Ex. No. | Formula | R1 | R2 | Purity | rt (min) | [M + H]+ |
| 379 | C25H28N4O3S | 4-methoxyphenyl | tetrahydrofuranylpropyl | 91 | 6.4 | 465.2 |
| 380 | C25H28N4O2S | 4-methoxyphenyl | isobutyl | 90 | 7.0 | 449.2 |
| 381 | C29H29N5OS | 4-dimethylaminophenyl | benzyl | 85 | 6.4 | 248.7 |
| 382 | C29H28ClN5OS | 4-dimethylaminophenyl | 2-chlorobenzyl | 85 | 6.9 | 265.7 |
| 383 | C29H27Cl2N5OS | 4-dimethylaminophenyl | 3,4-dichlorobenzyl | 84 | 7.3 | 282.6 |
| 384 | C30H29N5O3S | 4-dimethylaminophenyl | benzo[1,3]dioxol-5-ylmethyl | 85 | 6.3 | 270.7 |
| 385 | C29H28FN5OS | 4-dimethylaminophenyl | 4-fluorobenzyl | 88 | 6.5 | 257.7 |

-continued
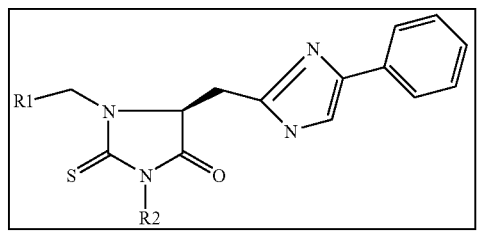
| Ex. No. | Formula | R1 | R2 | Purity | rt (min) | [M + H]+ |
|---|---|---|---|---|---|---|
| 386 | C30H31N5OS | 4-(dimethylamino)phenyl | 2-phenylethyl | 84 | 6.7 | 255.6 |
| 387 | C30H30ClN5OS | 4-(dimethylamino)phenyl | 2-(4-chlorophenyl)ethyl | 87 | 7.2 | 272.7 |
| 388 | C32H35N5O3S | 4-(dimethylamino)phenyl | 2-(3,4-dimethoxyphenyl)ethyl | 82 | 6.4 | 285.8 |
| 389 | C31H33N5OS | 4-(dimethylamino)phenyl | 3-phenylpropyl | 81 | 6.9 | 262.7 |
| 390 | C27H27N5O2S | 4-(dimethylamino)phenyl | furan-2-ylmethyl | 89 | 5.9 | 243.7 |

-continued

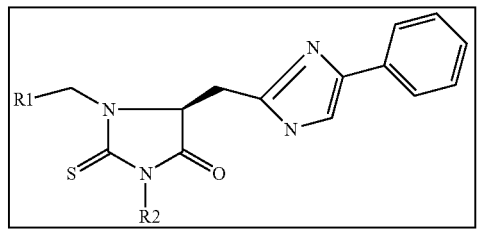

| Ex. No. | Formula | R1 | R2 | Purity | rt (min) | [M + H]+ |
|---|---|---|---|---|---|---|
| 391 | C27H31N5O2S | 4-(dimethylamino)phenyl | tetrahydrofuran-2-ylmethyl | 43 + 43 | 5.68 + 5.86 | 245.7 |
| 392 | C27H31N5OS | 4-(dimethylamino)phenyl | cyclopentyl | 83 | 6.4 | 237.7 |
| 393 | C28H33N5OS | 4-(dimethylamino)phenyl | cyclohexyl | 83 | 6.7 | 244.7 |
| 394 | C29H35N5OS | 4-(dimethylamino)phenyl | cyclohexylmethyl | 85 | 7.0 | 251.7 |
| 395 | C28H34N6O2S | 4-(dimethylamino)phenyl | 2-morpholinoethyl | 87 | 4.6 | 259.8 |
| 396 | C29H36N6O2S | 4-(dimethylamino)phenyl | 3-morpholinopropyl | 84 | 4.6 | 267.2 |
| 397 | C25H29N5O2S | 4-(dimethylamino)phenyl | 2-methoxyethyl | 74 | 5.4 | 232.7 |

-continued
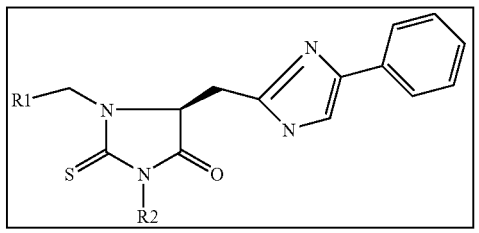
| Ex. No. | Formula | R1 | R2 | Purity | rt (min) | [M + H]+ |
|---|---|---|---|---|---|---|
| 398 | C26H31N5O2S | 4-dimethylamino-phenyl | O-propyl ether | 83 | 5.6 | 239.7 |
| 399 | C26H31N5OS | 4-dimethylamino-phenyl | isobutyl | 87 | 6.3 | 231.8 |
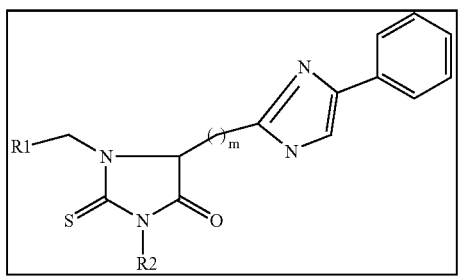
| Ex. No. | Formula | m | R1 | R2 | Purity | rt (min) | [M + H]+ |
|---|---|---|---|---|---|---|---|
| 400 | C30H34N6O3S | 2 | indol-3-yl | CH2CH2-NHBoc | 83% | 7.8 | 559.2 |
| 401 | C31H36N6O3S | 2 | indol-3-yl | (CH2)3-NHBoc | 82% | 7.9 | 573.2 |
| 402 | C32H38N6O3S | 2 | indol-3-yl | (CH2)4-NHBoc | 82% | 8.0 | 587.3 |

-continued
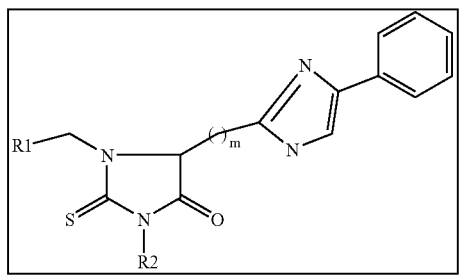
| Ex. No. | Formula | m | R1 | R2 | Purity | rt (min) | [M + H]+ |
|---|---|---|---|---|---|---|---|
| 403 | C33H40N6O3S | 2 | indole | NHBoc-(CH2)5- | 81% | 8.3 | 601.3 |
| 404 | C34H42N6O3S | 2 | indole | NHBoc-(CH2)6- | 80% | 8.5 | 615.3 |
| 405 | C26H31N5O3S2 | 2 | thiophene | NHBoc-(CH2)2- | 81% | 7.6 | 526.2 |
| 406 | C27H33N5O3S2 | 2 | thiophene | NHBoc-(CH2)3- | 83% | 7.8 | 540.2 |
| 407 | C28H35N5O3S2 | 2 | thiophene | NHBoc-(CH2)4- | 88% | 7.9 | 554.2 |
| 408 | C29H37N5O3S2 | 2 | thiophene | NHBoc-(CH2)5- | 86% | 8.2 | 568.2 |
| 409 | C30H39N5O3S2 | 2 | thiophene | NHBoc-(CH2)6- | 86% | 8.4 | 582.3 |
| 410 | C29H35N5O4S | 2 | methoxyphenyl | NHBoc-(CH2)2- | 87% | 7.7 | 550.3 |

-continued
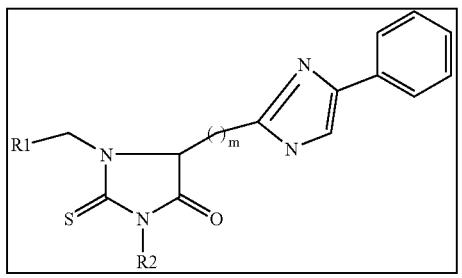
| Ex. No. | Formula | m | R1 | R2 | Purity | rt (min) | [M + H]+ |
|---|---|---|---|---|---|---|---|
| 411 | C30H37N5O4S | 2 | 4-methoxyphenyl | -(CH2)3-NHBoc | 87% | 7.9 | 564.3 |
| 412 | C31H39N5O4S | 2 | 4-methoxyphenyl | -(CH2)4-NHBoc | 92% | 8.0 | 578.3 |
| 413 | C32H41N5O4S | 2 | 4-methoxyphenyl | -(CH2)5-NHBoc | 89% | 8.3 | 592.3 |
| 414 | C33H43N5O4S | 2 | 4-methoxyphenyl | -(CH2)6-NHBoc | 88% | 8.5 | 606.3 |
| 415 | C30H38N6O3S | 2 | 4-(dimethylamino)phenyl | -(CH2)2-NHBoc | 83% | 7.0 | 563.3 |
| 416 | C31H40N6O3S | 2 | 4-(dimethylamino)phenyl | -(CH2)3-NHBoc | 85% | 7.2 | 577.3 |
| 417 | C32H42N6O3S | 2 | 4-(dimethylamino)phenyl | -(CH2)4-NHBoc | 88% | 7.4 | 591.3 |
| 418 | C33H44N6O3S | 2 | 4-(dimethylamino)phenyl | -(CH2)5-NHBoc | 88% | 7.7 | 303.3 |

-continued
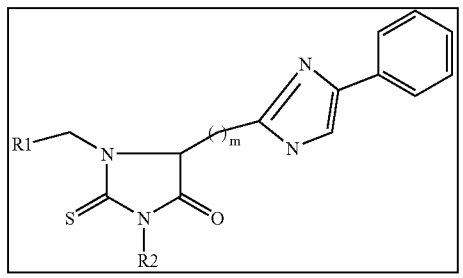
| Ex. No. | Formula | m | R1 | R2 | Purity | rt (min) | [M + H]+ |
|---|---|---|---|---|---|---|---|
| 419 | C34H46N6O3S | 2 | 4-(dimethylamino)phenyl | *-(CH2)6-NHBoc | 88% | 7.9 | 310.4 |
| 420 | C29H32N6O3S | 2 | indol-3-yl | *-(CH2)2-NHBoc | 78% | 7.9 | 545.2 |
| 421 | C30H34N6O3S | 2 | indol-3-yl | *-(CH2)3-NHBoc | 81% | 8.0 | 559.2 |
| 422 | C31H36N6O3S | 2 | indol-3-yl | *-(CH2)4-NHBoc | 84% | 8.1 | 573.3 |
| 423 | C32H38N6O3S | 2 | indol-3-yl | *-(CH2)5-NHBoc | 82% | 8.3 | 587.3 |
| 424 | C33H40N6O3S | 2 | indol-3-yl | *-(CH2)6-NHBoc | 86% | 8.5 | 601.3 |
| 425 | C25H29N5O3S2 | 2 | thien-3-yl | *-(CH2)2-NHBoc | 80% | 7.7 | 512.2 |
| 426 | C26H31N5O3S2 | 2 | thien-3-yl | *-(CH2)3-NHBoc | 82% | 7.8 | 526.2 |

-continued
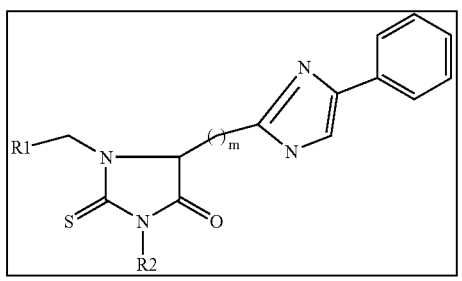
| Ex. No. | Formula | m | R1 | R2 | Purity | rt (min) | [M + H]+ |
|---|---|---|---|---|---|---|---|
| 427 | C27H33N5O3S2 | 2 | 3-thienyl | *-(CH2)2-NH-C(O)-O-C(CH3)3 | 87% | 7.9 | 540.2 |
| 428 | C28H35N5O3S2 | 2 | 3-thienyl | *-(CH2)3-NH-C(O)-O-C(CH3)3 | 86% | 8.2 | 554.2 |
| 429 | C29H37N5O3S2 | 2 | 3-thienyl | *-(CH2)4-NH-C(O)-O-C(CH3)3 | 84% | 8.4 | 568.2 |
| 430 | C28H33N5O4S | 2 | 4-methoxyphenyl | *-(CH2)2-NH-C(O)-O-C(CH3)3 | 86% | 7.8 | 536.3 |
| 431 | C29H35N5O4S | 2 | 4-methoxyphenyl | *-(CH2)3-NH-C(O)-O-C(CH3)3 | 85% | 7.9 | 550.3 |
| 432 | C30H37N5O4S | 2 | 4-methoxyphenyl | *-(CH2)4-NH-C(O)-O-C(CH3)3 | 92% | 8.0 | 564.3 |
| 433 | C31H39N5O4S | 2 | 4-methoxyphenyl | *-(CH2)5-NH-C(O)-O-C(CH3)3 | 90% | 8.2 | 578.3 |
| 434 | C32H41N5O4S | 2 | 4-methoxyphenyl | *-(CH2)6-NH-C(O)-O-C(CH3)3 | 90% | 8.5 | 592.3 |

-continued
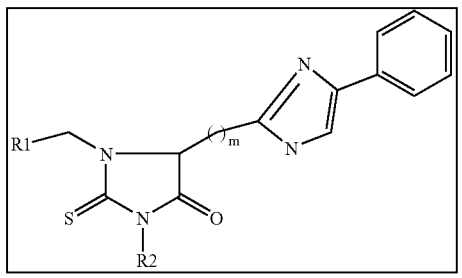
| Ex. No. | Formula | m | R1 | R2 | Purity | rt (min) | [M + H]+ |
|---|---|---|---|---|---|---|---|
| 435 | C29H36N6O3S | 2 | 4-(dimethylamino)phenyl | NHBoc-ethyl | 80% | 6.9 | 549.3 |
| 436 | C30H38N6O3S | 2 | 4-(dimethylamino)phenyl | NHBoc-propyl | 78% | 7.1 | 563.3 |
| 437 | C31H40N6O3S | 2 | 4-(dimethylamino)phenyl | NHBoc-butyl | 84% | 7.3 | 577.3 |
| 438 | C32H42N6O3S | 2 | 4-(dimethylamino)phenyl | NHBoc-pentyl | 83% | 7.5 | 296.3 |
| 439 | C33H44N6O3S | 2 | 4-(dimethylamino)phenyl | NHBoc-hexyl | 85% | 7.8 | 303.3 |
| 440 | C25H26N6OS | 1 | indol-3-yl | cyanomethyl | 76% | 5.4 | 459.2 |
| 441 | C26H28N6OS | 1 | indol-3-yl | cyanoethyl | 61% | 5.4 | 473.3 |
| 442 | C27H30N6OS | 1 | indol-3-yl | cyanopropyl | 75% | 5.6 | 244.2 |

-continued
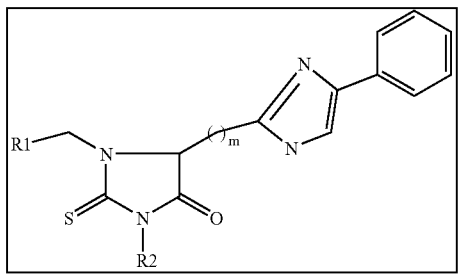
| Ex. No. | Formula | m | R1 | R2 | Purity | rt (min) | [M + H]+ |
|---|---|---|---|---|---|---|---|
| 443 | C28H32N6OS | 1 | indol-3-yl | -CH2CH2CH2CH2N | 32% | 5.7 | 251.1 |
| 444 | C29H34N6OS | 1 | indol-3-yl | *-CH2CH2CH2CH2CH2N | 59% | 5.9 | 258.3 |
| 445 | C21H23N5OS2 | 1 | thien-3-yl | *-CH2CH2N | 78% | 5.1 | 426.2 |
| 446 | C22H25N5OS2 | 1 | thien-3-yl | -CH2CH2CH2N | 79% | 5.2 | 440.2 |
| 447 | C23H27N5OS2 | 1 | thien-3-yl | *-CH2CH2CH2CH2N | 84% | 5.4 | 227.6 |
| 448 | C24H29N5OS2 | 1 | thien-3-yl | -CH2CH2CH2CH2CH2N | 84% | 5.5 | 234.7 |
| 449 | C25H31N5OS2 | 1 | thien-3-yl | *-CH2CH2CH2CH2CH2CH2N | 83% | 5.7 | 241.7 |
| 450 | C24H27N5O2S | 1 | 4-methoxyphenyl | *-CH2CH2N | 88% | 5.3 | 450.2 |
| 451 | C25H29N5O2S | 1 | 4-methoxyphenyl | -CH2CH2CH2N | 96% | 5.4 | 464.2 |

-continued
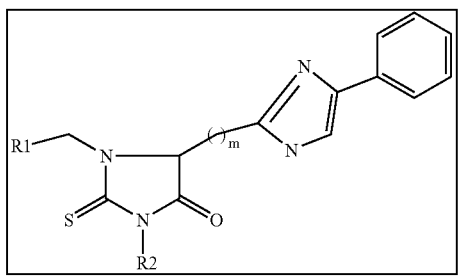
| Ex. No. | Formula | m | R1 | R2 | Purity | rt (min) | [M + H]+ |
|---|---|---|---|---|---|---|---|
| 452 | C26H31N5O2S | 1 | 4-methoxyphenyl-CH2 | *-CH2CH2CH2-N | 90% | 5.6 | 239.7 |
| 453 | C27H33N5O2S | 1 | 4-methoxyphenyl-CH2 | -CH2CH2CH2CH2-N | 90% | 5.7 | 246.7 |
| 454 | C28H35N5O2S | 1 | 4-methoxyphenyl-CH2 | *-(CH2)5-N | 91% | 5.9 | 253.7 |
| 455 | C25H30N6OS | 1 | 4-(dimethylamino)phenyl-CH2 | *-CH2-N | 84% | 4.8 | 232.2 |
| 456 | C26H32N6OS | 1 | 4-(dimethylamino)phenyl-CH2 | -CH2CH2CH2-N | 89% | 4.9 | 238.8 |
| 457 | C27H34N6OS | 1 | 4-(dimethylamino)phenyl-CH2 | *-CH2CH2CH2CH2-N | 86% | 5.0 | 246.1 |
| 458 | C28H36N6OS | 1 | 4-(dimethylamino)phenyl-CH2 | -(CH2)5-N | 93% | 5.2 | 252.9 |
| 459 | C29H38N6OS | 1 | 4-(dimethylamino)phenyl-CH2 | *-(CH2)6-N | 93% | 5.4 | 260.1 |

-continued
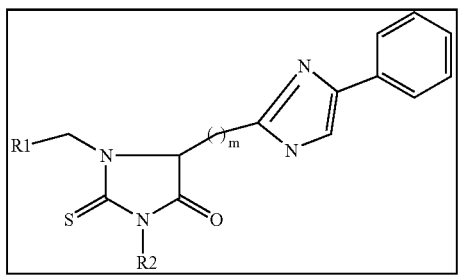
| Ex. No. | Formula | m | R1 | R2 | Purity | rt (min) | [M + H]+ |
|---|---|---|---|---|---|---|---|
| 460 | C24H24N6OS | 1 | indol-3-yl | *-CH2-N | 68% | 5.6 | 445.2 |
| 461 | C25H26N6OS | 1 | indol-3-yl | *-(CH2)2-N | 55% | 5.5 | 459.2 |
| 462 | C26H28N6OS | 1 | indol-3-yl | *-(CH2)3-N | 55% | 5.6 | 473.3 |
| 463 | C27H30N6OS | 1 | indol-3-yl | *-(CH2)4-N | 48% | 5.7 | 487.3 |
| 464 | C28N32N6OS | 1 | indol-3-yl | *-(CH2)5-N | 44% | 5.9 | 501.2 |
| 465 | C20H21N5OS2 | 1 | thien-3-yl | *-CH2-N | 84% | 5.3 | 412.1 |
| 466 | C21H23N5OS2 | 1 | thien-3-yl | *-(CH2)2-N | 86% | 5.2 | 426.2 |
| 467 | C22H25N5OS2 | 1 | thien-3-yl | *-(CH2)3-N | 90% | 5.3 | 440.2 |

-continued
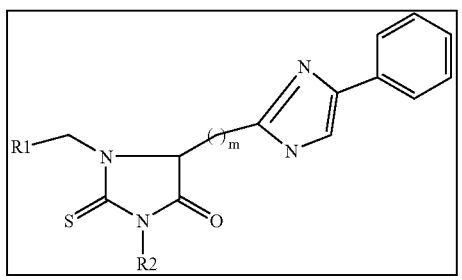
| Ex. No. | Formula | m | R1 | R2 | Purity | rt (min) | [M + H]+ |
|---|---|---|---|---|---|---|---|
| 468 | C23H27N5OS2 | 1 | 3-thienyl | ~~~N | 79% | 5.5 | 227.7 |
| 469 | C24H29N5OS2 | 1 | 3-thienyl | *~~~~N | 91% | 5.7 | 234.8 |
| 470 | C23H25N5O2S | 1 | 4-methoxyphenyl | *~N | 92% | 5.5 | 436.2 |
| 471 | C24H27N5O2S | 1 | 4-methoxyphenyl | ~~N | 88% | 5.4 | 450.2 |
| 472 | C25H29N5O2S | 1 | 4-methoxyphenyl | *~~N | 93% | 5.5 | 464.3 |
| 473 | C26H31N5O2S | 1 | 4-methoxyphenyl | ~~~N | 92% | 5.6 | 478.3 |
| 474 | C27H33N5O2S | 1 | 4-methoxyphenyl | *~~~N | 95% | 5.8 | 246.7 |
| 475 | C24H28N6OS | 1 | 4-(dimethylamino)phenyl | *~N | 87% | 4.9 | 224.7 |
| 476 | C25H30N6OS | 1 | 4-(dimethylamino)phenyl | ~~N | 80% | 4.8 | 231.9 |

-continued
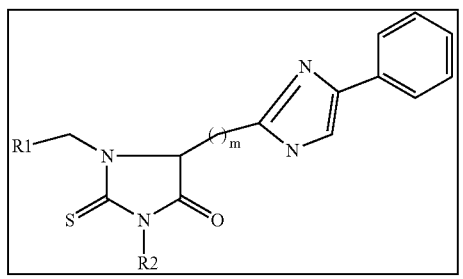
| Ex. No. | Formula | m | R1 | R2 | Purity | rt (min) | [M + H]+ |
|---|---|---|---|---|---|---|---|
| 477 | C26H32N6OS | 1 | N,N-dimethylamino-phenyl | pyrrolidinyl-propyl | 84% | 4.9 | 238.9 |
| 478 | C27H34N6OS | 1 | N,N-dimethylamino-phenyl | piperidinyl-butyl | 90% | 5.0 | 245.7 |
| 479 | C28H36N6OS | 1 | N,N-dimethylamino-phenyl | piperidinyl-pentyl | 91% | 5.2 | 505.3 |
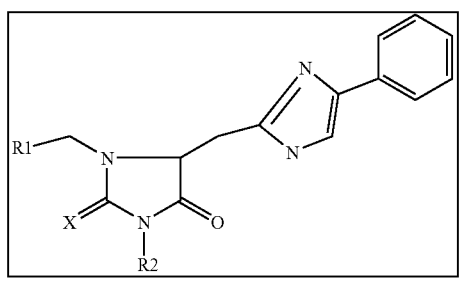
| Ex. No. | Formula | X | R1 | R2 | Purity | rt (min) | [M + H]+ |
|---|---|---|---|---|---|---|---|
| 480 | C30H34N6O3S | S | (S)-indol-3-ylmethyl | Boc-aminoethyl | 86% | 5.4 | 559.2 |
| 481 | C31H36N6O3S | S | (S)-indol-3-ylmethyl | Boc-aminobutyl | 88% | 5.5 | 573.2 |

-continued
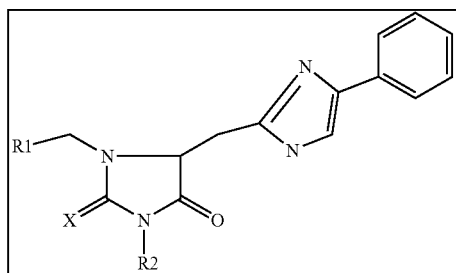
| Ex. No. | Formula | X | R1 | R2 | Purity | rt (min) | [M + H]+ |
|---|---|---|---|---|---|---|---|
| 482 | C32H38N6O3S | S | indol-3-ylmethyl (S) | *-(CH2)4-NH-C(O)O-tBu | 88% | 5.5 | 587.3 |
| 483 | C33H40N6O3S | S | indol-3-ylmethyl (S) | *-(CH2)5-NH-C(O)O-tBu | 89% | 5.7 | 601.3 |
| 484 | C34H42N6O3S | S | indol-3-ylmethyl (S) | *-(CH2)6-NH-C(O)O-tBu | 91% | 5.8 | 615.3 |
| 485 | C35H36N5O3S | S | indol-3-ylmethyl (S) | *-C6H4-CH2-NH-C(O)O-tBu | 91% | 5.6 | 621.3 |
| 486 | C31H34N6O4S | S | 1-acetyl-indol-3-ylmethyl (S) | *-(CH2)2-NH-C(O)O-tBu | 66% | 5.6 | 587.2 |
| 487 | C32H36N6O4S | S | 1-acetyl-indol-3-ylmethyl (S) | *-(CH2)3-NH-C(O)O-tBu | 73% | 5.6 | 601.2 |

-continued
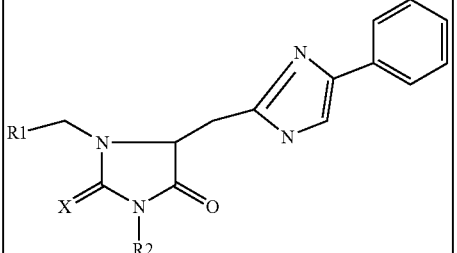
| Ex. No. | Formula | X | R1 | R2 | Purity | rt (min) | [M + H]+ |
|---|---|---|---|---|---|---|---|
| 488 | C33H38N6O4S | S | 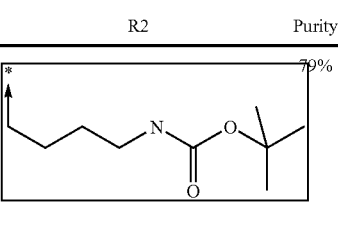 | 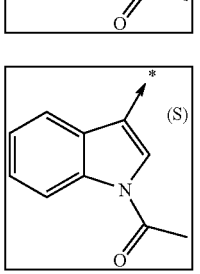 | 79% | 5.7 | 615.3 |
| 489 | C34H40N6O4S | S | 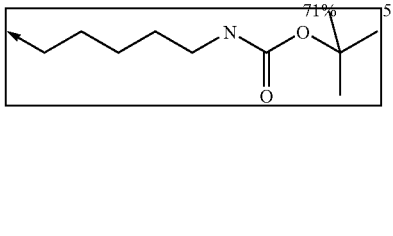 | 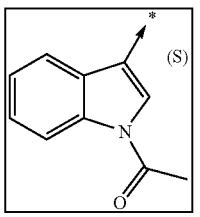 | 71% | 5.9 | 629.3 |
| 490 | C35H42N6O4S | S | 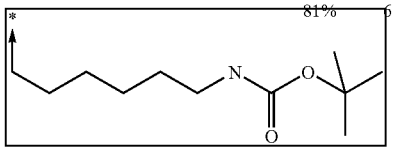 | 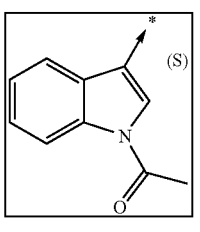 | 81% | 6.0 | 643.3 |
| 491 | C36H36N6O4S | S |  | 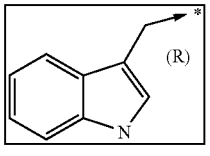 | 60% | 5.8 | 649.3 |
| 492 | C30H34N6O3S | S | 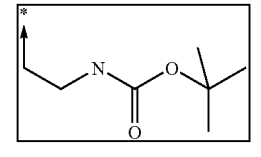 | 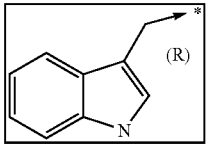 | 83% | 5.4 | 559.2 |
| 493 | C31H36N6O3S | S | 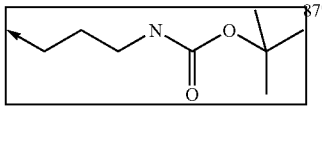 | | 87% | 5.5 | 573.2 |

-continued

| Ex. No. | Formula | X | R1 | R2 | Purity | rt (min) | [M + H]+ |
|---|---|---|---|---|---|---|---|
| 494 | C32H36N6O3S | S | indol-3-ylmethyl (R) | -(CH2)4-NH-C(O)O-tBu | 87% | 5.5 | 587.3 |
| 495 | C33H40N6O3S | S | indol-3-ylmethyl (R) | -(CH2)5-NH-C(O)O-tBu | 87% | 5.7 | 601.3 |
| 496 | C34H42N6O3S | S | indol-3-ylmethyl (R) | -(CH2)6-NH-C(O)O-tBu | 88% | 5.8 | 615.3 |
| 497 | C35H36N6O3S | S | indol-3-ylmethyl (R) | 4-(NH-C(O)O-tBu)-benzyl | 89% | 5.6 | 621.3 |
| 498 | C31H34N6O4S | S | 1-acetyl-indol-3-ylmethyl (R) | -(CH2)2-NH-C(O)O-tBu | 71% | 5.6 | 587.2 |
| 499 | C32H36N6O4S | S | 1-acetyl-indol-3-ylmethyl (R) | -(CH2)3-NH-C(O)O-tBu | 45% | 5.6 | 601.2 |

-continued
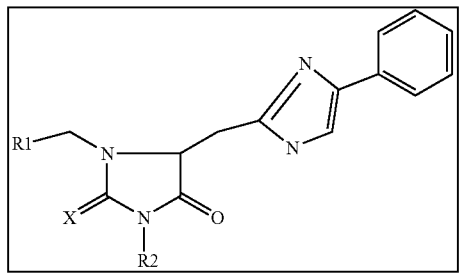
| Ex. No. | Formula | X | R1 | R2 | Purity | rt (min) | [M + H]+ |
|---|---|---|---|---|---|---|---|
| 500 | C33H38N6O4S | S | 1-acetyl-indol-3-yl (R) | *-(CH2)4-NH-C(O)-O-tBu | 75% | 5.7 | 615.3 |
| 501 | C34H40N6O4S | S | 1-acetyl-indol-3-yl (R) | *-(CH2)5-NH-C(O)-O-tBu | 68% | 5.9 | 629.3 |
| 502 | C35H42N6O4S | S | 1-acetyl-indol-3-yl (R) | *-(CH2)6-NH-C(O)-O-tBu | 76% | 6.0 | 643.3 |
| 503 | C36H36N6O4S | S | 1-acetyl-indol-3-yl (R) | *-C6H4-CH2-NH-C(O)-O-tBu | 55% | 5.8 | 649.3 |
| 504 | C30H34N6O4 | O | indol-3-yl (S) | *-(CH2)2-NH-C(O)-O-tBu | 88% | 4.9 | 543.3 |
| 505 | C31H36N6O4 | O | indol-3-yl (S) | *-(CH2)3-NH-C(O)-O-tBu | 88% | 5.0 | 557.3 |

-continued
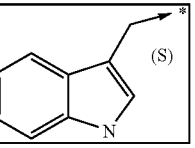
| Ex. No. | Formula | X | R1 | R2 | Purity | rt (min) | [M + H]+ |
|---|---|---|---|---|---|---|---|
| 506 | C32H38N6O4 | O | 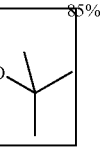 | 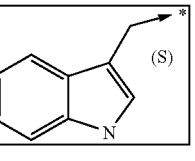 | 85% | 5.0 | 571.3 |
| 507 | C33H40N6O4 | O | 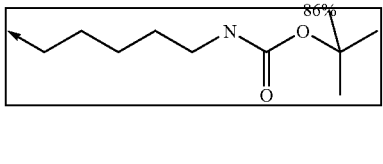 | 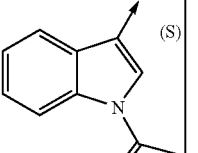 | 86% | 5.2 | 585.3 |
| 508 | C31H34N6O5 | O | 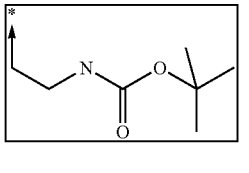 | 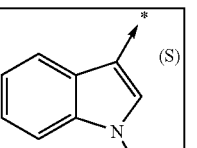 | 79% | 4.9 | 571.2 |
| 509 | C32H36N6O5 | O | 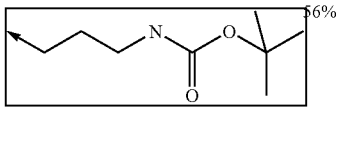 | 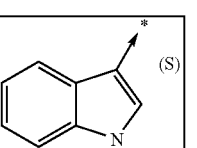 | 66% | 5.0 | 585.3 |
| 510 | C33H38N6O5 | O | 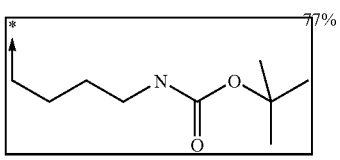 | 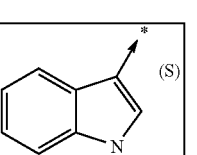 | 77% | 5.1 | 599.3 |
| 511 | C34H40N6O5 | O | 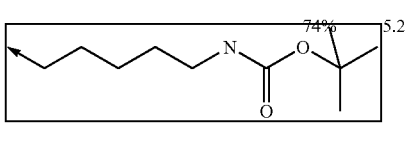 | | 74% | 5.2 | 613.3 |

-continued
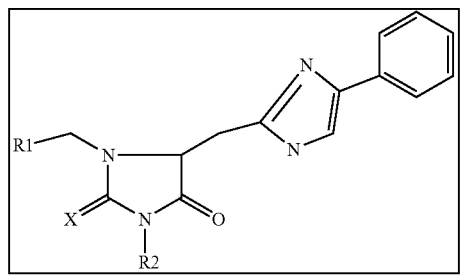
| Ex. No. | Formula | X | R1 | R2 | Purity | rt (min) | [M + H]+ |
|---|---|---|---|---|---|---|---|
| 512 | C30H34N6O4 | O | indol-3-ylmethyl (R) | *CH2CH2-NH-C(O)O-tBu | 90% | 4.9 | 543.3 |
| 513 | C31H36N6O4 | O | indol-3-ylmethyl (R) | *(CH2)3-NH-C(O)O-tBu | 90% | 5.0 | 557.3 |
| 514 | C32H38N6O4 | O | indol-3-ylmethyl (R) | *(CH2)4-NH-C(O)O-tBu | 89% | 5.0 | 571.3 |
| 515 | C33H40N6O4 | O | indol-3-ylmethyl (R) | *(CH2)5-NH-C(O)O-tBu | 91% | 5.2 | 585.3 |
| 516 | C31H34N6O5 | O | 1-acetyl-indol-3-ylmethyl (R) | *CH2CH2-NH-C(O)O-tBu | 76% | 4.9 | 571.2 |
| 517 | C32H36N6O5 | O | 1-acetyl-indol-3-ylmethyl (R) | *(CH2)3-NH-C(O)O-tBu | 81% | 5.0 | 585.3 |

-continued
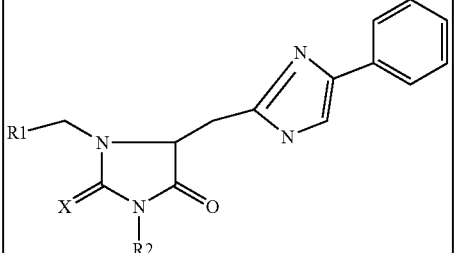
| Ex. No. | Formula | X | R1 | R2 | Purity | rt (min) | [M + H]+ |
|---|---|---|---|---|---|---|---|
| 518 | C33H38N6O5 | O | 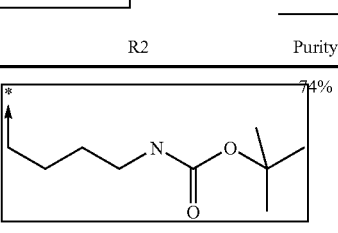 | 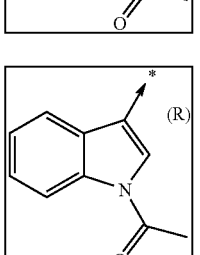 | 74% | 5.1 | 599.3 |
| 519 | C34H40N6O5 | O | 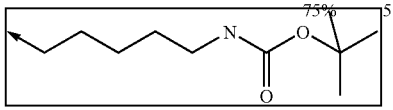 | 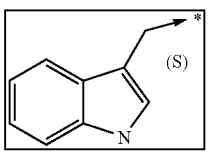 | 75% | 5.2 | 613.3 |
| 520 | C25H26N6OS | S | 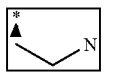 | 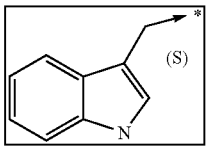 | 93% | 6.8 | 459.2 |
| 521 | C26H28N6OS | S | 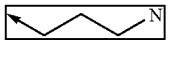 | 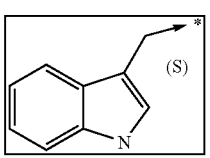 | 93% | 6.6 | 473.2 |
| 522 | C27H30N6OS | S | 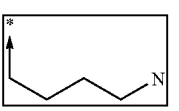 | 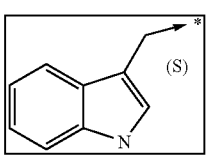 | 90% | 6.7 | 487.2 |
| 523 | C28H32N6OS | S | 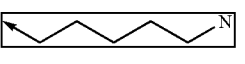 | 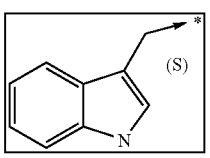 | 92% | 6.8 | 501.2 |
| 524 | C29H34N6OS | S | 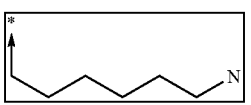 | | 92% | 6.9 | 515.2 |

-continued
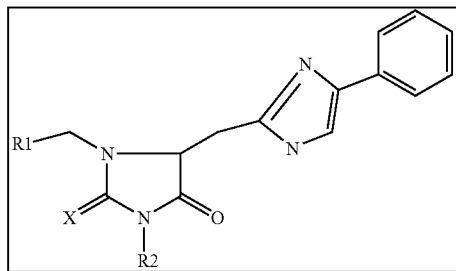
| Ex. No. | Formula | X | R1 | R2 | Purity | rt (min) | [M + H]+ |
|---|---|---|---|---|---|---|---|
| 525 | C30H28N6OS | S | indol-3-yl-CH2 (S) | 4-(CH2N)phenyl | 89% | 6.8 | 521.2 |
| 526 | C26H26N6O2S | S | 1-acetylindol-3-yl (S) | CH2CH2N | 63% | 7.1 | 487.2 |
| 527 | C27H28N6O2S | S | 1-acetylindol-3-yl (S) | (CH2)3N | 87% | 6.8 | 501.2 |
| 528 | C28H30N6O2S | S | 1-acetylindol-3-yl (S) | (CH2)4N | 85% | 6.9 | 515.2 |
| 529 | C29H32N6O2S | S | 1-acetylindol-3-yl (S) | (CH2)5N | 79% | 7.0 | 529.2 |

-continued

| Ex. No. | Formula | X | R1 | R2 | Purity | rt (min) | [M + H]+ |
|---|---|---|---|---|---|---|---|
| 530 | C30H34N6O2S | S | 1-acetyl-indol-3-yl (S) | hexyl-NH | 91% | 7.2 | 543.2 |
| 531 | C31H28N6O2S | S | 1-acetyl-indol-3-yl (S) | 4-(aminomethyl)phenyl | 80% | 7.1 | 549.2 |
| 532 | C25H26N6OS | S | indol-3-ylmethyl (R) | ethyl-NH | 91% | 6.8 | 459.2 |
| 533 | C26H28N6OS | S | indol-3-ylmethyl (R) | propyl-NH | 89% | 6.6 | 473.2 |
| 534 | C27H30N6OS | S | indol-3-ylmethyl (R) | butyl-NH | 93% | 6.7 | 487.2 |
| 535 | C28H32N6OS | S | indol-3-ylmethyl (R) | pentyl-NH | 91% | 6.8 | 501.2 |
| 536 | C29H34N6OS | S | indol-3-ylmethyl (R) | hexyl-NH | 91% | 6.9 | 515.2 |

-continued
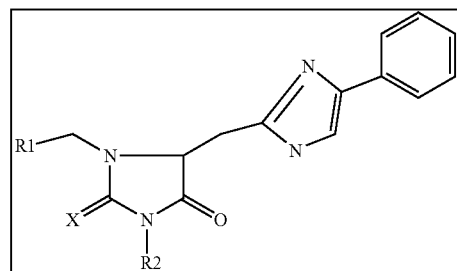
| Ex. No. | Formula | X | R1 | R2 | Purity | rt (min) | [M + H]+ |
|---|---|---|---|---|---|---|---|
| 537 | C30H28N6OS | S | 3-(R)-indolylmethyl | 4-(aminomethyl)phenyl | 87% | 6.8 | 521.2 |
| 538 | C26H26N6O2S | S | 1-acetyl-3-(R)-indolylmethyl | 2-aminoethyl | 90% | 7.0 | 487.2 |
| 539 | C27H28N6O2S | S | 1-acetyl-3-(R)-indolylmethyl | 3-aminopropyl | 61% | 6.8 | 501.2 |
| 540 | C28H30N6O2S | S | 1-acetyl-3-(R)-indolylmethyl | 4-aminobutyl | 87% | 6.9 | 515.2 |
| 541 | C29H32N6O2S | S | 1-acetyl-3-(R)-indolylmethyl | 5-aminopentyl | 83% | 7.0 | 529.2 |

-continued
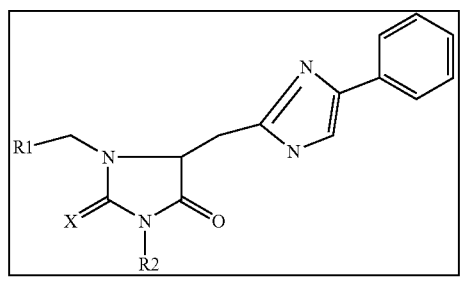
| Ex. No. | Formula | X | R1 | R2 | Purity | rt (min) | [M + H]+ |
|---|---|---|---|---|---|---|---|
| 542 | C30H34N6O2S | S | N-acetylindol-3-yl (R) | hexyl-N | 93% | 7.2 | 543.2 |
| 543 | C31H28N6O2S | S | N-acetylindol-3-yl (R) | 4-methylbenzyl-N | 76% | 7.1 | 549.2 |
| 544 | C25H26N6O2 | O | indol-3-yl (S) | ethyl-N | 91% | 6.1 | 443.2 |
| 545 | C26H28N6O2 | O | indol-3-yl (S) | propyl-N | 90% | 6.1 | 457.2 |
| 546 | C27H30N6O2 | O | indol-3-yl (S) | butyl-N | 87% | 6.1 | 471.2 |
| 547 | C28H32N6O2 | O | indol-3-yl (S) | hexyl-N | 88% | 6.2 | 485.2 |

-continued
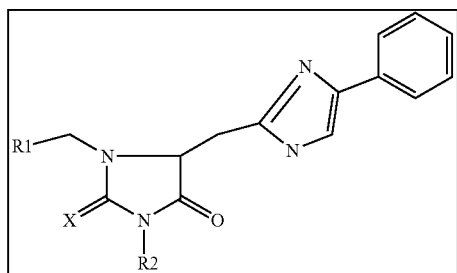
| Ex. No. | Formula | X | R1 | R2 | Analyses | | |
|---|---|---|---|---|---|---|---|
| | | | | | Purity | rt (min) | [M + H]+ |
| 548 | C26H26N6O3 | O | 1-acetylindol-3-yl (S) | *–CH2–CH2–N | 93% | 6.2 | 471.2 |
| 549 | C27H28N6O3 | O | 1-acetylindol-3-yl (S) | *–(CH2)3–N | 91% | 6.1 | 485.2 |
| 550 | C28H30N6O3 | O | 1-acetylindol-3-yl (S) | *–(CH2)4–N | 81% | 6.2 | 499.2 |
| 551 | C29H32N6O3 | O | 1-acetylindol-3-yl (S) | *–(CH2)5–N | 82% | 6.3 | 513.2 |
| 552 | C25H26N6O2 | O | indol-3-yl (R) | *–CH2–CH2–N | 91% | 6.1 | 443.2 |
| 553 | C26H28N6O2 | O | indol-3-yl (R) | *–(CH2)3–N | 91% | 6.1 | 457.2 |

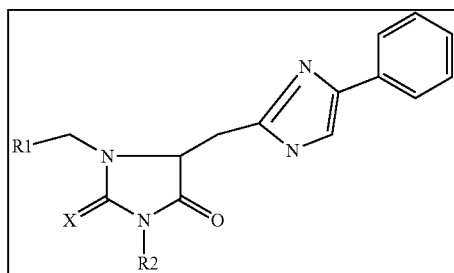
| Ex. No. | Formula | X | R1 | R2 | Purity | rt (min) | [M + H]+ |
|---|---|---|---|---|---|---|---|
| 554 | C27H30N6O2 | O | indol-3-yl-CH2- (R) | *-CH2CH2CH2CH2-N | 89% | 6.1 | 471.2 |
| 555 | C28H32N6O2 | O | indol-3-yl-CH2- (R) | *-CH2CH2CH2CH2CH2-N | 91% | 6.1 | 485.2 |
| 556 | C26H26N6O3 | O | 1-acetyl-indol-3-yl-CH2- (R) | *-CH2CH2-N | 93% | 6.2 | 471.2 |
| 557 | C27H28N6O3 | O | 1-acetyl-indol-3-yl-CH2- (R) | *-CH2CH2CH2-N | 95% | 6.1 | 485.2 |
| 558 | C28H30N6O3 | O | 1-acetyl-indol-3-yl-CH2- (R) | *-CH2CH2CH2CH2-N | 85% | 6.2 | 499.2 |
| 559 | C29H32N6O3 | O | 1-acetyl-indol-3-yl-CH2- (R) | *-CH2CH2CH2CH2CH2-N | 85% | 6.3 | 513.2 |

-continued
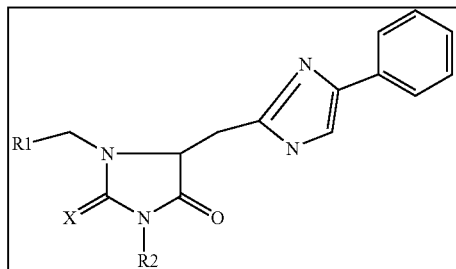
| Ex. No. | Formula | X | R1 | R2 | Purity | rt (min) | [M + H]+ |
|---|---|---|---|---|---|---|---|
| 560 | C24H24N6OS | S | indol-3-yl (R) | *-CH2-N (aziridine) | 84% | 3.6 | 445.2 |
| 561 | C26H28N6OS | S | indol-3-yl (R) | *-(CH2)3-N | 92% | 3.5 | 473.3 |
| 562 | C27H30N6OS | S | indol-3-yl (R) | *-(CH2)4-N | 83% | 3.6 | 487.3 |
| 563 | C28H32N6OS | S | indol-3-yl (R) | *-(CH2)5-N | 88% | 3.7 | 501.3 |
| 564 | C29H26N6OS | S | indol-3-yl (R) | *-C6H4-CH2-N | 59% | 3.7 | 507.2 |
| 565 | C24H24N6O2 | O | indol-3-yl (R) | *-CH2-N (aziridine) | 87% | 3.2 | 429.2 |
| 566 | C25H26N6O2 | O | indol-3-yl (R) | *-(CH2)2-N | 92% | 3.1 | 443.3 |

-continued
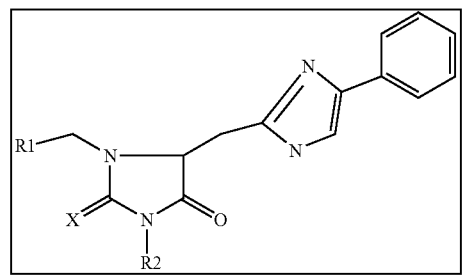
| | | | | | Analyses | | |
|---|---|---|---|---|---|---|---|
| Ex. No. | Formula | X | R1 | R2 | Purity | rt (min) | [M + H]+ |
| 567 | C26H28N6O2 | O | indole (R) | *-CH2CH2CH2CH2-N | 97% | 3.1 | 457.3 |
| 568 | C27H30N6O2 | O | indole (R) | -CH2CH2CH2CH2CH2-N | 90% | 3.1 | 471.3 |
| 569 | C24H24N6O2 | O | indole (R) | *-CH2-N | 91% | 3.1 | 429.2 |
| 570 | C25H26N6O2 | O | indole (R) | -CH2CH2CH2-N | 97% | 3.1 | 443.3 |
| 571 | C26H28N6O2 | O | indole (R) | *-CH2CH2CH2CH2-N | 95% | 3.1 | 457.3 |
| 572 | C27H30N6O2 | O | indole (R) | -CH2CH2CH2CH2CH2-N | 95% | 3.2 | 471.3 |

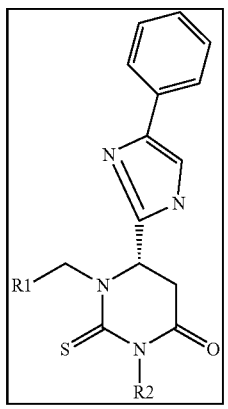
| Ex. No. | Formula | R1 | R2 | Purity | rt (min) | [M + H]+ |
|---|---|---|---|---|---|---|
| 573 | C29H25N5OS | indol-3-yl | benzyl | 93% | 6.7 | 492.2 |
| 574 | C29H24ClN5OS | indol-3-yl | 2-chlorobenzyl | 93% | 7.2 | 526.2 |
| 575 | C29H23Cl2N5OS | indol-3-yl | 3,4-dichlorobenzyl | 93% | 7.6 | 560.1 |
| 576 | C30H27N5OS | indol-3-yl | 4-methylbenzyl | 94% | 7.0 | 506.2 |
| 577 | C29H24FN5OS | indol-3-yl | 4-fluorobenzyl | 95% | 6.9 | 510.3 |

-continued
| | | | | | | |
|---|---|---|---|---|---|---|
| 578 | C30H27N5OS | 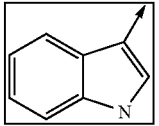 | | 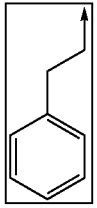 | 90% | 6.9 | 506.3 |
| 579 | C30H26ClN5OS | 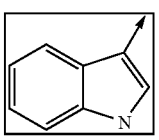 | | 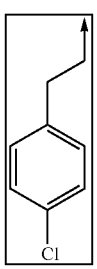 | 92% | 7.4 | 540.2 |
| 580 | C32H31N5O3S | 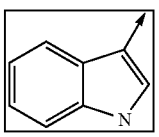 | | 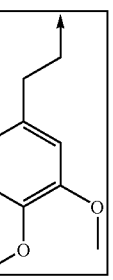 | 88% | 6.4 | 566.3 |
| 581 | C31H29N5OS | 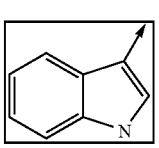 | | 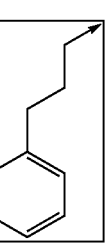 | 87% | 7.1 | 520.2 |
| 582 | C27H23N5O2S | 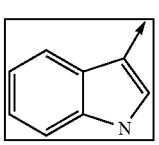 | | 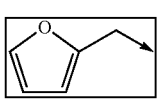 | 93% | 6.2 | 482.2 |
| 583 | C27H27N5O2S | 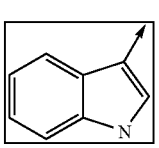 | | 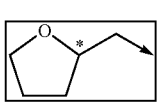 | 38 + 45% | 5.6 + 5.71 | 486.3 |
| 584 | C28H30N6O2S | 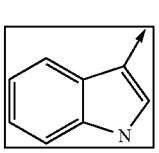 | | 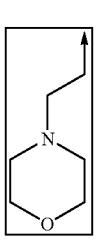 | 87% | 4.6 | 515.3 |

| | | | | | | |
|---|---|---|---|---|---|---|
| 585 | C29H32N6O2S | 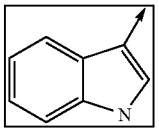 | 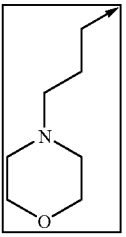 | 84% | 4.5 | 529.3 |
| 586 | C29H34N6OS | 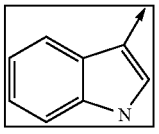 | 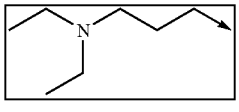 | 89% | 4.7 | 515.3 |
| 587 | C25H25N5O2S | 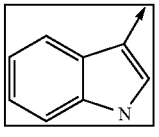 |  | 90% | 5.18 m | 460.3 |
| 588 | C26H27N5O2S | 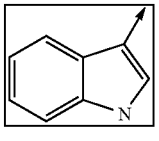 | 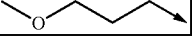 | 87% | 5.6 | 474.3 |
| 589 | C25H22N4OS2 | 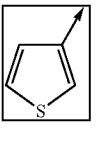 | 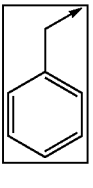 | 89% | 6.7 | 459.2 |
| 590 | C25H21ClN4OS2 | 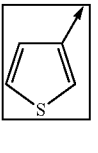 | 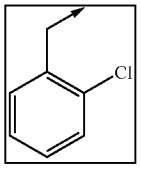 | 87% | 7.2 | 493.2 |
| 591 | C25H20Cl2N4OS2 | 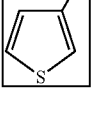 | 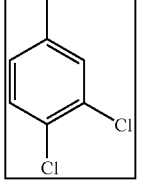 | 90% | 7.6 | 527.1 |
| 592 | C26H24N4OS2 | 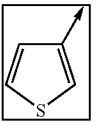 |  | 83% | 7.0 | 473.2 |

| | | | | | | |
|---|---|---|---|---|---|---|
| 593 | C25H21FN4OS2 | 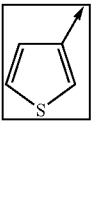 | 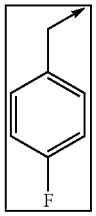 | 88% | 6.9 | 477.2 |
| 594 | C26H24N4OS2 | 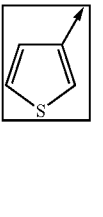 | 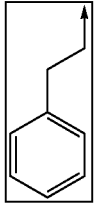 | 80% | 7.0 | 473.2 |
| 595 | C26H23ClN4OS2 | 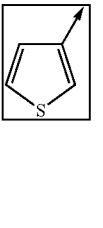 | 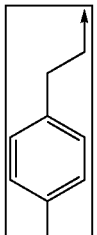 | 79% | 7.4 | 507.2 |
| 596 | C28H28N4O3S2 | 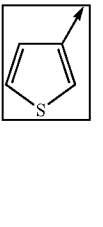 | 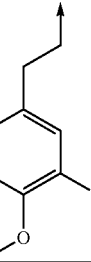 | 82% | 6.4 | 533.2 |
| 597 | C27H26N4OS2 | 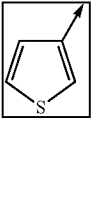 | 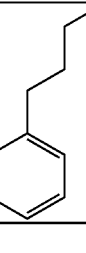 | 79% | 7.2 | 487.2 |
| 598 | C23H20N4O2S2 | 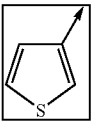 | 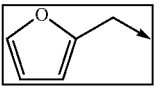 | 80% | 6.2 | 449.2 |
| 599 | C23H24N4O2S2 | 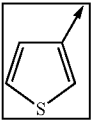 | 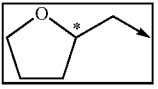 | 31 + 32% | 5.7 + 5.86 | 453.2 |

-continued

| | | | | | | |
|---|---|---|---|---|---|---|
| 600 | C24H27N5O2S2 | thiophene | morpholine-ethyl | 80% | 4.3 | 241.7 |
| 601 | C25H29N5O2S2 | thiophene | morpholine-propyl | 81% | 4.3 | 248.8 |
| 602 | C25H31N5OS2 | thiophene | N,N-diethylaminopropyl | 81% | 4.5 | 482.3 |
| 603 | C21H22N4O2S2 | thiophene | methoxyethyl | 79% | 5.6 | 427.1 |
| 604 | C22H24N4O2S2 | thiophene | methoxypropyl | 78% | 5.9 | 441.2 |
| 605 | C28H26N4O2S | 4-methoxyphenyl | benzyl | 89% | 6.8 | 483.2 |
| 606 | C28H25ClN4O2S | 4-methoxyphenyl | 2-chlorobenzyl | 90% | 7.2 | 517.2 |
| 607 | C28H24Cl2N4O2S | 4-methoxyphenyl | 3,4-dichlorobenzyl | 91% | 7.7 | 551.1 |

-continued
| | | | | | | |
|---|---|---|---|---|---|---|
| 608 | C29H28N4O2S | 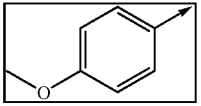 | 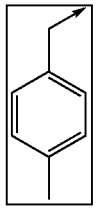 | 88% | 7.0 | 497.3 |
| 609 | C28H25FN4O2S | 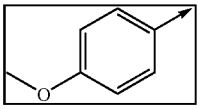 | 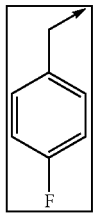 | 89% | 6.9 | 501.2 |
| 610 | C29H28N4O2S | 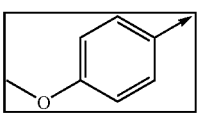 | 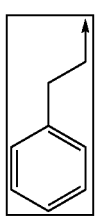 | 87% | 7.0 | 497.3 |
| 611 | C29H27ClN4O2S | 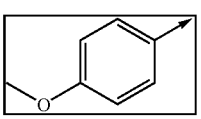 | 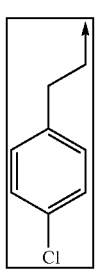 | 90% | 7.5 | 531.2 |
| 612 | C31H32N4O4S | 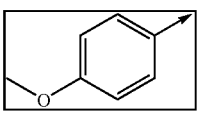 | 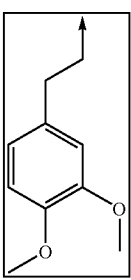 | 91% | 6.5 | 557.2 |
| 613 | C30H30N4O2S | 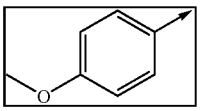 | 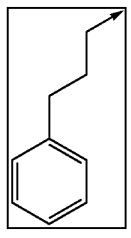 | 87% | 7.2 | 511.3 |
| 614 | C26H24N4O3S | 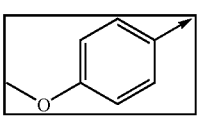 | 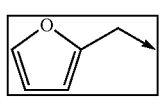 | 89% | 6.3 | 473.2 |

-continued
| | | | | | | |
|---|---|---|---|---|---|---|
| 615 | C26H28N4O3S | 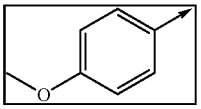 | 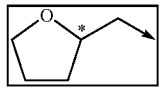 | 39 + 43% | 5.7 + 5.85 | 477.2 |
| 616 | C27H31N5O3S | 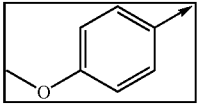 | 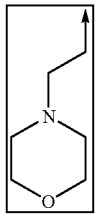 | 34% | 4.5 | 506.3 |
| 617 | C28H33N5O3S | 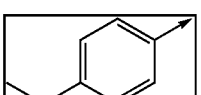 | 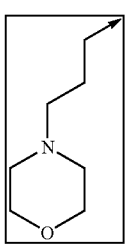 | 79% | 4.4 | 520.3 |
| 618 | C28H35N5O2S | 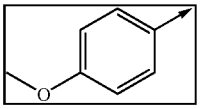 | 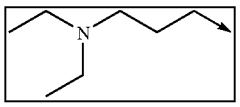 | 76% | 4.6 | 506.3 |
| 619 | C24H26N4O3S | 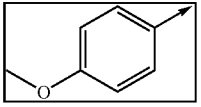 | 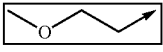 | 85% | 5.7 | 451.2 |
| 620 | C25H28N4O3S | 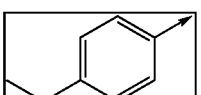 | 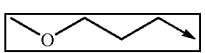 | 84% | 5.9 | 465.2 |
| 621 | C29H29N5OS | 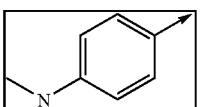 | 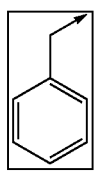 | 89% | 5.9 | 248.8 |
| 622 | C29H28ClN5OS | 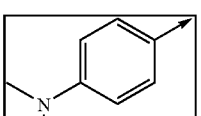 | 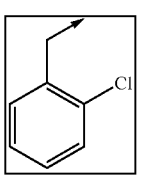 | 89% | 6.4 | 265.7 |
| 623 | C29H27Cl2N5OS | 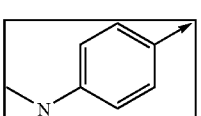 | 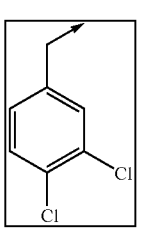 | 93% | 6.9 | 282.7 |

-continued
| | | | | | | | |
|---|---|---|---|---|---|---|---|
| 624 | C30H31N5OS | 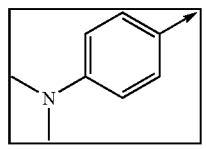 | | 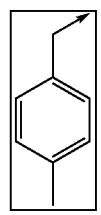 | 90% | 6.2 | 255.8 |
| 625 | C29H28FN5OS | 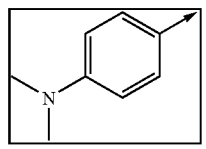 | | 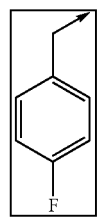 | 92% | 6.1 | 257.8 |
| 626 | C30H31N5OS | 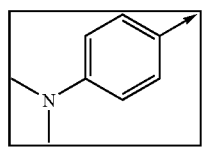 | | 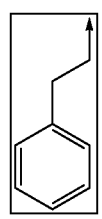 | 87% | 6.2 | 255.8 |
| 627 | C30H30ClN5OS | 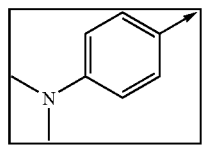 | | 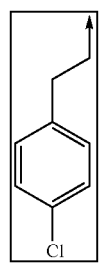 | 90% | 6.8 | 272.7 |
| 628 | C32H35N5O3S | 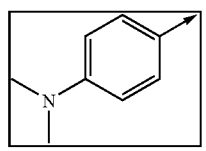 | | 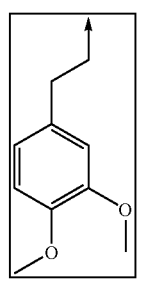 | 87% | 5.6 | 285.8 |
| 629 | C31H33N5OS | 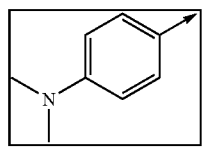 | | 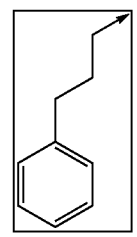 | 88% | 6.4 | 262.8 |

| | | | | | | |
|---|---|---|---|---|---|---|
| 630 | C27H27N5O2S | 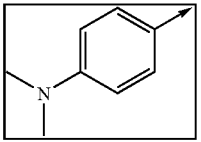 | 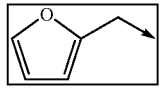 | 89% | 5.4 | 243.7 |
| 631 | C27H31N5O2S | 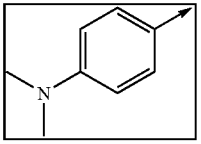 | 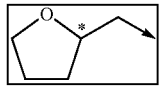 | 31 + 37% | 5.26 + 5.33 | 245.6 |
| 632 | C28H34N6O2S | 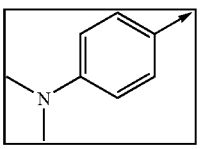 | 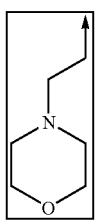 | 79% | 3.7 | 260.3 |
| 633 | C29H36N6O2S | 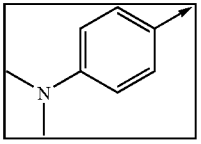 | 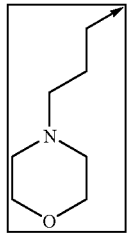 | 77% | 3.7 | 267.3 |
| 634 | C29H38N6OS | 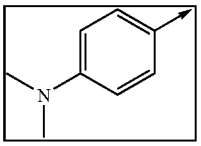 | 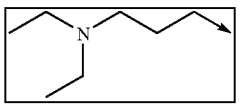 | 78% | 3.9 | 260.2 |
| 635 | C25H29N5O2S | 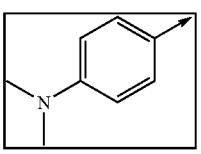 | 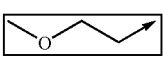 | 80% | 4.9 | 232.7 |
| 636 | C26H31N5O2S | 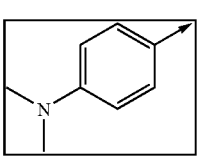 | 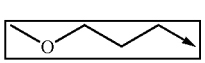 | 79% | 5.0 | 239.7 |
| 637 | C28H23F3N4O2S | 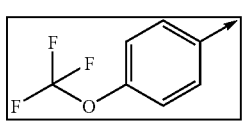 | 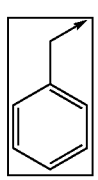 | 88% | 7.4 | 537.2 |

-continued

| | | | | | | | |
|---|---|---|---|---|---|---|---|
| 638 | C28H22ClF3N4O2S | 4-(trifluoromethoxy)phenyl | | 2-chlorobenzyl | 90% | 7.8 | 571.1 |
| 639 | C28H21Cl2F3N4O2S | 4-(trifluoromethoxy)phenyl | | 3,4-dichlorobenzyl | 92% | 8.3 | 605.1 |
| 640 | C29H25F3N4O2S | 4-(trifluoromethoxy)phenyl | | 4-methylbenzyl | 89% | 7.6 | 551.2 |
| 641 | C28H22F4N4O2S | 4-(trifluoromethoxy)phenyl | | 4-fluorobenzyl | 189% | 7.5 | 555.2 |
| 642 | C29H25F3N4O2S | 4-(trifluoromethoxy)phenyl | | 2-phenylethyl | 88% | 7.7 | 551.2 |
| 643 | C29H24ClF3N4O2S | 4-(trifluoromethoxy)phenyl | | 2-(4-chlorophenyl)ethyl | 90% | 8.1 | 585.1 |

-continued

| # | Formula | R1 | R2 | Yield | RT | MS |
|---|---|---|---|---|---|---|
| 644 | C31H29F3N4O4S | 4-(trifluoromethoxy)phenyl | 3,4-dimethoxyphenethyl | 92% | 7.2 | 611.2 |
| 645 | C30H27F3N4O2S | 4-(trifluoromethoxy)phenyl | phenylpropyl | 86% | 7.8 | 565.2 |
| 646 | C26H21F3N4O3S | 4-(trifluoromethoxy)phenyl | furan-2-ylmethyl | 88% | 7.0 | 527.2 |
| 647 | C26H25F3N4O3S | 4-(trifluoromethoxy)phenyl | (tetrahydrofuran-2-yl)methyl* | 44 + 42% | 6.59 + 6.7 | 531.2 |
| 648 | C27H28F3N5O3S | 4-(trifluoromethoxy)phenyl | 2-morpholinoethyl | 81% | 5.0 | 280.8 |
| 649 | C28H30F3N5O3S | 4-(trifluoromethoxy)phenyl | 3-morpholinopropyl | 82% | 5.0 | 287.8 |
| 650 | C28H32F3N5O2S | 4-(trifluoromethoxy)phenyl | 3-(diethylamino)propyl | 86% | 5.2 | 280.8 |

-continued
| | | | | | | |
|---|---|---|---|---|---|---|
| 651 | C24H23F3N4O3S |  | | 90% | 6.6 | 505.2 |
| 652 | C25H25F3N4O3S |  | | 88% | 6.8 | 519.2 |
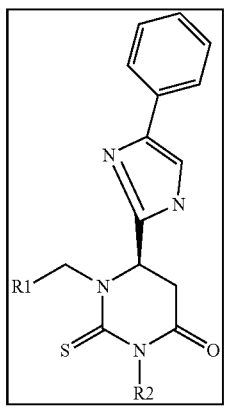
| | | | | Analyses | | |
|---|---|---|---|---|---|---|
| Ex. No. | Formula | R1 | R2 | Purity | rt (min) | [M + H]+ |
| 653 | C29H32N6O3S | 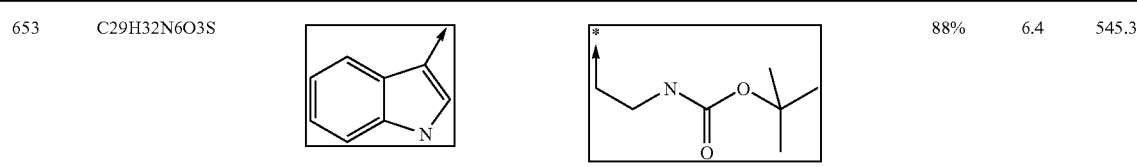 | | 88% | 6.4 | 545.3 |
| 654 | C30H34N6O3S | 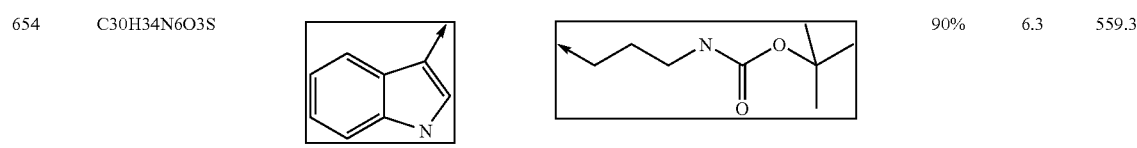 | | 90% | 6.3 | 559.3 |
| 655 | C31H36N6O3S | 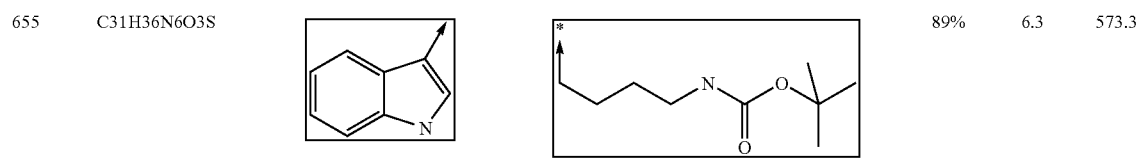 | | 89% | 6.3 | 573.3 |
| 656 | C32H38N6O3S | 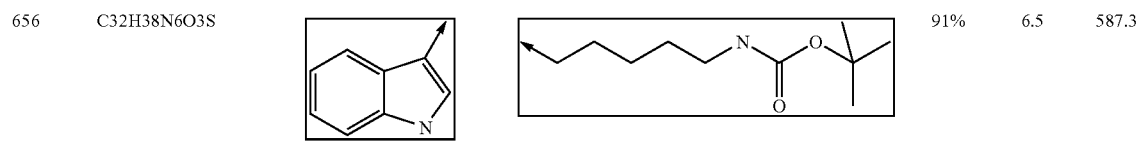 | | 91% | 6.5 | 587.3 |
| 657 | C33H40N6O3S | 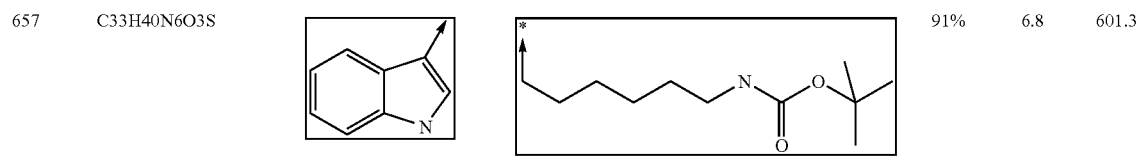 | | 91% | 6.8 | 601.3 |

| | | | | | | |
|---|---|---|---|---|---|---|
| 658 | C25H29N5O3S2 | 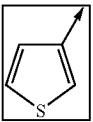 | 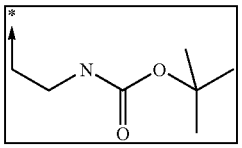 | 78% | 6.7 | 512.3 |
| 659 | C26H31N5O3S2 | 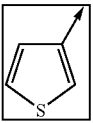 | 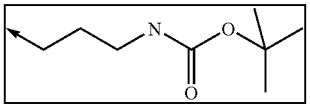 | 87% | 6.5 | 526.3 |
| 660 | C27H33N5O3S2 | 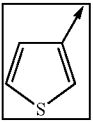 | 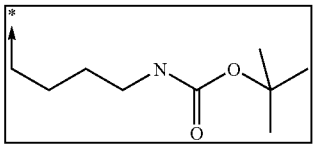 | 86% | 6.6 | 540.3 |
| 661 | C28H35N5O3S2 | 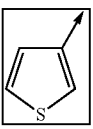 | 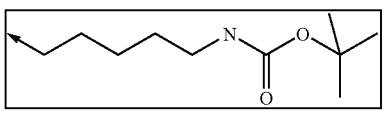 | 84% | 6.8 | 554.3 |
| 662 | C29H37N5O3S2 | 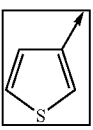 | 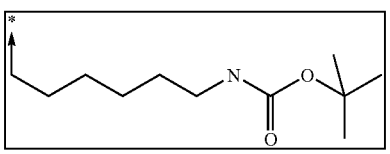 | 83% | 7.0 | 568.3 |
| 663 | C28H33N5O4S | 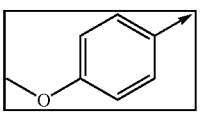 | 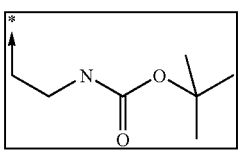 | 83% | 6.7 | 536.3 |
| 664 | C29H35N5O4S | 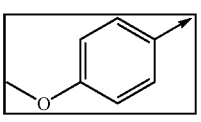 | 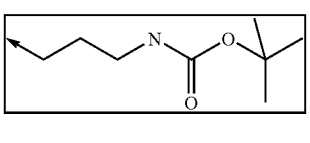 | 88% | 6.6 | 550.3 |
| 665 | C30H37N5O4S | 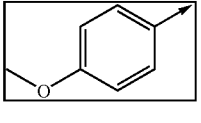 | 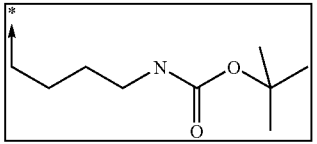 | 84% | 6.6 | 564.3 |
| 666 | C31H39N5O4S | 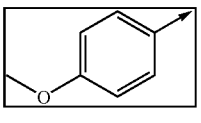 | 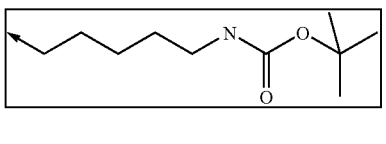 | 86% | 6.8 | 578.3 |
| 667 | C32H41N5O4S | 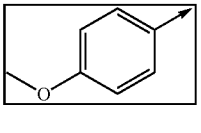 | 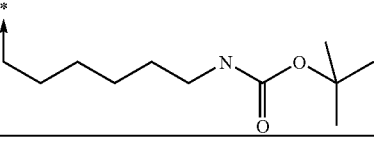 | 86% | 7.0 | 592.3 |

| | | | | | | |
|---|---|---|---|---|---|---|
| 668 | C29H36N6O3S | 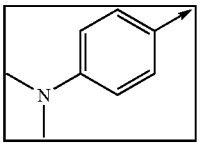 | 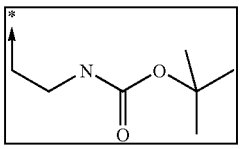 | 82% | 5.8 | 549.3 |
| 669 | C30H38N6O3S | 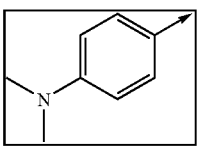 | 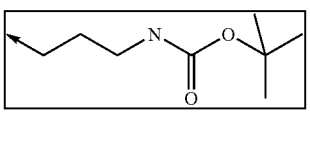 | 80% | 5.7 | 563.3 |
| 670 | C31H40N6O3S | 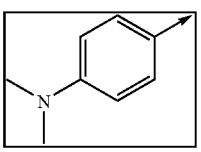 | 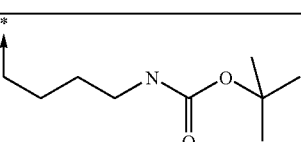 | 84% | 5.8 | 577.3 |
| 671 | C32H42N6O3S | 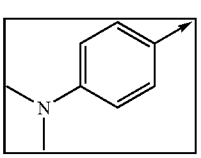 | 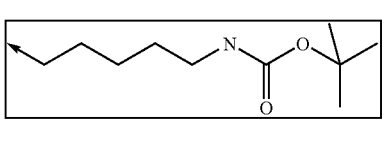 | 84% | 6.0 | 591.4 |
| 672 | C33H44N6O3S | 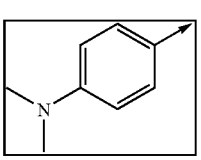 | 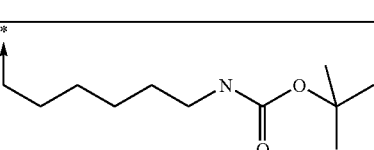 | 84% | 6.3 | 605.4 |
| 673 | C28H30F3N5O4S | 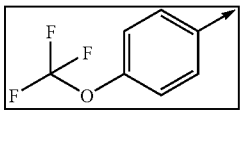 | 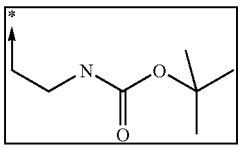 | 82% | 7.5 | 590.3 |
| 674 | C29H32F3N5O4S | 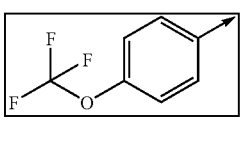 | 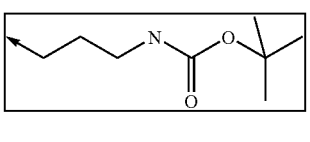 | 81% | 7.3 | 604.3 |
| 675 | C30H34F3N5O4S | 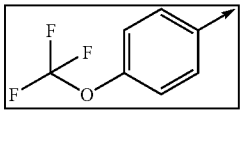 | 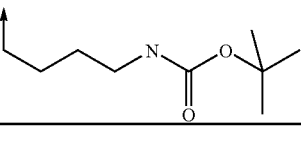 | 84% | 7.4 | 618.3 |
| 676 | C31H36F3N5O4S | 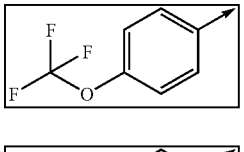 | 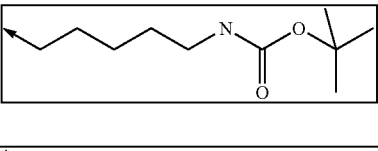 | 86% | 7.5 | 632.3 |
| 677 | C32H38F3N5O4S | 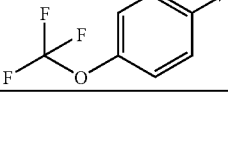 | 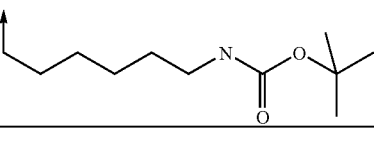 | 88% | 7.7 | 646.3 |

-continued
| | | R1 | R2 | | | |
|---|---|---|---|---|---|---|
| 678 | C29H34N6O4S | 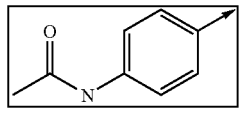 | 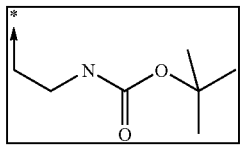 | 81% | 5.8 | 563.3 |
| 679 | C30H36N6O4S | 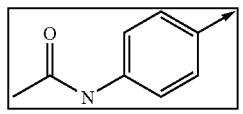 | 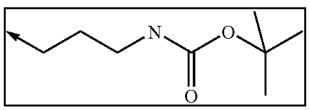 | 81% | 5.8 | 577.3 |
| 680 | C31H38N6O4S | 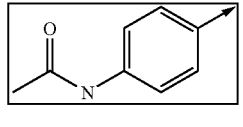 | 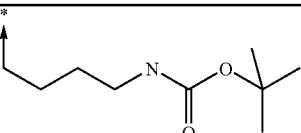 | 82% | 5.8 | 591.3 |
| 681 | C32H40N6O4S | 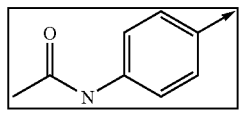 | 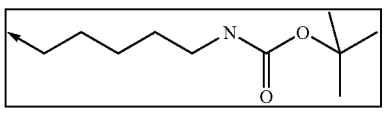 | 82% | 6.0 | 605.3 |
| 682 | C33H42N6O4S | 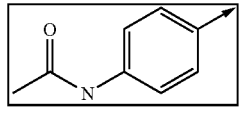 | 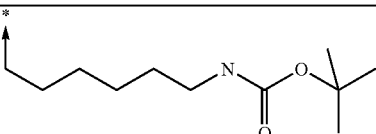 | 83% | 6.2 | 619.4 |
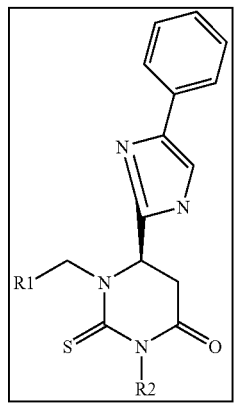
| | | | | | Analyses | |
|---|---|---|---|---|---|---|
| Ex. No. | Formula | R1 | R2 | Purity | rt (min) | [M + H]+ |
| 683 | C27H30N6O5S | 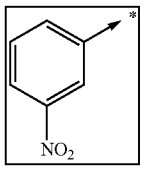 | 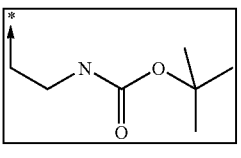 | 77% | 6.9 | 551.3 |

-continued
| | | | | | | |
|---|---|---|---|---|---|---|
| 684 | C28H32N6O5S | 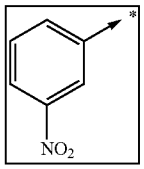 | 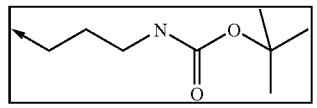 | 75% | 6.8 | 565.3 |
| 685 | C29H34N6O5S | 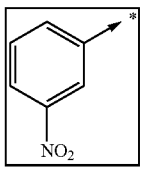 | 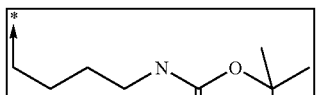 | 81% | 6.9 | 579.3 |
| 686 | C30H36N6O5S | 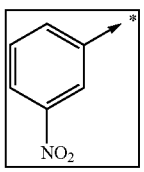 | 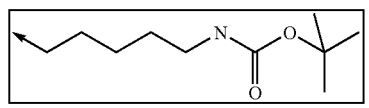 | 82% | 7.0 | 593.3 |
| 687 | C31H38N6O5S | 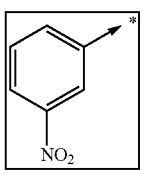 | 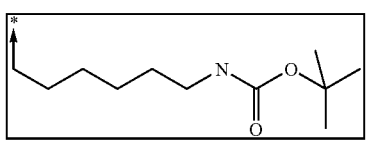 | 82% | 7.3 | 607.3 |
| 688 | C27H37N5O3S | 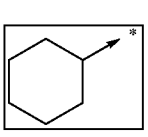 | 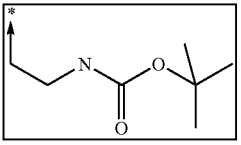 | 77% | 7.5 | 512.3 |
| 689 | C28H39N5O3S | 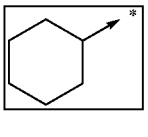 | 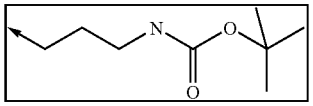 | 71% | 7.3 | 526.4 |
| 690 | C29H41N5O3S | 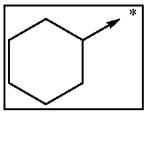 | 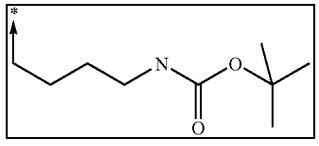 | 76% | 7.3 | 540.3 |
| 691 | C30H43N5O3S | 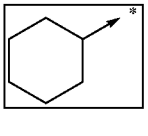 | 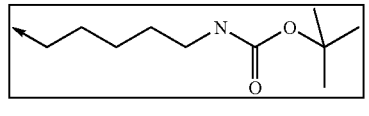 | 74% | 7.5 | 554.4 |
| 692 | C31H45N5O3S | 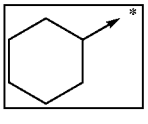 | 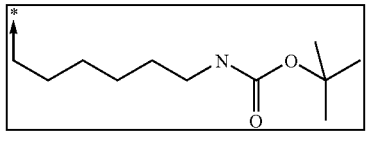 | 74% | 7.7 | 568.4 |
| 693 | C24H24N6OS | 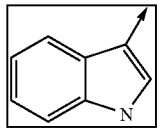 |  | 47% | 4.2 | 445.3 |

-continued
| | | | | | | |
|---|---|---|---|---|---|---|
| 694 | C25H26N6OS | 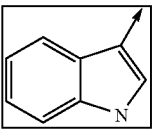 | 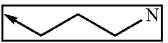 | 45% | 3.9 | 459.3 |
| 695 | C26H28N6OS | 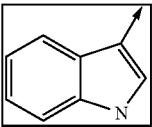 | 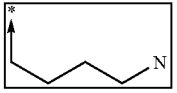 | 52% | 4.0 | 473.3 |
| 696 | C27H30N6OS | 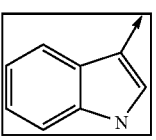 | 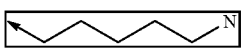 | 43% | 4.1 | 487.3 |
| 697 | C28H32N6OS | 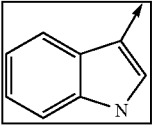 | 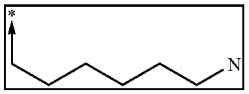 | 38% | 4.3 | 501.3 |
| 698 | C20H21N5OS2 | 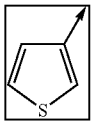 |  | 78% | 4.1 | 412.2 |
| 699 | C21H23N5OS2 | 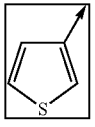 | 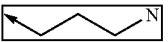 | 81% | 4.0 | 426.3 |
| 700 | C22H25N5OS2 | 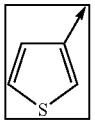 | 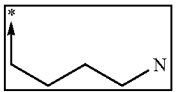 | 84% | 4.1 | 440.2 |
| 701 | C23H27N5OS2 | 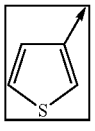 |  | 86% | 4.2 | 454.3 |
| 702 | C24H29N5OS2 | 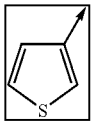 | 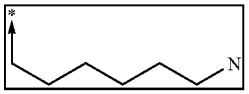 | 85% | 4.3 | 468.3 |
| 703 | C23H25N5O2S | 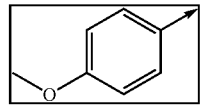 |  | 82% | 4.2 | 436.3 |
| 704 | C24H27N5O2S | 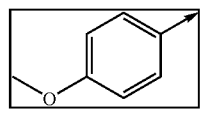 | 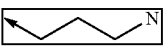 | 84% | 4.1 | 450.3 |

-continued
| | | | | | | |
|---|---|---|---|---|---|---|
| 705 | C25H29N5O2S | 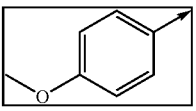 |  | 88% | 4.2 | 464.3 |
| 706 | C26H31N5O2S | 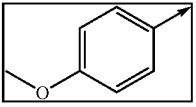 |  | 88% | 4.3 | 478.3 |
| 707 | C27H33N5O2S | 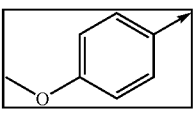 | 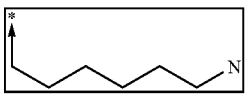 | 87% | 4.4 | 492.3 |
| 708 | C24H28N6OS | 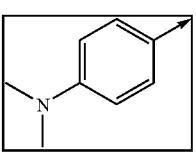 |  | 80% | 3.5 | 449.3 |
| 709 | C25H30N6OS | 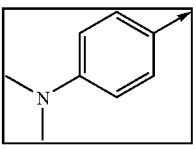 | 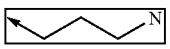 | 83% | 3.4 | 436.3 |
| 710 | C26H32N6OS | 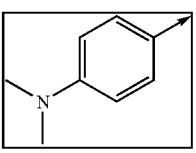 | 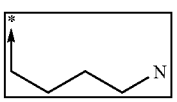 | 84% | 3.5 | 477.3 |
| 711 | C27H34N6OS | 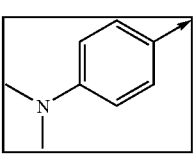 |  | 84% | 3.6 | 491.3 |
| 712 | C28H36N6OS | 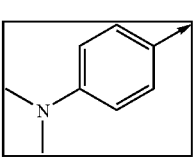 | 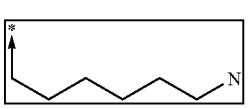 | 85% | 3.8 | 505.3 |
| 713 | C23H22F3N5O2S | 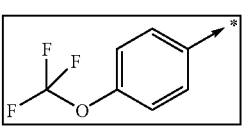 |  | 83% | 4.8 | 490.3 |
| 714 | C24H24F3N5O2S | 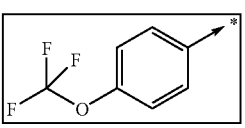 | 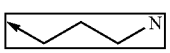 | 84% | 4.8 | 504.2 |
| 715 | C25H26F3N5O2S | 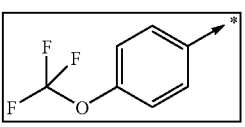 | 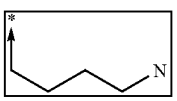 | 88% | 4.8 | 518.2 |

| | | | | | | |
|---|---|---|---|---|---|---|
| 716 | C26H28F3N5O2S | 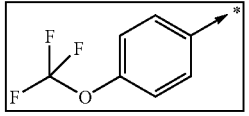 |  | 91% | 4.9 | 532.2 |
| 717 | C27H30F3N5O2S | 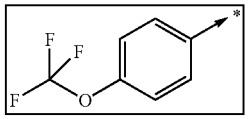 |  | 90% | 5.0 | 546.2 |
| 718 | C24H26N6O2S | 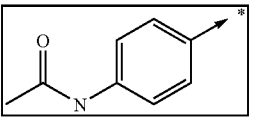 |  | 70% | 3.6 | 463.3 |
| 719 | C25H28N6O2S | 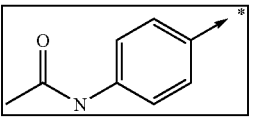 | 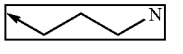 | 82% | 3.5 | 477.3 |
| 720 | C26H30N6O2S | 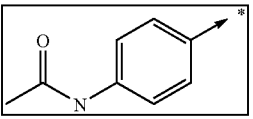 |  | 83% | 3.5 | 491.3 |
| 721 | C27H32N6O2S | 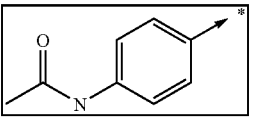 | 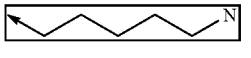 | 89% | 3.7 | 505.3 |
| 722 | C28H34N6O2S | 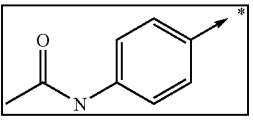 |  | 89% | 3.8 | 519.3 |
| 723 | C22H22N6O3S | 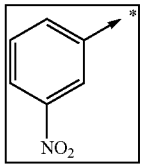 |  | 81% | 4.3 | 451.2 |
| 724 | C23H24N6O3S | 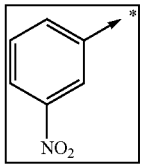 | 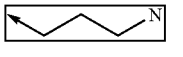 | 80% | 4.3 | 465.2 |

| | | | | | | |
|---|---|---|---|---|---|---|
| 725 | C24H26N6O3S | 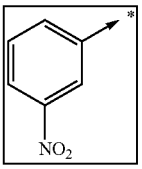 | 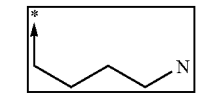 | 89% | 4.3 | 479.2 |
| 726 | C25H28N6O3S | 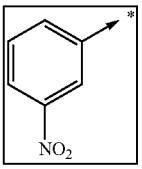 |  | 86% | 4.4 | 493.3 |
| 727 | C26H30N6O3S | 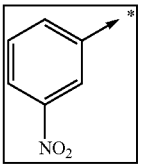 | 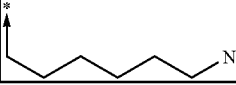 | 86% | 4.5 | 507.3 |
| 728 | C22H29N5OS | 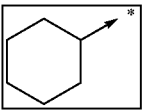 |  | 79% | 4.8 | 412.3 |
| 729 | C23H31N5OS | 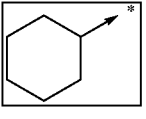 | 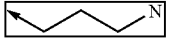 | 75% | 4.6 | 426.3 |
| 730 | C24H33N5OS | 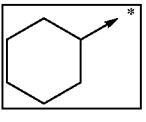 | 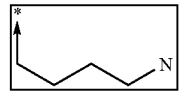 | 78% | 4.6 | 440.3 |
| 731 | C25H35N5OS | 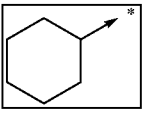 |  | 78% | 4.7 | 454.3 |
| 732 | C26H37N5OS | 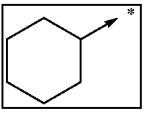 | 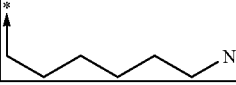 | 83.8% | 5.0 | 468.2 |

-continued
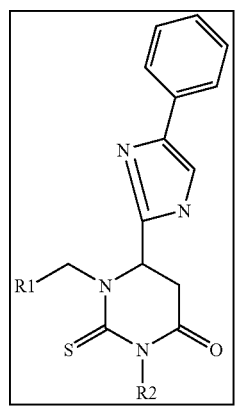
| Ex. No. | Formula | R1 | R2 | Purity | rt (min) | [M + H]+ |
|---|---|---|---|---|---|---|
| 733 | C28H24N6OS | indol-3-yl | 4-pyridyl | 45% | 4.7 | 493.2 |
| 734 | C29H26N6OS | indol-3-yl | 4-pyridylmethyl | 57% | 4.2 | 507.3 |
| 735 | C24H21N5OS2 | thien-3-yl | 4-pyridyl | 69% | 4.7 | 460.2 |
| 736 | C25H23N5OS2 | thien-3-yl | 4-pyridylmethyl | 77% | 4.2 | 474.2 |
| 737 | C27H25N5O2S | 4-methoxyphenyl | 4-pyridyl | 73% | 4.8 | 484.3 |

-continued
| | | | | | | |
|---|---|---|---|---|---|---|
| 738 | C28H27N5O2S | 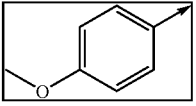 | 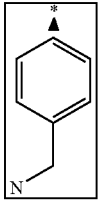 | 76% | 4.3 | 497.3 |
| 739 | C28H28N6OS | 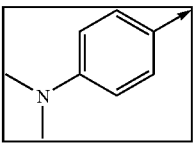 | 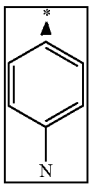 | 67% | 3.9 | 497.3 |
| 740 | C29H30N6OS | 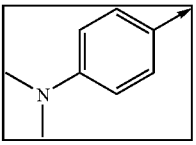 | 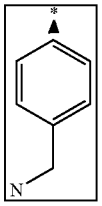 | 62% | 3.6 | 511.3 |
| 741 | C27H22F3N5O2S | 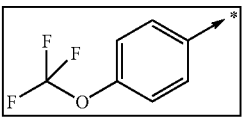 | 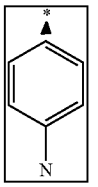 | 61% | 5.7 | 538.2 |
| 742 | C28H24F3N5O2S | 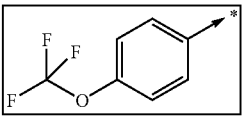 | 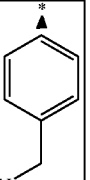 | 75% | 4.9 | 552.2 |
| 743 | C28H26N6O2S | 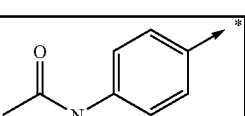 | 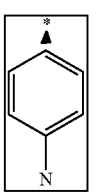 | 57% | 4.0 | 511.2 |
| 744 | C29H28N6O2S | 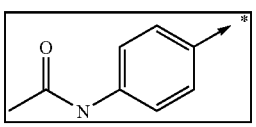 | 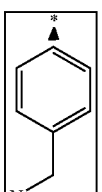 | 60% | 3.7 | 525.3 |

-continued
| | | | | | | |
|---|---|---|---|---|---|---|
| 745 | C26H22N6O3S | 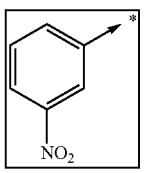 | 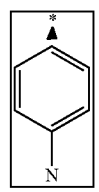 | 70% | 5.0 | 499.2 |
| 746 | C27H24N6O3S | 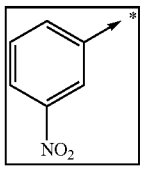 | 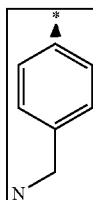 | 65% | 4.4 | 513.2 |
| 747 | C26H29N5OS | 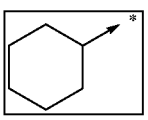 | 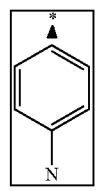 | 78% | 5.4 | 460.3 |
| 748 | C27H31N5OS | 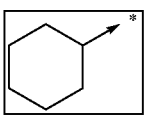 | 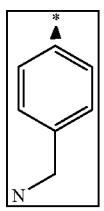 | 80% | 4.7 | 474.3 |
| 749 | C34H34N6O3S | 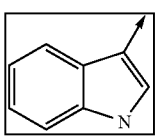 | 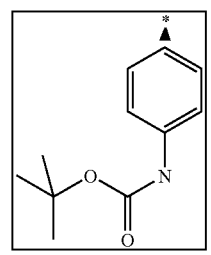 | 86% | 6.6 | 593.3 |
| 750 | C33H32N6O3S | 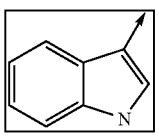 | 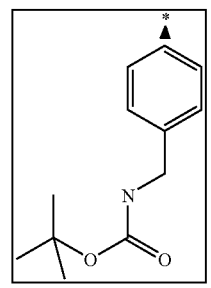 | 82% | 6.5 | 607.3 |

-continued
| | | | | | | |
|---|---|---|---|---|---|---|
| 751 | C30H31N5O3S2 | 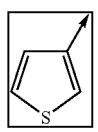 | 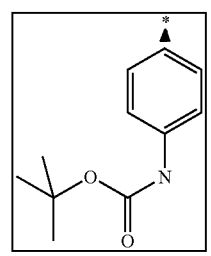 | 77% | 6.7 | 560.2 |
| 752 | C29H29N5O3S2 | 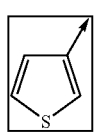 | 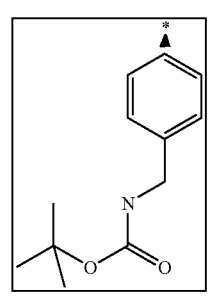 | 77% | 6.7 | 574.2 |
| 753 | C33H35N5O4S | 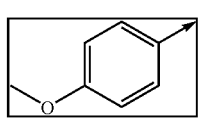 | 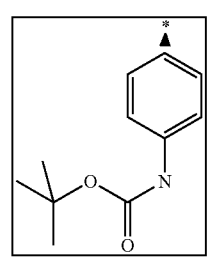 | 81% | 6.8 | 584.3 |
| 754 | C32H33NSO4S | 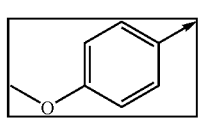 | 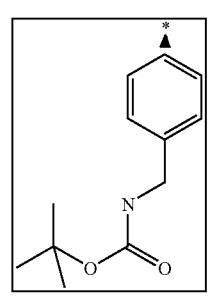 | 76% | 6.7 | 598.3 |
| 755 | C34H38N6O3S | 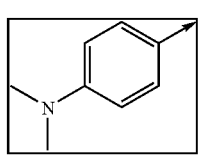 | 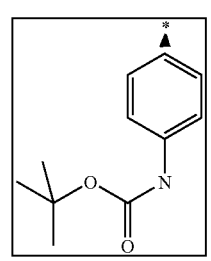 | 77% | 5.9 | 597.3 |

-continued
| | | | | | | | |
|---|---|---|---|---|---|---|---|
| 756 | C33H36N6O3S | 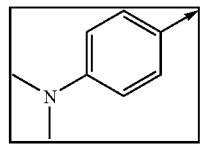 | 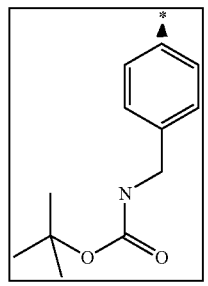 | 74% | 5.8 | 611.3 | |
| 757 | C33H32F3N5O4S | 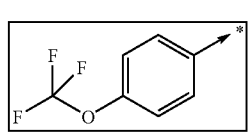 | 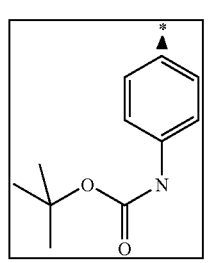 | 76% | 7.4 | 638.3 | |
| 758 | C32H30F3N5O4S | 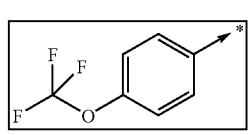 | 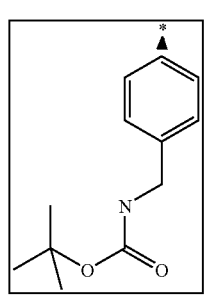 | 74% | 7.3 | 652.3 | |
| 759 | C34H36N6O4S | 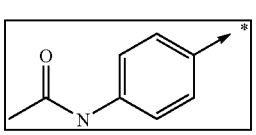 | 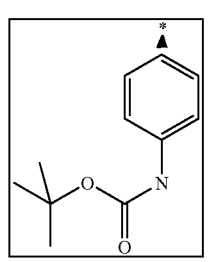 | 78% | 6.1 | 611.3 | |
| 760 | C33H34N6O4S | 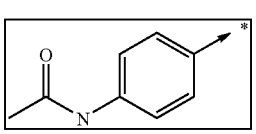 | 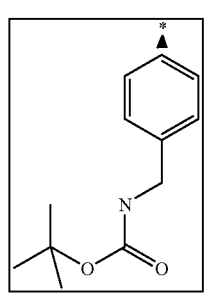 | 76% | 6.0 | 625.3 | |

-continued
| | | | | | | |
|---|---|---|---|---|---|---|
| 761 | C32H32N6O5S | 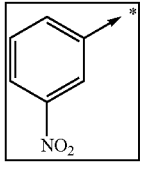 | 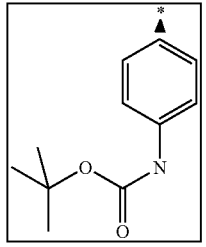 | 74% | 6.9 | 599.2 |
| 762 | C31H30N6O5S | 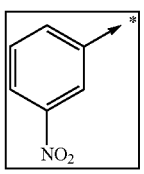 | 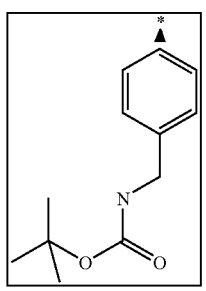 | 69% | 6.8 | 613.3 |
| 763 | C32H39N5O3S | 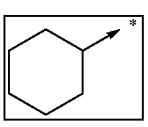 | 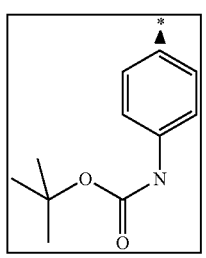 | 78% | 7.3 | 560.3 |
| 764 | C31H37N5O3S | 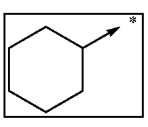 | 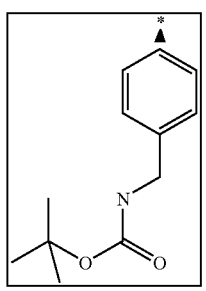 | 74% | 7.5 | 574.3 |
| 765 | C31H34N6O4S | 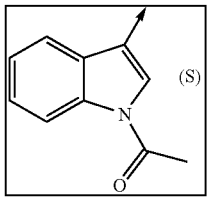 | 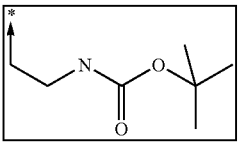 | 76% | 6.9 | 587.2 |
| 766 | C32H36N6O4S | 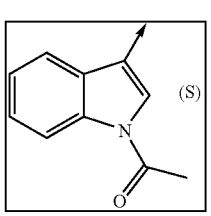 | 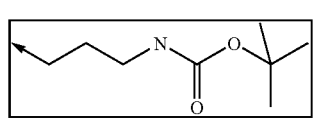 | 88% | 6.8 | 601.3 |

| | | | | | | |
|---|---|---|---|---|---|---|
| 767 | C33H38N6O4S | 1-acetylindol-3-yl (S) | *-(CH2)4-NH-C(O)-O-C(CH3)3 | 81% | 6.8 | 615.3 |
| 768 | C34H40N6O4S | 1-acetylindol-3-yl (S) | *-(CH2)5-NH-C(O)-O-C(CH3)3 | 84% | 7.0 | 629.3 |
| 769 | C35H42N6O4S | 1-acetylindol-3-yl (S) | *-(CH2)6-NH-C(O)-O-C(CH3)3 | 78% | 7.2 | 643.4 |
| 770 | C36H36N6O4S | 1-acetylindol-3-yl (S) | *-(p-C6H4)-CH2-NH-C(O)-O-C(CH3)3 | 83% | 6.8 | 649.3 |
| 771 | C31H34N6O4S | 1-acetylindol-3-yl (S) | *-(CH2)2-NH-C(O)-O-C(CH3)3 | 81% | 6.9 | 587.2 |
| 772 | C32H36N6O4S | 1-acetylindol-3-yl (R) | *-(CH2)3-NH-C(O)-O-C(CH3)3 | 76% | 6.8 | 601.3 |
| 773 | C33H38N6O4S | 1-acetylindol-3-yl (R) | *-(CH2)4-NH-C(O)-O-C(CH3)3 | 82% | 6.8 | 615.3 |

-continued

| | | | | | | |
|---|---|---|---|---|---|---|
| 774 | C34H40N6O4S | [indole (R), N-acetyl] | [hexyl-NH-C(O)-O-tBu] | 84% | 7.0 | 629.3 |
| 775 | C35H42N6O4S | [indole (R), N-acetyl] | [heptyl-NH-C(O)-O-tBu] | 13% | 7.2 | 643.3 |
| 776 | C36H36N6O4S | [indole (R), N-acetyl] | [4-(CH2-NH-C(O)-O-tBu)-phenyl] | 71% | 6.8 | 649.3 |
| 777 | C26H26N6O2S | [indole (S), N-acetyl] | [CH2-CH2-NH2] | 84% | 4.4 | 487.3 |
| 778 | C27H28N6O2S | [indole (S), N-acetyl] | [(CH2)3-NH2] | 85% | 4.4 | 501.3 |
| 779 | C28H30N6O2S | [indole (S), N-acetyl] | [(CH2)4-NH2] | 65% | 4.4 | 515.3 |
| 780 | C29H32N6O2S | [indole (S), N-acetyl] | [(CH2)5-NH2] | 75% | 4.6 | 529.3 |

-continued

| | | | | | | |
|---|---|---|---|---|---|---|
| 781 | C30H34N6O2S | 1-acetylindol-3-yl (S) | hexyl-N | 84% | 4.7 | 543.3 |
| 782 | C31H28N6O2S | 1-acetylindol-3-yl (S) | 4-(CH2-N)-phenyl | 82% | 4.5 | 549.3 |
| 783 | C26H26N6O2S | 1-acetylindol-3-yl (R) | ethyl-N | 87% | 4.4 | 487.3 |
| 784 | C27H28N6O2S | 1-acetylindol-3-yl (R) | propyl-N | 87% | 4.4 | 501.3 |
| 785 | C28H30N6O2S | 1-acetylindol-3-yl (R) | butyl-N | 83% | 4.4 | 515.3 |
| 786 | C29H32N6O2S | 1-acetylindol-3-yl (R) | pentyl-N | 91% | 4.5 | 529.3 |
| 787 | C30H34N6O2S | 1-acetylindol-3-yl (R) | hexyl-N | 84% | 4.7 | 543.3 |

| | | | | | | |
|---|---|---|---|---|---|---|
| 788 | C31H28N6O2S | 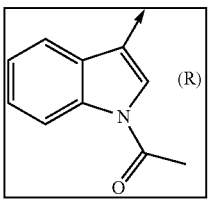 | 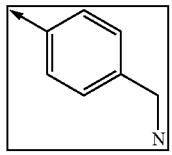 | 79% | 4.5 | 549.3 |
| 789 | C24H24N6OS | 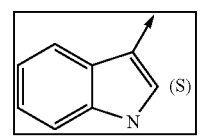 | 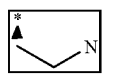 | 42% | 4.3 | 445.3 |
| 790 | C25H26N6OS | 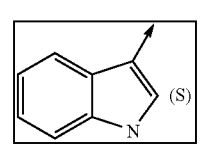 | 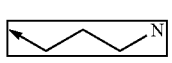 | 72% | 4.1 | 459.3 |
| 791 | C26H28N6OS | 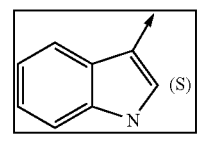 | 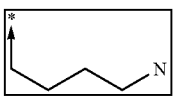 | 87% | 4.1 | 473.4 |
| 792 | C27H30N6OS | 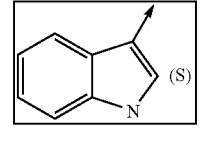 |  | 88% | 4.3 | 487.4 |
| 793 | C28H32N6OS | 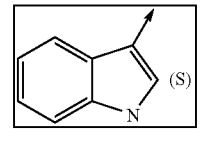 | 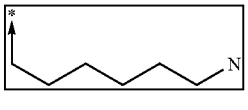 | 92% | 4.4 | 501.4 |
| 794 | C29H26N6OS | 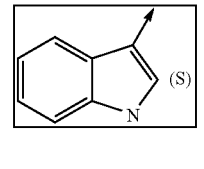 | 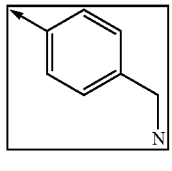 | 78% | 4.3 | 507.3 |
| 795 | C24H24N6OS | 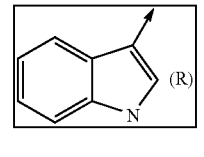 | 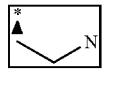 | 46% | 4.3 | 445.3 |
| 796 | C25H26N6OS | 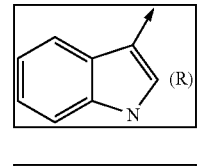 |  | 71% | 4.1 | 459.3 |
| 797 | C26H28N6OS | 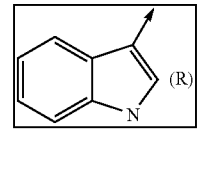 | 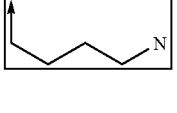 | 93% | 4.1 | 473.4 |

-continued
| Ex. No. | Formula | | | Purity | rt (min) | [M + H]+ |
|---|---|---|---|---|---|---|
| 798 | C27H30N6OS | indol-3-yl (R) | chain with N | 94% | 4.3 | 487.4 |
| 799 | C28H32N6OS | indol-3-yl (R) | chain with N | 86% | 4.5 | 501.4 |
| 800 | C29H26N6OS | indol-3-yl (R) | benzyl-N | 77% | | 507.3 |
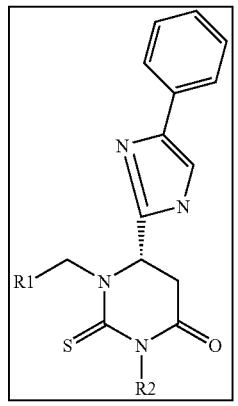
| | | | | | Analyses | |
|---|---|---|---|---|---|---|
| Ex. No. | Formula | R1 | R2 | Purity | rt (min) | [M + H]+ |
| 801 | C30H30N4OS | 4-isopropylphenyl | benzyl | 96% | 7.7 | 495.3 |
| 802 | C30H29ClN4OS | 4-isopropylphenyl | 2-chlorobenzyl | 97% | 8.1 | 529.3 |
| 803 | C30H28Cl2N4OS | 4-isopropylphenyl | 3,4-dichlorobenzyl | 99% | 8.6 | 563.2 |

| | | | | | | |
|---|---|---|---|---|---|---|
| 804 | C31H32N4OS | 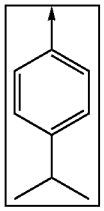 | 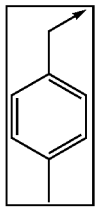 | 95% | 7.9 | 509.3 |
| 805 | C30H29FN4OS | 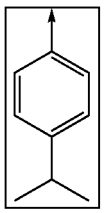 | 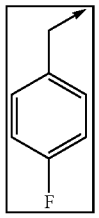 | 96% | 7.8 | 513.3 |
| 806 | C31H32N4OS | 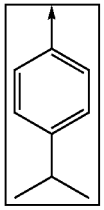 | 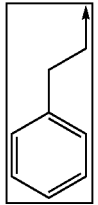 | 93% | 7.9 | 509.3 |
| 807 | C31H31ClN4OS | 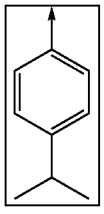 | 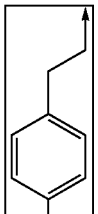 | 95% | 8.4 | 543.3 |
| 808 | C33H36N4O3S | 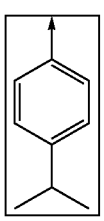 | 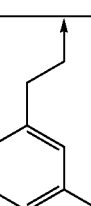 | 93% | 7.4 | 569.3 |
| 809 | C32H34N4OS | 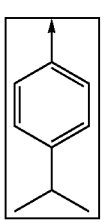 | 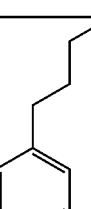 | 94% | 8.1 | 523.3 |

| | | | | | | |
|---|---|---|---|---|---|---|
| 810 | C28H28N4O2S | 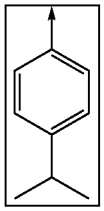 | 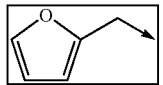 | 96% | 7.2 | 485.3 |
| 811 | C28H32N4O2S | 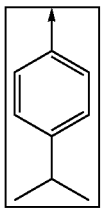 | 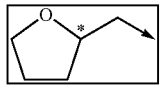 | 37 + 44% | 6.7 + 6.84 | 489.3 |
| 812 | C29H35N5O2S | 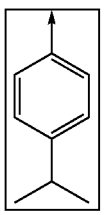 | 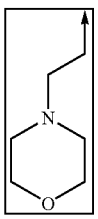 | 88% | 5.3 | 518.3 |
| 813 | C30H37N5O2S | 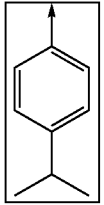 | 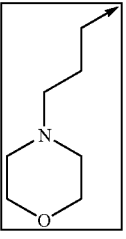 | 94% | 5.3 | 532.4 |
| 814 | C30H39N5OS | 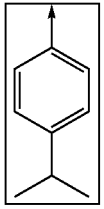 | 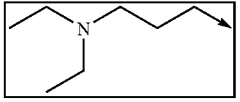 | 89% | 5.4 | 518.4 |
| 815 | C26H30N4O2S | 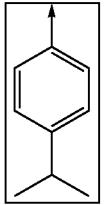 |  | 92% | 6.7 | 463.3 |
| 816 | C27H32N4O2S | 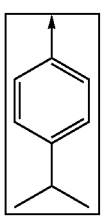 |  | 91% | 6.9 | 477.3 |

-continued
| | | | | | | |
|---|---|---|---|---|---|---|
| 817 | C29H27N5O2S | 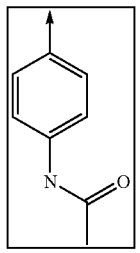 | 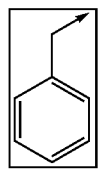 | 93% | 6.0 | 510.3 |
| 818 | C29H26ClN5O2S | 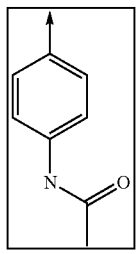 | 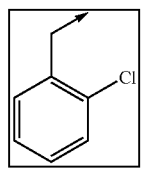 | 87% | 6.5 | 544.2 |
| 819 | C29H25Cl2N5O2S | 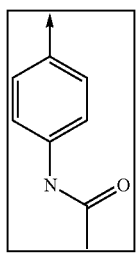 | 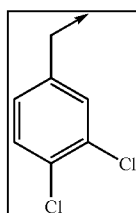 | 74% | 6.9 | 578.2 |
| 820 | C20H29N5O2S | 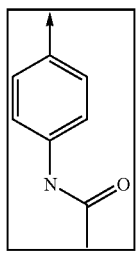 | 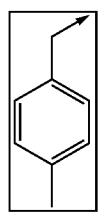 | 94% | 6.2 | 524.3 |
| 821 | C29H26FN5O2S | 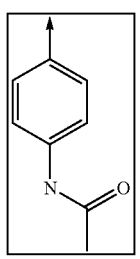 | 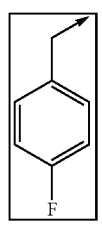 | 94% | 6.2 | 528.3 |
| 822 | C30H29N5O2S | 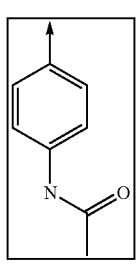 | 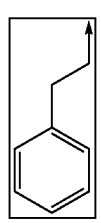 | 93% | 6.3 | 524.3 |

| | | | | | | |
|---|---|---|---|---|---|---|
| 823 | C30H28ClN5O2S | 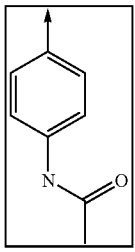 | 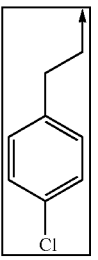 | 93% | 6.7 | 558.2 |
| 824 | C32H33N5O4S | 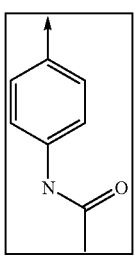 | 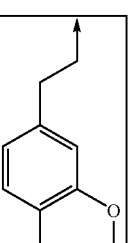 | 91% | 5.7 | 584.3 |
| 825 | C31H31N5O2S | 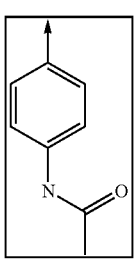 | 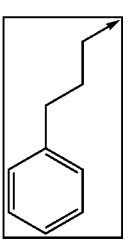 | 89% | 6.5 | 538.3 |
| 826 | C27H25N5O3S | 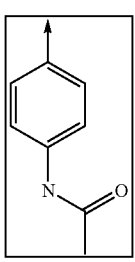 | 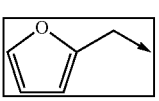 | 90% | 5.5 | 500.3 |
| 827 | C27H29N5O3S | 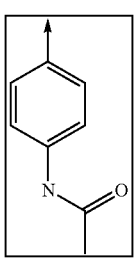 | 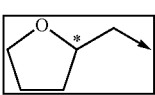 | 27% + 24 | 4.99 + 5.1 | 504.3 |
| 828 | C28H32N6O3S | 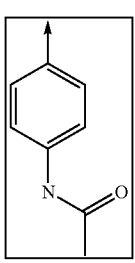 | 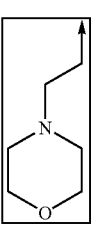 | 85% | 3.9 | 533.3 |

| | | | | | | |
|---|---|---|---|---|---|---|
| 829 | C29H34N6O3S | 4-acetamidophenyl | 4-morpholinobutyl | 87% | 3.9 | 547.3 |
| 830 | C29H36N6O2S | 4-acetamidophenyl | 4-(diethylamino)butyl | 88% | 4.1 | 533.3 |
| 831 | C25H27N5O3S | 4-acetamidophenyl | 2-methoxyethyl | 92% | 4.9 | 478.3 |
| 832 | C26H29N5O3S | 4-acetamidophenyl | 3-methoxypropyl | 93% | 5.1 | 492.3 |
| 833 | C27H23N5O3S | 3-nitrophenyl | benzyl | 93% | 7.0 | 498.3 |
| 834 | C27H22ClN5O3S | 3-nitrophenyl | 2-chlorobenzyl | 85% | 7.4 | 532.2 |

-continued
| | | | | | | |
|---|---|---|---|---|---|---|
| 835 | C27H21Cl2N5O3S | 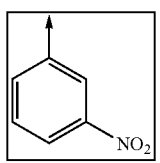 | 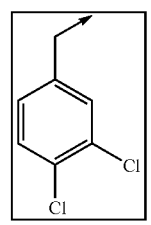 | 88% | 7.8 | 566.1 |
| 836 | C28H25N5O3S | 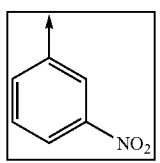 | 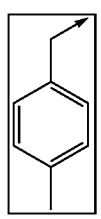 | 90% | 7.3 | 512.3 |
| 837 | C27H22FN5O3S | 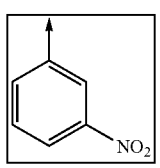 | 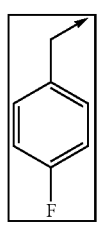 | 88% | 7.1 | 516.2 |
| 838 | C28H25N5O3S | 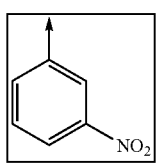 | 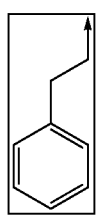 | 90% | 7.3 | 512.3 |
| 839 | C28H24ClN5O3S | 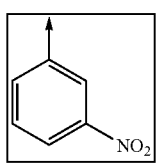 | 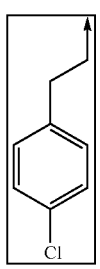 | 91% | 7.8 | 546.2 |
| 840 | C30H29N5O5S | 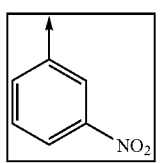 | 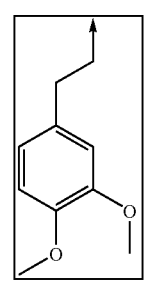 | 92% | 6.8 | 572.2 |

-continued

| | | | | | | |
|---|---|---|---|---|---|---|
| 841 | C29H27N5O3S | 3-NO2-phenyl | phenylpropyl | 94% | 7.5 | 526.3 |
| 842 | C25H21N5O4S | 3-NO2-phenyl | furan-2-ylmethyl | 89% | 6.6 | 488.2 |
| 843 | C25H25N5O4S | 3-NO2-phenyl | (tetrahydrofuran-2-yl)methyl* | 46% + 45 | 6.24 + 6.4 | 492.3 |
| 844 | C26H28N6O4S | 3-NO2-phenyl | morpholinoethyl | 82% | 4.6 | 521.3 |
| 845 | C27H30N6O4S | 3-NO2-phenyl | morpholinopropyl | 84% | 4.6 | 535.3 |
| 846 | C27H32N6O3S | 3-NO2-phenyl | diethylaminopropyl | 76% | 4.8 | 521.3 |
| 847 | C23H23N5O4S | 3-NO2-phenyl | methoxyethyl | 90% | 6.1 | 466.2 |
| 848 | C24H25N5O4S | 3-NO2-phenyl | methoxypropyl | 90% | 6.3 | 480.3 |

-continued
| | | | | | | |
|---|---|---|---|---|---|---|
| 849 | C24H21N5OS2 | 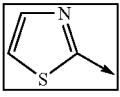 | 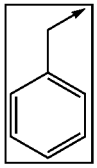 | 87% | 6.1 | 460.2 |
| 850 | C24H20ClN5OS2 | 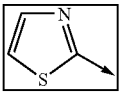 | 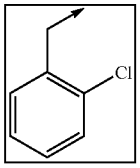 | 53% | 6.6 | 494.1 |
| 851 | C24H19Cl2N5OS2 | 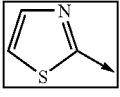 | 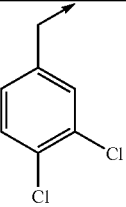 | 85% | 7.0 | 528.0 |
| 852 | C25H23N5OS2 | 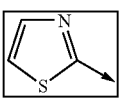 | 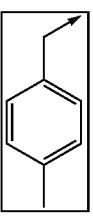 | 79% | 6.2 | 474.1 |
| 853 | C24H20FN5OS2 | 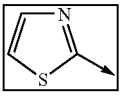 | 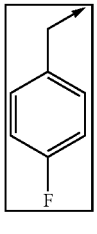 | 76% | 6.2 | 478.1 |
| 854 | C25H23N5OS2 | 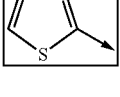 | 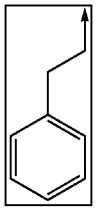 | 74% | 6.4 | 474.1 |
| 855 | C25H22ClN5OS2 | 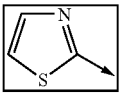 | 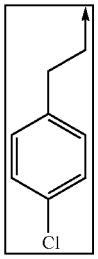 | 82% | 6.9 | 508.1 |

-continued
| | | | | | | |
|---|---|---|---|---|---|---|
| 856 | C27H27N5O3S2 | 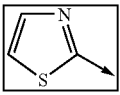 | 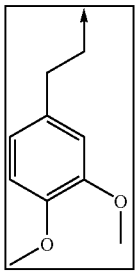 | 73% | 5.8 | 534.1 |
| 857 | C26H25N5OS2 | 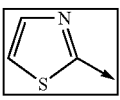 | 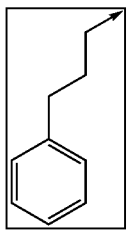 | 74% | 6.6 | 488.1 |
| 858 | C22H19N5O2S2 | 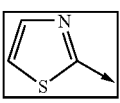 | 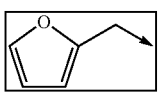 | 77% | 5.5 | 450.1 |
| 859 | C22H23N5O2S2 | 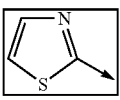 | 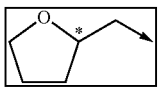 | 23 + 25% | 5.2 + 5.33 | 454.1 |
| 860 | C23H26N6O2S2 | 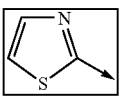 | 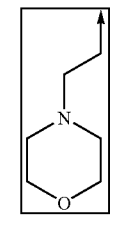 | 78% | 3.9 | 483.2 |
| 861 | C24H28N6O2S2 | 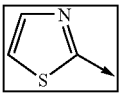 | 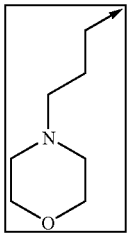 | 68% | 3.9 | 497.2 |
| 862 | C24H30N6OS2 | 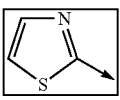 | 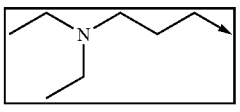 | 59% | 4.1 | 483.2 |
| 863 | C20H21N5O2S2 | 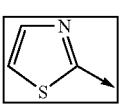 |  | 68% | 5.0 | 428.1 |
| 864 | C21H23N5O2S2 | 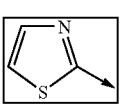 | 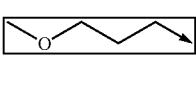 | 65% | 5.3 | 442.1 |

-continued
| | | | | | | | |
|---|---|---|---|---|---|---|---|
| 865 | C27H30N4OS |  | | 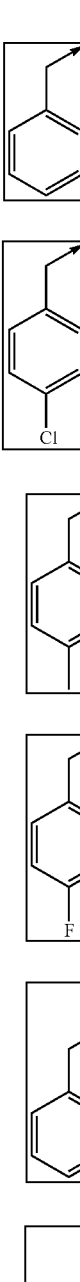 | 97% | 7.4 | 459.2 |
| 866 | C27H29ClN4OS |  | | 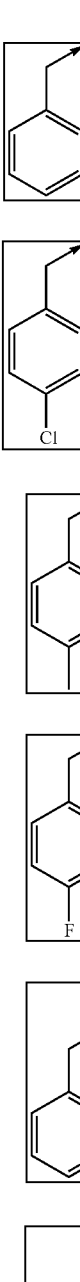 | 98% | 7.9 | 493.2 |
| 867 | C27H28Cl2N4OS |  | | 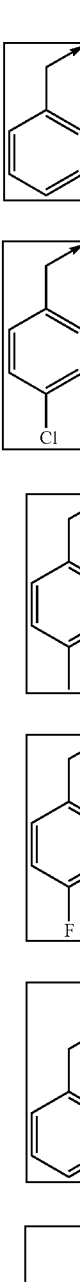 | 97% | 8.4 | 527.1 |
| 868 | C28H32N4OS |  | | 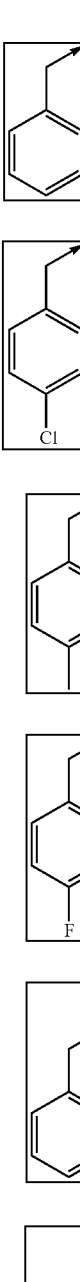 | 98% | 7.6 | 473.2 |
| 869 | C27H29FN4OS |  | | 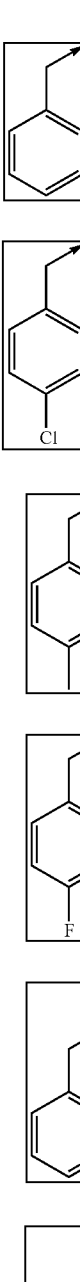 | 96% | 7.6 | 477.2 |
| 870 | C28H32N4OS |  | | 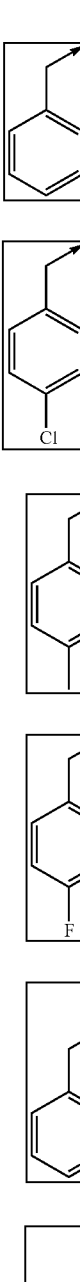 | 94% | 7.7 | 473.2 |
| 871 | C28H31ClN4OS |  | | 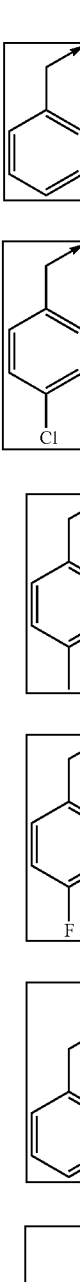 | 96% | 8.3 | 507.2 |

-continued

| | | | | | | |
|---|---|---|---|---|---|---|
| 872 | C30H36N4O3S | | | 94% | 7.2 | 533.2 |
| 873 | C29H34N4OS | | | 91% | 7.9 | 487.2 |
| 874 | C25H28N4O2S | | | 95% | 6.9 | 449.2 |
| 875 | C25H32N4O2S | | | 38 + 8% | 6.9 + 7.04 | 453.2 |
| 876 | C26H35N5O2S | | | 94% | 5.0 | 482.2 |
| 877 | C27H37N5O2S | | | 93% | 5.0 | 496.3 |
| 878 | C27H39N5OS | | | 94% | 5.2 | 482.3 |

| | | | | | | |
|---|---|---|---|---|---|---|
| 879 | C23H30N4O2S | 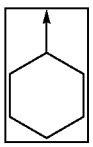 | 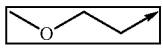 | 95% | 6.5 | 427.2 |
| 880 | C24H32N4O2S | 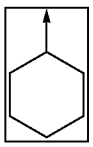 |  | 97% | 6.7 | 441.2 |
| 881 | C29H27ClN4OS | 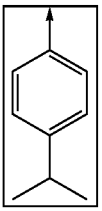 | 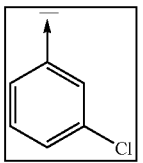 | 78% | 7.7 | 515.2 |
| 882 | C29H28N4OS | 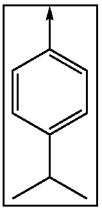 | 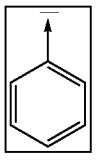 | 59% | 7.2 | 481.2 |
| 883 | C21H32N4OS | 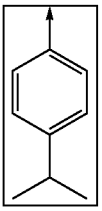 | 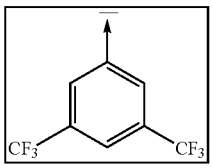 | 63% | 8.6 | 617.2 |
| 884 | C31H30N4O2S | 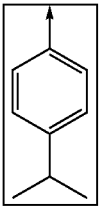 | 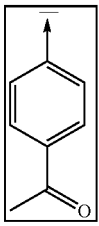 | 61% | 7.1 | 523.2 |
| 885 | C32H34N4OS | 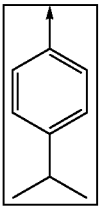 | 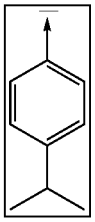 | 60% | 7.9 | 523.3 |

-continued

| | | | | | | |
|---|---|---|---|---|---|---|
| 886 | C31H33N5OS | 4-isopropylphenyl | 4-(dimethylamino)phenyl | 28% | 6.7 | 524.2 |
| 887 | C29H27N5O3S | 4-isopropylphenyl | 4-nitrophenyl | 53% | 7.6 | 526.2 |
| 888 | C29H27BrN4OS | 4-isopropylphenyl | 4-bromophenyl | 68% | 7.8 | 559.1 |
| 889 | C29H26F2N4OS | 4-isopropylphenyl | 2,6-difluorophenyl | 62% | 7.3 | 517.2 |
| 890 | C29H27N7OS | 4-isopropylphenyl | 4-azidophenyl | 64% | 7.6 | 522.2 |
| 891 | C30H27N5OS | 4-isopropylphenyl | 3-cyanophenyl | 66% | 7.3 | 506.2 |
| 892 | C20H28N4O3S | 4-isopropylphenyl | benzo[1,3]dioxol-5-yl | 62% | 7.1 | 525.2 |

-continued
| | | | | | | | |
|---|---|---|---|---|---|---|---|
| 893 | C29H26ClN5O3S | 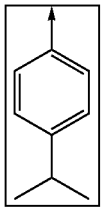 | 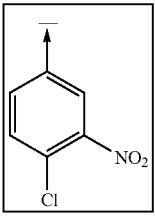 | | 55% | 7.9 | 560.1 |
| 894 | C33H36N4OS | 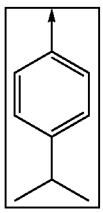 | 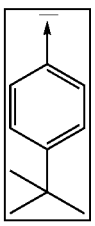 | | 59% | 8.1 | 537.3 |
| 895 | C30H30N4OS | 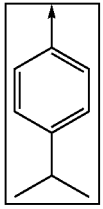 | 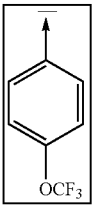 | | 67% | 7.9 | 565.2 |
| 896 | C31H32N4OS | 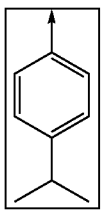 | 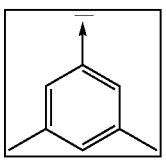 | | 57% | 7.7 | 509.2 |
| 897 | C28H24ClN5O2S | 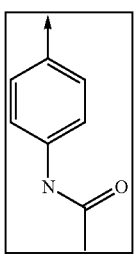 | 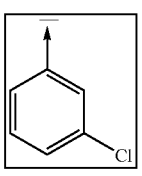 | | 64% | 6.2 | 530.1 |
| 898 | C28H25N5O2S | 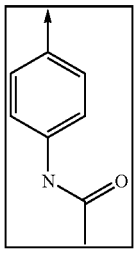 | 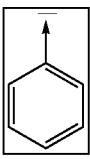 | | 64% | 5.6 | 496.2 |

-continued
| | | | | | | | |
|---|---|---|---|---|---|---|---|
| 899 | C30H29N5O2S | 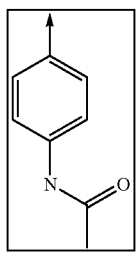 | | 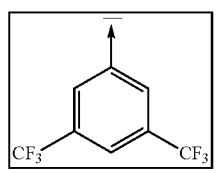 | 52% | 7.1 | 632.2 |
| 900 | C30H27N5O3S | 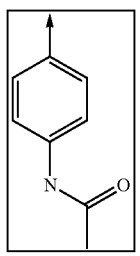 | | 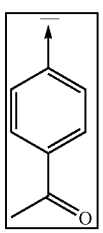 | 57% | 5.5 | 538.2 |
| 901 | C31H31NSO2S | 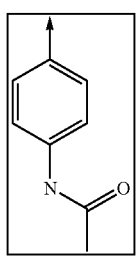 | | 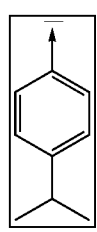 | 65% | 6.4 | 538.2 |
| 902 | C30H30N6O2S | 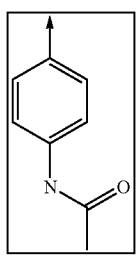 | | 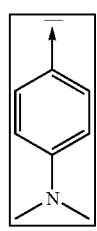 | 29% | 5.0 | 539.2 |
| 903 | C28H24N6O4S | 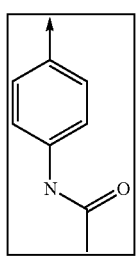 | | 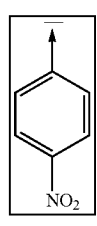 | 51% | 6.0 | 541.2 |
| 904 | C28H24BrN5O2S | 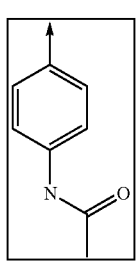 | | 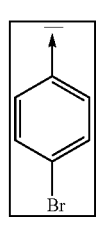 | 72% | 6.3 | 574.0 |

-continued
| | | | | | | |
|---|---|---|---|---|---|---|
| 905 | C28H23F2N5O2S | 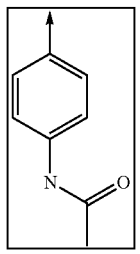 | 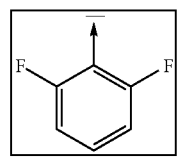 | 66% | 5.7 | 532.2 |
| 906 | C28H24N8O2S | 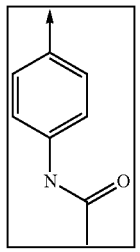 | 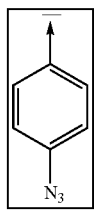 | 52% | 6.1 | 537.2 |
| 907 | C29H24N6O2S | 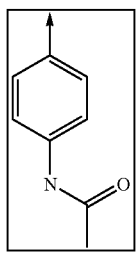 | 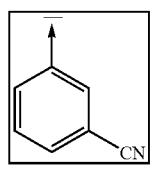 | 65% | 5.7 | 521.1 |
| 908 | C29H25N5O4S | 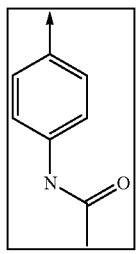 | 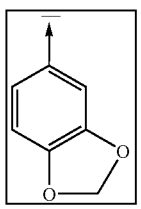 | 66% | 5.5 | 540.1 |
| 909 | C28H23ClN6O4S | 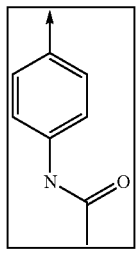 | 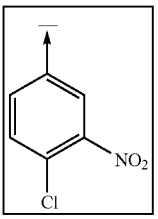 | 55% | 6.4 | 575.1 |
| 910 | C32H33N5O2S | 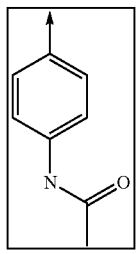 | 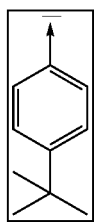 | 64% | 6.6 | 552.2 |

-continued

| # | Formula | Ar1 | Ar2 | % | t | MS |
|---|---|---|---|---|---|---|
| 911 | C29H27N5O2S | 4-(NHC(O)CH3)-C6H4 | 4-OCF3-C6H4 | 68% | 6.5 | 580.1 |
| 912 | C30H29N5O2S | 4-(NHC(O)CH3)-C6H4 | 3,5-dimethyl-C6H3 | 68% | 6.1 | 524.2 |
| 913 | C26H20ClN5O3S | 3-NO2-C6H4 | 3-Cl-C6H4 | 60% | 7.0 | 518.1 |
| 914 | C26H21N5O3S | 3-NO2-C6H4 | C6H5 | 63% | 6.6 | 484.2 |
| 915 | C28H25N5O3S | 3-NO2-C6H4 | 3,5-(CF3)2-C6H3 | 41% | 7.8 | 620.1 |
| 916 | C28H23N5O4S | 3-NO2-C6H4 | 4-C(O)CH3-C6H4 | 51% | 6.4 | 526.1 |
| 917 | C29H27N5O3S | 3-NO2-C6H4 | 4-iPr-C6H4 | 64% | 7.3 | 526.2 |

-continued
| | | | | | | |
|---|---|---|---|---|---|---|
| 918 | C28H26N6O3S | 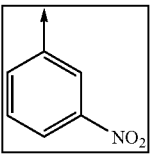 | 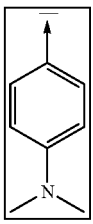 | 21% | 6.2 | 527.2 |
| 919 | C26H20N6O5S | 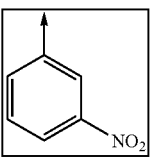 | 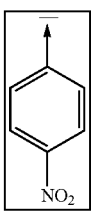 | 27% | 6.8 | 529.1 |
| 920 | C26H20BrN5O3S | 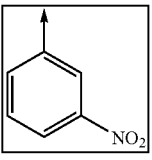 | 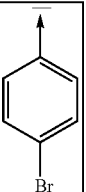 | 61% | 7.2 | 562.0 |
| 921 | C26H19F2N5O3S | 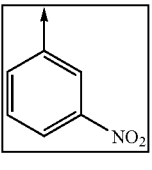 | 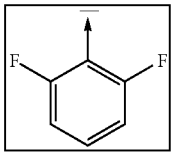 | 55% | 6.6 | 520.1 |
| 922 | C26H20N8O3S | 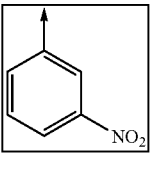 | 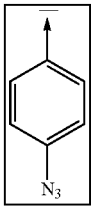 | 61% | 7.0 | 525.1 |
| 923 | C27H20N6O3S | 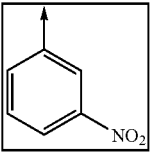 | 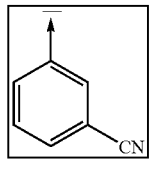 | 50% | 6.6 | 509.1 |
| 924 | C27H21N5O5S | 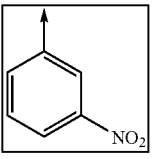 | 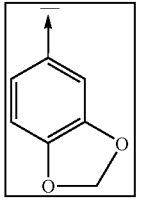 | 68% | 6.5 | 528.1 |

-continued
| | | | | | | |
|---|---|---|---|---|---|---|
| 925 | C26H19ClN6O5S | 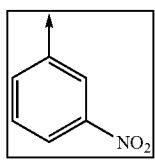 | 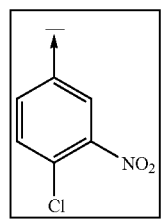 | 44% | 7.2 | 563.1 |
| 926 | C30H29N5O3S | 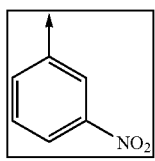 | 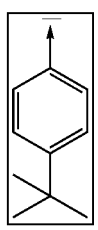 | 60% | 7.5 | 540.2 |
| 927 | C27H23N5O3S | 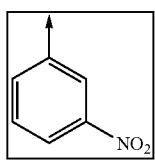 | 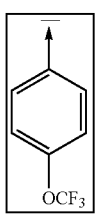 | 62% | 7.3 | 568.1 |
| 928 | C28H25N5O3S | 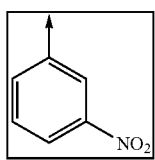 | 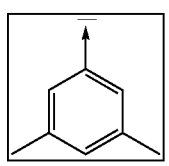 | 60% | 7.0 | 512.2 |
| 929 | C23H18ClN5OS2 | 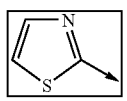 | 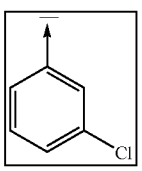 | 28% | 6.4 | 480.1 |
| 930 | C23H19N5OS2 | 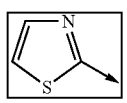 | 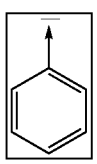 | 22% | 5.8 | 446.1 |
| 931 | C25H23N5OS2 | 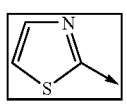 | 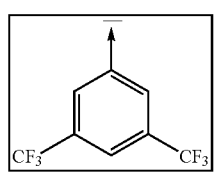 | 34% | 7.3 | 582.1 |

-continued
| | | | | | | |
|---|---|---|---|---|---|---|
| 932 | C25H21N5O2S2 | 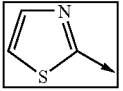 | 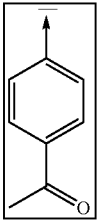 | 25% | 5.7 | 488.1 |
| 933 | C26H25N5OS2 | 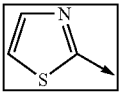 | 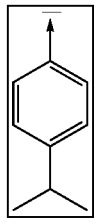 | 21% | 6.6 | 488.1 |
| 934 | C25H24N6OS2 | 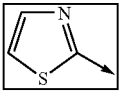 | 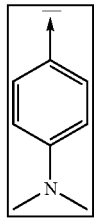 | 13% | 5.3 | 489.1 |
| 935 | C23H18N6O3S2 | 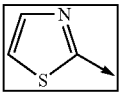 | 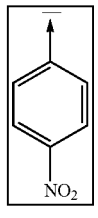 | 23% | 6.2 | 491.1 |
| 936 | C23H18BrN5OS2 | 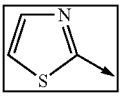 | 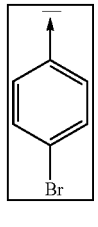 | 38% | 6.5 | 524.0 |
| 937 | C23H17F2N5OS2 | 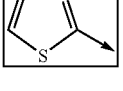 | 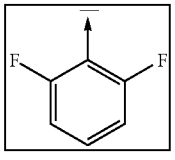 | 58% | 5.8 | 482.1 |
| 938 | C23H18N8OS2 | 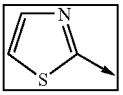 | 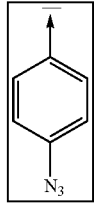 | 28% | 6.3 | 487.1 |

-continued

| # | Formula | R1 | R2 | % | t | M |
|---|---|---|---|---|---|---|
| 939 | C24H18N6OS2 | thiazol-2-yl | 3-cyanophenyl | 32% | 5.9 | 471.1 |
| 940 | C24H19N5O3S2 | thiazol-2-yl | benzo[1,3]dioxol-5-yl | 23% | 5.7 | 490.1 |
| 941 | C23H17ClN6O3S2 | thiazol-2-yl | 4-chloro-3-nitrophenyl | 33% | 6.7 | 525.0 |
| 942 | C27H27N5OS2 | thiazol-2-yl | 4-tert-butylphenyl | 29% | 6.8 | 502.2 |
| 943 | C24H21N5OS2 | thiazol-2-yl | 4-(trifluoromethoxy)phenyl | 35% | 6.7 | 530.1 |
| 944 | C25H23N5OS2 | thiazol-2-yl | 3,5-dimethylphenyl | 16% | 6.3 | 474.1 |
| 945 | C26H27ClN4OS | cyclohexyl | 3-chlorophenyl | 61% | 7.5 | 479.2 |
| 946 | C26H28N4OS | cyclohexyl | phenyl | 54% | 7.0 | 445.2 |

-continued

| | | | | | | |
|---|---|---|---|---|---|---|
| 947 | C28H32N4OS | cyclohexyl | 3,5-bis(CF3)phenyl | 61% | 8.4 | 581.1 |
| 948 | C28H30N4O2S | cyclohexyl | 4-acetylphenyl | 49% | 6.9 | 487.2 |
| 949 | C29H34N4OS | cyclohexyl | 4-isopropylphenyl | 57% | 7.7 | 487.2 |
| 950 | C28H33N5OS | cyclohexyl | 4-(dimethylamino)phenyl | 16% | 6.4 | 488.2 |
| 951 | C26H27N5O3S | cyclohexyl | 4-nitrophenyl | 44% | 7.4 | 490.2 |
| 952 | C26H27BrN4OS | cyclohexyl | 4-bromophenyl | 70% | 7.6 | 523.1 |
| 953 | C26H26F2N4OS | cyclohexyl | 2,6-difluorophenyl | 61% | 7.0 | 481.2 |

-continued

| | | | | | | |
|---|---|---|---|---|---|---|
| 954 | C26H27N7OS | cyclohexyl | 4-N3-phenyl | 66% | 7.4 | 486.2 |
| 955 | C27H27N5OS | cyclohexyl | 3-CN-phenyl | 68% | 7.1 | 470.2 |
| 956 | C27H28N4O3S | cyclohexyl | 3,4-methylenedioxyphenyl | 63% | 6.9 | 489.2 |
| 957 | C26H26ClN5O3S | cyclohexyl | 4-Cl-3-NO2-phenyl | 66% | 7.7 | 524.1 |
| 958 | C30H36N4OS | cyclohexyl | 4-tBu-phenyl | 58% | 7.9 | 501.3 |
| 959 | C27H30N4OS | cyclohexyl | 4-OCF3-phenyl | 64% | 7.7 | 529.2 |
| 960 | C28H32N4OS | cyclohexyl | 3,5-dimethylphenyl | 46% | 7.5 | 473.2 |

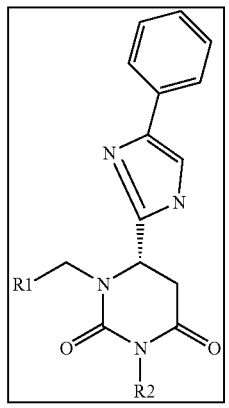
| Ex. No. | Formula | R1 | R2 | Purity | rt (min) | [M + H]+ |
|---|---|---|---|---|---|---|
| 961 | C30H30N4O3 | 4-isopropylphenyl | 3-methoxyphenyl | 57% | 10.5 | 495.2 |
| 962 | C30H27F3N4O2 | 4-isopropylphenyl | 3-(trifluoromethyl)phenyl | 69% | 11.6 | 533.2 |
| 963 | C29H28N4O2 | 4-isopropylphenyl | phenyl | 69% | 10.4 | 465.2 |
| 964 | C29H27N5O4 | 4-isopropylphenyl | 3-nitrophenyl | 61% | 11.0 | 510.2 |
| 965 | C30H29ClN4O2 | 4-isopropylphenyl | 3-chloro-4-methylphenyl | 74% | 11.6 | 513.2 |

-continued
| 966 | C32H32N4O4 | 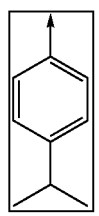 | 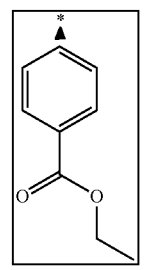 | 52% | 11.0 | 537.2 |
| 967 | C29H27BrN4O2 | 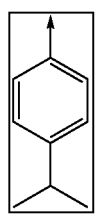 | 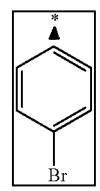 | 76% | 11.2 | 543.1 |
| 968 | C29H27FN4O2 | 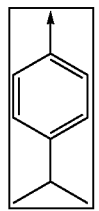 | 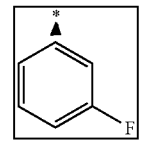 | 60% | 10.7 | 483.2 |
| 969 | C29H26Cl2N4O2 | 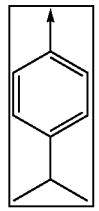 | 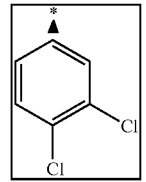 | 68% | 11.9 | 533.1 |
| 970 | C31H30N4O3 | 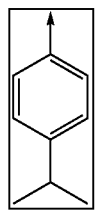 | 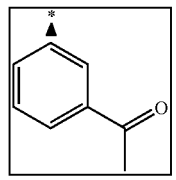 | 71% | 10.3 | 507.2 |
| 971 | C30H30N4O2S | 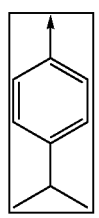 | 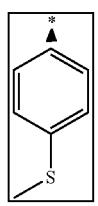 | 72% | 10.9 | 511.2 |

| | | | | | | |
|---|---|---|---|---|---|---|
| 972 | C30H27F3N4O3 | 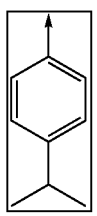 | 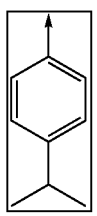 | 77% | 11.6 | 549.2 |
| 973 | C29H27BrN4O2 | | | 66% | 11.3 | 543.1 |
| 974 | C32H34N4O2 | 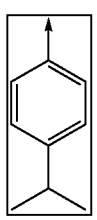 | | 85% | 11.5 | 507.3 |
| 975 | C29H26F2N4O2 | 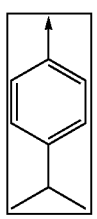 | | 72% | 10.8 | 501.2 |
| 976 | C32N34N4O5 | 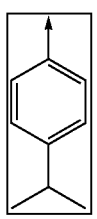 | | 71% | 10.3 | 555.2 |
| 977 | C29H27N5O4 | 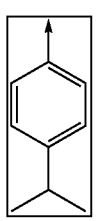 | 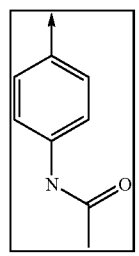 | 72% | 8.0 | 510.2 |

| | | | | | | |
|---|---|---|---|---|---|---|
| 978 | C29H24F3N5O3 | 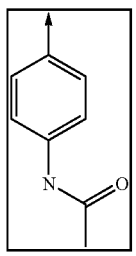 | 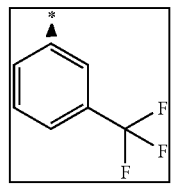 | 70% | 9.3 | 548.2 |
| 979 | C28H25N5O3 | 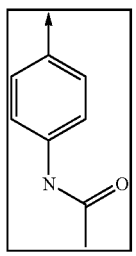 | 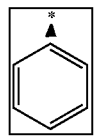 | 79% | 7.8 | 480.2 |
| 980 | C28H24N6O5 | 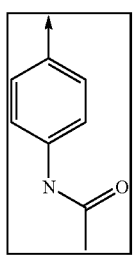 | 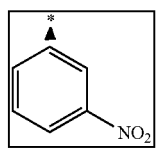 | 62% | 8.6 | 525.2 |
| 981 | C29H26ClN5O3 | 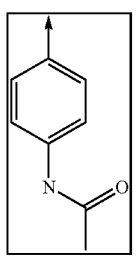 | 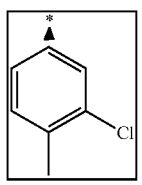 | 71% | 9.1 | 528.2 |
| 982 | C31H29N5O5 | 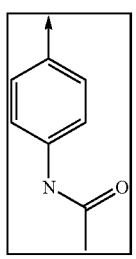 | 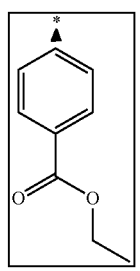 | 65% | 8.6 | 552.2 |
| 983 | C28H24BrN5O3 | 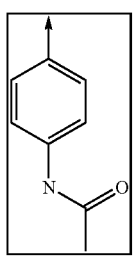 | 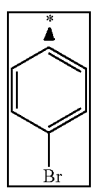 | 82% | 8.8 | 558.1 |

| | | | | | | |
|---|---|---|---|---|---|---|
| 984 | C28H24FN5O3 | 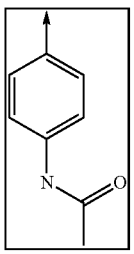 | | | 73% | 8.2 | 498.2 |
| 985 | C28H23Cl2N5O3 | 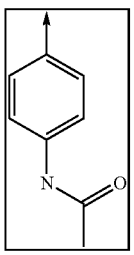 | | | 66% | 9.5 | 548.1 |
| 986 | C30H27N5O4 | 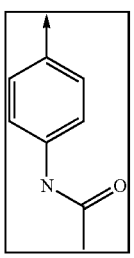 | | | 81% | 7.7 | 522.2 |
| 987 | C29H27N5O3S | 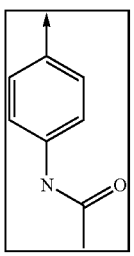 | | | 79% | 8.4 | 526.2 |
| 988 | C29H24F3N5O4 | 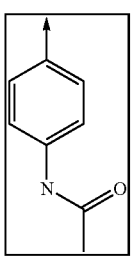 | | | 83% | 9.3 | 564.2 |
| 989 | C28H24BrN5O3 | 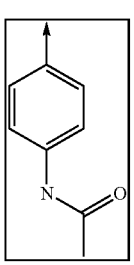 | | | 69% | 8.8 | 558.1 |

| | | | | | | |
|---|---|---|---|---|---|---|
| 990 | C31H31N5O3 | 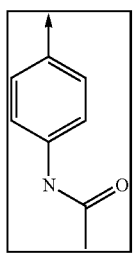 | 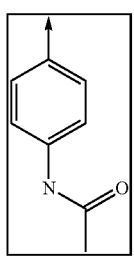 | 84% | 9.2 | 522.3 |
| 991 | C28H23F2N5O3 | | | 86% | 8.1 | 516.2 |
| 992 | C31H31N5O6 | 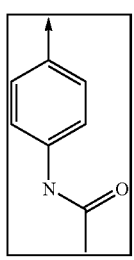 | | 60% | 7.7 | 570.2 |
| 993 | C27H23N5O5 | 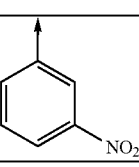 | | 76% | 9.5 | 498.2 |
| 994 | C27H20F3N5O4 | 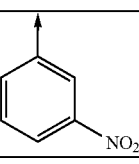 | | 71% | 10.7 | 536.1 |
| 995 | C26H21N5O4 | 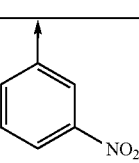 | | 85% | 9.4 | 488.2 |
| 996 | C26H20N6O6 | 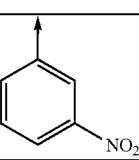 | | 56% | 10.0 | 513.2 |

-continued

| | | | | | | | |
|---|---|---|---|---|---|---|---|
| 997 | C27H22ClN5O4 | | 3-NO2-phenyl | | 2-Cl,methyl-phenyl | 77% | 10.7 | 516.1 |
| 998 | C29H25N5O6 | | 3-NO2-phenyl | | ethyl benzoate | 64% | 10.2 | 540.2 |
| 999 | C26H20BrN5O4 | | 3-NO2-phenyl | | 4-Br-phenyl | 83% | 10.4 | 546.0 |
| 1000 | C26H20FN5O4 | | 3-NO2-phenyl | | 3-F-phenyl | 74% | 9.8 | 486.2 |
| 1001 | C26H19Cl2N5O4 | | 3-NO2-phenyl | | 2,3-diCl-phenyl | 69% | 11.0 | 536.1 |
| 1002 | C28H23N5O5 | | 3-NO2-phenyl | | 3-acetyl-phenyl | 81% | 9.3 | 510.2 |
| 1003 | C27H23N5O4S | | 3-NO2-phenyl | | 4-SMe-phenyl | 79% | 10.1 | 514.1 |

-continued
| | | | | | | |
|---|---|---|---|---|---|---|
| 1004 | C27H20F3N5O5 | 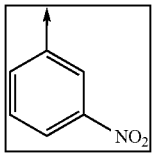 | 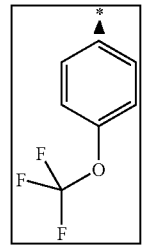 | 74% | 10.8 | 552.1 |
| 1005 | C26H20BrN5O4 | 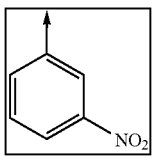 | 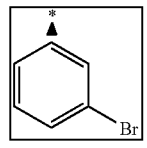 | 66% | 10.4 | 546.0 |
| 1008 | C29H27N5O4 | 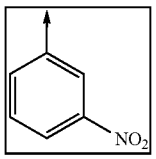 | 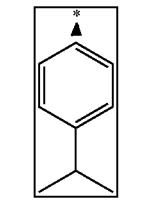 | 84% | 10.8 | 510.2 |
| 1007 | C26H19F2N5O4 | 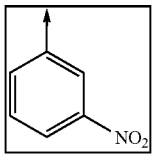 | 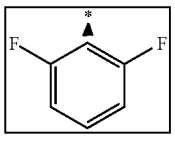 | 76% | 9.8 | 504.1 |
| 1008 | C29H27N5O7 | 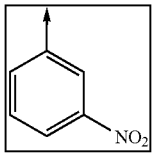 | 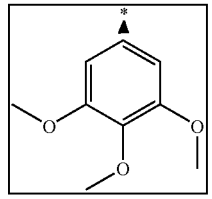 | 74% | 9.3 | 558.2 |
| 1009 | C24H21N5O3S | 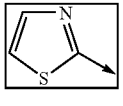 | 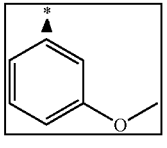 | 60% | 8.2 | 460.1 |
| 1010 | C24H18F3N5O2S | 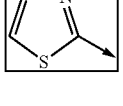 | 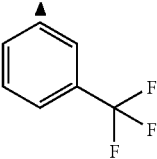 | 65% | 9.5 | 498.1 |
| 1011 | C23H19N5O2S | 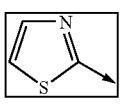 | 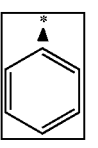 | 77% | 8.0 | 430.1 |

-continued
| | | | | | | |
|---|---|---|---|---|---|---|
| 1012 | C23H18N6O4S | 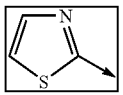 | 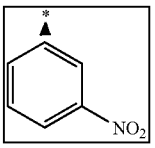 | 60% | 8.7 | 475.1 |
| 1013 | C24H20ClN5O2S | 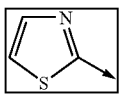 | 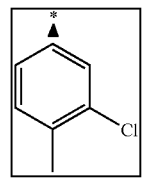 | 62% | 9.4 | 478.1 |
| 1014 | C26H23N5O4S | 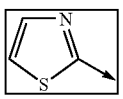 | 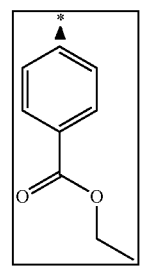 | 63% | 8.9 | 502.2 |
| 1015 | C23H18BrN5O2S | 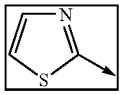 | 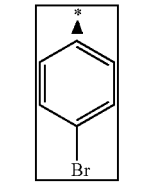 | 79% | 9.1 | 508.0 |
| 1016 | C23H18FN5O2S | 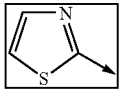 | 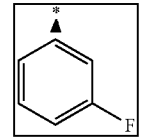 | 63% | 8.4 | 448.1 |
| 1017 | C23H17Cl2N5O2S | 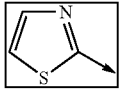 | 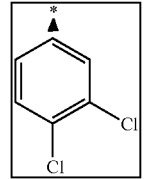 | 54% | 9.8 | 498.1 |
| 1018 | C25H21N5O3S | 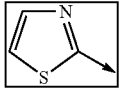 | 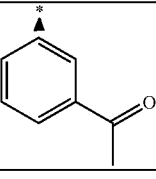 | 62% | 8.0 | 472.1 |
| 1019 | C24H21N5O2S2 | 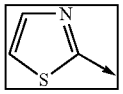 | 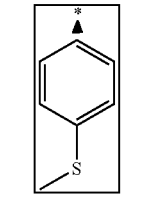 | 73% | 8.8 | 476.1 |

-continued
| | | | | | | | |
|---|---|---|---|---|---|---|---|
| 1020 | C24H18F3N5O3S | 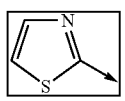 | | 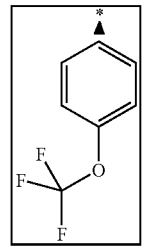 | 70% | 9.6 | 514.1 |
| 1021 | C23H18BrN5O2S | 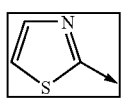 | | 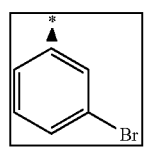 | 60% | 9.2 | 508.0 |
| 1022 | C26H25N5O2S | 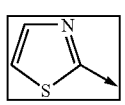 | | 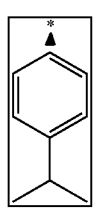 | 74% | 9.6 | 472.2 |
| 1023 | C23H17F2N5O2S | 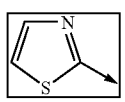 | | 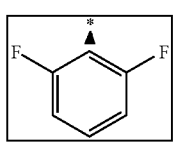 | 62% | 8.3 | 466.1 |
| 1024 | C26H25N5O5S | 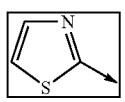 | | 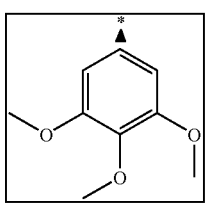 | 64% | 8.0 | 520.1 |
| 1025 | C27H22F2N4O3 | 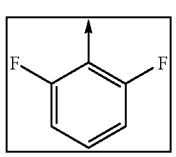 | | 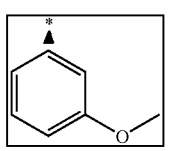 | 76% | 9.4 | 489.2 |
| 1026 | C27H19F5N4O2 | 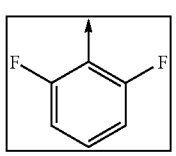 | | 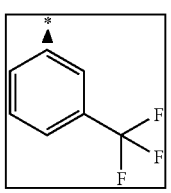 | 77% | 10.6 | 527.1 |
| 1027 | C26H20F2N4O2 | 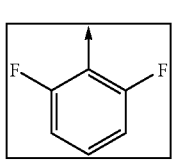 | | 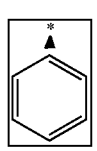 | 87% | 9.2 | 459.2 |

-continued
| | | | | | | |
|---|---|---|---|---|---|---|
| 1028 | C26H19F2N5O4 | 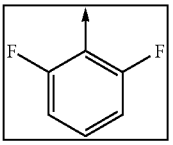 | 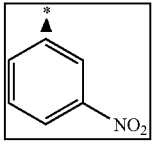 | 79% | 9.9 | 504.1 |
| 1029 | C27H21ClF2N4O2 | 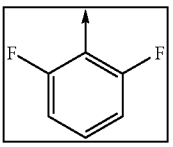 | 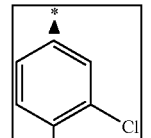 | 74% | 10.6 | 507.1 |
| 1030 | C29H24F2N4O4 | 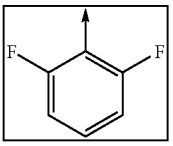 | 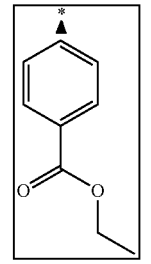 | 89% | 10.1 | 531.2 |
| 1031 | C26H19BrF2N4O2 | 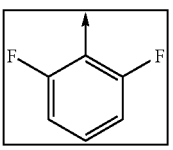 | 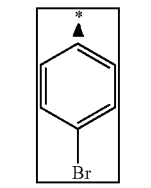 | 82% | 10.3 | 537.1 |
| 1032 | C26H19F3N4O2 | 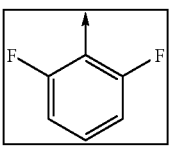 | 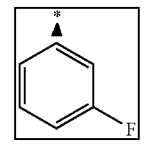 | 79% | 9.7 | 477.1 |
| 1033 | C26H18Cl2F2N4O2 | 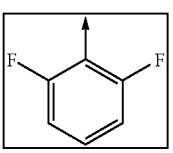 | 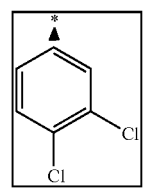 | 69% | 11.0 | 527.1 |
| 1034 | C28H22F2N4O3 | 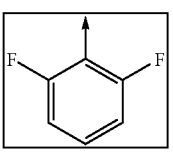 | 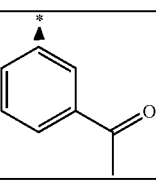 | 82% | 9.2 | 501.2 |
| 1035 | C27H22F2N4O2S | 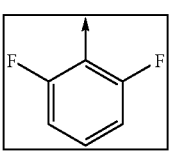 | 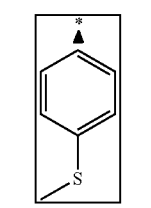 | 76% | 9.9 | 505.1 |

-continued
| Ex. No. | Formula | | | Purity | rt (min) | [M + H]+ |
|---|---|---|---|---|---|---|
| 1036 | C27H19F5N4O3 | 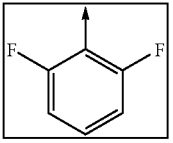 | 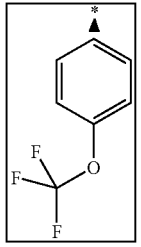 | 83% | 10.7 | 543.1 |
| 1037 | C26H19BrF2N4O2 | 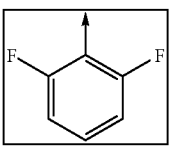 | 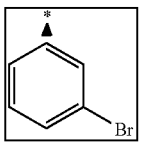 | 68% | 10.4 | 537.1 |
| 1038 | C29H26F2N4O2 | 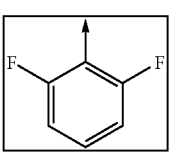 | 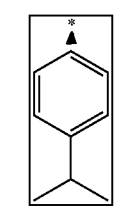 | 86% | 10.7 | 501.2 |
| 1039 | C26H18F4N4O2 | 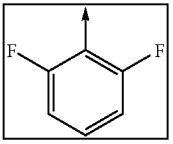 | 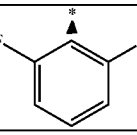 | 80% | 9.6 | 495.1 |
| 1040 | C29H26F2N4O5 | 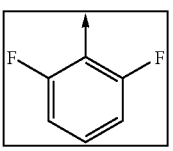 | 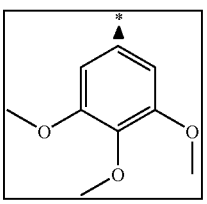 | 43% | 9.2 | 549.2 |
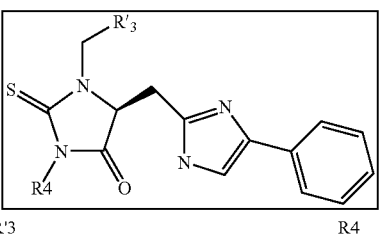
| Ex. No. | Formula | R'3 | R4 | Purity | Analyses rt (min) | [M + H]+ |
|---|---|---|---|---|---|---|
| 1041 | C26H33N5OS2 | 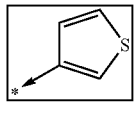 | 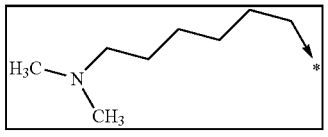 | 56 | 3.69 | 496.3 |
| 1042 | C29H37N5O2S | 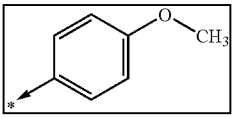 | 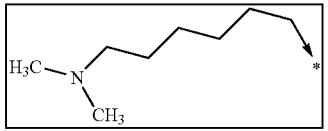 | 74 | 3.78 | 520.3 |

-continued
| Ex. No. | Formula | R'3 | R4 | Purity | rt (min) | [M + H]+ |
|---|---|---|---|---|---|---|
| 1043 | C30H36N6OS | 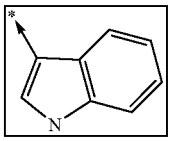 | 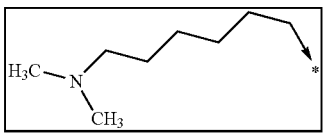 | 76 | 3.77 | 529.3 |
| 1044 | C31H38N6OS | 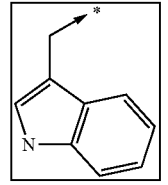 | 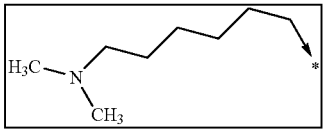 | 73 | 3.85 | 543.3 |
| 1045 | C30H39N5OS | 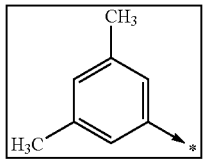 | 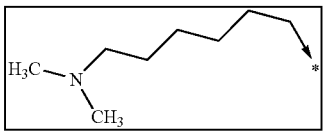 | 63 | 4.19 | 518.3 |
| 1046 | C30H36N6OS | 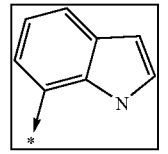 | 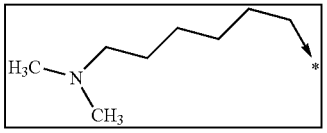 | 71 | 4.01 | 529.3 |
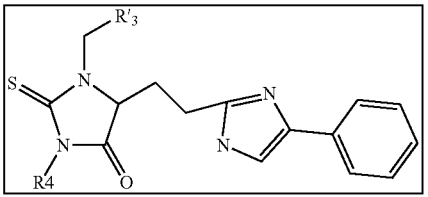
| Ex. No. | Formula | R'3 | R4 | Purity | rt (min) | [M + H]+ |
|---|---|---|---|---|---|---|
| 1047 | C27H35N5OS2 | 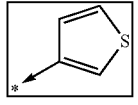 | 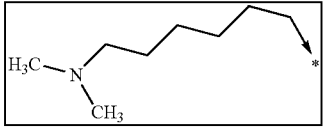 | 69 | 3.65 | 510.3 |
| 1048 | C30H39N5O2S | 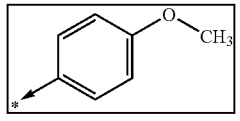 | 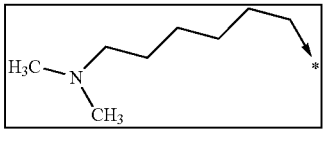 | 75 | 3.75 | 534.3 |
| 1049 | C31H42N6OS | 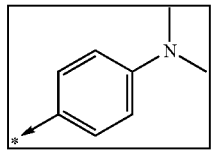 | 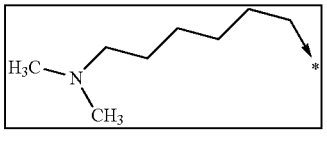 | 71 | 3.49 | 547.3 |
| 1050 | C31H38N6OS | 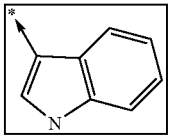 | 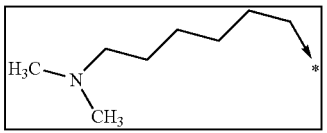 | 66 | 3.74 | 543.3 |

-continued
| Ex. No. | Formula | R'3 | R4 | Purity | rt (min) | [M + H]+ |
|---|---|---|---|---|---|---|
| 1051 | C31H38N6OS | 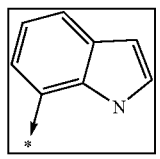 | 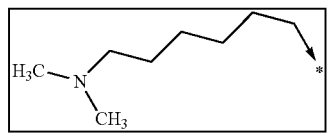 | 87 | 3.89 | 543.3 |
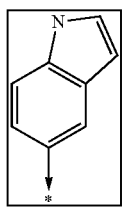
| Ex. No. | Formula | R'3 | R4 | Purity | Analyses rt (min) | [M + H]+ |
|---|---|---|---|---|---|---|
| 1052 | C30H36N6OS | 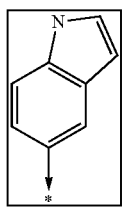 | 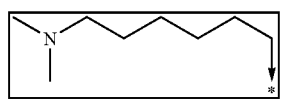 | 83.38 | 4.71 | 529.3 |
| 1053 | C26H33N5OS2 | 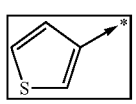 | 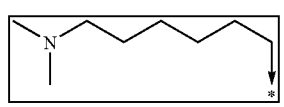 | 72.31 | 4.41 | 496.3 |
| 1054 | C29H37N5O2S | 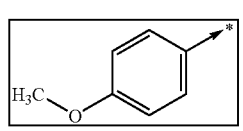 | 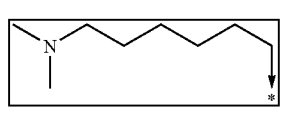 | 71.47 | 4.5 | 520.3 |
| 1055 | C30H40N6OS | 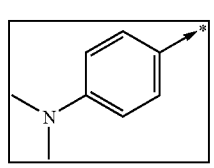 | 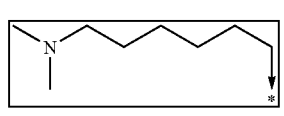 | 62.38 | 3.86 | 533.3 |
| 1056 | C25H32N6OS2 | 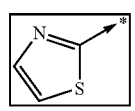 | 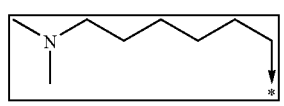 | 25.6 | 3.9 | 497.2 |
| 1057 | C28H33F2N5OS | 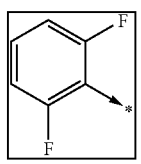 | 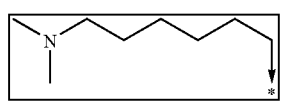 | 63.2 | 4.5 | 526.3 |

-continued

| | | | | | | |
|---|---|---|---|---|---|---|
| 1058 | C31H41N5OS | 4-isopropylphenyl | N-methyl hexyl chain | 69.01 | 5.17 | 532.4 |
| 1059 | C28H34N6O3S | 3-nitrophenyl | N-methyl hexyl chain | 73.01 | 4.58 | 535.3 |
| 1060 | C28H41N5OS | cyclohexyl | N-methyl hexyl chain | 44.6 | 4.9 | 496.4 |
| 1061 | C29H34F3N5O2S | 4-(trifluoromethoxy)phenyl | N-methyl hexyl chain | 80.9 | 5.1 | 574.2 |
| 1062 | C30H39N5OS | 3,5-dimethylphenyl | N-methyl hexyl chain | 58.64 | 4.91 | 518.3 |
| 1063 | C36H42N6OS | 9-ethylcarbazol-3-yl | N-methyl hexyl chain | 54.23 | 5.3 | 607.3 |
| 1064 | C28H34BrN5OS | 4-bromophenyl | N-methyl hexyl chain | 76.51 | 4.86 | 568.2 |
| 1065 | C28H33Cl2N5OS | 3,4-dichlorophenyl | N-methyl hexyl chain | 74.91 | 5.03 | 558.2 |
| 1066 | C29H34F3N5OS | 3-(trifluoromethyl)phenyl | N-methyl hexyl chain | 66.26 | 4.93 | 558.2 |

| | | | | | | |
|---|---|---|---|---|---|---|
| 1067 | C28H34N6O3S | 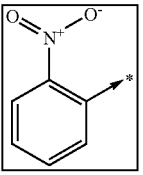 | 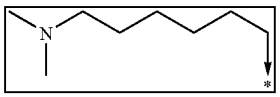 | 40 | 4.6 | 535.2 |
| 1068 | C32H37N5OS | 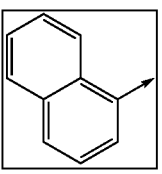 | 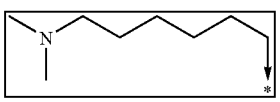 | 73.1 | 4.9 | 540.3 |
| 1069 | C29H34N6O5S | 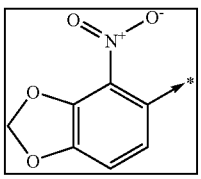 | 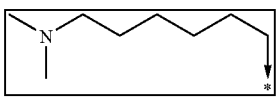 | 55.8 | 4.58 | 579.2 |
| 1070 | C34H39N5OS | 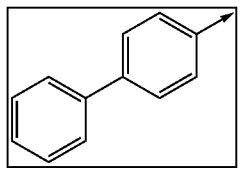 | 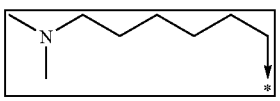 | 64.6 | 5.2 | 566.3 |
| 1071 | C29H34N6OS | 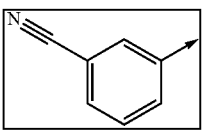 | 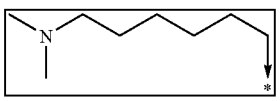 | 70.75 | 4.38 | 515.3 |
| 1072 | C29H37N5OS | 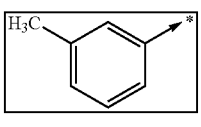 | 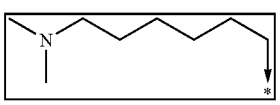 | 64.36 | 4.68 | 504.3 |
| 1073 | C35H41N5O2S | 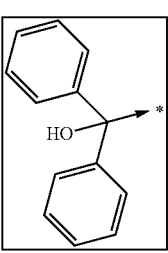 | 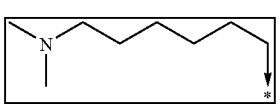 | 40.5 | 5 | 596.3 |
| 1074 | C31H38N6OS | 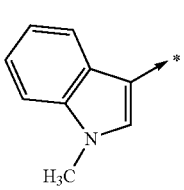 | 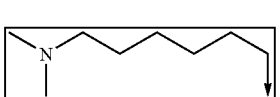 | 80.4 | 4 | 543.3 |

-continued
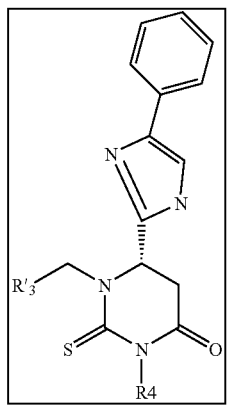
| Ex. No. | Formula | R'3 | R4 | Purity | rt (min) | [M + H]+ |
|---|---|---|---|---|---|---|
| 1075 | C26H32N6O3S2 | thiazol-2-yl | *-(CH2)4-NH-C(O)-O-tBu | 45.2% | 6.1 | 541.3 |
| 1076 | C27H34N6O3S2 | thiazol-2-yl | *-(CH2)5-NH-C(O)-O-tBu | 35.3% | 6.3 | 555.3 |
| 1077 | C28H36N6O3S2 | thiazol-2-yl | *-(CH2)6-NH-C(O)-O-tBu | 39.9% | 6.5 | 569.3 |
| 1078 | C30H38N6O3S2 | thiazol-2-yl | *-cyclohexyl-CH2-NH-C(O)-O-tBu | 14.9 + 22.82% | 6.7 + 6.76 | 595.3 |
| 1079 | C32H41N5O3S | 4-isopropylphenyl | *-(CH2)4-NH-C(O)-O-tBu | 70.3% | 7.5 | 576.4 |
| 1080 | C33H43N5O3S | 4-isopropylphenyl | *-(CH2)5-NH-C(O)-O-tBu | 71.9% | 7.7 | 590.4 |
| 1081 | C34H45N5O3S | 4-isopropylphenyl | *-(CH2)6-NH-C(O)-O-tBu | 72.7% | 7.9 | 604.4 |

| | | | | | |
|---|---|---|---|---|---|
| 1082 | C36H47N5O3S | (4-isopropylphenyl) | (cyclohexyl-CH2-NH-Boc) | 34.6 + 34.7% | 8.1 + 8.28 | 630.4 |
| 1083 | C29H33F2N5O3S | (2,6-difluorophenyl) | (propyl-NH-Boc) | 60.6% | 6.9 | 570.3 |
| 1084 | C30H35F2N5O3S | (2,6-difluorophenyl) | (butyl-NH-Boc) | 62.7% | 7.1 | 584.3 |
| 1085 | C31H37F2N5O3S | (2,6-difluorophenyl) | (pentyl-NH-Boc) | 65.5% | 7.3 | 598.3 |
| 1086 | C33H39F2N5O3S | (2,6-difluorophenyl) | (cyclohexyl-CH2-NH-Boc) | 33.92% + 32.4% | 7.5 + 4.6 | 624.3 |
| 1087 | C29H34BrN5O3S | (4-bromophenyl) | (butyl-NH-Boc) | 65.6% | 7.3 | 612.2 |
| 1088 | C30H36BrN5O3S | (4-bromophenyl) | (pentyl-NH-Boc) | 68.6% | 7.5 | 626.2 |
| 1089 | C31H38BrN5O3S | (4-bromophenyl) | (hexyl-NH-Boc) | 75.2% | 7.7 | 640.3 |

| | | | | | | |
|---|---|---|---|---|---|---|
| 1090 | C33H40BrN5O3S | 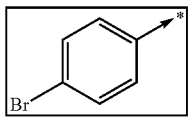 | 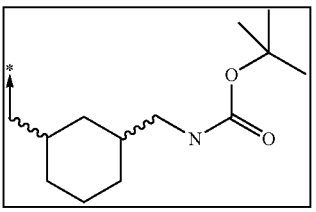 | 37.14% + 37.1% | 7.88 + 8.0 | 666.3 |
| 1091 | C29H34BrN5O3S | 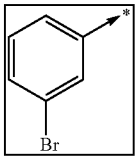 | 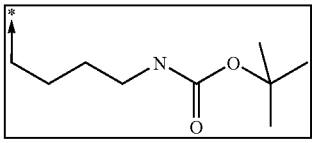 | 71.9% | 7.3 | 612.2 |
| 1092 | C30H36BrN5O3S | 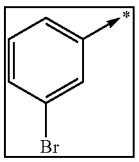 | 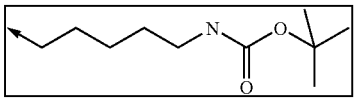 | 76.2% | 7.4 | 626.2 |
| 1093 | C31H38BrN5O3S | 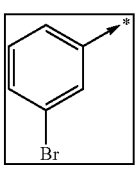 | 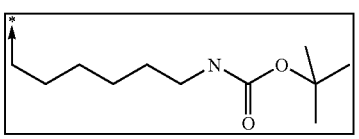 | 77.0% | 7.6 | 640.3 |
| 1094 | C33H40BrN5O3S | 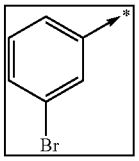 | 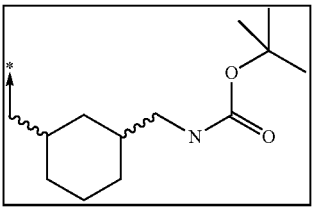 | 39.4 + 39.64% m | 7.8 + 8.0 | 666.3 |
| 1095 | C29H33Cl2N5O3S | 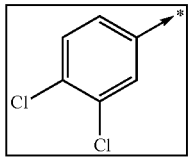 | 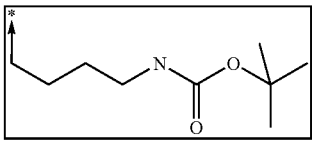 | 72.1% | 7.6 | 602.2 |
| 1096 | C30H35Cl2N5O3S | 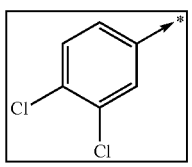 | 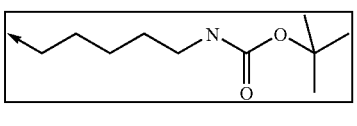 | 74.9% | 7.7 | 616.3 |
| 1097 | C31H37Cl2N5O3S | 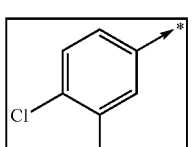 | 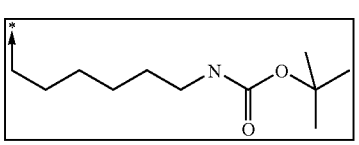 | 76.4% | 7.9 | 630.3 |

| | | | | | | |
|---|---|---|---|---|---|---|
| 1098 | C33H39Cl2N5O3S | 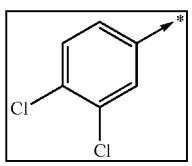 | 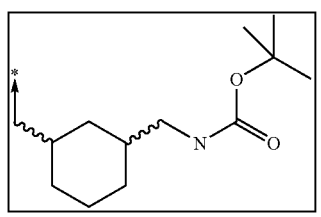 | 39.6% + 39.16% | 8.1 + 8.4 | 656.3 |
| 1099 | C30H34F3N5O3S | 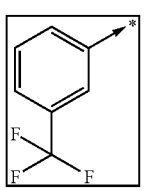 | 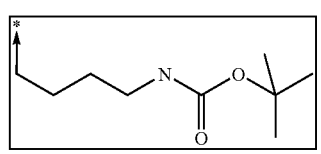 | 64.3% | 7.3 | 602.3 |
| 1100 | C31H36F3N5O3S | 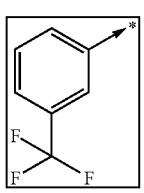 | 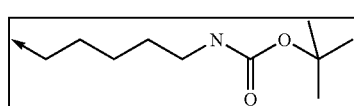 | 71.3% | 7.5 | 616.3 |
| 1101 | C32H38F3N5O3S | 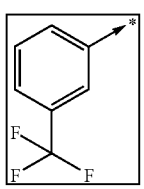 | 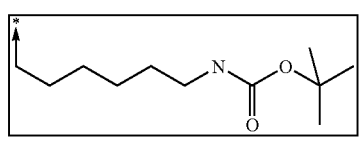 | 71.6% | 7.6 | 630.3 |
| 1102 | C34H40F3N5O3S | 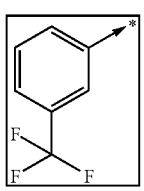 | 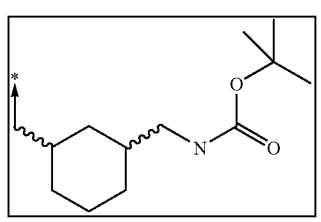 | 34.8 + 34.91% | 8.0 + 7.8 | 656.4 |
| 1103 | C29H34N6O5S | 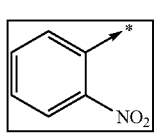 | 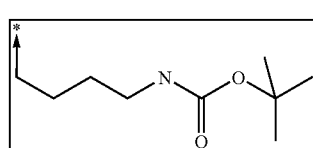 | 63.2% | 6.9 | 579.3 |
| 1104 | C30H36N6O5S | 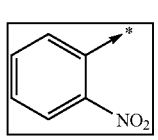 | 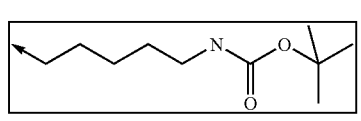 | 66.1% | 7.1 | 593.3 |
| 1105 | C31H38N6O5S | 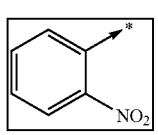 | 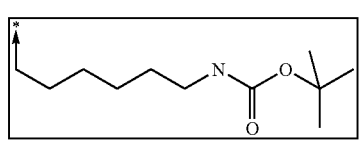 | 66.1% | 7.3 | 607.3 |

-continued

| | | | | | | |
|---|---|---|---|---|---|---|
| 1106 | C33H40N6O5S | | | 33.7% + 24.4% | 7.5 + 7.6 | 633.4 |
| 1107 | C33H37N5O3S | | | 84.0% | 7.2 | 584.4 |
| 1108 | C34H39N5O3S | | | 86.3% | 7.4 | 598.4 |
| 1109 | C35H41N5O3S | | | 86.2% | 7.6 | 612.4 |
| 1110 | C37H43N5O3S | | | 43.1% + 43.4% | 7.9 + 8.12 | 638.4 |
| 1111 | C36H41N5O4S | | | 58.2% | 7.3 | 640.4 |
| 1112 | C37H43N5O4S | | | 61.1% | 7.5 | 654.4 |

| | | | | | | |
|---|---|---|---|---|---|---|
| 1113 | C38H45N5O4S | (diphenyl-O) | (hexyl-NH-C(O)-O-tBu) | 67.6% | 7.7 | 668.4 |
| 1114 | C40H47N5O4S | (diphenyl-O) | (cyclohexyl-CH2-NH-C(O)-O-tBu) | 38.1% + 38.5% | 7.9 + 8.1 | 694.4 |
| 1115 | C21H24N6OS2 | (thiazol-2-yl) | (butyl-N) | 74.0% | 3.9 | 441.2 |
| 1116 | C22H26N6OS2 | (thiazol-2-yl) | (pentyl-N) | 80.2% | 4.0 | 455.3 |
| 1117 | C23H28N6OS2 | (thiazol-2-yl) | (hexyl-N) | 47.3% | 4.2 | 469.3 |
| 1118 | C25H30N6OS2 | (thiazol-2-yl) | (cyclohexyl-CH2-N) | 18.31% + 14% | 4.2 + 4.3 | 495.3 |
| 1119 | C27H33N5OS | (4-iPr-phenyl) | (butyl-N) | 76.8% | 5.1 | 476.4 |
| 1120 | C28H35N5OS | (4-iPr-phenyl) | (pentyl-N) | 77.9% | 5.3 | 490.4 |
| 1121 | C29H37N5OS | (4-iPr-phenyl) | (hexyl-N) | 75.6% | 5.4 | 504.4 |

-continued
| | | | | | | |
|---|---|---|---|---|---|---|
| 1122 | C31H39N5OS | 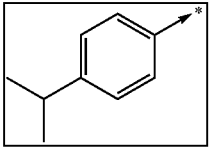 | 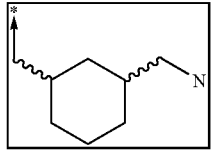 | 38.42% + 26.7% m | 5.5 + 5.7 | 530.4 |
| 1123 | C24H25F2N5OS | 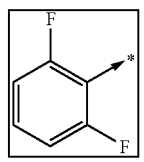 | 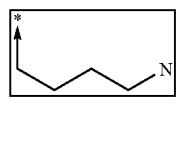 | 68.1% | 4.5 | 470.3 |
| 1124 | C25H27F2N5OS | 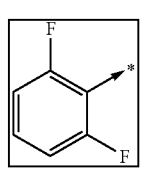 |  | 66.9% | 4.7 | 484.3 |
| 1125 | C26H29F2N5OS | 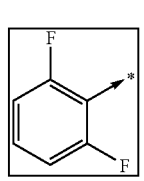 | 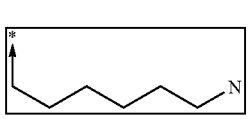 | 70.0% | 4.8 | 498.3 |
| 1126 | C28H31F2N5OS | 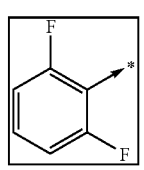 | 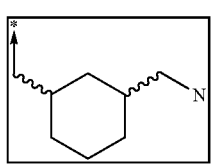 | 25.0% | 4.9 | 524.3 |
| 1127 | C24H26BrN5OS | 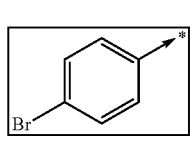 | 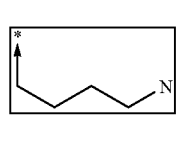 | 72.7% | 4.9 | 512.2 |
| 1128 | C25H28BrN5OS | 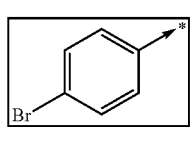 |  | 78.5% | 5.0 | 526.2 |
| 1129 | C26H30BrN5OS | 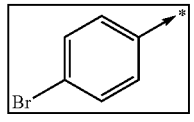 | 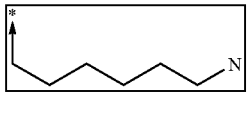 | 80.2% | 5.1 | 540.2 |
| 1130 | C28H32BrN5OS | 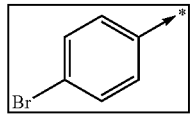 | 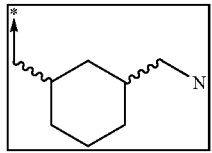 | 39.21% + 27% | 5.3 + 5.4 | 566.2 |

-continued

| | | | | | | |
|---|---|---|---|---|---|---|
| 1131 | C24H26BrN5OS | 3-bromophenyl | *-CH2CH2CH2CH2-N | 77.9% | 4.9 | 512.2 |
| 1132 | C25H28BrN5OS | 3-bromophenyl | *-(CH2)5-N | 81.4% | 5.0 | 526.2 |
| 1133 | C26H30BrN5OS | 3-bromophenyl | *-(CH2)6-N | 78.25%* | 5.1 | 540.2 |
| 1134 | C26H32BrN5OS | 3-bromophenyl | *-cyclohexyl-CH2-N | 31.02% + 27.9 | 5.2 + 5.4 | 566.2 |
| 1135 | C24H25Cl2N5OS | 3,4-dichlorophenyl | *-(CH2)4-N | 79.9% | 5.1 | 502.2 |
| 1136 | C25H27Cl2N5OS | 3,4-dichlorophenyl | *-(CH2)5-N | 81.2% | 5.2 | 516.2 |
| 1137 | C26H29Cl2N5OS | 3,4-dichlorophenyl | *-(CH2)6-N | 80.1% | 5.3 | 530.2 |
| 1138 | C28H31Cl2N5OS | 3,4-dichlorophenyl | *-cyclohexyl-CH2-N | 33.63% + 28.8% | 5.4 + 5.6 | 556.2 |
| 1139 | C25H26F3N5OS | 3-(trifluoromethyl)phenyl | *-(CH2)4-N | 73.7% | 4.9 | 502.3 |

| | | | | | | |
|---|---|---|---|---|---|---|
| 1140 | C26H28F3N5OS | 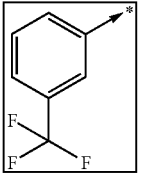 |  | 80.8% | 5.1 | 516.2 |
| 1141 | C27H30F3N5OS | 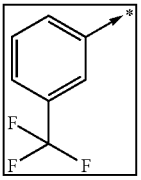 | 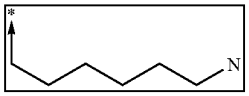 | 76.86%* | 5.2 | 530.3 |
| 1142 | C29H32F3N5OS | 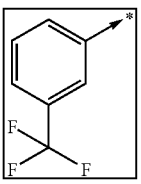 | 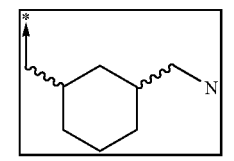 | 27.7% + 27.3 | 5.3 + 5.4 | 556.3 |
| 1143 | C24H26N6O3S | 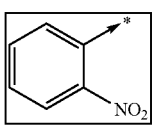 | 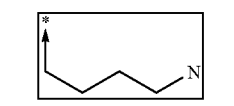 | 70.7% | 4.6 | 479.3 |
| 1144 | C25H28N6O3S | 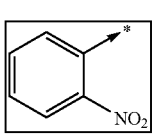 |  | 72.3% | 4.7 | 493.3 |
| 1145 | C26H30N6O3S | 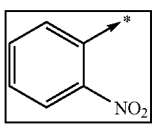 | 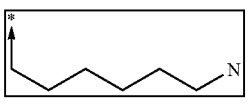 | 72.4% | 4.8 | 507.3 |
| 1146 | C28H32N6O3S | 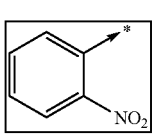 | 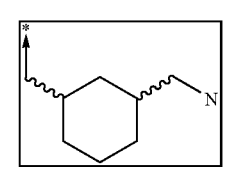 | 27.5% + 26.5% | 4.9 + 5.3 | 533.3 |
| 1147 | C28H29N5OS | 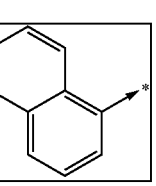 | 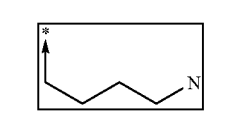 | 88.2% | 4.8 | 484.3 |
| 1148 | C29H31N5OS | 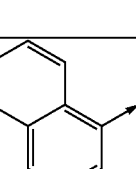 |  | 89.1% | 5.0 | 498.3 |

-continued
| | | | | | | |
|---|---|---|---|---|---|---|
| 1149 | C30H33N5OS | 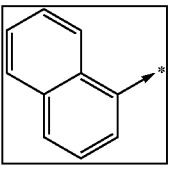 | 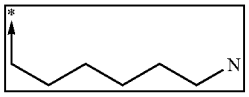 | 89.9% | 5.1 | 512.3 |
| 1150 | C32H35N5OS | 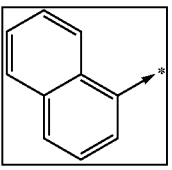 | 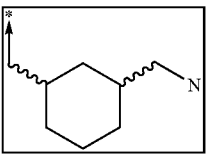 | 46.67% + 31.0 | 5.3 + 5.5 | 538.3 |
| 1151 | C31H33N5O2S | 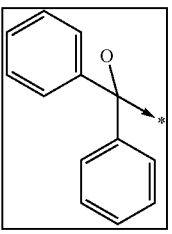 | 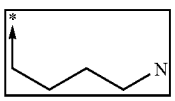 | 46.0% | 5.0 | 540.3 |
| 1152 | C32H35N5O2S | 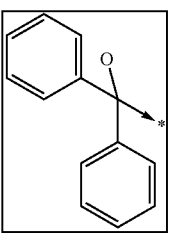 |  | 46.6% | 5.1 | 554.2 |
| 1153 | C33H37N5O2S | 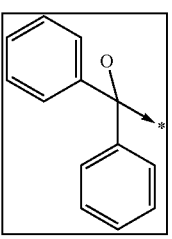 | 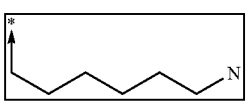 | 54.2% | 5.2 | 568.3 |
| 1154 | C35H39N5O2S | 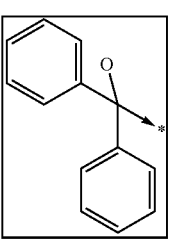 | 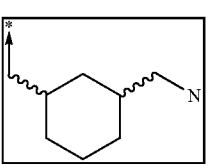 | 28 + 21% | 5.3 + 5.5 | 594.3 |

-continued
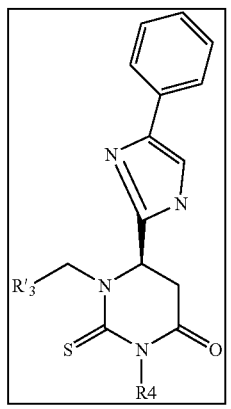
| Ex. No. | Formula | R'3 | R4 | Purity | rt (min) | [M + H]+ |
|---|---|---|---|---|---|---|
| 1155 | C29H34N6O5S | 4-NO2-phenyl | *-(CH2)4-NH-C(O)-O-tBu | 82% | 6.5 | 579.3 |
| 1156 | C30H36N6O5S | 4-NO2-phenyl | *-(CH2)5-NH-C(O)-O-tBu | 85% | 6.7 | 593.3 |
| 1157 | C31H38N6O5S | 4-NO2-phenyl | *-(CH2)6-NH-C(O)-O-tBu | 84% | 6.9 | 607.4 |
| 1158 | C33H40N6O5S | 4-NO2-phenyl | *-cyclohexyl-CH2-NH-C(O)-O-tBu | 42 + 42% | 7.1 + 7.28 | 633.4 |
| 1159 | C30H34N6O7S | 2-NO2-benzodioxol | *-(CH2)4-NH-C(O)-O-tBu | 78% | 6.5 | 623.3 |

-continued
| | | | | | | |
|---|---|---|---|---|---|---|
| 1160 | C30H36N6O7S | 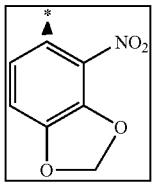 | 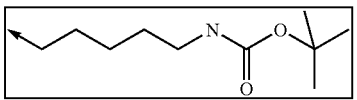 | 82% | 6.7 | 637.3 |
| 1161 | C32H38N6O7S | 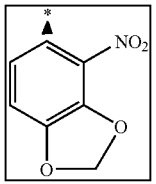 | 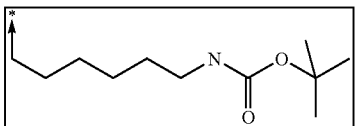 | 80% | 6.9 | 651.3 |
| 1162 | C34H40N6O7S | 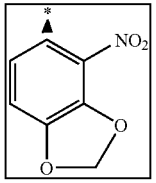 | 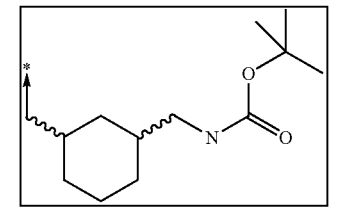 | 34 + 41% | 7.1 + 7.2 | 677.4 |
| 1163 | C35H39N5O3S | 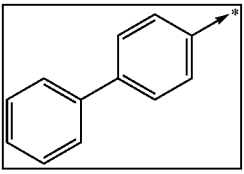 | 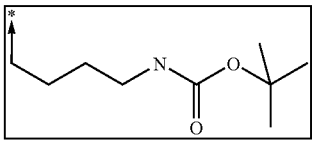 | 83% | 7.1 | 610.4 |
| 1164 | C36H41N5O3S | 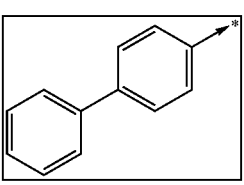 | 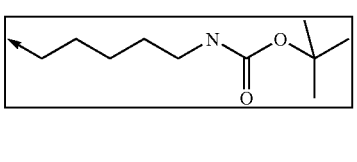 | 84% | 7.3 | 624.4 |
| 1165 | C37H43N5O3S | 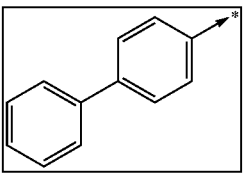 | 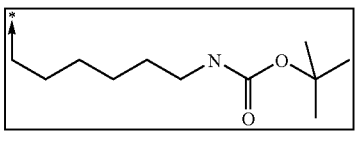 | 85% | 7.5 | 638.4 |
| 1166 | C39H45N5O3S | 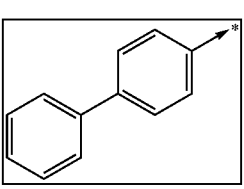 | 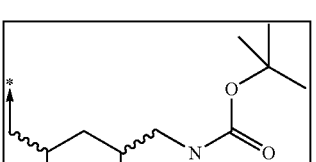 | 41 + 42% | 7.7 + 7.9 | 664.4 |
| 1167 | C33H37N5O3S | 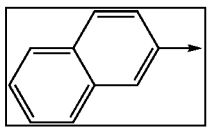 | 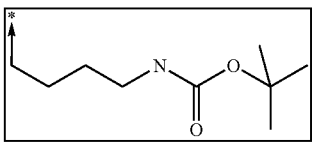 | 91% | 6.9 | 584.4 |

| | | | | | | |
|---|---|---|---|---|---|---|
| 1168 | C34H39N5O3S | 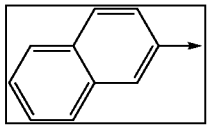 | 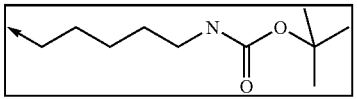 | 90% | 7.1 | 598.4 |
| 1169 | C35H41N5O3S | 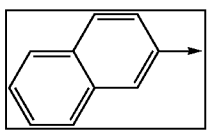 | 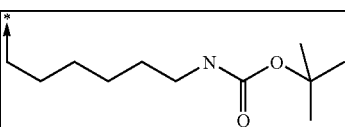 | 89% | 7.3 | 612.4 |
| 1170 | C37H43N5O3S | 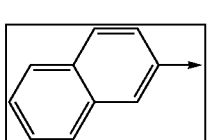 | 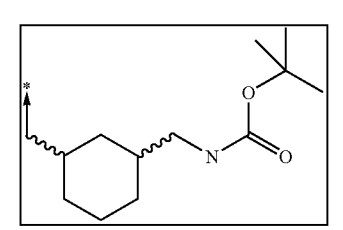 | 41 + 42% | 7.5 + 7.7 | 638.4 |
| 1171 | C30H34N6O3S | 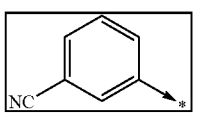 | 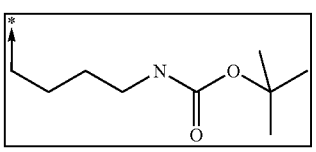 | 85% | 6.4 | 559.3 |
| 1172 | C31H36N6O3S | 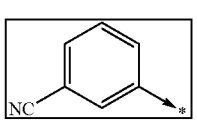 | 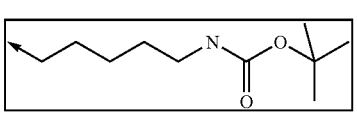 | 87% | 6.5 | 573.3 |
| 1173 | C32H38N6O3S | 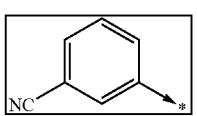 | 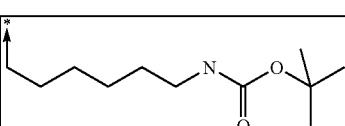 | 81% | 6.8 | 587.4 |
| 1174 | C34H40N6O3S | 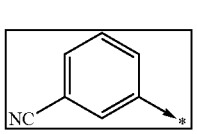 | 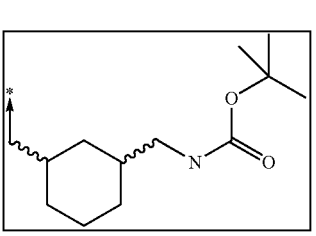 | 42 + 43% | 6.9 + 7.1 | 613.4 |
| 1175 | C37H43N5O5S | 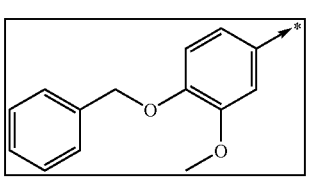 | 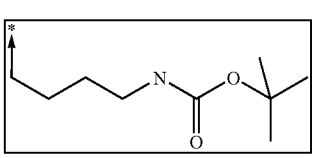 | 86% | 6.9 | 670.4 |
| 1176 | C38H45N5O5S | 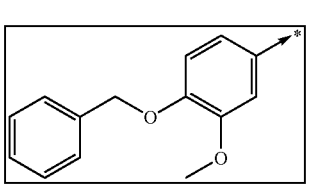 | 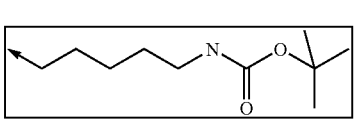 | 82% | 7.1 | 684.5 |

| | | | | | | |
|---|---|---|---|---|---|---|
| 1177 | C39H47N5O5S | 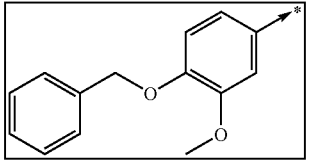 | 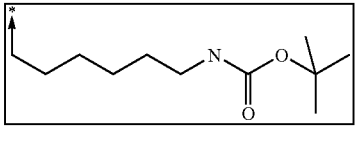 | 86% | 7.3 | 698.5 |
| 1178 | C41H49N5O5S | 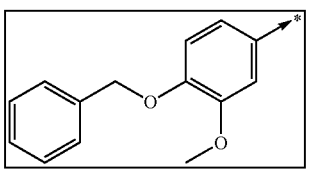 | 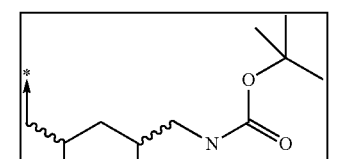 | 38.3 + 38.4% | 7.5 + 7.62 | 724.4 |
| 1179 | C31H39N5O3S | 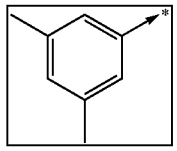 | 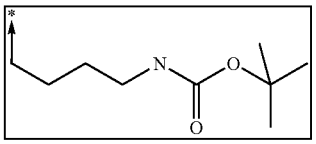 | 86% | 6.9 | 562.4 |
| 1180 | C32H41N5O3S | 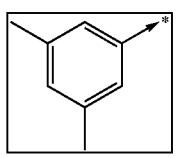 | 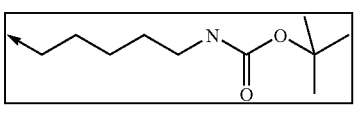 | 87% | 7.1 | 576.4 |
| 1181 | C33H43N5O3S | 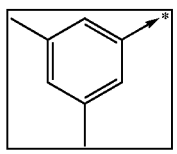 | 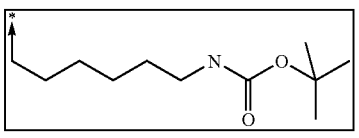 | 86% | 7.3 | 590.4 |
| 1182 | C35H45N5O3S | 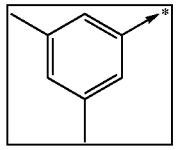 | 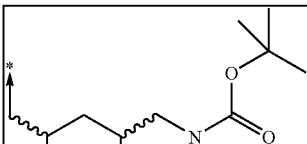 | 38 + 39% | 7.5 + 7.64 | 616.4 |
| 1183 | C37H42N6O3S | 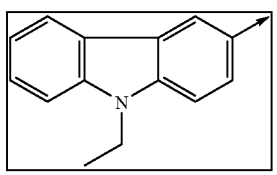 | 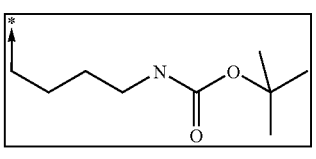 | 85% | 7.2 | 651.4 |
| 1184 | C38H44N6O3S | 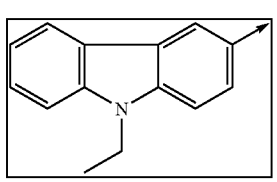 | 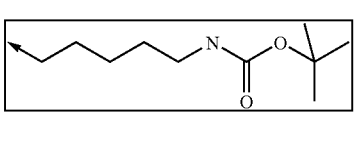 | 88% | 7.3 | 665.4 |

| | | | | | | |
|---|---|---|---|---|---|---|
| 1185 | C39H46N6O3S | 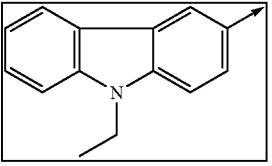 | 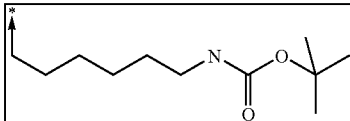 | 88% | 7.5 | 679.4 |
| 1186 | C41H48N6O3S | 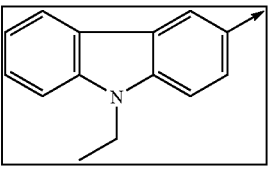 | 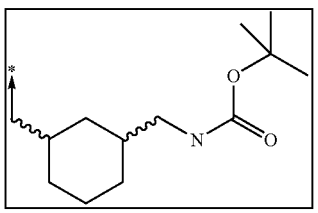 | 38.4 + 38.5% | 7.8 + 7.98 | 705.4 |
| 1187 | C36H39N5O3S | 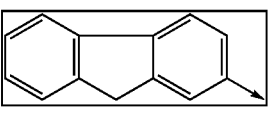 | 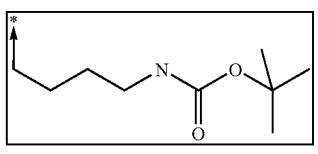 | 86% | 7.2 | 622.4 |
| 1188 | C37H41N5O3S | 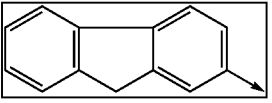 | 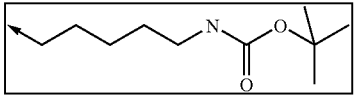 | 87% | 7.4 | 636.4 |
| 1189 | C38H43N5O3S | 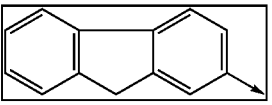 | 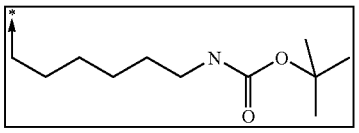 | 82% | 7.6 | 650.4 |
| 1190 | C40H45N5O3S | 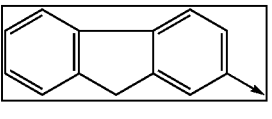 | 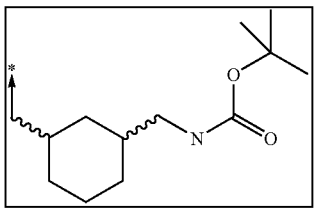 | 40.6 + 40.9% | 7.8 + 8.01 | 676.4 |
| 1191 | C31H36N6O3S | 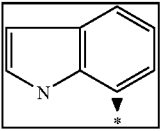 | 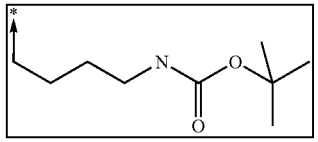 | 85.41%* | 6.8 } | |
| 1192 | C32H38N6O3S | 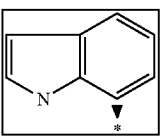 | 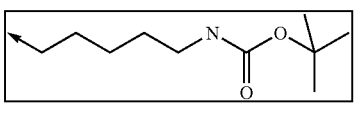 | 89% | 6.8 | 587.4 |
| 1193 | C33H40N6O3S | 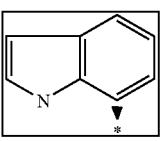 | 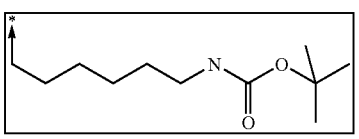 | 90% | 7.0 | 601.4 |

-continued

| | | | | | | |
|---|---|---|---|---|---|---|
| 1194 | C35H42N6O3S | (indole structure) | (cyclohexyl-CH2-NH-C(O)-O-tBu structure) | 43.1 + 44.5% | 7.3 + 7.45 | 627.4 |
| 1195 | C24H26N6O3S | (nitrobenzene structure) | (butyl-NH-C(O)-O-tBu structure) | 87% | 4.3 | 479.3 |
| 1196 | C25H28N6O3S | (nitrobenzene structure) | (pentyl-NH-C(O)-O-tBu structure) | 92% | 4.4 | 493.3 |
| 1197 | C26H30N6O3S | (nitrobenzene structure) | (hexyl-NH-C(O)-O-tBu structure) | 92% | 4.6 | 507.3 |
| 1198 | C28H32N6O3S | (nitrobenzene structure) | (cyclohexyl-CH2-NH-C(O)-O-tBu structure) | 35 + 33.9% | 4.7 + 4.8 | 533.3 |
| 1199 | C25H26N6O5S | (nitro-methylenedioxybenzene structure) | (butyl-N structure) | 82% | 4.3 | 523.2 |
| 1200 | C26H28N6O5S | (nitro-methylenedioxybenzene structure) | (pentyl-N structure) | 86% | 4.5 | 537.3 |

-continued
| | | | | | | |
|---|---|---|---|---|---|---|
| 1201 | C27H30N6O5S | 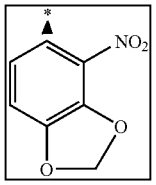 | 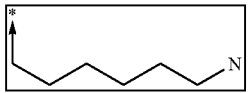 | 83% | 4.6 | 551.3 |
| 1202 | C29H32N6O5S | 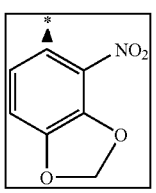 | 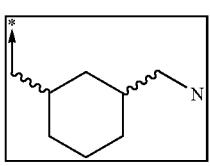 | 35 + 33.9% | 4.7 + 4.8 | 577.3 |
| 1203 | C30H31N5OS | 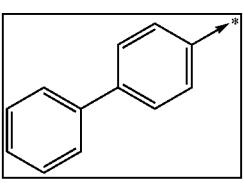 | 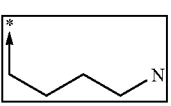 | 88% | 4.9 | 510.3 |
| 1204 | C31H33N5OS | 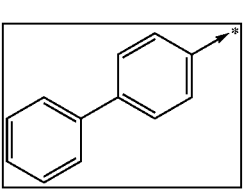 |  | 90% | 5.0 | 524.3 |
| 1205 | C32H35N5OS | 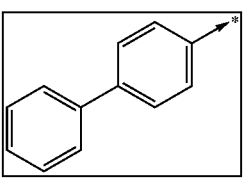 | 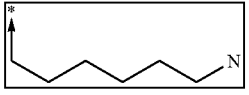 | 89% | 5.2 | 538.3 |
| 1206 | C34H37N5OS | 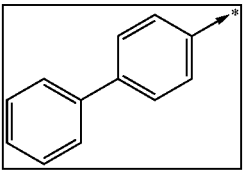 | 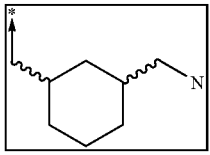 | 43 + 31% | 5.3 + 5.4 | 564.3 |
| 1207 | C28H29N5OS | 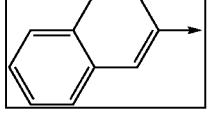 | 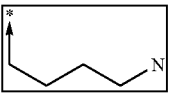 | 92% | 4.7 | 484.3 |
| 1208 | C29H31N5OS | 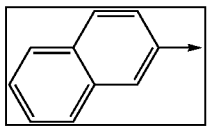 | 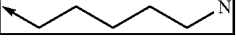 | 93% | 4.8 | 498.3 |
| 1209 | C30H33N5OS | 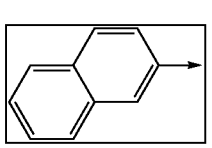 | 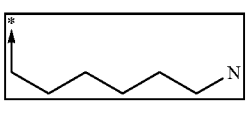 | 92% | 4.9 | 512.3 |

-continued

| | | | | | | |
|---|---|---|---|---|---|---|
| 1210 | C32H35N5OS | naphthalen-2-yl | cyclohexyl-CH2-N | 43 + 30.1% | 5.1 | 538.3 |
| 1211 | C25H26N6OS | 3-cyanophenyl | -(CH2)3-N | 87% | 4.1 | 459.3 |
| 1212 | C26H28N6OS | 3-cyanophenyl | -(CH2)4-N | 86% | 4.2 | 473.3 |
| 1213 | C27H30N6OS | 3-cyanophenyl | -(CH2)5-N | 82% | 4.4 | 487.3 |
| 1214 | C29H32N6OS | 3-cyanophenyl | cyclohexyl-CH2-N | 40 + 36% | 4.5 + 4.6 | 513.3 |
| 1215 | C32H35N5O3S | 4-benzyloxy-3-methoxyphenyl | -(CH2)3-N | 87% | 4.8 | 570.3 |
| 1216 | C33H37N5O3S | 4-benzyloxy-3-methoxyphenyl | -(CH2)4-N | 84% | 4.9 | 584.3 |
| 1217 | C34H39N5O3S | 4-benzyloxy-3-methoxyphenyl | -(CH2)5-N | 86% | 5.0 | 598.3 |
| 1218 | C36H41N5O3S | 4-benzyloxy-3-methoxyphenyl | cyclohexyl-CH2-N | 32% + 29% | 5.2 + 5.3 | 624.4 |
| 1219 | C26H31N5OS | 3,5-dimethylphenyl | -(CH2)3-N | 90% | 4.6 | 462.3 |

| | | | | | | |
|---|---|---|---|---|---|---|
| 1220 | C27H33N5OS | | | 92% | 4.7 | 476.4 |
| 1221 | C28H35N5OS | | | 91% | 4.9 | 490.4 |
| 1222 | C30H37N5OS | | | 42 + 29.9% | 5.0 + 5.2 | 516.3 |
| 1223 | C32H34N6OS | | | 80% | 5.0 | 551.3 |
| 1224 | C33H36N6OS | | | 90% | 5.1 | 565.3 |
| 1225 | C34H38N6OS | | | 85% | 5.3 | 579.4 |
| 1226 | C36H40N6OS | | | 37% + 27 | 5.45.6 | 605.4 |
| 1227 | C31H31N5OS | | | 90% | 5.0 | 522.3 |
| 1228 | C32H33N5OS | | | 91% | 5.1 | 536.3 |
| 1229 | C33H35N5OS | | | 90% | 5.2 | 550.3 |

| | | | | | | |
|---|---|---|---|---|---|---|
| 1230 | C35H37N5OS | (fluorene structure) | (cyclohexyl-N structure) | 42% + 30.8 | 5.4 + 5.5 | 576.3 |
| 1231 | C26H28N6OS | (indole structure) | (chain-N structure) | 68% | 4.4 | 473.4 |
| 1232 | C27H30N6OS | (indole structure) | (chain-N structure) | 56% | 4.5 | 487.4 |
| 1233 | C28H32N6OS | (indole structure) | (chain-N structure) | 40% | 4.7 | 613.2 |
| 1234 | C30H34N6OS | (indole structure) | (cyclohexyl-N structure) | 40% | 4.8 | 527.4 |

Pharmacological Properties of the Compounds of the Invention

The compounds of the present invention can and have been tested as regards their affinity for different sub-types of somatostatin receptors according to the procedures described below.

Study of the affinity for the sub-types of human somatostatin receptors:

The affinity of a compound of the invention for sub-types of somatostatin receptors 1 to 5 ($sst_1$, $sst_2$, $sst_3$, $sst_4$ and $sst_5$, respectively) is determined by measurement of the inhibition of the bond of [$^{125}$I-Tyr$^{11}$]SRIF-14 to transfected CHO-K1 cells.

The gene of the $sst_1$, receptor of human somatostatin has been cloned in the form of a genomic fragment. A segment PstI-XmnI of 1.5 Kb containing 100 bp of the non transcribed 5' region, 1.17 Kb of the coding region in totality, and 230 bp of the non transcribed 3' region is modified by the addition of the linker BglII. The resulting DNA fragment is subcloned in the BamHI site of a pCMV-81 in order to produce the expression plasmid in mammals (provided by Dr. Graeme Bell, Univ. Chicago). A cloned cell line expressing in a stable fashion the $sst_1$ receptor is obtained by transfection in CHO-K1 cells (ATCC) using the calcium phosphate co-precipitation method. The plasmid pRSV-neo (ATCC) is included as selection marker. Cloned cell lines were selected in an RPMI 1640 medium containing 0.5 mg/ml of G418 (Gibco), followed by circular cloning and multiplication in culture.

The gene of the $sst_2$ receptor of human somatostatin, isolated in the form of a genomic fragment of DNA of 1.7 Kb BamHI-HindIII and subcloned in a plasmid vector pGEM3Z (Promega), was provided by Dr. G. Bell (Univ. of Chicago). The expression vector of the mammalian cells is constructed by inserting the BamHl-HindlI fragment of 1.7 Kb in endonuclease restriction sites compatible with the plasmid pCMV5. A cloned cell line is obtained by transfection in CHO-K1 cells using the calcium phosphate co-precipitation method. The plasmid pRSV-neo is included as selection marker.

The $sst_3$ receptor is isolated as a genomic fragment, and the complete coding sequence is contained in a BamHI/HindIII fragment of 2.4 Kb. The expression plasmid in mammals, pCMV-h3, is constructed by insertion of the NcoI-HindIII fragment of 2.0 Kb in the EcoR1 site of the vector pCMV after modification of the terminations and addition of EcoR1 linkers. A cloned cell line expressing in a stable fashion the $sst_3$ receptor is obtained by transfection in CHO-K1 cells (ATCC) by the calcium phosphate co-precipitation method. The plasmid pRSV-neo (ATCC) is included as selection marker. Cloned cell lines were selected in an RPMI 1640 medium containing 0.5 mg/ml of G418 (Gibco), followed by circular cloning and multiplication in culture.

The expression plasmid of the human $sst_4$ receptor, pCMV-HX, was provided by Dr. Graeme Bell (Univ. Chicago). This vector contains the genomic fragment coding for the human $sst_4$ receptor of 1.4 Kb NheI-NheI, 456 pb of the non transcribed 5' region, and 200 pb of the non transcribed 3' region, cloned in the XbaI/EcoR1 sites of PCMV-HX. A cloned cell line expressing in a stable fashion the sst$_4$ receptor is obtained by transfection in CHO-K1 cells (ATCC). by the calcium phosphate co-precipitation method. The plasmid pRSV-neo (ATCC) is included as selection marker. The cloned cell lines were selected in an RPMI 1640 medium containing 0.5 mg/ml of G418 (Gibco), followed by circular cloning and multiplication in culture.

The gene corresponding to the human sst$_5$ receptor, obtained by the PCR method using a genomic clone as probe, was provided by Dr. Graeme Bell (Univ. Chicago). The resulting PCR fragment of 1.2 Kb contains 21 base pairs of the non transcribed 5' region, the coding region in totality, and 55 pb of the non transcribed 3' region. The clone is inserted in an EcoR1 site of the plasmid pBSSK(+). The insert is recovered in the form of a HindIII-XbaI fragment of 1.2 Kb for subcloning in an expression vector in mammals, pCVM5. A cloned cell line expressing in a stable fashion the sst$_5$ receptor is obtained by transfection in CHO-K1 cells (ATCC) by the calcium phosphate co-precipitation method. The plasmid pRSV-neo (ATCC) is included as selection marker. The cloned cell lines were selected in an RPMI 1640 medium containing 0.5 mg/ml of G418 (Gibco), followed by circular cloning and multiplication in culture.

The CHO-K1 cells which express in a stable fashion the human sst receptors are cultured in an RPMI 1640 medium containing 10% of foetal calf serum and 0.4 mg/ml of geneticin. The cells are collected with 0.5 mM EDTA and centrifuged at 500 g for approximately 5 minutes at approximately 4° C. The pellet is resuspended in Tris 50 mM at pH 7.4 and centrifuged twice at 500 g for approximately 5 minutes at approximately 4° C. The cells are lysed by sonication and centrifuged at 39000 g for approximately 10 minutes at 4° C. The pellet is resuspended in the same buffer and centrifuged at 50000 g for approximately 10 minutes at approximately 4° C. and the membranes in the pellet obtained are stored at −80° C.

The competitive inhibition tests of the bond with [$^{125}$I-Tyr$^{11}$]SRIF-14 are carried out in duplicate using 96-well polypropylene plates. The cell membranes (10 μg protein/well) are incubated with [$^{125}$I-Tyr$^{11}$]SRIF-14 (0.05 nM) for approximately 60 min. at approximately 37° C. in a 50 mM HEPES buffer (pH 7.4) containing BSA 0.2%, MgCl$_2$ 5 mM, Trasylol 200 KIU/ml, bacitricin 0.02 mg/ml, phenylmethyl-sulphonyl fluoride 0.02 mg/ml.

The bound [$^{125}$I-Tyr ]SRIF-14 is separated from the free [$^{125}$I-Tyr $^{11}$]SRIF-14 by immediate filtration through GFIC glass fibre filter plates (Unifilter, Packard) pre-impregnated with 0.1% of polyethylenimine (P.E.I.), using a Filtermate 196 (Packard). The filters are washed with 50 mM HEPES buffer at approximately 0-4° C. for approximately 4 seconds and their radioactivity is determined using a counter (Packard Top Count).

The specific bond is obtained by subtracting the non-specific bond (determined in the presence of 0.1 μM of SRIF-14) from the total bond. The data relative to the bond are analyzed by computer-aided.non-linear regression analysis (MDL) and the values of the inhibition constants (Ki) are determined.

Determination of the agonist or antagonist character of a compound of the present invention is carried out using the test described below.

Functional Test: Inhibition of Production of Intracellular cAMP:

CHO-K1 cells expressing the sub-types of human somatostatin receptors (SRIF-14) are cultured in 24-well plates in an RPMI 1640 medium with 10% of foetal calf serum and 0.4 mg/ml of geneticin. The medium is changed the day preceding the experiment.

The cells at a rate of 10$^5$ cells/well are washed twice with 0.5 ml of new RPMI medium comprising 0.2% BSA completed. by 0.5 mM of 3-isobutyl-1-methylxanthine (IBMX) and incubated for approximately 5 min at approximately 37° C.

The production of cyclic AMP is stimulated by the addition of 1 mM of forskolin (FSK) for 15-30 minutes at approximately 37 ° C.

The inhibitor effect of the somatostatin of an agonist compound is measured by the simultaneous addition of FSK (1 μM), SRIF-14 (10$^{-12}$ to 10$^{-6}$ M) and of the compound to be tested (10$^{-10}$ M to 10$^{-5}$ M).

The antagonist effect of a compound is measured by the simultaneous addition of FSK (1 μM), SRIF-14 (1 to 10 nM) and of the compound to be tested (10$^{10-10}$ M to 10$^{-5}$ M).

The reaction medium is eliminated and 200 ml of 0.1 N HCl are added. The quantity of cAMP is measured by a radioimmunological test (FlashPlate SMP001A kit, New England Nuclear).

Results:

The tests carried out according to the protocols described above have demonstrated that the compounds of general formula (I) defined in the present Application have a good affinity for at least one of the sub-types of somatostatin receptors, the inhibition constant K$_i$ being lower than micromolar for certain exemplified compounds, and in particular for the compounds shown in the Tables I and II below.

TABLE I

| R'3 | R'4 | K$_i$ |
|---|---|---|
| indol-3-yl-methyl* | (CH$_2$)$_3$NH$_2$ | <1 μM |
|  | (CH$_2$)$_4$NH$_2$ | <1 μM |
|  | (CH$_2$)$_5$NH$_2$ | <1 μM |
|  | (CH$_2$)$_6$NH$_2$ | <1 μM |
| indol-3-yl-methyl* | (CH$_2$)$_3$NH$_2$ | <1 μM |
|  | (CH$_2$)$_4$NH$_2$ | <1 μM |
|  | (CH$_2$)$_5$NH$_2$ | <1 μM |
|  | (CH$_2$)$_6$NH$_2$ | <1 μM |

TABLE II

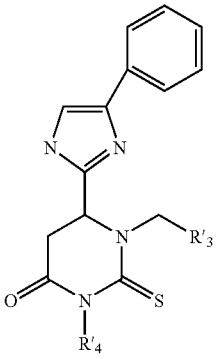

| R'3 | R'4 | $K_i$ |
|---|---|---|
| 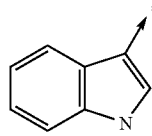 | $(CH_2)_4NH_2$<br>$(CH_2)_5NH_2$<br>$(CH_2)_6NH_2$<br>$(CH_2)_6NMe_2$ | <1 μM<br><1 μM<br><1 μM |
| 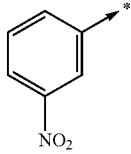 | $(CH_2)_5NH_2$<br>$(CH_2)_6NH_2$<br>$(CH_2)_6NMe_2$ | <1 μM<br><1 μM<br><1 μM |
| 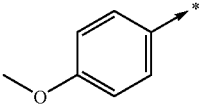 | $(CH_2)_5NH_2$<br>$(CH_2)_6NH_2$<br>$(CH_2)_6NMe_2$ | <1 μM<br><1 μM<br><1 μM |
| 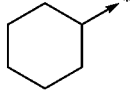 | $(CH_2)_5NH_2$<br>$(CH_2)_6NH_2$<br>$(CH_2)_6NMe_2$ | <1 μM<br><1 μM<br><1 μM |
| 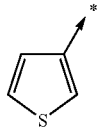 | $(CH_2)_5NH_2$<br>$(CH_2)_6NH_2$<br>$(CH_2)_6NMe_2$ | <1 μM<br><1 μM<br><1 μM |
| 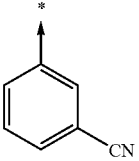 | $(CH_2)_6NMe_2$ | <1 μM |

The invention claimed is:

1. A method of treating a disorder selected from the group consisting of acromegaly, hypophyseal adenomas, endocrine gastroenteropancreatic tumors bleeding in warm-blooded animals comprising administering to warm-blooded animals in need thereof an amount of a compound of the formula

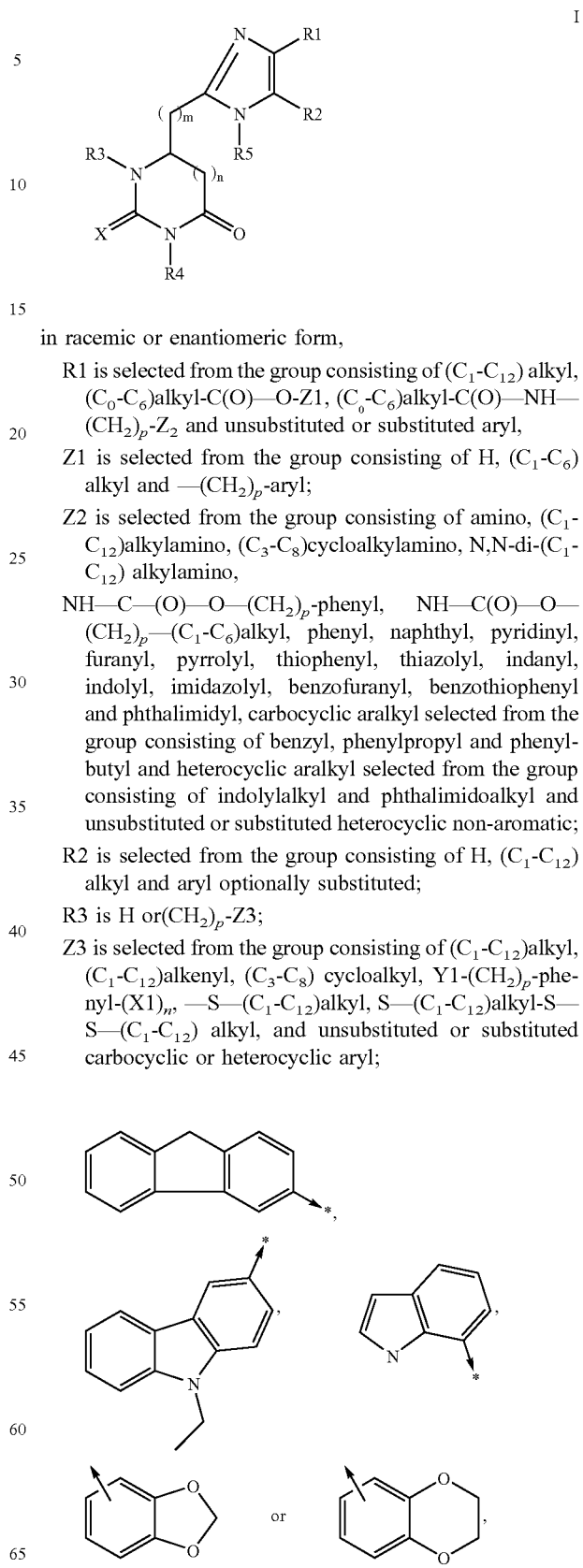

in racemic or enantiomeric form,

R1 is selected from the group consisting of $(C_1-C_{12})$ alkyl, $(C_0-C_6)$alkyl-C(O)—O-Z1, $(C_0-C_6)$alkyl-C(O)—NH—$(CH_2)_p$-Z2 and unsubstituted or substituted aryl, Z1 is selected from the group consisting of H, $(C_1-C_6)$ alkyl and —$(CH_2)_p$-aryl;

Z2 is selected from the group consisting of amino, $(C_1-C_{12})$alkylamino, $(C_3-C_8)$cycloalkylamino, N,N-di-$(C_1-C_{12})$ alkylamino, NH—C—(O)—O—$(CH_2)_p$-phenyl, NH—C(O)—O—$(CH_2)_p$—$(C_1-C_6)$alkyl, phenyl, naphthyl, pyridinyl, furanyl, pyrrolyl, thiophenyl, thiazolyl, indanyl, indolyl, imidazolyl, benzofuranyl, benzothiophenyl and phthalimidyl, carbocyclic aralkyl selected from the group consisting of benzyl, phenylpropyl and phenylbutyl and heterocyclic aralkyl selected from the group consisting of indolylalkyl and phthalimidoalkyl and unsubstituted or substituted heterocyclic non-aromatic;

R2 is selected from the group consisting of H, $(C_1-C_{12})$ alkyl and aryl optionally substituted;

R3 is H or $(CH_2)_p$-Z3;

Z3 is selected from the group consisting of $(C_1-C_{12})$alkyl, $(C_1-C_{12})$alkenyl, $(C_3-C_8)$ cycloalkyl, Y1-$(CH_2)_p$-phenyl-$(X1)_n$, —S—$(C_1-C_{12})$alkyl, S—$(C_1-C_{12})$alkyl-S—S—$(C_1-C_{12})$ alkyl, and unsubstituted or substituted carbocyclic or heterocyclic aryl;

bis-arylalkyl or

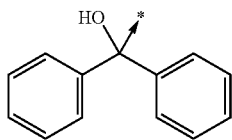

Y1 is O, S, NH or is absent;
R4 is (CH$_2$)$_p$-Z4;
Z4 is selected from the group consisting of amino, (C$_1$-C$_{12}$)alkyl, (C$_3$-C$_8$)cycloalkyl, (C$_1$-C$_{12}$)alkylamino, N,N-di-(C$_1$-C$_{12}$)alkylamino, amino (C$_3$-C$_6$) cycloalkyl, amino (C$_1$-C$_6$) alkyl (C$_3$-C$_8$) cycloalkyl (C$_1$-C$_6$) alkyl, carbocyclic or heterocyclic aminoaryl, (C$_1$-C$_{12}$) alkoxy, (C$_1$-C$_{12}$) alkenyl, N—C(O)O(C$_1$-C$_6$) alkyl, unsubstituted or substituted carbocyclic or heterocyclic aryl, unsubstituted or substituted heterocyclic non-aromatic radical, bis-arylalkyl, di-arylalkyl,

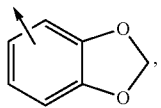 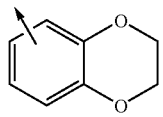

and N (R6)(R7), R6 and R7 taken together with the nitrogen atom which they carry form together a heterocycle of 5 to 7 ring members;
R5 is selected from the group consisting of H, —(CH$_2$)$_p$—C(O)—(CH$_2$)$_p$-Z5, —(CH$_2$)$_p$-Z5, —(CH$_2$)$_p$—OZ5 or —(C$_0$-C$_6$)alkyl-C(O)—NH—(CH$_2$)$_p$-Z5,
Z5 is unsubstituted or substituted member selected from the group consisting of —(C$_1$-C$_{12}$) alkyl, benzo[b]thiophene, phenyl, naphthyl, benzo[b]furanyl, thiophene, isoxazolyl, indolyl,

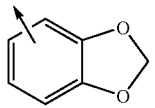 and 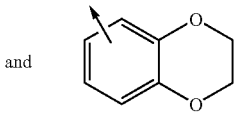

it being understood that the above substitutes of Z5 are selected from the group consisting of Cl, F, Br, I, CF$_3$, NO$_2$, OH, NH$_2$, CN, N$_3$, —OCF$_3$, (C$_1$-C$_{12}$) alkyl, (C$_1$-C$_{12}$) alkoxy, —(CH$_2$)$_p$-phenyl-(X$_1$)$_q$, —NH—CO—(C$_1$-C$_6$) alkyl, —NH—C(O)O—(C$_1$-C$_6$) alkyl, —S—(C$_1$-C$_6$) alkyl, —S-phenyl-(X1)$_q$, —O—(CH$_2$)$_p$-phenyl-(X1)$_q$, —(CH$_2$)$_p$—C(O)—O—(C$_1$-C$_6$) alkyl, —(CH$_2$)$_p$—C(O)—(C$_1$-C$_6$) alkyl, —O—(CH$_2$)$_p$—NH$_2$, —O—(CH$_2$)$_p$—NH—(C$_1$-C$_6$) alkyl, —O—(CH$_2$)$_p$—N-di((C$_1$-C$_6$) alkyl) and (C$_0$-C$_{12}$) alkyl-(X1)$_q$;
X1, each time that it occurs, is independently selected from the group consisting of H, Cl, F, Br, I, CF$_3$, NO$_2$, OH, NH$_2$, CN, N$_3$, —OCF$_3$, (C$_1$-C$_{12}$) alkyl, (C$_1$-C$_{12}$) alkoxy, —S—(C$_1$-C$_6$) alkyl, —(CH$_2$)$_p$-amino, —(CH$_2$)$_p$—NH—(C$_1$-C$_6$) alkyl, —(CH$_2$)$_p$—N-di-((C$_1$-C$_6$) alkyl, —(CH$_2$)$_p$-phenyl and —(CH$_2$)$_p$—NH—(C$_3$-C$_6$)-cycloalkyl;
p each time that it occurs is independently an integer from 0 to 6;
q each time that it occurs is independently an integer from 1 to 5;
X is O or S;
n in the chemical structure is 0;
n in Z3 is 0; and
m is 1, 2 or 3;
or a pharmaceutically acceptable salt of said compound sufficient to treat said disorder.

2. The method of claim 1, wherein
R1 is unsubstituted or substituted aryl;
R2 is H or alkyl;
R3 is selected from the group consisting of

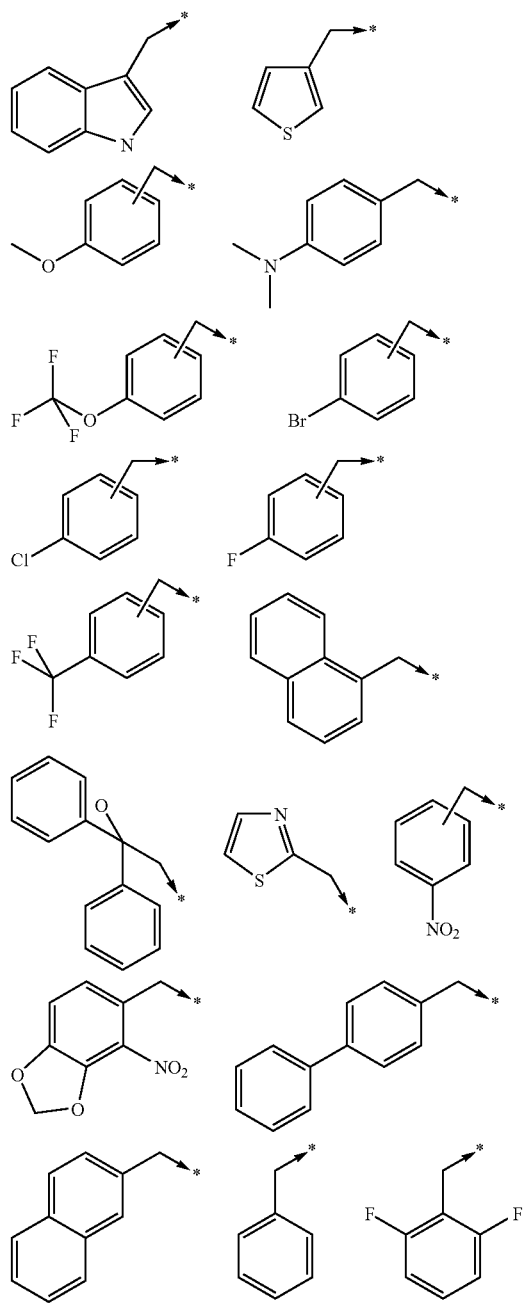

-continued
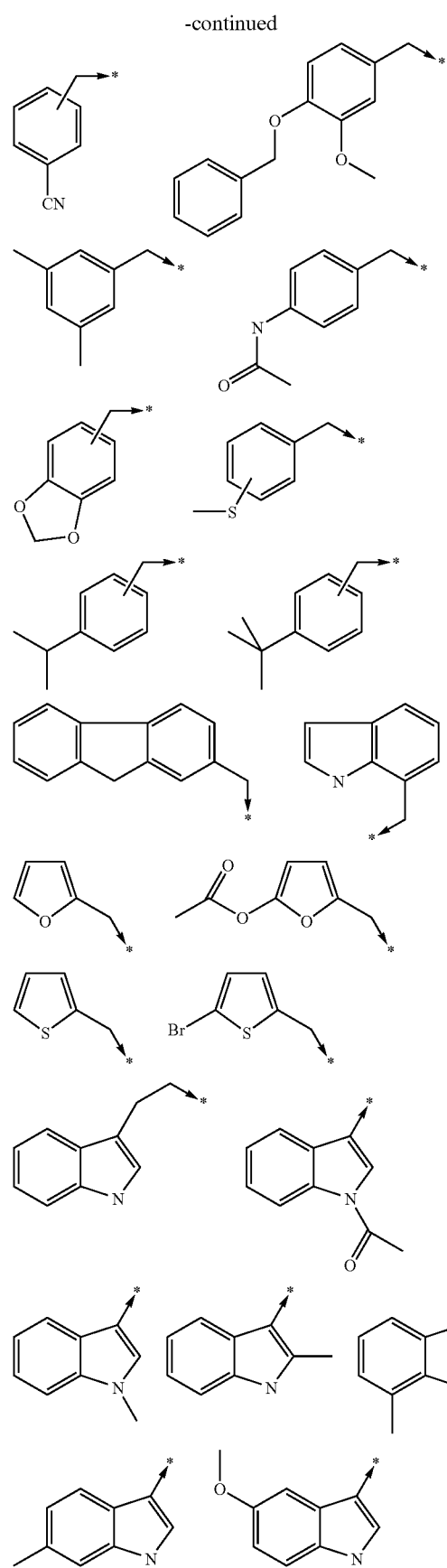
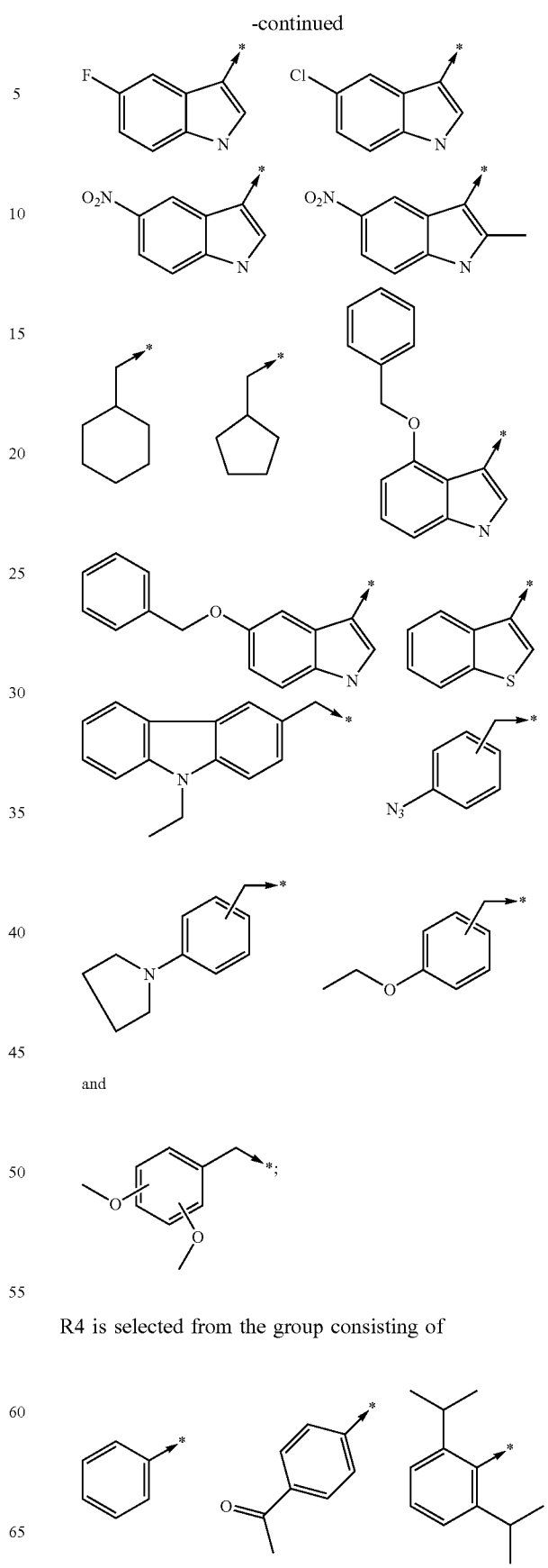
and
R4 is selected from the group consisting of

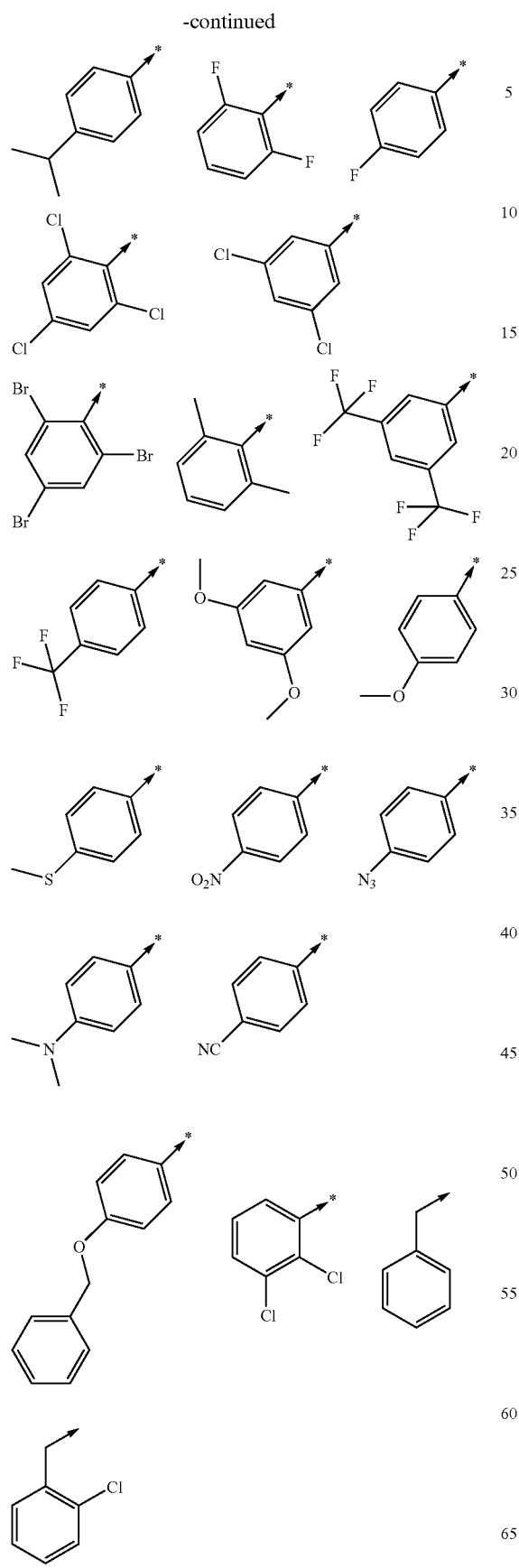
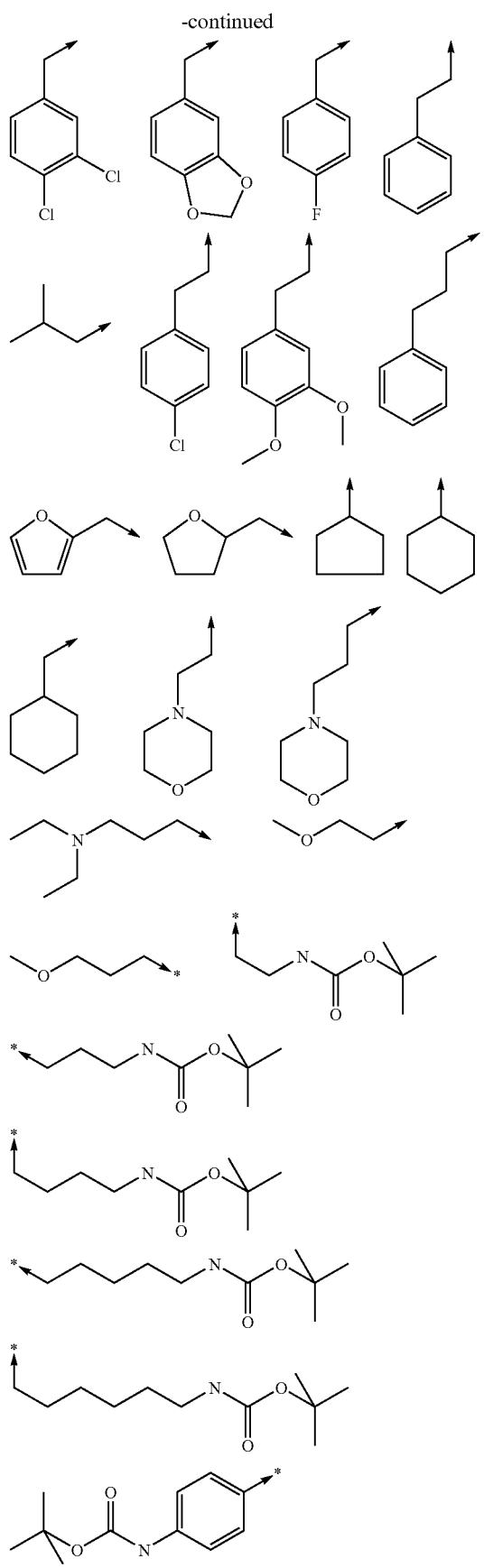

-continued

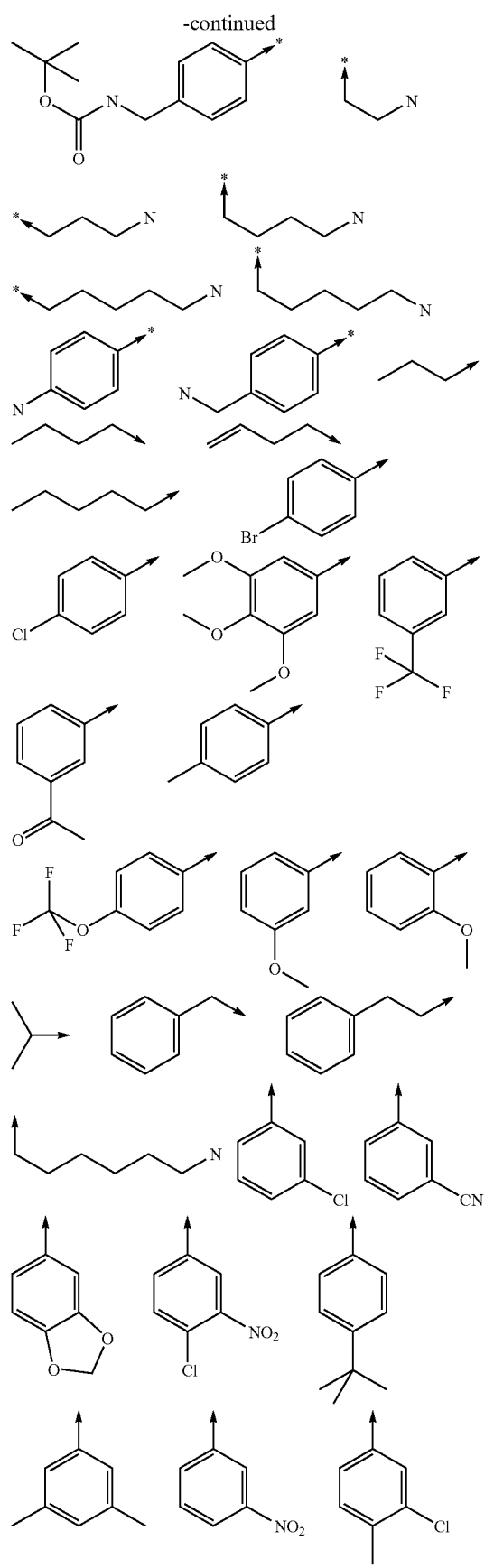

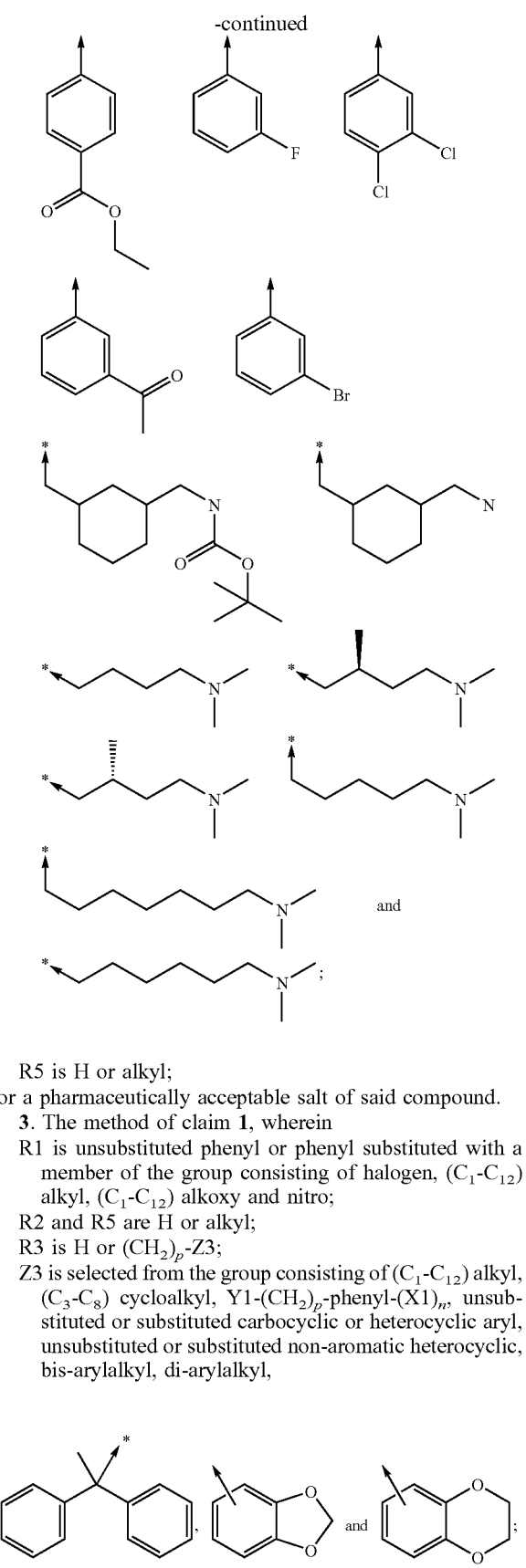

R5 is H or alkyl;
or a pharmaceutically acceptable salt of said compound.

3. The method of claim 1, wherein
R1 is unsubstituted phenyl or phenyl substituted with a member of the group consisting of halogen, ($C_1$-$C_{12}$) alkyl, ($C_1$-$C_{12}$) alkoxy and nitro;
R2 and R5 are H or alkyl;
R3 is H or $(CH_2)_p$-Z3;
Z3 is selected from the group consisting of ($C_1$-$C_{12}$) alkyl, ($C_3$-$C_8$) cycloalkyl, Y1-$(CH_2)_p$-phenyl-$(X1)_n$, unsubstituted or substituted carbocyclic or heterocyclic aryl, unsubstituted or substituted non-aromatic heterocyclic, bis-arylalkyl, di-arylalkyl, Y1 represents O, S, NH or is absent;

R4 is $(CH_2)_p$-Z4;

Z4 is selected from the group consisting of amino, $(C_1$-$C_{12})$ alkyl, $(C_3$-$C_8)$ cycloalkyl, $(C_1$-$C_{12})$ alkylamino, N,N-di-$(C_1$-$C_{12})$ alkylamino, amino $(C_3$-$C_6)$ cycloalkyl, amino $(C_1$-$C_6)$ alkyl $(C_3$-$C_8)$ cycloalkyl $(C_1$-$C_6)$ alkyl, carbocyclic or heterocyclic aminoaryl, an unsubstituted or substituted carbocyclic and heterocyclic aryl, unsubstituted or substituted non-aromatic heterocyclic, bis-arylalkyl, di-arylalkyl,

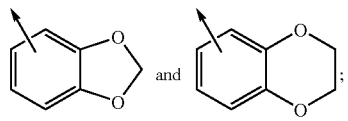

it being understood that the substituent of substituted phenyl is at least one member of the group consisting of Cl, F, Br, I, $CF_3$, $NO_2$, OH, $NH_2$, CN, $N_3$, —$OCF_3$, $(C_1$-$C_{12})$ alkoxy, —$(CH_2)_p$-phenyl-$(X1)_q$, —NH—CO—$(C_1$-$C_6)$ alkyl, —NH—C(O)—$(C_1$-$C_6)$ alkyl, —S—$(C_1C_6)$ alkyl, —S-phenyl-$(X1)_q$, —O—$(CH_2)_p$-phenyl-$(X1)_q$, —$(CH_2)_p$—C(O)—O—$(C_1$-$C_6)$ alkyl, —$(CH_2)_p$—C(O)—$(C_1$-$C_6)$ alkyl, —O—$(CH_2)_p$—$NH_2$, —O$(CH_2)_p$—NH —$(C_1$-$C_6)$alkyl, —O—$(CH_2)_p$—N-di-$((C_{1-6})$ alkyl and $(C_0$-$C_{12})$ alkyl-$(X1)_q$;

X1, each time that it occurs, is selected from the group consisting of H, Cl, F, Br, I, $CF_3$, $NO_2$, OH, $NH_2$, CN, $N_3$, —$OCF_3$, $(C_1$-$C_{12})$ alkyl, $(C_1$-$C_{12})$ alkoxy, —S—$(C_1$-$C_6)$ alkyl, —$(CH_2)_p$-amino, —$(CH_2)_p$—NH—$(C_1$-$C_6)$ alkyl, —$(CH_2)_p$—N-di-$((C_1$-$C_6)$ alkyl), —$(CH_2)_p$-phenyl and —$(CH_2)_p$—NH—$(C_3$-$C_6)$ cycloalkyl;

p each time that it occurs is independently an integer from 0 to 6; and q each time that it occurs is independently an integer from 1 to 5.

4. The method of claim 3, wherein

R1 is phenyl or phenyl substituted by a member selected from the group consisting of halogen, $(C_1$-$C_{12})$ alkyl, $(C_1$-$C_{12})$ alkoxy and nitro;

R2 and R5 are H or alkyl;

R3 is $(C_2)_p$-Z3,

Z3 is selected from the group Z3 is selected from the group consisting of $(C_3$-$C_8)$ cycloalkyl, unsubstituted or substituted phenyl, naphthyl, furanyl, thiophene, indolyl, pyrrolyl and benzothiophene;

R4 is $(CH_2)_p$-Z4;

Z4 is selected from the group consisting of amino, $(C_1$-$C_{12})$ alkylamino, N,N-di-$(C_1$-$C_{12})$ alkylamino and amino $(C_1$-$C_6)$ alkyl $(C_3$-$C_6)$ cycloalkyl-$(C_1$-$C_6)$ alkyl;

X is S;

p each time that it occurs is independently an integer from 0 to 6;

n is 0; and m is 1, 2 or 3.

5. The method of claim 4 selected from the compounds of formulae

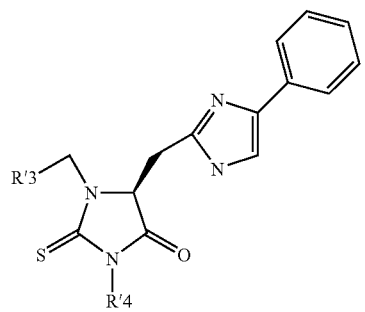

(I)b and

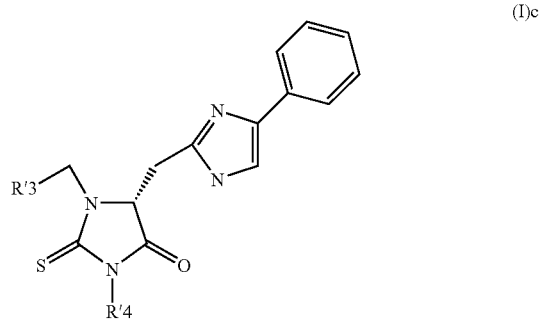

(I)c wherein R'3 is selected from

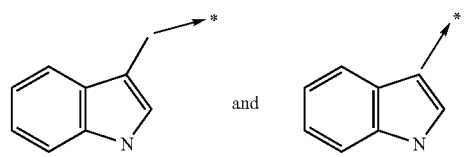

and R'3 is selected from

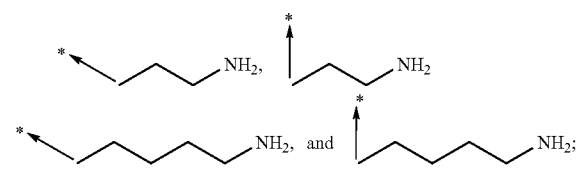

or a pharmaceutically acceptable salt or said compound.

* * * * *